US012616462B2

(12) United States Patent
Stone et al.

(10) Patent No.: US 12,616,462 B2
(45) Date of Patent: May 5, 2026

(54) SOFT TISSUE REPAIR DEVICE AND METHOD

(71) Applicant: Biomet Sports Medicine, LLC, Warsaw, IN (US)

(72) Inventors: Kevin T. Stone, Winona Lake, IN (US); Nathan M. Sautter, North Manchester, IN (US); Brian K. Berelsman, Warsaw, IN (US); Jeffery D. Arnett, Gilbert, AZ (US); Joshua A. Butters, Chandler, AZ (US); Dylan M. Hushka, Chandler, AZ (US); Nicholas R. Slater, Chandler, AZ (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 351 days.

(21) Appl. No.: 18/531,396

(22) Filed: Dec. 6, 2023

(65) Prior Publication Data

US 2024/0130727 A1     Apr. 25, 2024

Related U.S. Application Data

(60) Continuation of application No. 17/392,971, filed on Aug. 3, 2021, now abandoned, which is a (Continued)

(51) Int. Cl.
A61B 17/04          (2006.01)
(52) U.S. Cl.
CPC ...... A61B 17/0469 (2013.01); A61B 17/0401 (2013.01); A61B 2017/0409 (2013.01)
(58) Field of Classification Search
CPC .......... A61B 17/0469; A61B 17/06166; A61B 17/0401; A61B 2017/0406;
(Continued)

(56) References Cited

U.S. PATENT DOCUMENTS 26,501  A     12/1859   Kendrick et al.
64,499  A      5/1867   Daubert
(Continued)

FOREIGN PATENT DOCUMENTS

AU        4957264  A      3/1966
AU         440266  A1    10/1967
(Continued)

OTHER PUBLICATIONS

US 6,238,418 B1, 05/2001, Schwartz (withdrawn)
(Continued)

*Primary Examiner* — Dianne Dornbusch
(74) *Attorney, Agent, or Firm* — SCHWEGMAN LUNDBERG & WOESSNER, P.A.

(57)          ABSTRACT

A soft tissue repair device can include a housing having a handle, a deployment system having an actuation member, and an insertion system having an inserter and a slider. The slider can be coupled to the actuation member and movable relative to the inserter between deployed and retracted positions. First and second anchors can be carried on an external surface of the slider such that the anchors are spaced apart and portions of the anchors are coaxial with the slider and each other. A flexible strand can couple the anchors. The insertion system can cooperate with the deployment system to move the slider to the deployed position to deploy the first anchor upon activating the actuation member a first time, and to move the slider to the deployed position from the retracted position to deploy the second anchor upon actuating the actuation member a second time after the first time.

22 Claims, 19 Drawing Sheets

Related U.S. Application Data continuation of application No. 16/255,300, filed on Jan. 23, 2019, now Pat. No. 11,109,857, which is a continuation of application No. 15/332,590, filed on Oct. 24, 2016, now Pat. No. 10,265,064, which is a continuation of application No. 13/645,964, filed on Oct. 5, 2012, now Pat. No. 9,504,460, which is a division of application No. 12/570,854, filed on Sep. 30, 2009, now Pat. No. 8,303,604.

(58) Field of Classification Search
CPC .... A61B 2017/0409; A61B 2017/0417; A61B 2017/0445
See application file for complete search history.

(56) References Cited

U.S. PATENT DOCUMENTS

| | | | |
|---|---|---|---|
| 65,499 | A | 6/1867 | Miller |
| 126,366 | A | 4/1872 | Wills |
| 233,475 | A | 10/1880 | Cook et al. |
| 261,501 | A | 7/1882 | Vandermark |
| 268,407 | A | 12/1882 | Hughes |
| 330,087 | A | 11/1885 | Binns |
| 394,739 | A | 12/1888 | Toulmin |
| 401,677 | A | 4/1889 | Autenrieth |
| 417,805 | A | 12/1889 | Beaman |
| 445,875 | A | 2/1891 | Brickell |
| 487,304 | A | 12/1892 | Todd |
| 687,221 | A | 11/1901 | Gaff et al. |
| 762,710 | A | 6/1904 | Hall |
| 837,767 | A | 12/1906 | Aims |
| 838,203 | A | 12/1906 | Neil |
| 1,059,631 | A | 4/1913 | Popovics |
| 1,131,155 | A | 3/1915 | Murphy |
| 1,153,450 | A | 9/1915 | Schaff |
| 1,346,940 | A | 7/1920 | Collins |
| 1,505,470 | A | 8/1924 | Kelm |
| 1,635,066 | A | 7/1927 | Wells |
| 1,950,799 | A | 3/1934 | Jones |
| 2,042,403 | A | 5/1936 | Andrew |
| 2,065,659 | A | 12/1936 | Cullen |
| 2,108,206 | A | 2/1938 | Meeker |
| 2,121,193 | A | 6/1938 | Erich |
| 2,242,003 | A | 5/1941 | Lorenzo |
| 2,267,925 | A | 12/1941 | Johnston |
| 2,302,986 | A | 11/1942 | Vollrath |
| 2,329,398 | A | 9/1943 | Duffy |
| 2,379,629 | A | 7/1945 | Eweson |
| 2,397,216 | A | 3/1946 | Stellin |
| RE22,857 | E | 3/1947 | Ogburn |
| 2,526,959 | A | 10/1950 | Lorenzo |
| 2,528,456 | A | 10/1950 | Thomas |
| 2,549,382 | A | 4/1951 | Mitterway |
| 2,562,419 | A | 7/1951 | Ferris |
| 2,581,564 | A | 1/1952 | Jaime |
| 2,600,395 | A | 6/1952 | Joseph et al. |
| 2,610,631 | A | 9/1952 | Calicchio |
| 2,665,597 | A | 1/1954 | Hill |
| 2,669,774 | A | 2/1954 | Mitchell |
| 2,698,986 | A | 1/1955 | Brown |
| 2,760,488 | A | 8/1956 | Pierce |
| 2,833,284 | A | 5/1958 | Springer |
| 2,846,712 | A | 8/1958 | Moe |
| 2,860,393 | A | 11/1958 | Brock |
| 2,880,728 | A | 4/1959 | Rights |
| 2,881,762 | A | 4/1959 | Lowrie |
| 2,883,096 | A | 4/1959 | Horace |
| 2,913,042 | A | 11/1959 | John |
| 2,947,504 | A | 8/1960 | Ruhlman |
| 3,000,009 | A | 9/1961 | Selstad |
| 3,003,155 | A | 10/1961 | Mielzynski |
| 3,013,559 | A | 12/1961 | Thomas |
| 3,037,619 | A | 6/1962 | Ernest |
| 3,039,460 | A | 6/1962 | Chandler |
| 3,081,781 | A | 3/1963 | Stermer |
| 3,090,386 | A | 5/1963 | William |
| 3,103,666 | A | 9/1963 | Bone |
| 3,123,077 | A | 3/1964 | Alcamo |
| 3,125,095 | A | 3/1964 | Kaufman et al. |
| 3,209,422 | A | 10/1965 | Arthur |
| 3,223,083 | A | 12/1965 | Cobey |
| 3,234,938 | A | 2/1966 | Robinson |
| 3,240,379 | A | 3/1966 | Bremer et al. |
| 3,250,271 | A | 5/1966 | Jack |
| 3,399,432 | A | 9/1968 | Merser |
| 3,409,014 | A | 11/1968 | Grant |
| RE26,501 | E | 12/1968 | Himmelstein et al. |
| 3,435,475 | A | 4/1969 | Bisk |
| 3,467,089 | A | 9/1969 | Hasson |
| 3,470,834 | A | 10/1969 | Bone |
| 3,470,875 | A | 10/1969 | Johnson |
| 3,500,820 | A | 3/1970 | Almen |
| 3,507,274 | A | 4/1970 | Soichet |
| 3,513,484 | A | 5/1970 | Hausner |
| 3,515,132 | A | 6/1970 | Mcknight |
| 3,522,803 | A | 8/1970 | Majzlin |
| 3,527,223 | A | 9/1970 | Shein |
| 3,533,406 | A | 10/1970 | Tatum |
| 3,541,591 | A | 11/1970 | Hoegerman |
| 3,545,008 | A | 12/1970 | Bader, Jr. |
| 3,547,389 | A | 12/1970 | Mitchell |
| 3,579,831 | A | 5/1971 | Stevens et al. |
| 3,590,616 | A | 7/1971 | Schussler |
| 3,608,095 | A | 9/1971 | Barry |
| 3,618,447 | A | 11/1971 | Goins |
| 3,628,530 | A | 12/1971 | Schwartz |
| 3,643,649 | A | 2/1972 | Amato |
| 3,648,705 | A | 3/1972 | Lary |
| 3,650,274 | A | 3/1972 | Edwards et al. |
| 3,656,483 | A | 4/1972 | Rudel |
| 3,659,597 | A | 5/1972 | Wolfers |
| 3,664,345 | A | 5/1972 | Dabbs et al. |
| 3,665,560 | A | 5/1972 | Bennett et al. |
| 3,675,639 | A | 7/1972 | Cimber |
| 3,683,422 | A | 8/1972 | Stemmer et al. |
| 3,692,022 | A | 9/1972 | Ewing |
| 3,695,271 | A | 10/1972 | Chodorow |
| 3,699,969 | A | 10/1972 | Allen |
| 3,716,058 | A | 2/1973 | Tanner |
| 3,744,488 | A | 7/1973 | Cox |
| 3,752,516 | A | 8/1973 | Mumma |
| 3,757,629 | A | 9/1973 | Schneider |
| 3,763,856 | A | 10/1973 | Blomberg |
| 3,771,520 | A | 11/1973 | Lerner |
| 3,777,748 | A | 12/1973 | Abramson |
| 3,786,801 | A | 1/1974 | Sartorius |
| 3,802,438 | A | 4/1974 | Wolvek |
| 3,807,407 | A | 4/1974 | Schweizer |
| 3,810,456 | A | 5/1974 | Karman |
| 3,825,010 | A | 7/1974 | Mc Donald |
| 3,840,017 | A | 10/1974 | Violante |
| 3,842,824 | A | 10/1974 | Neufeld |
| 3,842,840 | A | 10/1974 | Schweizer |
| 3,845,772 | A | 11/1974 | Smith |
| 3,867,933 | A | 2/1975 | Kitrilakis |
| 3,867,944 | A | 2/1975 | Samuels |
| 3,871,368 | A | 3/1975 | Johnson et al. |
| 3,871,379 | A | 3/1975 | Clarke |
| 3,874,388 | A | 4/1975 | King et al. |
| 3,875,648 | A | 4/1975 | Bone |
| 3,877,570 | A | 4/1975 | Barry |
| 3,880,156 | A | 4/1975 | Hoff |
| 3,881,475 | A | 5/1975 | Gordon et al. |
| 3,889,666 | A | 6/1975 | Lerner |
| 3,892,240 | A | 7/1975 | Park |
| 3,896,500 | A | 7/1975 | Rambert et al. |
| 3,896,810 | A | 7/1975 | Akiyama |
| 3,907,442 | A | 9/1975 | Reid |
| 3,910,281 | A | 10/1975 | Kletschka |
| 3,918,444 | A | 11/1975 | Hoff et al. |
| 3,918,455 | A | 11/1975 | Coplan |
| 3,927,666 | A | 12/1975 | Hoff |
| 3,931,667 | A | 1/1976 | Merser et al. |

(56)                    References Cited

U.S. PATENT DOCUMENTS

| | | | |
|---|---|---|---|
| 3,933,153 | A | 1/1976 | Csatary et al. |
| 3,937,217 | A | 2/1976 | Kosonen |
| 3,943,932 | A | 3/1976 | Woo |
| 3,946,446 | A | 3/1976 | Schofield |
| 3,946,728 | A | 3/1976 | Bettex |
| 3,946,740 | A | 3/1976 | Bassett |
| 3,949,755 | A | 4/1976 | Vauquois |
| 3,953,896 | A | 5/1976 | Treace |
| 3,954,103 | A | 5/1976 | Garcia-Roel et al. |
| 3,961,632 | A | 6/1976 | Moossun |
| 3,973,560 | A | 8/1976 | Emmett |
| 3,976,079 | A | 8/1976 | Samuels et al. |
| 3,977,050 | A | 8/1976 | Perez |
| 3,979,799 | A | 9/1976 | Merser et al. |
| 3,985,138 | A | 10/1976 | Jarvik |
| 3,990,619 | A | 11/1976 | Russell |
| 4,005,707 | A | 2/1977 | Moulding, Jr. |
| 4,006,747 | A | 2/1977 | Kronenthal et al. |
| 4,007,743 | A | 2/1977 | Blake |
| 4,013,071 | A | 3/1977 | Rosenberg |
| 4,026,281 | A | 5/1977 | Mayberry et al. |
| 4,036,101 | A | 7/1977 | Burnett |
| 4,050,100 | A | 9/1977 | Barry |
| 4,054,954 | A | 10/1977 | Nakayama et al. |
| 4,084,478 | A | 4/1978 | Simmons |
| 4,085,466 | A | 4/1978 | Goodfellow et al. |
| 4,094,313 | A | 6/1978 | Komamura et al. |
| 4,099,750 | A | 7/1978 | Mcgrew |
| 4,103,690 | A | 8/1978 | Harris |
| RE29,819 | E | 10/1978 | Bone |
| 4,121,487 | A | 10/1978 | Bone |
| 4,143,656 | A | 3/1979 | Holmes |
| 4,144,876 | A | 3/1979 | Deleo |
| 4,146,022 | A | 3/1979 | Johnson et al. |
| 4,149,277 | A | 4/1979 | Bokros |
| 4,157,714 | A | 6/1979 | Foltz et al. |
| 4,158,250 | A | 6/1979 | Ringwald |
| 4,160,453 | A | 7/1979 | Miller |
| 4,164,225 | A | 8/1979 | Johnson et al. |
| 4,172,458 | A | 10/1979 | Pereyra |
| 4,175,555 | A | 11/1979 | Herbert |
| 4,185,636 | A | 1/1980 | Gabbay et al. |
| 4,196,883 | A | 4/1980 | Einhorn et al. |
| 4,207,627 | A | 6/1980 | Cloutier |
| 4,210,148 | A | 7/1980 | Stivala |
| 4,235,161 | A | 11/1980 | Kunreuther |
| 4,235,238 | A | 11/1980 | Ogiu et al. |
| 4,237,779 | A | 12/1980 | Kunreuther |
| 4,243,037 | A | 1/1981 | Smith |
| 4,249,525 | A | 2/1981 | Krzeminski |
| 4,263,913 | A | 4/1981 | Malmin |
| 4,265,246 | A | 5/1981 | Barry |
| 4,273,117 | A | 6/1981 | Neuhauser |
| 4,275,490 | A | 6/1981 | Bivins |
| 4,275,717 | A | 6/1981 | Bolesky |
| 4,287,807 | A | 9/1981 | Pacharis et al. |
| 4,291,698 | A | 9/1981 | Fuchs et al. |
| 4,301,551 | A | 11/1981 | Dore et al. |
| 4,302,397 | A | 11/1981 | Frainier et al. |
| 4,307,723 | A | 12/1981 | Finney |
| 4,312,337 | A | 1/1982 | Donohue |
| 4,316,469 | A | 2/1982 | Kapitanov |
| 4,319,428 | A | 3/1982 | Fox |
| 4,326,531 | A | 4/1982 | Shimonaka |
| 4,344,193 | A | 8/1982 | Kenny |
| 4,345,601 | A | 8/1982 | Fukuda |
| 4,349,027 | A | 9/1982 | Difrancesco |
| 4,388,921 | A | 6/1983 | Sutter et al. |
| 4,400,833 | A | 8/1983 | Kurland |
| 4,402,445 | A | 9/1983 | Green |
| 4,409,974 | A | 10/1983 | Freedland et al. |
| 4,438,769 | A | 3/1984 | Pratt et al. |
| 4,441,489 | A | 4/1984 | Evans et al. |
| 4,454,875 | A | 6/1984 | Pratt et al. |
| 4,462,395 | A | 7/1984 | Johnson |
| 4,463,753 | A | 8/1984 | Gustilo |
| 4,473,102 | A | 9/1984 | Ohman et al. |
| 4,484,570 | A | 11/1984 | Sutter et al. |
| 4,489,446 | A | 12/1984 | Reed |
| 4,489,464 | A | 12/1984 | Massari et al. |
| 4,493,323 | A | 1/1985 | Albright et al. |
| 4,496,468 | A | 1/1985 | House et al. |
| 4,505,274 | A | 3/1985 | Speelman |
| 4,509,516 | A | 4/1985 | Richmond |
| 4,531,522 | A | 7/1985 | Bedi et al. |
| 4,532,926 | A | 8/1985 | O'holla |
| 4,534,350 | A | 8/1985 | Golden et al. |
| 4,535,764 | A | 8/1985 | Ebert |
| 4,537,185 | A | 8/1985 | Stednitz |
| 4,549,545 | A | 10/1985 | Levy |
| 4,549,652 | A | 10/1985 | Free |
| 4,561,432 | A | 12/1985 | Mazor |
| 4,564,007 | A | 1/1986 | Coombs |
| 4,570,623 | A | 2/1986 | Ellison et al. |
| 4,573,844 | A | 3/1986 | Smith |
| 4,576,608 | A | 3/1986 | Homsy |
| 4,584,722 | A | 4/1986 | Levy et al. |
| 4,587,963 | A | 5/1986 | Leibinger et al. |
| 4,590,928 | A | 5/1986 | Hunt et al. |
| 4,595,007 | A | 6/1986 | Mericle |
| 4,596,249 | A | 6/1986 | Freda et al. |
| 4,597,766 | A | 7/1986 | Hilal et al. |
| 4,602,635 | A | 7/1986 | Mulhollan et al. |
| 4,602,636 | A | 7/1986 | Noiles |
| 4,604,997 | A | 8/1986 | De et al. |
| 4,605,414 | A | 8/1986 | Czajka |
| 4,616,650 | A | 10/1986 | Green et al. |
| 4,621,640 | A | 11/1986 | Mulhollan et al. |
| 4,624,254 | A | 11/1986 | Mcgarry et al. |
| 4,632,100 | A | 12/1986 | Somers et al. |
| 4,635,637 | A | 1/1987 | Schreiber |
| 4,636,121 | A | 1/1987 | Miller |
| 4,640,271 | A | 2/1987 | Lower |
| 4,641,652 | A | 2/1987 | Hutterer et al. |
| 4,649,916 | A | 3/1987 | Frimberger |
| 4,649,952 | A | 3/1987 | Jobe |
| 4,653,486 | A | 3/1987 | Coker |
| 4,653,487 | A | 3/1987 | Maale |
| 4,653,489 | A | 3/1987 | Tronzo |
| 4,655,771 | A | 4/1987 | Wallsten |
| 4,655,777 | A | 4/1987 | Dunn |
| 4,662,068 | A | 5/1987 | Polonsky |
| 4,667,662 | A | 5/1987 | Titone et al. |
| 4,667,675 | A | 5/1987 | Davis |
| 4,669,473 | A | 6/1987 | Richards et al. |
| 4,683,895 | A | 8/1987 | Pohndorf |
| 4,688,561 | A | 8/1987 | Reese |
| 4,690,169 | A | 9/1987 | Jobe |
| 4,696,300 | A | 9/1987 | Anderson |
| 4,705,040 | A | 11/1987 | Mueller et al. |
| 4,708,132 | A | 11/1987 | Silvestrini |
| 4,711,639 | A | 12/1987 | Grundei |
| 4,714,474 | A | 12/1987 | Brooks, Jr. et al. |
| 4,714,475 | A | 12/1987 | Grundei et al. |
| 4,716,893 | A | 1/1988 | Fischer et al. |
| 4,719,671 | A | 1/1988 | Ito et al. |
| 4,719,917 | A | 1/1988 | Barrows et al. |
| 4,723,540 | A | 2/1988 | Gilmer, Jr. |
| 4,724,839 | A | 2/1988 | Bedi et al. |
| 4,728,329 | A | 3/1988 | Mansat |
| 4,728,332 | A | 3/1988 | Albrektsson |
| 4,730,615 | A | 3/1988 | Sutherland et al. |
| 4,736,746 | A | 4/1988 | Anderson |
| 4,738,255 | A | 4/1988 | Goble et al. |
| 4,739,751 | A | 4/1988 | Sapega et al. |
| 4,741,330 | A | 5/1988 | Hayhurst |
| 4,741,336 | A | 5/1988 | Failla et al. |
| 4,744,353 | A | 5/1988 | Mcfarland |
| 4,744,793 | A | 5/1988 | Parr et al. |
| 4,750,492 | A | 6/1988 | Jacobs |
| 4,751,922 | A | 6/1988 | Dipietropolo |
| 4,754,685 | A | 7/1988 | Kite et al. |
| 4,760,843 | A | 8/1988 | Fischer et al. |
| 4,760,844 | A | 8/1988 | Kyle |

(56)                    References Cited

U.S. PATENT DOCUMENTS

| | | | |
|---|---|---|---|
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,779,372 A | 10/1988 | Pozo Obeso |
| 4,781,190 A | 11/1988 | Lee |
| 4,784,126 A | 11/1988 | Hourahane |
| 4,787,882 A | 11/1988 | Claren |
| 4,790,297 A | 12/1988 | Luque |
| 4,790,850 A | 12/1988 | Dunn et al. |
| 4,793,363 A | 12/1988 | Ausherman et al. |
| 4,795,468 A | 1/1989 | Hodorek et al. |
| 4,809,695 A | 3/1989 | Gwathmey et al. |
| 4,813,406 A | 3/1989 | Ogle, II |
| 4,813,416 A | 3/1989 | Pollak et al. |
| 4,823,780 A | 4/1989 | Odensten et al. |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,836,080 A | 6/1989 | Kite, III et al. |
| 4,838,282 A | 6/1989 | Strasser et al. |
| 4,841,960 A | 6/1989 | Garner |
| 4,846,835 A | 7/1989 | Grande |
| 4,851,005 A | 7/1989 | Hunt et al. |
| 4,858,601 A | 8/1989 | Glisson |
| 4,858,603 A | 8/1989 | Clemow et al. |
| 4,858,608 A | 8/1989 | Mcquilkin |
| 4,860,513 A | 8/1989 | Whitman |
| 4,863,383 A | 9/1989 | Grafelmann |
| 4,863,471 A | 9/1989 | Mansat |
| 4,870,957 A | 10/1989 | Goble et al. |
| 4,872,450 A | 10/1989 | Austad |
| 4,873,976 A | 10/1989 | Schreiber |
| 4,884,572 A | 12/1989 | Bays et al. |
| 4,887,601 A | 12/1989 | Richards |
| 4,889,110 A | 12/1989 | Galline et al. |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,917,700 A | 4/1990 | Aikins |
| 4,919,667 A | 4/1990 | Richmond |
| 4,922,897 A | 5/1990 | Sapega et al. |
| 4,923,461 A | 5/1990 | Caspari et al. |
| 4,927,421 A | 5/1990 | Goble et al. |
| 4,946,377 A | 8/1990 | Kovach |
| 4,946,467 A | 8/1990 | Ohi et al. |
| 4,946,468 A | 8/1990 | Li |
| 4,950,270 A | 8/1990 | Bowman et al. |
| 4,950,285 A | 8/1990 | Wilk |
| 4,959,069 A | 9/1990 | Brennan et al. |
| 4,960,381 A | 10/1990 | Niznick |
| 4,961,741 A | 10/1990 | Hayhurst |
| 4,962,929 A | 10/1990 | Melton, Jr. |
| 4,968,315 A | 11/1990 | Gatturna |
| 4,968,317 A | 11/1990 | Tormala et al. |
| 4,969,886 A | 11/1990 | Cziffer et al. |
| 4,974,488 A | 12/1990 | Spralja |
| 4,974,656 A | 12/1990 | Judkins |
| 4,976,736 A | 12/1990 | White et al. |
| 4,978,350 A | 12/1990 | Wagenknecht |
| 4,979,956 A | 12/1990 | Silvestrini |
| 4,983,176 A | 1/1991 | Cushman et al. |
| 4,983,184 A | 1/1991 | Steinemann |
| 4,983,240 A | 1/1991 | Orkin et al. |
| 4,988,351 A | 1/1991 | Paulos et al. |
| 4,994,074 A | 2/1991 | Bezwada et al. |
| 4,997,433 A | 3/1991 | Goble et al. |
| 5,002,545 A | 3/1991 | Whiteside et al. |
| 5,002,550 A | 3/1991 | Li |
| 5,002,562 A | 3/1991 | Oberlander |
| 5,002,574 A | 3/1991 | May et al. |
| 5,007,921 A | 4/1991 | Brown |
| 5,019,093 A | 5/1991 | Kaplan et al. |
| 5,020,713 A | 6/1991 | Kunreuther |
| 5,026,398 A | 6/1991 | May et al. |
| 5,028,569 A | 7/1991 | Cihon |
| 5,030,224 A | 7/1991 | Wright |
| 5,030,235 A | 7/1991 | Campbell, Jr. |
| 5,035,701 A | 7/1991 | Kabbara |
| 5,037,422 A | 8/1991 | Hayhurst et al. |
| 5,037,426 A | 8/1991 | Goble et al. |
| 5,041,129 A | 8/1991 | Hayhurst et al. |
| 5,046,513 A | 9/1991 | Gatturna et al. |
| 5,047,030 A | 9/1991 | Draenert |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A | 11/1991 | Gilbertson et al. |
| 5,067,962 A | 11/1991 | Campbell et al. |
| 5,071,420 A | 12/1991 | Paulos et al. |
| 5,074,874 A | 12/1991 | Yoon et al. |
| 5,078,731 A | 1/1992 | Hayhurst |
| 5,078,843 A | 1/1992 | Pratt |
| 5,080,050 A | 1/1992 | Dale |
| 5,080,675 A | 1/1992 | Lawes et al. |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,087,309 A | 2/1992 | Melton, Jr. |
| 5,089,012 A | 2/1992 | Prou |
| 5,092,727 A | 3/1992 | Moghe |
| 5,092,866 A | 3/1992 | Breard et al. |
| 5,098,433 A | 3/1992 | Freedland |
| 5,098,435 A | 3/1992 | Stednitz et al. |
| 5,100,415 A | 3/1992 | Hayhurst |
| 5,100,417 A | 3/1992 | Cerier |
| 5,108,433 A | 4/1992 | May et al. |
| 5,112,335 A | 5/1992 | Laboureau et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,783 A | 7/1992 | Moghe et al. |
| 5,127,785 A | 7/1992 | Faucher |
| 5,129,901 A | 7/1992 | Decoste |
| 5,129,902 A | 7/1992 | Goble et al. |
| 5,129,904 A | 7/1992 | Illi |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,151,104 A | 9/1992 | Kenna |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,171,274 A | 12/1992 | Fluckiger et al. |
| 5,176,682 A | 1/1993 | Chow |
| 5,178,629 A | 1/1993 | Kammerer |
| 5,183,458 A | 2/1993 | Marx |
| 5,190,545 A | 3/1993 | Corsi et al. |
| 5,192,282 A | 3/1993 | Draenert |
| 5,197,987 A | 3/1993 | Koch et al. |
| 5,199,135 A | 4/1993 | Gold |

(56)                    References Cited

U.S. PATENT DOCUMENTS

| | | | |
|---|---|---|---|
| 5,203,784 | A | 4/1993 | Ross et al. |
| 5,203,787 | A | 4/1993 | Noblitt et al. |
| 5,207,679 | A | 5/1993 | Li |
| 5,209,753 | A | 5/1993 | Biedermann et al. |
| 5,209,805 | A | 5/1993 | Spraggins |
| 5,211,647 | A | 5/1993 | Schmieding |
| 5,211,650 | A | 5/1993 | Noda |
| 5,214,987 | A | 6/1993 | Fenton, Sr. |
| 5,217,495 | A | 6/1993 | Kaplan et al. |
| 5,219,359 | A | 6/1993 | McQuilkin et al. |
| 5,222,976 | A | 6/1993 | Yoon |
| 5,224,940 | A | 7/1993 | Dann et al. |
| 5,224,946 | A | 7/1993 | Hayhurst et al. |
| 5,226,914 | A | 7/1993 | Caplan et al. |
| 5,230,699 | A | 7/1993 | Grasinger |
| 5,232,436 | A | 8/1993 | Janevski |
| 5,234,435 | A | 8/1993 | Seagrave, Jr. |
| 5,235,238 | A | 8/1993 | Nomura et al. |
| 5,236,445 | A | 8/1993 | Hayhurst et al. |
| 5,236,461 | A | 8/1993 | Forte |
| 5,242,447 | A | 9/1993 | Borzone |
| 5,246,441 | A | 9/1993 | Ross et al. |
| 5,249,899 | A | 10/1993 | Wilson |
| 5,250,053 | A | 10/1993 | Snyder |
| 5,258,015 | A | 11/1993 | Li et al. |
| 5,258,016 | A | 11/1993 | Dipoto et al. |
| 5,258,040 | A | 11/1993 | Bruchman et al. |
| 5,261,908 | A | 11/1993 | Campbell, Jr. |
| 5,268,001 | A | 12/1993 | Nicholson et al. |
| 5,269,160 | A | 12/1993 | Wood |
| 5,269,783 | A | 12/1993 | Sander |
| 5,269,806 | A | 12/1993 | Sardelis et al. |
| 5,269,809 | A | 12/1993 | Hayhurst et al. |
| 5,279,311 | A | 1/1994 | Snyder |
| 5,281,422 | A | 1/1994 | Badylak et al. |
| 5,282,809 | A | 2/1994 | Kammerer et al. |
| 5,282,832 | A | 2/1994 | Toso et al. |
| 5,282,867 | A | 2/1994 | Mikhail |
| 5,282,868 | A | 2/1994 | Bahler |
| 5,285,040 | A | 2/1994 | Brandberg et al. |
| 5,290,217 | A | 3/1994 | Campos |
| 5,290,243 | A | 3/1994 | Chodorow et al. |
| 5,306,301 | A | 4/1994 | Graf et al. |
| 5,312,410 | A | 5/1994 | Miller et al. |
| 5,312,422 | A | 5/1994 | Trott |
| 5,312,438 | A | 5/1994 | Johnson |
| 5,314,429 | A | 5/1994 | Goble |
| 5,318,566 | A | 6/1994 | Miller |
| 5,318,575 | A | 6/1994 | Chesterfield et al. |
| 5,318,577 | A | 6/1994 | Li |
| 5,318,578 | A | 6/1994 | Hasson |
| 5,320,115 | A | 6/1994 | Kenna |
| 5,320,626 | A | 6/1994 | Schmieding |
| 5,320,633 | A | 6/1994 | Allen et al. |
| 5,324,308 | A | 6/1994 | Pierce |
| 5,330,489 | A | 7/1994 | Green et al. |
| 5,330,534 | A | 7/1994 | Herrington et al. |
| 5,333,625 | A | 8/1994 | Klein |
| 5,334,204 | A | 8/1994 | Clewett et al. |
| 5,336,229 | A | 8/1994 | Noda |
| 5,336,231 | A | 8/1994 | Adair |
| 5,336,240 | A | 8/1994 | Metzler et al. |
| 5,339,870 | A | 8/1994 | Green et al. |
| 5,342,369 | A | 8/1994 | Harryman, II |
| 5,344,460 | A | 9/1994 | Turanyi et al. |
| 5,346,462 | A | 9/1994 | Barber |
| 5,350,380 | A | 9/1994 | Goble et al. |
| RE34,762 | E | 10/1994 | Goble et al. |
| 5,354,292 | A | 10/1994 | Braeuer et al. |
| 5,354,298 | A | 10/1994 | Lee et al. |
| 5,354,299 | A | 10/1994 | Coleman |
| 5,356,412 | A | 10/1994 | Golds et al. |
| 5,356,413 | A | 10/1994 | Martins et al. |
| 5,356,417 | A | 10/1994 | Golds |
| 5,358,511 | A | 10/1994 | Gatturna et al. |
| 5,358,530 | A | 10/1994 | Hodorek |
| 5,358,531 | A | 10/1994 | Goodfellow et al. |
| 5,360,431 | A | 11/1994 | Puno et al. |
| 5,362,294 | A | 11/1994 | Seitzinger |
| 5,362,911 | A | 11/1994 | Cevasco et al. |
| 5,364,400 | A | 11/1994 | Rego, Jr. et al. |
| 5,366,461 | A | 11/1994 | Blasnik |
| 5,368,599 | A | 11/1994 | Hirsch et al. |
| 5,370,646 | A | 12/1994 | Reese et al. |
| 5,370,661 | A | 12/1994 | Branch |
| 5,370,662 | A | 12/1994 | Stone et al. |
| 5,372,146 | A | 12/1994 | Branch |
| 5,372,604 | A | 12/1994 | Trott |
| 5,372,821 | A | 12/1994 | Badylak et al. |
| 5,374,268 | A | 12/1994 | Sander |
| 5,374,269 | A | 12/1994 | Rosenberg |
| 5,376,118 | A | 12/1994 | Kaplan et al. |
| 5,379,492 | A | 1/1995 | Glesser |
| 5,383,878 | A | 1/1995 | Roger et al. |
| 5,383,904 | A | 1/1995 | Totakura et al. |
| 5,385,567 | A | 1/1995 | Goble |
| 5,391,171 | A | 2/1995 | Schmieding |
| 5,391,176 | A | 2/1995 | De |
| 5,391,182 | A | 2/1995 | Chin |
| 5,393,302 | A | 2/1995 | Clark et al. |
| RE34,871 | E | 3/1995 | Mcguire et al. |
| 5,395,374 | A | 3/1995 | Miller et al. |
| 5,395,401 | A | 3/1995 | Bahler |
| 5,397,356 | A | 3/1995 | Goble et al. |
| 5,403,328 | A | 4/1995 | Shallman |
| 5,403,329 | A | 4/1995 | Hinchcliffe |
| 5,403,348 | A | 4/1995 | Bonutti |
| 5,405,359 | A | 4/1995 | Pierce |
| 5,411,550 | A | 5/1995 | Herweck et al. |
| 5,415,658 | A | 5/1995 | Kilpela et al. |
| 5,417,690 | A | 5/1995 | Sennett et al. |
| 5,417,691 | A | 5/1995 | Hayhurst |
| 5,417,698 | A | 5/1995 | Green et al. |
| 5,417,712 | A | 5/1995 | Whittaker et al. |
| 5,423,819 | A | 6/1995 | Small et al. |
| 5,423,821 | A | 6/1995 | Pasque |
| 5,423,823 | A | 6/1995 | Schmieding |
| 5,423,824 | A | 6/1995 | Akerfeldt et al. |
| 5,423,860 | A | 6/1995 | Lizardi et al. |
| 5,425,733 | A | 6/1995 | Schmieding |
| 5,425,766 | A | 6/1995 | Bowald |
| 5,433,751 | A | 7/1995 | Christel et al. |
| 5,437,680 | A | 8/1995 | Yoon |
| 5,437,685 | A | 8/1995 | Blasnik |
| 5,439,684 | A | 8/1995 | Prewett et al. |
| 5,441,508 | A | 8/1995 | Gazielly et al. |
| 5,443,468 | A | 8/1995 | Johnson |
| 5,443,482 | A | 8/1995 | Stone et al. |
| 5,443,483 | A | 8/1995 | Kirsch |
| 5,443,509 | A | 8/1995 | Boucher et al. |
| 5,445,833 | A | 8/1995 | Badylak et al. |
| 5,447,512 | A | 9/1995 | Wilson et al. |
| 5,449,361 | A | 9/1995 | Preissman |
| 5,451,203 | A | 9/1995 | Lamb |
| 5,454,811 | A | 10/1995 | Huebner |
| 5,454,821 | A | 10/1995 | Harm et al. |
| 5,456,685 | A | 10/1995 | Huebner |
| 5,456,721 | A | 10/1995 | Legrand |
| 5,456,722 | A | 10/1995 | Mcleod et al. |
| 5,458,601 | A | 10/1995 | Young, Jr. et al. |
| 5,458,604 | A | 10/1995 | Schmieding |
| 5,462,542 | A | 10/1995 | Alesi, Jr. |
| 5,462,560 | A | 10/1995 | Stevens |
| 5,464,426 | A | 11/1995 | Bonutti |
| 5,464,427 | A | 11/1995 | Curtis et al. |
| 5,464,440 | A | 11/1995 | Johansson |
| 5,466,237 | A | 11/1995 | Byrd, III et al. |
| 5,467,786 | A | 11/1995 | Allen et al. |
| 5,470,334 | A | 11/1995 | Ross et al. |
| 5,470,337 | A | 11/1995 | Moss |
| 5,470,338 | A | 11/1995 | Whitfield et al. |
| 5,470,354 | A | 11/1995 | Hershberger et al. |
| 5,472,452 | A | 12/1995 | Trott |
| 5,474,565 | A | 12/1995 | Trott |

(56)                    References Cited

U.S. PATENT DOCUMENTS

| | | | |
|---|---|---|---|
| 5,474,568 A | 12/1995 | Scott et al. |
| 5,474,572 A | 12/1995 | Hayhurst |
| 5,476,465 A | 12/1995 | Preissman |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,480,446 A | 1/1996 | Goodfellow et al. |
| 5,484,442 A | 1/1996 | Melker et al. |
| 5,486,197 A | 1/1996 | Le et al. |
| 5,486,359 A | 1/1996 | Caplan et al. |
| 5,489,210 A | 2/1996 | Hanosh |
| 5,490,750 A | 2/1996 | Gundy |
| 5,495,974 A | 3/1996 | Deschenes et al. |
| 5,496,290 A | 3/1996 | Ackerman |
| 5,496,331 A | 3/1996 | Xu et al. |
| 5,496,348 A | 3/1996 | Bonutti |
| 5,498,302 A | 3/1996 | Davidson |
| 5,500,000 A | 3/1996 | Feagin et al. |
| 5,505,735 A | 4/1996 | Li |
| 5,505,736 A | 4/1996 | Reimels et al. |
| 5,507,754 A | 4/1996 | Green et al. |
| 5,514,059 A | 5/1996 | Romney |
| 5,520,691 A | 5/1996 | Branch |
| 5,520,694 A | 5/1996 | Dance et al. |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,843 A | 6/1996 | Zang |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,531,759 A | 7/1996 | Kensey et al. |
| 5,534,011 A | 7/1996 | Greene, Jr. et al. |
| 5,534,012 A | 7/1996 | Bonutti |
| 5,534,033 A | 7/1996 | Simpson |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,664 A | 10/1996 | Durlacher et al. |
| 5,562,668 A | 10/1996 | Johnson |
| 5,562,669 A | 10/1996 | Mcguire |
| 5,562,683 A | 10/1996 | Chan |
| 5,562,685 A | 10/1996 | Mollenauer et al. |
| 5,562,686 A | 10/1996 | Sauer et al. |
| 5,569,252 A | 10/1996 | Justin et al. |
| 5,569,269 A | 10/1996 | Hart et al. |
| 5,569,305 A | 10/1996 | Bonutti |
| 5,569,306 A | 10/1996 | Thal |
| 5,570,706 A | 11/1996 | Howell |
| 5,571,090 A | 11/1996 | Sherts |
| 5,571,104 A | 11/1996 | Li |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,547 A | 11/1996 | LeVeen et al. |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,607,430 A | 3/1997 | Bailey |
| 5,613,971 A | 3/1997 | Lower et al. |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,745 A | 5/1997 | Schwartz |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle |
| 5,643,273 A | 7/1997 | Clark |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | Mcdevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,960 A | 7/1997 | Pavletic |
| 5,649,963 A | 7/1997 | Mcdevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,677 A | 9/1997 | Wimmer |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |
| 5,673,546 A | 10/1997 | Abraham et al. |
| 5,674,224 A | 10/1997 | Howell et al. |
| 5,679,723 A | 10/1997 | Cooper |
| 5,681,334 A | 10/1997 | Evans et al. |
| 5,681,352 A | 10/1997 | Clancy, III et al. |
| 5,683,404 A | 11/1997 | Johnson |
| 5,683,419 A | 11/1997 | Thal |
| 5,688,284 A | 11/1997 | Chervitz et al. |
| 5,688,285 A | 11/1997 | Yamada |
| 5,690,655 A | 11/1997 | Hart et al. |
| 5,690,676 A | 11/1997 | Dipoto et al. |
| 5,690,678 A | 11/1997 | Johnson |
| 5,693,046 A | 12/1997 | Songer et al. |
| 5,695,497 A | 12/1997 | Stahelin |
| 5,697,929 A | 12/1997 | Mellinger |
| 5,697,969 A | 12/1997 | Schmitt et al. |
| 5,699,657 A | 12/1997 | Paulson |
| 5,700,277 A | 12/1997 | Nash et al. |
| 5,702,397 A | 12/1997 | Goble et al. |
| 5,702,422 A | 12/1997 | Stone |
| 5,702,462 A | 12/1997 | Oberlander |
| 5,702,464 A | 12/1997 | Lackey et al. |
| 5,707,373 A | 1/1998 | Sevrain et al. |
| 5,709,708 A | 1/1998 | Thal et al. |
| 5,711,969 A | 1/1998 | Patel et al. |
| 5,713,005 A | 1/1998 | Proebsting |
| 5,713,897 A | 2/1998 | Goble et al. |

(56) References Cited

U.S. PATENT DOCUMENTS

| | | | |
|---|---|---|---|
| 5,713,904 A | 2/1998 | Errico et al. |
| 5,713,905 A | 2/1998 | Goble et al. |
| 5,713,921 A | 2/1998 | Bonutti |
| 5,715,578 A | 2/1998 | Knudson |
| 5,716,359 A | 2/1998 | Ojima et al. |
| 5,716,397 A | 2/1998 | Myers |
| 5,716,616 A | 2/1998 | Prockop et al. |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,722,976 A | 3/1998 | Brown |
| 5,723,331 A | 3/1998 | Tubo et al. |
| 5,725,529 A | 3/1998 | Nicholson et al. |
| 5,725,549 A | 3/1998 | Lam |
| 5,725,556 A | 3/1998 | Moser et al. |
| 5,725,557 A | 3/1998 | Gatturna et al. |
| 5,725,581 A | 3/1998 | Branemark |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,260 A | 4/1998 | Songer et al. |
| 5,741,281 A | 4/1998 | Martin |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | De et al. |
| 5,755,791 A | 5/1998 | Whitson et al. |
| 5,766,176 A | 6/1998 | Duncan |
| 5,766,218 A | 6/1998 | Arnott |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,776,200 A | 7/1998 | Johnson et al. |
| 5,782,845 A | 7/1998 | Shewchuk |
| 5,782,862 A | 7/1998 | Bonutti |
| 5,782,864 A | 7/1998 | Lizardi |
| 5,782,866 A | 7/1998 | Wenstrom, Jr. |
| 5,782,925 A | 7/1998 | Collazo et al. |
| 5,785,714 A | 7/1998 | Morgan et al. |
| 5,786,217 A | 7/1998 | Tubo et al. |
| 5,792,142 A | 8/1998 | Galitzer |
| 5,792,149 A | 8/1998 | Sherts et al. |
| 5,796,127 A | 8/1998 | Hayafuji et al. |
| 5,797,913 A | 8/1998 | Dambreville et al. |
| 5,797,915 A | 8/1998 | Pierson, III et al. |
| 5,797,916 A | 8/1998 | McDowell |
| 5,797,928 A | 8/1998 | Kogasaka |
| 5,800,407 A | 9/1998 | Eldor |
| 5,800,447 A | 9/1998 | Wenstrom, Jr. |
| 5,800,543 A | 9/1998 | Mcleod et al. |
| 5,810,824 A | 9/1998 | Chan |
| 5,810,848 A * | 9/1998 | Hayhurst ............... A61B 17/04 |
| | | 606/232 |
| 5,811,094 A | 9/1998 | Caplan et al. |
| 5,814,056 A | 9/1998 | Prosst et al. |
| 5,814,069 A | 9/1998 | Schulze et al. |
| 5,814,070 A | 9/1998 | Borzone et al. |
| 5,814,071 A | 9/1998 | Mcdevitt et al. |
| 5,814,072 A | 9/1998 | Bonutti |
| 5,814,073 A | 9/1998 | Bonutti |
| 5,817,095 A | 10/1998 | Smith |
| 5,823,980 A | 10/1998 | Kopfer |
| 5,824,011 A | 10/1998 | Stone et al. |
| 5,824,066 A | 10/1998 | Gross |
| 5,827,285 A | 10/1998 | Bramlet |
| 5,830,234 A | 11/1998 | Wojciechowicz et al. |
| 5,836,955 A | 11/1998 | Buelna et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,849,012 A | 12/1998 | Abboudi |
| 5,860,947 A | 1/1999 | Stamler |
| 5,860,973 A | 1/1999 | Michelson |
| 5,860,978 A | 1/1999 | Mcdevitt et al. |
| 5,868,740 A | 2/1999 | LaVeen et al. |
| 5,868,748 A | 2/1999 | Burke |
| 5,868,789 A | 2/1999 | Huebner |
| 5,871,456 A | 2/1999 | Armstrong et al. |
| 5,871,484 A | 2/1999 | Spievack et al. |
| 5,871,486 A | 2/1999 | Huebner |
| 5,871,490 A | 2/1999 | Schulze et al. |
| 5,871,542 A | 2/1999 | Goodfellow et al. |
| 5,871,543 A | 2/1999 | Hofmann |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,920 A | 5/1999 | Desatnick et al. |
| 5,899,938 A | 5/1999 | Sklar et al. |
| 5,906,934 A | 5/1999 | Grande et al. |
| 5,908,421 A | 6/1999 | Beger |
| 5,908,436 A | 6/1999 | Cuschieri et al. |
| 5,910,148 A | 6/1999 | Reimels et al. |
| 5,911,721 A | 6/1999 | Nicholson et al. |
| 5,916,557 A | 6/1999 | Berlowitz-Tarrant et al. |
| 5,918,604 A | 7/1999 | Whelan |
| 5,919,232 A | 7/1999 | Chaffringeon et al. |
| 5,921,986 A | 7/1999 | Bonutti |
| 5,925,008 A | 7/1999 | Douglas |
| 5,928,231 A | 7/1999 | Klein et al. |
| 5,928,267 A | 7/1999 | Bonutti et al. |
| 5,928,286 A | 7/1999 | Ashby et al. |
| RE36,289 E | 8/1999 | Le et al. |
| 5,931,838 A | 8/1999 | Vito |
| 5,931,844 A | 8/1999 | Thompson et al. |
| 5,931,869 A | 8/1999 | Boucher et al. |
| 5,935,119 A | 8/1999 | Guy et al. |
| 5,935,129 A | 8/1999 | Mcdevitt et al. |
| 5,935,133 A | 8/1999 | Wagner et al. |
| 5,935,134 A | 8/1999 | Pedlick et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,947,999 A | 9/1999 | Groiso |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | Dipoto et al. |
| 5,961,520 A | 10/1999 | Beck, Jr. et al. |
| 5,961,521 A | 10/1999 | Roger |
| 5,961,524 A | 10/1999 | Crombie |
| 5,963,869 A | 10/1999 | Fehnel |
| 5,964,764 A | 10/1999 | West, Jr. et al. |
| 5,964,767 A | 10/1999 | Tapia et al. |
| 5,964,769 A | 10/1999 | Wagner et al. |
| 5,964,783 A | 10/1999 | Grafton et al. |
| 5,964,808 A | 10/1999 | Blaha et al. |
| 5,968,045 A | 10/1999 | Frazier |
| 5,968,047 A | 10/1999 | Reed |
| 5,968,077 A | 10/1999 | Wojciechowicz et al. |
| 5,968,078 A | 10/1999 | Grotz |
| 5,968,099 A | 10/1999 | Badorf et al. |

(56)             References Cited

U.S. PATENT DOCUMENTS

| | | | |
|---|---|---|---|
| 5,970,697 A | 10/1999 | Jacobs et al. |
| 5,972,006 A | 10/1999 | Sciaino, Jr. |
| 5,976,125 A | 11/1999 | Graham |
| 5,976,127 A | 11/1999 | Lax |
| 5,980,473 A | 11/1999 | Korakianitis et al. |
| 5,980,524 A | 11/1999 | Justin et al. |
| 5,980,539 A | 11/1999 | Kontos |
| 5,980,548 A | 11/1999 | Evans et al. |
| 5,980,558 A | 11/1999 | Wiley |
| 5,980,559 A | 11/1999 | Bonutti |
| 5,989,252 A | 11/1999 | Fumex |
| 5,989,256 A | 11/1999 | Kuslich et al. |
| 5,989,282 A | 11/1999 | Bonutti |
| 5,989,294 A | 11/1999 | Marlow |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |
| 5,997,575 A | 12/1999 | Whitson et al. |
| 6,001,100 A | 12/1999 | Sherman et al. |
| 6,001,106 A | 12/1999 | Ryan et al. |
| 6,004,351 A | 12/1999 | Tomita et al. |
| 6,004,352 A | 12/1999 | Buni |
| 6,007,538 A | 12/1999 | Levin |
| 6,007,567 A | 12/1999 | Bonutti |
| 6,010,525 A | 1/2000 | Bonutti et al. |
| 6,013,103 A | 1/2000 | Kaufman et al. |
| 6,016,727 A | 1/2000 | Morgan |
| 6,019,767 A | 2/2000 | Howell |
| 6,022,352 A | 2/2000 | Vandewalle |
| 6,022,373 A | 2/2000 | Li |
| 6,023,661 A | 2/2000 | Sottery |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,036,695 A | 3/2000 | Smith |
| 6,039,753 A | 3/2000 | Meislin |
| 6,041,485 A | 3/2000 | Pedlick et al. |
| 6,042,601 A | 3/2000 | Smith |
| 6,042,609 A | 3/2000 | Giordano et al. |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger |
| 6,056,772 A | 5/2000 | Bonutti |
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,066,146 A | 5/2000 | Carroll et al. |
| 6,066,173 A | 5/2000 | Mckernan et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,083,257 A | 7/2000 | Taylor et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,102,934 A | 8/2000 | Li |
| 6,106,545 A | 8/2000 | Egan et al. |
| 6,110,128 A | 8/2000 | Andelin et al. |
| 6,110,207 A | 8/2000 | Eichhorn et al. |
| 6,113,604 A | 9/2000 | Whittaker et al. |
| 6,117,160 A | 9/2000 | Bonutti |
| 6,117,162 A | 9/2000 | Schmieding et al. |
| 6,123,710 A | 9/2000 | Pinczewski et al. |
| 6,127,596 A | 10/2000 | Brown et al. |
| 6,132,433 A | 10/2000 | Whelan |
| 6,132,437 A | 10/2000 | Omurtag |
| 6,136,010 A | 10/2000 | Modesitt et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,150,163 A | 11/2000 | McPherson et al. |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,171,310 B1 | 1/2001 | Giordano et al. |
| 6,174,324 B1 | 1/2001 | Egan et al. |
| 6,179,840 B1 | 1/2001 | Bowman |
| 6,183,461 B1 | 2/2001 | Matsuura et al. |
| 6,183,737 B1 | 2/2001 | Zaleske et al. |
| 6,187,025 B1 | 2/2001 | Machek |
| 6,190,348 B1 | 2/2001 | Tiemann |
| 6,190,401 B1 | 2/2001 | Green et al. |
| 6,190,411 B1 | 2/2001 | Lo |
| 6,190,415 B1 | 2/2001 | Cooke et al. |
| 6,193,754 B1 | 2/2001 | Seedhom |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,200,606 B1 | 3/2001 | Peterson et al. |
| 6,200,685 B1 | 3/2001 | Davidson |
| 6,203,556 B1 | 3/2001 | Evans et al. |
| 6,203,563 B1 | 3/2001 | Fernandez |
| 6,203,565 B1 | 3/2001 | Bonutti et al. |
| 6,203,572 B1 | 3/2001 | Johnson et al. |
| 6,203,576 B1 | 3/2001 | Afriat et al. |
| 6,206,883 B1 | 3/2001 | Tunc |
| 6,210,376 B1 | 4/2001 | Grayson |
| 6,210,381 B1 | 4/2001 | Morse |
| 6,210,445 B1 | 4/2001 | Zawadzki |
| 6,214,007 B1 | 4/2001 | Anderson |
| 6,214,012 B1 | 4/2001 | Karpman et al. |
| 6,217,580 B1 | 4/2001 | Levin |
| 6,221,107 B1 | 4/2001 | Steiner |
| 6,228,096 B1 | 5/2001 | Marchand |
| 6,231,592 B1 | 5/2001 | Bonutti et al. |
| 6,234,980 B1 | 5/2001 | Bell |
| 6,235,057 B1 | 5/2001 | Roger et al. |
| 6,235,058 B1 | 5/2001 | Huene |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,024 B1 | 6/2001 | Montagnino et al. |
| 6,245,081 B1 | 6/2001 | Bowman |
| 6,254,604 B1 | 7/2001 | Howell |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |

(56) References Cited

U.S. PATENT DOCUMENTS

| | | | |
|---|---|---|---|
| 6,283,996 | B1 | 9/2001 | Chervitz et al. |
| 6,287,307 | B1 | 9/2001 | Abboudi |
| 6,287,325 | B1 | 9/2001 | Bonutti |
| 6,293,929 | B1 | 9/2001 | Smith et al. |
| 6,293,961 | B2 | 9/2001 | Schwartz et al. |
| 6,296,659 | B1 | 10/2001 | Foerster |
| 6,299,615 | B1 | 10/2001 | Huebner |
| 6,302,888 | B1 | 10/2001 | Mellinger et al. |
| 6,302,899 | B1 | 10/2001 | Johnson et al. |
| 6,302,915 | B1 | 10/2001 | Cooney, III et al. |
| 6,303,158 | B1 | 10/2001 | Odgaard et al. |
| 6,306,156 | B1 | 10/2001 | Clark |
| 6,306,158 | B1 | 10/2001 | Bartlett |
| 6,306,159 | B1 | 10/2001 | Schwartz et al. |
| 6,309,124 | B1 | 10/2001 | Gueret |
| 6,309,405 | B1 | 10/2001 | Bonutti |
| 6,312,448 | B1 | 11/2001 | Bonutti |
| 6,315,788 | B1 | 11/2001 | Roby |
| 6,319,224 | B1 | 11/2001 | Stout et al. |
| 6,319,271 | B1 | 11/2001 | Schwartz et al. |
| 6,328,758 | B1 | 12/2001 | Tornier et al. |
| 6,334,064 | B1 | 12/2001 | Fiddian-green |
| 6,342,060 | B1 | 1/2002 | Adams |
| 6,343,531 | B2 | 2/2002 | Amis |
| 6,355,066 | B1 | 3/2002 | Kim et al. |
| 6,358,270 | B1 | 3/2002 | Lemer |
| 6,364,897 | B1 | 4/2002 | Bonutti |
| 6,368,322 | B1 | 4/2002 | Luks et al. |
| 6,368,326 | B1 | 4/2002 | Dakin et al. |
| 6,368,343 | B1 | 4/2002 | Bonutti et al. |
| 6,371,124 | B1 | 4/2002 | Whelan |
| 6,379,361 | B1 | 4/2002 | Beck, Jr. et al. |
| 6,383,190 | B1 | 5/2002 | Preissman |
| 6,383,199 | B2 | 5/2002 | Carter et al. |
| 6,387,111 | B1 | 5/2002 | Barber |
| 6,387,113 | B1 | 5/2002 | Hawkins et al. |
| 6,387,129 | B2 | 5/2002 | Rieser et al. |
| 6,391,030 | B1 | 5/2002 | Wagner et al. |
| 6,398,785 | B2 | 6/2002 | Carchidi et al. |
| 6,406,456 | B1 | 6/2002 | Slate et al. |
| 6,406,479 | B1 | 6/2002 | Justin et al. |
| 6,409,743 | B1 | 6/2002 | Fenton, V |
| 6,413,260 | B1 | 7/2002 | Berrevoets et al. |
| 6,423,073 | B2 | 7/2002 | Bowman |
| 6,423,088 | B1 | 7/2002 | Fenton, V |
| 6,425,924 | B1 | 7/2002 | Rousseau |
| 6,428,562 | B2 | 8/2002 | Bonutti |
| 6,432,123 | B2 | 8/2002 | Schwartz et al. |
| 6,436,123 | B1 | 8/2002 | Magovern |
| 6,436,124 | B1 | 8/2002 | Anderson et al. |
| 6,440,134 | B1 | 8/2002 | Zaccherotti et al. |
| 6,440,136 | B1 | 8/2002 | Gambale et al. |
| 6,447,516 | B1 | 9/2002 | Bonutti |
| 6,451,030 | B2 | 9/2002 | Li et al. |
| 6,454,768 | B1 | 9/2002 | Jackson |
| 6,458,134 | B1 | 10/2002 | Songer et al. |
| 6,458,161 | B1 | 10/2002 | Gibbs et al. |
| 6,461,373 | B2 | 10/2002 | Wyman et al. |
| 6,464,690 | B1 | 10/2002 | Castaneda et al. |
| 6,464,713 | B2 | 10/2002 | Bonutti |
| 6,468,293 | B2 | 10/2002 | Bonutti et al. |
| 6,471,707 | B1 | 10/2002 | Miller et al. |
| 6,475,230 | B1 | 11/2002 | Bonutti et al. |
| 6,478,753 | B2 | 11/2002 | Reay-Young |
| 6,482,210 | B1 | 11/2002 | Skiba et al. |
| 6,485,504 | B1 | 11/2002 | Johnson et al. |
| 6,491,714 | B1 | 12/2002 | Bennett |
| 6,497,901 | B1 | 12/2002 | Royer |
| 6,500,184 | B1 | 12/2002 | Chan et al. |
| 6,500,195 | B2 | 12/2002 | Bonutti |
| 6,500,208 | B1 | 12/2002 | Metzger et al. |
| RE37,963 | E | 1/2003 | Thal |
| 6,503,267 | B2 | 1/2003 | Bonutti et al. |
| 6,506,190 | B1 | 1/2003 | Walshe |
| 6,508,820 | B2 | 1/2003 | Bales |
| 6,508,821 | B1 | 1/2003 | Schwartz et al. |
| 6,508,830 | B2 | 1/2003 | Steiner |
| 6,511,498 | B1 | 1/2003 | Fumex |
| 6,511,499 | B2 | 1/2003 | Schmieding et al. |
| 6,514,274 | B1 | 2/2003 | Boucher et al. |
| 6,517,542 | B1 | 2/2003 | Papay et al. |
| 6,517,552 | B1 | 2/2003 | Nord et al. |
| 6,517,564 | B1 | 2/2003 | Grafton et al. |
| 6,517,578 | B2 | 2/2003 | Hein |
| 6,517,579 | B1 | 2/2003 | Paulos et al. |
| 6,520,964 | B2 | 2/2003 | Tallarida et al. |
| 6,520,980 | B1 | 2/2003 | Foerster |
| 6,524,317 | B1 | 2/2003 | Ritchart et al. |
| 6,527,777 | B2 | 3/2003 | Justin |
| 6,527,794 | B1 | 3/2003 | Mcdevitt et al. |
| 6,527,795 | B1 | 3/2003 | Lizardi |
| 6,533,795 | B1 | 3/2003 | Tran et al. |
| 6,533,802 | B2 | 3/2003 | Bojarski et al. |
| 6,537,319 | B2 | 3/2003 | Whelan |
| 6,540,750 | B2 | 4/2003 | Burkhart |
| 6,540,769 | B1 | 4/2003 | Miller, III |
| 6,540,770 | B1 | 4/2003 | Tornier et al. |
| 6,540,783 | B1 | 4/2003 | Whittaker et al. |
| 6,543,094 | B2 | 4/2003 | D'addario |
| 6,544,281 | B2 | 4/2003 | Elattrache et al. |
| 6,547,564 | B1 | 4/2003 | Hansson |
| 6,547,778 | B1 | 4/2003 | Sklar et al. |
| 6,547,800 | B2 | 4/2003 | Foerster et al. |
| 6,551,330 | B1 | 4/2003 | Bain et al. |
| 6,551,343 | B1 | 4/2003 | Tormala et al. |
| 6,551,353 | B1 | 4/2003 | Baker et al. |
| 6,553,802 | B1 | 4/2003 | Jacob |
| 6,554,830 | B1 | 4/2003 | Chappius |
| 6,554,852 | B1 | 4/2003 | Oberlander |
| 6,554,862 | B2 | 4/2003 | Hays et al. |
| 6,558,389 | B2 | 5/2003 | Clark et al. |
| 6,562,071 | B2 | 5/2003 | Järvinen |
| 6,565,572 | B2 | 5/2003 | Chappius |
| 6,565,573 | B1 | 5/2003 | Ferrante |
| 6,569,167 | B1 | 5/2003 | Bobechko et al. |
| 6,569,186 | B1 | 5/2003 | Winters et al. |
| 6,569,187 | B1 | 5/2003 | Bonutti et al. |
| 6,572,635 | B1 | 6/2003 | Bonutti |
| 6,572,655 | B1 | 6/2003 | Johnson |
| 6,575,925 | B1 | 6/2003 | Noble |
| 6,579,295 | B1 | 6/2003 | Supinski |
| 6,582,453 | B1 | 6/2003 | Tran et al. |
| 6,585,730 | B1 | 7/2003 | Foerster |
| 6,585,740 | B2 | 7/2003 | Schlapfer et al. |
| 6,585,750 | B2 | 7/2003 | Bonutti et al. |
| 6,589,245 | B1 | 7/2003 | Weiler et al. |
| 6,589,246 | B1 | 7/2003 | Hack et al. |
| 6,592,609 | B1 | 7/2003 | Bonutti |
| 6,592,622 | B1 | 7/2003 | Ferguson |
| 6,595,911 | B2 | 7/2003 | Lovuolo |
| 6,599,289 | B1 | 7/2003 | Bojarski et al. |
| 6,599,319 | B2 | 7/2003 | Knudsen et al. |
| 6,605,096 | B1 | 8/2003 | Ritchart |
| 6,607,548 | B2 | 8/2003 | Pohjonen et al. |
| 6,610,064 | B1 | 8/2003 | Goble et al. |
| 6,610,079 | B1 | 8/2003 | Li et al. |
| 6,613,018 | B2 | 9/2003 | Bagga et al. |
| 6,616,694 | B1 | 9/2003 | Hart |
| 6,620,166 | B1 | 9/2003 | Wenstrom, Jr. et al. |
| 6,620,185 | B1 | 9/2003 | Harvie et al. |
| 6,620,195 | B2 | 9/2003 | Goble et al. |
| 6,620,329 | B2 | 9/2003 | Rosen et al. |
| 6,620,349 | B1 | 9/2003 | Lopez |
| 6,623,492 | B1 | 9/2003 | Berube et al. |
| 6,623,524 | B2 | 9/2003 | Schmieding |
| 6,626,910 | B1 | 9/2003 | Hugues |
| 6,626,919 | B1 | 9/2003 | Swanstrom |
| 6,626,930 | B1 | 9/2003 | Allen et al. |
| 6,629,977 | B1 | 10/2003 | Wolf |
| 6,629,997 | B2 | 10/2003 | Mansmann |
| 6,632,245 | B2 | 10/2003 | Kim |
| 6,635,073 | B2 | 10/2003 | Bonutti |
| 6,638,279 | B2 | 10/2003 | Bonutti |
| 6,638,286 | B1 | 10/2003 | Burbank et al. |

(56) References Cited

U.S. PATENT DOCUMENTS

| | | | |
|---|---|---|---|
| 6,638,312 | B2 | 10/2003 | Plouhar et al. |
| 6,641,596 | B1 | 11/2003 | Lizardi |
| 6,641,597 | B2 | 11/2003 | Burkhart et al. |
| 6,645,169 | B1 | 11/2003 | Slate et al. |
| 6,645,211 | B2 | 11/2003 | Magana |
| 6,645,227 | B2 | 11/2003 | Fallin et al. |
| 6,648,903 | B1 | 11/2003 | Pierson, III |
| 6,648,921 | B2 | 11/2003 | Anderson et al. |
| 6,652,450 | B2 | 11/2003 | Neisz et al. |
| 6,652,533 | B2 | 11/2003 | O'Neil |
| 6,652,560 | B1 | 11/2003 | Gerke et al. |
| 6,652,562 | B2 | 11/2003 | Collier et al. |
| 6,652,563 | B2 | 11/2003 | Dreyfuss |
| 6,656,182 | B1 | 12/2003 | Hayhurst |
| 6,656,183 | B2 | 12/2003 | Colleran et al. |
| 6,658,182 | B1 | 12/2003 | Gonthier |
| 6,660,008 | B1 | 12/2003 | Foerster et al. |
| 6,660,022 | B1 | 12/2003 | Li et al. |
| 6,663,634 | B2 | 12/2003 | Ahrens et al. |
| 6,663,656 | B2 | 12/2003 | Schmieding et al. |
| 6,666,868 | B2 | 12/2003 | Fallin |
| 6,666,877 | B2 | 12/2003 | Morgan et al. |
| 6,669,707 | B1 | 12/2003 | Swanstrom et al. |
| 6,679,889 | B1 | 1/2004 | West, Jr. et al. |
| 6,682,533 | B1 | 1/2004 | Dinsdale et al. |
| 6,682,549 | B2 | 1/2004 | Bartlett |
| 6,685,728 | B2 | 2/2004 | Sinnott et al. |
| 6,689,137 | B2 | 2/2004 | Reed |
| 6,689,153 | B1 | 2/2004 | Skiba |
| 6,689,154 | B2 | 2/2004 | Bartlett |
| 6,692,499 | B2 | 2/2004 | Tormala et al. |
| 6,692,516 | B2 | 2/2004 | West, Jr. et al. |
| 6,695,852 | B2 | 2/2004 | Gleason |
| 6,712,849 | B2 | 3/2004 | Re et al. |
| 6,712,859 | B2 | 3/2004 | Rousseau |
| 6,716,190 | B1 | 4/2004 | Glines et al. |
| 6,716,224 | B2 | 4/2004 | Singhatat |
| 6,716,234 | B2 | 4/2004 | Grafton et al. |
| 6,716,957 | B2 | 4/2004 | Tunc |
| 6,730,092 | B2 | 5/2004 | Songer |
| 6,730,124 | B2 | 5/2004 | Steiner |
| 6,736,799 | B1 | 5/2004 | Erbe et al. |
| 6,737,053 | B1 | 5/2004 | Goh et al. |
| 6,746,483 | B1 | 6/2004 | Bojarski et al. |
| 6,752,780 | B2 | 6/2004 | Stout et al. |
| 6,752,810 | B1 | 6/2004 | Gao et al. |
| 6,752,831 | B2 | 6/2004 | Sybert et al. |
| 6,755,836 | B1 | 6/2004 | Lewis |
| 6,755,868 | B2 | 6/2004 | Rousseau |
| 6,761,722 | B2 | 7/2004 | Cole et al. |
| 6,761,739 | B2 | 7/2004 | Shepard |
| 6,767,037 | B2 | 7/2004 | Wenstrom, Jr. |
| 6,770,076 | B2 | 8/2004 | Foerster |
| 6,770,084 | B1 | 8/2004 | Bain et al. |
| 6,773,450 | B2 | 8/2004 | Leung et al. |
| 6,779,701 | B2 | 8/2004 | Bailly et al. |
| 6,780,190 | B2 | 8/2004 | Maroney |
| 6,780,198 | B1 | 8/2004 | Gregoire et al. |
| 6,790,210 | B1 | 9/2004 | Cragg et al. |
| 6,793,595 | B1 | 9/2004 | Monnet |
| 6,802,862 | B1 | 10/2004 | Roger et al. |
| 6,808,502 | B2 | 10/2004 | Nguyen |
| 6,808,526 | B1 | 10/2004 | Magerl et al. |
| 6,814,741 | B2 | 11/2004 | Bowman et al. |
| 6,830,572 | B2 | 12/2004 | Mcdevitt et al. |
| 6,833,005 | B1 | 12/2004 | Mantas |
| 6,835,377 | B2 | 12/2004 | Goldberg et al. |
| 6,840,953 | B2 | 1/2005 | Martinek |
| 6,860,885 | B2 | 3/2005 | Bonutti |
| 6,860,895 | B1 | 3/2005 | Akerfeldt et al. |
| 6,863,671 | B1 | 3/2005 | Strobel et al. |
| 6,872,040 | B2 | 3/2005 | Deeg et al. |
| 6,872,210 | B2 | 3/2005 | Hearn |
| 6,875,216 | B2 | 4/2005 | Wolf |
| 6,884,249 | B2 | 4/2005 | May et al. |
| 6,887,243 | B2 | 5/2005 | Culbert |
| 6,887,259 | B2 | 5/2005 | Lizardi |
| 6,887,271 | B2 | 5/2005 | Justin et al. |
| 6,890,354 | B2 | 5/2005 | Steiner et al. |
| 6,893,448 | B2 | 5/2005 | O'quinn et al. |
| 6,896,686 | B2 | 5/2005 | Weber |
| 6,899,722 | B2 | 5/2005 | Bonutti |
| 6,902,573 | B2 | 6/2005 | Strobel et al. |
| 6,905,513 | B1 | 6/2005 | Metzger |
| 6,908,466 | B1 | 6/2005 | Bonutti et al. |
| 6,911,202 | B2 | 6/2005 | Amir et al. |
| 6,916,292 | B2 | 7/2005 | Morawski et al. |
| 6,916,321 | B2 | 7/2005 | Tenhuisen et al. |
| 6,921,402 | B2 | 7/2005 | Contiliano et al. |
| 6,923,823 | B1 | 8/2005 | Bartlett et al. |
| 6,923,824 | B2 | 8/2005 | Morgan et al. |
| 6,923,832 | B1 | 8/2005 | Sharkey et al. |
| 6,939,379 | B2 | 9/2005 | Sklar |
| 6,946,001 | B2 | 9/2005 | Sanford et al. |
| 6,949,102 | B2 | 9/2005 | Andrews |
| 6,951,565 | B2 | 10/2005 | Keane et al. |
| 6,960,214 | B2 | 11/2005 | Burkinshaw |
| 6,966,887 | B1 | 11/2005 | Chin |
| 6,966,916 | B2 | 11/2005 | Kumar |
| 6,969,391 | B1 | 11/2005 | Gazzani |
| 6,969,398 | B2 | 11/2005 | Stevens et al. |
| 6,972,027 | B2 | 12/2005 | Fallin et al. |
| 6,980,903 | B2 | 12/2005 | Daniels et al. |
| 6,984,237 | B2 | 1/2006 | Hatch et al. |
| 6,986,781 | B2 | 1/2006 | Smith |
| 6,989,034 | B2 | 1/2006 | Hammer et al. |
| 6,994,719 | B2 | 2/2006 | Grafton |
| 6,994,725 | B1 | 2/2006 | Goble |
| 7,001,429 | B2 | 2/2006 | Ferguson |
| 7,004,959 | B2 | 2/2006 | Bonutti |
| 7,008,451 | B2 | 3/2006 | Justin et al. |
| 7,011,682 | B2 | 3/2006 | Lashinski et al. |
| 7,033,397 | B2 | 4/2006 | Webster et al. |
| 7,048,754 | B2 | 5/2006 | Martin et al. |
| 7,052,499 | B2 | 5/2006 | Steger et al. |
| 7,060,101 | B2 | 6/2006 | O'Connor et al. |
| 7,066,942 | B2 | 6/2006 | Treace |
| 7,066,944 | B2 | 6/2006 | Laufer et al. |
| 7,081,126 | B2 | 7/2006 | Mcdevitt et al. |
| 7,083,638 | B2 | 8/2006 | Foerster |
| 7,087,064 | B1 | 8/2006 | Hyde |
| 7,087,073 | B2 | 8/2006 | Bonutti |
| 7,090,690 | B2 | 8/2006 | Foerster et al. |
| 7,097,654 | B1 | 8/2006 | Freedland |
| 7,101,395 | B2 | 9/2006 | Tremulis et al. |
| 7,105,010 | B2 | 9/2006 | Hart et al. |
| 7,105,026 | B2 | 9/2006 | Johnson et al. |
| 7,112,221 | B2 | 9/2006 | Harris |
| 7,118,578 | B2 | 10/2006 | West, Jr. et al. |
| 7,118,583 | B2 | 10/2006 | O'quinn et al. |
| 7,125,421 | B2 | 10/2006 | Tremulis et al. |
| 7,131,467 | B2 | 11/2006 | Gao et al. |
| 7,137,996 | B2 | 11/2006 | Steiner et al. |
| 7,141,066 | B2 | 11/2006 | Steiner et al. |
| 7,144,414 | B2 | 12/2006 | Harvie et al. |
| 7,148,209 | B2 | 12/2006 | Hoemann et al. |
| 7,153,127 | B2 | 12/2006 | Struble et al. |
| 7,153,307 | B2 | 12/2006 | Scribner |
| 7,153,312 | B1 | 12/2006 | Torrie et al. |
| 7,153,327 | B1 | 12/2006 | Metzger |
| 7,160,285 | B2 | 1/2007 | Sklar et al. |
| 7,160,333 | B2 | 1/2007 | Plouhar et al. |
| 7,172,626 | B1 | 2/2007 | Andrews |
| 7,179,259 | B1 | 2/2007 | Gibbs |
| 7,201,722 | B2 | 4/2007 | Krueger |
| 7,207,993 | B1 | 4/2007 | Baldwin et al. |
| 7,229,441 | B2 | 6/2007 | Trieu et al. |
| 7,235,091 | B2 | 6/2007 | Thornes |
| 7,255,675 | B2 | 8/2007 | Gertner et al. |
| 7,255,700 | B2 | 8/2007 | Kaiser et al. |
| 7,255,715 | B2 | 8/2007 | Metzger |
| 7,261,716 | B2 | 8/2007 | Strobel et al. |
| 7,264,634 | B2 | 9/2007 | Schmieding |
| 7,279,008 | B2 | 10/2007 | Brown et al. |

(56) References Cited

U.S. PATENT DOCUMENTS

| | | | |
|---|---|---|---|
| 7,285,124 | B2 | 10/2007 | Foerster |
| 7,291,177 | B2 | 11/2007 | Gibbs |
| 7,303,577 | B1 | 12/2007 | Dean |
| 7,306,417 | B2 | 12/2007 | Dorstewitz |
| 7,309,355 | B2 | 12/2007 | Donnelly et al. |
| 7,326,222 | B2 | 2/2008 | Dreyfuss et al. |
| 7,329,272 | B2 | 2/2008 | Burkhart et al. |
| 7,354,354 | B2 | 4/2008 | Palumbo et al. |
| 7,361,179 | B2 | 4/2008 | Rousseau et al. |
| 7,377,845 | B2 | 5/2008 | Stewart et al. |
| 7,390,329 | B2 | 6/2008 | Westra et al. |
| 7,390,332 | B2 | 6/2008 | Selvitelli et al. |
| 7,399,018 | B1 | 7/2008 | Khachaturian |
| 7,442,210 | B2 | 10/2008 | Segal et al. |
| 7,462,198 | B2 | 12/2008 | Webster et al. |
| 7,463,198 | B2 | 12/2008 | Deaett et al. |
| 7,465,308 | B2 | 12/2008 | Sikora et al. |
| 7,468,074 | B2 | 12/2008 | Caborn |
| 7,481,814 | B1 | 1/2009 | Metzger |
| 7,484,539 | B1 | 2/2009 | Huang |
| 7,485,149 | B1 | 2/2009 | White |
| 7,494,496 | B2 | 2/2009 | Swain et al. |
| 7,494,506 | B2 | 2/2009 | Brulez et al. |
| D587,807 | S | 3/2009 | Wolf et al. |
| 7,500,983 | B1 | 3/2009 | Kaiser et al. |
| 7,513,910 | B2 | 4/2009 | Buskirk et al. |
| 7,517,357 | B2 | 4/2009 | Abrams et al. |
| 7,572,275 | B2 | 8/2009 | Fallin et al. |
| 7,572,298 | B2 | 8/2009 | Roller et al. |
| 7,578,825 | B2 | 8/2009 | Huebner |
| 7,585,311 | B2 | 9/2009 | Green et al. |
| 7,588,587 | B2 | 9/2009 | Barbieri et al. |
| 7,591,823 | B2 | 9/2009 | Tipirneni |
| 7,597,705 | B2 | 10/2009 | Forsberg et al. |
| 7,601,165 | B2 | 10/2009 | Stone |
| 7,604,636 | B1 | 10/2009 | Walters et al. |
| 7,608,092 | B1 | 10/2009 | Schaffhasen |
| 7,608,098 | B1 | 10/2009 | Stone et al. |
| 7,615,076 | B2 | 11/2009 | Cauthen, III et al. |
| 7,621,937 | B2 | 11/2009 | Pipenhagen et al. |
| 7,632,287 | B2 | 12/2009 | Baker et al. |
| 7,651,509 | B2 | 1/2010 | Bojarski et al. |
| 7,658,750 | B2 | 2/2010 | Li |
| 7,658,751 | B2 | 2/2010 | Stone et al. |
| 7,670,279 | B2 | 3/2010 | Gertner |
| 7,678,123 | B2 | 3/2010 | Chanduszko |
| 7,686,810 | B2 | 3/2010 | West, Jr. et al. |
| 7,691,112 | B2 | 4/2010 | Chanduszko et al. |
| 7,695,493 | B2 | 4/2010 | Saadat et al. |
| 7,695,503 | B1 | 4/2010 | Kaiser |
| 7,703,372 | B1 | 4/2010 | Shakespeare |
| 7,713,188 | B2 | 5/2010 | Bouffier |
| 7,713,285 | B1 | 5/2010 | Stone et al. |
| 7,717,929 | B2 | 5/2010 | Fallman |
| 7,731,732 | B2 | 6/2010 | Ken |
| 7,736,364 | B2 | 6/2010 | Stone |
| 7,736,379 | B2 | 6/2010 | Ewers et al. |
| 7,749,250 | B2 | 7/2010 | Stone et al. |
| 7,758,594 | B2 | 7/2010 | Lamson et al. |
| 7,758,611 | B2 | 7/2010 | Kato |
| 7,762,942 | B2 | 7/2010 | Neisz et al. |
| 7,771,482 | B1 | 8/2010 | Karmon |
| 7,776,041 | B1 | 8/2010 | Walters |
| 7,780,701 | B1 | 8/2010 | Meridew et al. |
| 7,790,945 | B1 | 9/2010 | Watson, Jr. |
| 7,803,173 | B2 | 9/2010 | Burkhart et al. |
| 7,819,895 | B2 | 10/2010 | Ginn et al. |
| 7,828,820 | B2 | 11/2010 | Stone et al. |
| 7,828,850 | B2 | 11/2010 | Cauthen, III et al. |
| 7,856,698 | B2 | 12/2010 | Hays |
| 7,857,830 | B2 | 12/2010 | Stone et al. |
| 7,867,252 | B2 | 1/2011 | Criscuolo et al. |
| 7,867,264 | B2 | 1/2011 | Mcdevitt et al. |
| 7,875,058 | B2 | 1/2011 | Holmes, Jr. |
| 7,878,058 | B2 | 2/2011 | Blendinger et al. |
| 7,887,586 | B2 | 2/2011 | Linares |
| 7,896,907 | B2 | 3/2011 | Mcdevitt et al. |
| 7,905,903 | B2 | 3/2011 | Stone et al. |
| 7,905,904 | B2 | 3/2011 | Stone et al. |
| 7,909,851 | B2 | 3/2011 | Stone et al. |
| 7,914,539 | B2 | 3/2011 | Stone et al. |
| 7,938,847 | B2 | 5/2011 | Fanton et al. |
| 7,951,198 | B2 | 5/2011 | Sucec et al. |
| 7,955,388 | B2 | 6/2011 | Jensen et al. |
| 7,959,650 | B2 | 6/2011 | Kaiser et al. |
| 7,976,565 | B1 | 7/2011 | Meridew |
| 7,981,140 | B2 | 7/2011 | Burkhart |
| 7,998,203 | B2 | 8/2011 | Blum |
| 8,034,090 | B2 | 10/2011 | Stone et al. |
| 8,062,334 | B2 | 11/2011 | Green et al. |
| 8,066,776 | B2 | 11/2011 | O'Connor et al. |
| 8,075,574 | B2 | 12/2011 | May et al. |
| 8,075,626 | B2 | 12/2011 | Dun |
| 8,088,108 | B2 | 1/2012 | Kraft |
| 8,088,130 | B2 | 1/2012 | Kaiser et al. |
| 8,109,867 | B2 | 2/2012 | Rosenblatt |
| 8,114,127 | B2 | 2/2012 | West, Jr. |
| 8,114,128 | B2 | 2/2012 | Cauldwell et al. |
| 8,118,835 | B2 | 2/2012 | Weisel et al. |
| 8,118,836 | B2 | 2/2012 | Denham et al. |
| 8,118,868 | B2 | 2/2012 | May et al. |
| 8,128,658 | B2 | 3/2012 | Kaiser et al. |
| 8,137,354 | B2 | 3/2012 | Stone |
| 8,137,382 | B2 | 3/2012 | Denham et al. |
| 8,137,407 | B2 | 3/2012 | Todd et al. |
| 8,142,510 | B2 | 3/2012 | Lee et al. |
| 8,147,557 | B2 | 4/2012 | Lee et al. |
| 8,147,558 | B2 | 4/2012 | Lee et al. |
| 8,162,997 | B2 | 4/2012 | Struhl |
| 8,167,906 | B2 | 5/2012 | Cauldwell et al. |
| 8,177,810 | B2 | 5/2012 | Ferree |
| 8,202,295 | B2 | 6/2012 | Kaplan |
| 8,202,318 | B2 | 6/2012 | Willobee |
| 8,221,454 | B2 | 7/2012 | Schaffhasen |
| 8,231,654 | B2 | 7/2012 | Kaiser et al. |
| 8,251,998 | B2 | 8/2012 | Hoeppner et al. |
| 8,252,022 | B2 | 8/2012 | Holman et al. |
| 8,273,106 | B2 | 9/2012 | Stone et al. |
| 8,292,921 | B2 | 10/2012 | Stone et al. |
| 8,298,262 | B2 | 10/2012 | Stone et al. |
| 8,298,284 | B2 | 10/2012 | Cassani |
| 8,303,589 | B2 | 11/2012 | Tyber et al. |
| 8,303,604 | B2 | 11/2012 | Stone et al. |
| 8,317,825 | B2 | 11/2012 | Stone |
| 8,328,806 | B2 | 12/2012 | Tyber et al. |
| 8,333,788 | B2 | 12/2012 | Maiorino |
| 8,337,525 | B2 | 12/2012 | Stone et al. |
| 8,343,155 | B2 | 1/2013 | Fisher et al. |
| 8,343,227 | B2 | 1/2013 | Metzger et al. |
| 8,361,054 | B2 | 1/2013 | Ducharme et al. |
| 8,361,113 | B2 | 1/2013 | Stone et al. |
| 8,409,253 | B2 | 4/2013 | Stone et al. |
| 8,454,635 | B2 | 6/2013 | Paolitto et al. |
| 8,486,114 | B2 | 7/2013 | Gillard et al. |
| 8,500,818 | B2 | 8/2013 | Metzger et al. |
| 8,506,597 | B2 | 8/2013 | Kaiser et al. |
| 8,545,535 | B2 | 10/2013 | Hirotsuka et al. |
| 8,551,140 | B2 | 10/2013 | Denham et al. |
| 8,562,645 | B2 | 10/2013 | Stone et al. |
| 8,562,647 | B2 | 10/2013 | Kaiser et al. |
| 8,574,235 | B2 | 11/2013 | Stone |
| 8,579,901 | B1 | 11/2013 | Foerster |
| 8,579,944 | B2 | 11/2013 | Holloway et al. |
| 8,591,544 | B2 | 11/2013 | Jolly et al. |
| 8,597,327 | B2 | 12/2013 | Stone et al. |
| 8,608,777 | B2 | 12/2013 | Kaiser et al. |
| 8,632,566 | B2 | 1/2014 | Olson |
| 8,632,569 | B2 | 1/2014 | Stone et al. |
| 8,652,171 | B2 | 2/2014 | Stone et al. |
| 8,652,172 | B2 | 2/2014 | Denham et al. |
| 8,672,904 | B1 | 3/2014 | Schultz |
| 8,672,968 | B2 | 3/2014 | Stone et al. |
| 8,672,969 | B2 | 3/2014 | Stone et al. |
| 8,702,718 | B2 | 4/2014 | Bhatnagar et al. |

(56) References Cited

U.S. PATENT DOCUMENTS

| | | | |
|---|---|---|---|
| 8,715,297 | B1 | 5/2014 | Foerster et al. |
| 8,721,650 | B2 | 5/2014 | Fanton et al. |
| 8,721,684 | B2 | 5/2014 | Denham et al. |
| 8,771,316 | B2 | 7/2014 | Denham et al. |
| 8,771,352 | B2 | 7/2014 | Conner et al. |
| 8,777,956 | B2 | 7/2014 | Hoeppner et al. |
| 8,801,783 | B2 | 8/2014 | Stone et al. |
| 8,808,374 | B2 | 8/2014 | Eggli |
| 8,814,903 | B2 | 8/2014 | Sengun et al. |
| 8,828,067 | B2 | 9/2014 | Tipirneni et al. |
| 8,840,645 | B2 | 9/2014 | Denham et al. |
| 8,858,642 | B2 | 10/2014 | Metzger et al. |
| 8,894,715 | B2 | 11/2014 | Metzger et al. |
| 8,900,314 | B2 | 12/2014 | Metzger et al. |
| 8,926,613 | B2 | 1/2015 | Kaiser et al. |
| 8,932,331 | B2 | 1/2015 | Kaiser et al. |
| 8,936,621 | B2 | 1/2015 | Denham et al. |
| 8,961,548 | B2 | 2/2015 | Buser |
| 8,968,364 | B2 | 3/2015 | Berelsman |
| 8,998,949 | B2 | 4/2015 | Stone et al. |
| 9,005,287 | B2 | 4/2015 | Stone |
| 9,017,381 | B2 | 4/2015 | Kaiser et al. |
| 9,023,058 | B2 | 5/2015 | Jaramillo et al. |
| 9,028,509 | B2 | 5/2015 | Chu et al. |
| 9,078,644 | B2 | 7/2015 | Stone |
| 9,149,267 | B2 | 10/2015 | Norton et al. |
| 9,173,651 | B2 | 11/2015 | Stone et al. |
| 9,179,950 | B2 | 11/2015 | Zajac et al. |
| 9,198,673 | B2 | 12/2015 | Stone |
| 9,216,078 | B2 | 12/2015 | Conner et al. |
| 9,271,713 | B2 | 3/2016 | Denham et al. |
| 9,271,826 | B2 | 3/2016 | Eggli et al. |
| 9,289,285 | B2 | 3/2016 | Eggli |
| 9,314,235 | B2 | 4/2016 | Bojarski et al. |
| 9,314,241 | B2 | 4/2016 | Stone et al. |
| 9,357,991 | B2 | 6/2016 | Denham et al. |
| 9,357,992 | B2 | 6/2016 | Stone et al. |
| 9,370,350 | B2 | 6/2016 | Norton |
| 9,381,013 | B2 | 7/2016 | Norton |
| 9,402,621 | B2 | 8/2016 | Stone et al. |
| 9,408,599 | B2 | 8/2016 | Kaiser et al. |
| 9,414,833 | B2 | 8/2016 | Stone et al. |
| 9,414,925 | B2 | 8/2016 | Metzger et al. |
| 9,468,433 | B2 | 10/2016 | Denham et al. |
| 9,486,211 | B2 | 11/2016 | Stone et al. |
| 9,492,158 | B2 | 11/2016 | Stone et al. |
| 9,498,204 | B2 | 11/2016 | Denham et al. |
| 9,504,460 | B2 | 11/2016 | Stone et al. |
| 9,510,819 | B2 | 12/2016 | Stone et al. |
| 9,510,821 | B2 | 12/2016 | Denham et al. |
| 9,532,777 | B2 | 1/2017 | Kaiser et al. |
| 9,538,998 | B2 | 1/2017 | Stone et al. |
| 9,539,003 | B2 | 1/2017 | Stone et al. |
| 9,561,025 | B2 | 2/2017 | Stone et al. |
| 9,572,655 | B2 | 2/2017 | Denham |
| 9,585,651 | B2 | 3/2017 | Lam et al. |
| 9,603,591 | B2 | 3/2017 | Denham et al. |
| 9,622,736 | B2 | 4/2017 | Stone et al. |
| 9,642,661 | B2 | 5/2017 | Stone et al. |
| 9,681,940 | B2 | 6/2017 | Stone et al. |
| 9,724,090 | B2 | 8/2017 | Kaiser et al. |
| 9,743,919 | B2 | 8/2017 | Manos et al. |
| 9,757,119 | B2 | 9/2017 | Norton et al. |
| 9,763,656 | B2 | 9/2017 | Stone et al. |
| 9,782,245 | B2 | 10/2017 | Mujwid et al. |
| 9,788,876 | B2 | 10/2017 | Stone |
| 9,801,620 | B2 | 10/2017 | Kaiser et al. |
| 9,801,708 | B2 | 10/2017 | Denham et al. |
| 9,833,230 | B2 | 12/2017 | Stone |
| 9,861,351 | B2 | 1/2018 | Kaiser et al. |
| 9,918,826 | B2 | 3/2018 | Berelsman et al. |
| 9,918,827 | B2 | 3/2018 | Berelsman et al. |
| 9,993,241 | B2 | 6/2018 | Denham et al. |
| 10,004,489 | B2 | 6/2018 | Kaiser et al. |
| 10,004,493 | B2 | 6/2018 | Stone et al. |
| 10,004,588 | B2 | 6/2018 | Berelsman et al. |
| 10,022,118 | B2 | 7/2018 | Norton et al. |
| 10,092,288 | B2 | 10/2018 | Denham et al. |
| 10,098,629 | B2 | 10/2018 | Kaiser et al. |
| 10,154,837 | B2 | 12/2018 | Stone et al. |
| 10,167,582 | B1 | 1/2019 | Pilgeram et al. |
| 10,251,637 | B2 | 4/2019 | Stone et al. |
| 10,265,064 | B2 | 4/2019 | Stone et al. |
| 10,265,159 | B2 | 4/2019 | Denham et al. |
| 10,321,906 | B2 | 6/2019 | Stone et al. |
| 10,349,931 | B2 | 7/2019 | Stone |
| 10,363,028 | B2 | 7/2019 | Norton |
| 10,368,856 | B2 | 8/2019 | Stone et al. |
| 10,398,428 | B2 | 9/2019 | Denham et al. |
| 10,398,430 | B2 | 9/2019 | Stone et al. |
| 10,441,264 | B2 | 10/2019 | Stone et al. |
| 10,517,587 | B2 | 12/2019 | Denham et al. |
| 10,517,714 | B2 | 12/2019 | Stone et al. |
| 10,542,967 | B2 | 1/2020 | Kaiser et al. |
| 10,595,851 | B2 | 3/2020 | Kaiser et al. |
| 10,603,029 | B2 | 3/2020 | Kaiser et al. |
| 10,610,217 | B2 | 4/2020 | Stone et al. |
| 10,675,073 | B2 | 6/2020 | Stone et al. |
| 10,687,803 | B2 | 6/2020 | Denham et al. |
| 10,695,045 | B2 | 6/2020 | Kaiser et al. |
| 10,695,052 | B2 | 6/2020 | Denham et al. |
| 10,702,259 | B2 | 7/2020 | Stone et al. |
| 10,716,557 | B2 | 7/2020 | Denham et al. |
| 10,729,421 | B2 | 8/2020 | Stone et al. |
| 10,729,423 | B2 | 8/2020 | Kaiser et al. |
| 10,729,430 | B2 | 8/2020 | Denham et al. |
| 10,743,925 | B2 | 8/2020 | Stone et al. |
| 10,758,221 | B2 | 9/2020 | Berelsman et al. |
| 10,835,232 | B2 | 11/2020 | Stone et al. |
| 10,932,770 | B2 | 3/2021 | Stone et al. |
| 10,973,507 | B2 | 4/2021 | Stone et al. |
| 10,987,099 | B2 | 4/2021 | Stone et al. |
| 11,039,826 | B2 | 6/2021 | Denham et al. |
| 11,065,103 | B2 | 7/2021 | Berelsman et al. |
| 11,096,684 | B2 | 8/2021 | Stone et al. |
| 11,109,857 | B2 | 9/2021 | Stone et al. |
| 11,116,495 | B2 | 9/2021 | Stone et al. |
| 11,185,320 | B2 | 11/2021 | Kaiser et al. |
| 11,241,305 | B2 | 2/2022 | Denham et al. |
| 11,259,792 | B2 | 3/2022 | Denham et al. |
| 11,259,794 | B2 | 3/2022 | Stone et al. |
| 11,284,884 | B2 | 3/2022 | Denham et al. |
| 11,311,287 | B2 | 4/2022 | Stone et al. |
| 11,317,907 | B2 | 5/2022 | Denham et al. |
| 11,376,115 | B2 | 7/2022 | Stone et al. |
| 11,446,019 | B2 | 9/2022 | Stone et al. |
| 11,471,147 | B2 | 10/2022 | Kaiser et al. |
| 11,534,157 | B2 | 12/2022 | Norton |
| 11,534,159 | B2 | 12/2022 | Denham et al. |
| 11,589,859 | B2 | 2/2023 | Kaiser et al. |
| 11,612,391 | B2 | 3/2023 | Stone et al. |
| 11,617,572 | B2 | 4/2023 | Stone et al. |
| 11,672,527 | B2 | 6/2023 | Stone et al. |
| 11,723,648 | B2 | 8/2023 | Stone et al. |
| 11,730,464 | B2 | 8/2023 | Stone et al. |
| 11,786,236 | B2 | 10/2023 | Denham et al. |
| 11,819,205 | B2 | 11/2023 | Stone et al. |
| 2001/0002439 | A1 | 5/2001 | Bonutti et al. |
| 2001/0010005 | A1 | 7/2001 | Kammerer et al. |
| 2001/0014825 | A1 | 8/2001 | Burke et al. |
| 2001/0019649 | A1 | 9/2001 | Field et al. |
| 2001/0027341 | A1 | 10/2001 | Gianotti |
| 2001/0029387 | A1 | 10/2001 | Wolf et al. |
| 2001/0037131 | A1 | 11/2001 | Schmieding et al. |
| 2001/0037153 | A1 | 11/2001 | Charles, Jr. et al. |
| 2001/0041916 | A1 | 11/2001 | Bonutti |
| 2001/0041937 | A1 | 11/2001 | Rieser et al. |
| 2001/0041938 | A1 | 11/2001 | Hein |
| 2001/0044627 | A1 | 11/2001 | Justin |
| 2001/0044639 | A1 | 11/2001 | Levinson |
| 2001/0047206 | A1 | 11/2001 | Sklar et al. |
| 2001/0051815 | A1 | 12/2001 | Esplin |
| 2001/0051816 | A1 | 12/2001 | Enzerink et al. |
| 2001/0053934 | A1 | 12/2001 | Schmieding |

(56)　　　　References Cited

U.S. PATENT DOCUMENTS

| | | |
|---|---|---|
| 2001/0056299 A1 | 12/2001 | Thompson |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | Elattrache et al. |
| 2002/0019649 A1 | 2/2002 | Sikora et al. |
| 2002/0029048 A1 | 3/2002 | Miller |
| 2002/0029066 A1 | 3/2002 | Foerster |
| 2002/0032465 A1 | 3/2002 | Lemer |
| 2002/0045902 A1 | 4/2002 | Bonutti |
| 2002/0052628 A1 | 5/2002 | Bowman |
| 2002/0055780 A1 | 5/2002 | Sklar |
| 2002/0058966 A1 | 5/2002 | Tormala et al. |
| 2002/0068254 A1 | 6/2002 | Campbell |
| 2002/0077629 A1 | 6/2002 | Hoffman et al. |
| 2002/0077659 A1 | 6/2002 | Johnson et al. |
| 2002/0082220 A1 | 6/2002 | Hoemann et al. |
| 2002/0091391 A1 | 7/2002 | Cole et al. |
| 2002/0099411 A1 | 7/2002 | Bartlett |
| 2002/0111591 A1 | 8/2002 | Mckinnon et al. |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0156475 A1 | 10/2002 | Lerch et al. |
| 2002/0161401 A1 | 10/2002 | Steiner |
| 2002/0161439 A1 | 10/2002 | Strobel et al. |
| 2002/0165548 A1 | 11/2002 | Jutley |
| 2002/0165611 A1 | 11/2002 | Enzerink et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0177853 A1 | 11/2002 | Chervitz et al. |
| 2002/0188298 A1 | 12/2002 | Chan |
| 2002/0193830 A1 | 12/2002 | Bonutti |
| 2003/0004545 A1 | 1/2003 | Burkhart et al. |
| 2003/0009235 A1 | 1/2003 | Manrique et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0050667 A1 | 3/2003 | Grafton et al. |
| 2003/0065361 A1 | 4/2003 | Dreyfuss |
| 2003/0065391 A1 | 4/2003 | Re et al. |
| 2003/0065402 A1 | 4/2003 | Anderson et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Archibald, III |
| 2003/0088251 A1 | 5/2003 | Braun et al. |
| 2003/0088272 A1 | 5/2003 | Smith |
| 2003/0093156 A1 | 5/2003 | Metzger et al. |
| 2003/0105477 A1 | 6/2003 | Schwartz et al. |
| 2003/0105489 A1 | 6/2003 | Eichhorn et al. |
| 2003/0114929 A1 | 6/2003 | Knudsen |
| 2003/0120309 A1 | 6/2003 | Colleran et al. |
| 2003/0130670 A1 | 7/2003 | Anderson et al. |
| 2003/0130694 A1 | 7/2003 | Bojarski et al. |
| 2003/0130695 A1 | 7/2003 | Mcdevitt et al. |
| 2003/0135214 A1 | 7/2003 | Fetto |
| 2003/0135239 A1 | 7/2003 | Gabriel et al. |
| 2003/0135265 A1 | 7/2003 | Stinson |
| 2003/0135963 A1 | 7/2003 | Holbrook et al. |
| 2003/0139752 A1 | 7/2003 | Pasricha et al. |
| 2003/0139775 A1 | 7/2003 | Grafton |
| 2003/0149448 A1 | 8/2003 | Foerster et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0176920 A1 | 9/2003 | Sklar et al. |
| 2003/0181925 A1 | 9/2003 | Bain et al. |
| 2003/0187510 A1 | 10/2003 | Hyde |
| 2003/0195528 A1 | 10/2003 | Ritchart |
| 2003/0195564 A1 | 10/2003 | Tran et al. |
| 2003/0195565 A1 | 10/2003 | Bonutti |
| 2003/0208209 A1 | 11/2003 | Gambale et al. |
| 2003/0208210 A1 | 11/2003 | Dreyfuss et al. |
| 2003/0212456 A1 | 11/2003 | Lipchitz et al. |
| 2003/0216809 A1 | 11/2003 | Ferguson |
| 2003/0220646 A1 | 11/2003 | Thelen et al. |
| 2003/0220660 A1 | 11/2003 | Kortenbach et al. |
| 2003/0225459 A1 | 12/2003 | Hammer et al. |
| 2003/0229361 A1 | 12/2003 | Jackson |
| 2003/0229396 A1 | 12/2003 | Andrews |
| 2003/0236555 A1 | 12/2003 | Thornes |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0013380 A1 | 1/2004 | Jimenez |
| 2004/0015171 A1 | 1/2004 | Bojarski et al. |
| 2004/0015172 A1 | 1/2004 | Biedermann et al. |
| 2004/0024456 A1 | 2/2004 | Charles, Jr. et al. |
| 2004/0024457 A1 | 2/2004 | Boyce et al. |
| 2004/0039389 A1 | 2/2004 | Hugh, Jr. et al. |
| 2004/0044351 A1 | 3/2004 | Searle |
| 2004/0044391 A1 | 3/2004 | Porter |
| 2004/0059357 A1 | 3/2004 | Koseki |
| 2004/0073176 A1 | 4/2004 | Utterberg |
| 2004/0087981 A1 | 5/2004 | Berube et al. |
| 2004/0092936 A1 | 5/2004 | Miller et al. |
| 2004/0093031 A1 | 5/2004 | Burkhart et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0098099 A1 | 5/2004 | McCullagh et al. |
| 2004/0111117 A1 | 6/2004 | Colleran et al. |
| 2004/0122431 A1 | 6/2004 | Biedermann et al. |
| 2004/0122454 A1 | 6/2004 | Wang et al. |
| 2004/0122456 A1 | 6/2004 | Saadat et al. |
| 2004/0127907 A1 | 7/2004 | Dakin et al. |
| 2004/0133206 A1 | 7/2004 | Stevens et al. |
| 2004/0133211 A1 | 7/2004 | Raskin et al. |
| 2004/0133238 A1 | 7/2004 | Cerier |
| 2004/0133239 A1 | 7/2004 | Singhatat |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0138755 A1 | 7/2004 | O'connor et al. |
| 2004/0143344 A1 | 7/2004 | Malaviya et al. |
| 2004/0144535 A1 | 7/2004 | Kalman et al. |
| 2004/0147932 A1 | 7/2004 | Burkinshaw et al. |
| 2004/0147958 A1 | 7/2004 | Lam et al. |
| 2004/0148030 A1 | 7/2004 | Ek |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0181234 A1 | 9/2004 | Mcdevitt et al. |
| 2004/0182968 A1 | 9/2004 | Gentry |
| 2004/0187314 A1 | 9/2004 | Johnson |
| 2004/0193185 A1 | 9/2004 | Mcbrayer |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225183 A1 | 11/2004 | Michlitsch et al. |
| 2004/0225292 A1 | 11/2004 | Sasso et al. |
| 2004/0225305 A1 | 11/2004 | Ewers et al. |

(56) References Cited

U.S. PATENT DOCUMENTS

| | | |
|---|---|---|
| 2004/0230302 A1 | 11/2004 | May et al. |
| 2004/0236353 A1 | 11/2004 | Bain et al. |
| 2004/0236373 A1 | 11/2004 | William, III |
| 2004/0243139 A1 | 12/2004 | Lewis et al. |
| 2004/0243178 A1 | 12/2004 | Haut et al. |
| 2004/0243180 A1 | 12/2004 | Donnelly et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267317 A1 | 12/2004 | Higgins et al. |
| 2004/0267361 A1 | 12/2004 | Donnelly et al. |
| 2004/0267362 A1 | 12/2004 | Hwang et al. |
| 2005/0004670 A1 | 1/2005 | Gebhardt et al. |
| 2005/0021087 A1 | 1/2005 | Koseki |
| 2005/0021148 A1 | 1/2005 | Gibbs |
| 2005/0027307 A1 | 2/2005 | Schwartz et al. |
| 2005/0033289 A1 | 2/2005 | Warren et al. |
| 2005/0033362 A1 | 2/2005 | Grafton |
| 2005/0033363 A1 | 2/2005 | Bojarski et al. |
| 2005/0038426 A1 | 2/2005 | Chan |
| 2005/0049598 A1 | 3/2005 | West, Jr. et al. |
| 2005/0055027 A1 | 3/2005 | Yeung et al. |
| 2005/0055037 A1 | 3/2005 | Fathauer |
| 2005/0064042 A1 | 3/2005 | Vunjak-novakovic et al. |
| 2005/0065521 A1 | 3/2005 | Steger et al. |
| 2005/0065526 A1 | 3/2005 | Drew et al. |
| 2005/0070906 A1 | 3/2005 | Clark et al. |
| 2005/0070928 A1 | 3/2005 | Heino et al. |
| 2005/0074495 A1 | 4/2005 | Schwartz et al. |
| 2005/0076478 A1 | 4/2005 | Miyazaki et al. |
| 2005/0085819 A1 | 4/2005 | Ellis et al. |
| 2005/0090827 A1 | 4/2005 | Gedebou |
| 2005/0090828 A1 | 4/2005 | Alford |
| 2005/0090862 A1 | 4/2005 | Mcdevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0107882 A1 | 5/2005 | Stone et al. |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1 | 6/2005 | Pipenhagen et al. |
| 2005/0125036 A1 | 6/2005 | Roby |
| 2005/0125073 A1 | 6/2005 | Orban et al. |
| 2005/0130301 A1 | 6/2005 | Mckay et al. |
| 2005/0131413 A1 | 6/2005 | O'driscoll et al. |
| 2005/0137600 A1 | 6/2005 | Jacobs et al. |
| 2005/0137624 A1 | 6/2005 | Fallman |
| 2005/0143734 A1 | 6/2005 | Cachia et al. |
| 2005/0149033 A1 | 7/2005 | Mcguire et al. |
| 2005/0149118 A1 | 7/2005 | Koyfman et al. |
| 2005/0149119 A1 | 7/2005 | Koyfman et al. |
| 2005/0149122 A1 | 7/2005 | Mcdevitt et al. |
| 2005/0149187 A1 | 7/2005 | Clark et al. |
| 2005/0154471 A1 | 7/2005 | Aram et al. |
| 2005/0159812 A1 | 7/2005 | Dinger, III et al. |
| 2005/0160656 A1 | 7/2005 | Safwat et al. |
| 2005/0165416 A1 | 7/2005 | Bojarski et al. |
| 2005/0165482 A1 | 7/2005 | Goldhahn et al. |
| 2005/0171547 A1 | 8/2005 | Aram |
| 2005/0171603 A1 | 8/2005 | Justin et al. |
| 2005/0171604 A1 | 8/2005 | Michalow |
| 2005/0177237 A1 | 8/2005 | Shappley et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0192581 A1 | 9/2005 | Molz et al. |
| 2005/0192632 A1 | 9/2005 | Geissler et al. |
| 2005/0197711 A1 | 9/2005 | Cachia |
| 2005/0203620 A1 | 9/2005 | Steiner et al. |
| 2005/0209703 A1 | 9/2005 | Fell |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0229433 A1 | 10/2005 | Cachia |
| 2005/0234549 A1 | 10/2005 | Kladakis et al. |
| 2005/0240198 A1 | 10/2005 | Albertson et al. |
| 2005/0251153 A1 | 11/2005 | Sakamoto et al. |
| 2005/0251159 A1 | 11/2005 | Ewers et al. |
| 2005/0251177 A1 | 11/2005 | Saadat et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0261642 A1 | 11/2005 | Weston |
| 2005/0267479 A1 | 12/2005 | Morgan et al. |
| 2005/0267533 A1 | 12/2005 | Gertner |
| 2005/0277088 A1 | 12/2005 | Fischer et al. |
| 2005/0277939 A1 | 12/2005 | Miller, III |
| 2005/0277961 A1 | 12/2005 | Stone et al. |
| 2005/0277985 A1 | 12/2005 | Wert et al. |
| 2005/0283040 A1 | 12/2005 | Greenhalgh |
| 2005/0283156 A1 | 12/2005 | Schmieding et al. |
| 2005/0283158 A1 | 12/2005 | West, Jr. |
| 2005/0283192 A1 | 12/2005 | Torrie et al. |
| 2005/0283220 A1 | 12/2005 | Gobran et al. |
| 2005/0288710 A1 | 12/2005 | Fallin et al. |
| 2006/0004364 A1 | 1/2006 | Green et al. |
| 2006/0004410 A1 | 1/2006 | Nobis et al. |
| 2006/0004460 A1 | 1/2006 | Engh et al. |
| 2006/0015103 A1 | 1/2006 | Burke |
| 2006/0015106 A1 | 1/2006 | Lerch et al. |
| 2006/0015107 A1 | 1/2006 | Sklar |
| 2006/0030884 A1 | 2/2006 | Yeung et al. |
| 2006/0030948 A1 | 2/2006 | Manrique et al. |
| 2006/0036265 A1 | 2/2006 | Dant et al. |
| 2006/0052787 A1 | 3/2006 | Re et al. |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089525 A1 | 4/2006 | Mamo et al. |
| 2006/0089672 A1 | 4/2006 | Martinek |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli |
| 2006/0116685 A1 | 6/2006 | Urbanski et al. |
| 2006/0121084 A1 | 6/2006 | Borden et al. |
| 2006/0122608 A1 | 6/2006 | Fallin et al. |
| 2006/0122611 A1 | 6/2006 | Morales et al. |
| 2006/0135958 A1 | 6/2006 | Marissen et al. |
| 2006/0149258 A1 | 7/2006 | Sousa |
| 2006/0149266 A1 | 7/2006 | Cordasco |
| 2006/0155287 A1 | 7/2006 | Montgomery et al. |
| 2006/0155328 A1 | 7/2006 | Foerster |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0178701 A1 | 8/2006 | Schmieding |
| 2006/0178743 A1 | 8/2006 | Carter |
| 2006/0189993 A1 | 8/2006 | Stone |
| 2006/0190041 A1 | 8/2006 | Fallin et al. |
| 2006/0190042 A1 | 8/2006 | Stone et al. |

(56) References Cited

U.S. PATENT DOCUMENTS

| | | |
|---|---|---|
| 2006/0195101 A1 | 8/2006 | Stevens |
| 2006/0195106 A1 | 8/2006 | Jones et al. |
| 2006/0200235 A1 | 9/2006 | Bianchi et al. |
| 2006/0212055 A1 | 9/2006 | Karabey et al. |
| 2006/0229623 A1 | 10/2006 | Bonutti et al. |
| 2006/0229671 A1 | 10/2006 | Steiner et al. |
| 2006/0229673 A1* | 10/2006 | Forsberg ............ A61B 17/0057 |
| | | 606/232 |
| 2006/0229676 A1 | 10/2006 | Doll et al. |
| 2006/0235407 A1 | 10/2006 | Wang et al. |
| 2006/0235413 A1 | 10/2006 | Denham et al. |
| 2006/0241624 A1 | 10/2006 | Kizuka et al. |
| 2006/0241776 A1 | 10/2006 | Brown et al. |
| 2006/0241781 A1 | 10/2006 | Brown et al. |
| 2006/0247642 A1 | 11/2006 | Stone et al. |
| 2006/0253130 A1 | 11/2006 | Wolniewicz, III |
| 2006/0259048 A1 | 11/2006 | Koseki |
| 2006/0259076 A1 | 11/2006 | Burkhart |
| 2006/0264944 A1 | 11/2006 | Cole |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276818 A1 | 12/2006 | Buser et al. |
| 2006/0276841 A1 | 12/2006 | Barbieri et al. |
| 2006/0276896 A1 | 12/2006 | Fallin et al. |
| 2006/0280768 A1 | 12/2006 | Hwang et al. |
| 2006/0280803 A1 | 12/2006 | Kumar et al. |
| 2006/0282082 A1 | 12/2006 | Fanton et al. |
| 2006/0282083 A1 | 12/2006 | Fanton et al. |
| 2006/0282085 A1 | 12/2006 | Stone |
| 2006/0293709 A1 | 12/2006 | Bojarski et al. |
| 2007/0005068 A1 | 1/2007 | Sklar |
| 2007/0005080 A1 | 1/2007 | Wolniewicz, III et al. |
| 2007/0010857 A1 | 1/2007 | Sugimoto et al. |
| 2007/0016305 A1 | 1/2007 | Chudik |
| 2007/0021779 A1 | 1/2007 | Garvin et al. |
| 2007/0027476 A1 | 2/2007 | Harris et al. |
| 2007/0032800 A1 | 2/2007 | Ortiz et al. |
| 2007/0032823 A1 | 2/2007 | Tegg |
| 2007/0038218 A1 | 2/2007 | Grevious |
| 2007/0043371 A1 | 2/2007 | Teague |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0071568 A1 | 3/2007 | Dorstewitz |
| 2007/0073307 A1 | 3/2007 | Scribner et al. |
| 2007/0073319 A1 | 3/2007 | Mikkaichi et al. |
| 2007/0073322 A1 | 3/2007 | Mikkaichi et al. |
| 2007/0078435 A1 | 4/2007 | Stone et al. |
| 2007/0078517 A1 | 4/2007 | Engh et al. |
| 2007/0083236 A1 | 4/2007 | Sikora et al. |
| 2007/0088362 A1 | 4/2007 | Bonutti et al. |
| 2007/0093847 A1 | 4/2007 | Scribner et al. |
| 2007/0100350 A1 | 5/2007 | Deffenbaugh et al. |
| 2007/0112384 A1 | 5/2007 | Conlon et al. |
| 2007/0118217 A1 | 5/2007 | Brulez et al. |
| 2007/0123883 A1 | 5/2007 | Ellis et al. |
| 2007/0123984 A1 | 5/2007 | Hodorek |
| 2007/0129809 A1 | 6/2007 | Meridew et al. |
| 2007/0135843 A1 | 6/2007 | Burkhart |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0162120 A1 | 7/2007 | Bouffier |
| 2007/0167926 A1 | 7/2007 | Blott et al. |
| 2007/0167950 A1 | 7/2007 | Tauro et al. |
| 2007/0173948 A1 | 7/2007 | Meridew et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | Elattrache et al. |
| 2007/0191853 A1 | 8/2007 | Stone |
| 2007/0198022 A1 | 8/2007 | Lang et al. |
| 2007/0198036 A1 | 8/2007 | Sklar et al. |
| 2007/0219558 A1 | 9/2007 | Deutsch |
| 2007/0225715 A1 | 9/2007 | Deffenbaugh et al. |
| 2007/0225719 A1 | 9/2007 | Stone et al. |
| 2007/0225763 A1 | 9/2007 | Zwolinski et al. |
| 2007/0225805 A1 | 9/2007 | Schmieding |
| 2007/0233241 A1 | 10/2007 | Graf et al. |
| 2007/0239209 A1 | 10/2007 | Fallman |
| 2007/0239275 A1 | 10/2007 | Willobee |
| 2007/0244565 A1 | 10/2007 | Stchur |
| 2007/0250059 A1 | 10/2007 | Weisshaupt et al. |
| 2007/0250163 A1 | 10/2007 | Cassani |
| 2007/0250175 A1 | 10/2007 | Meridew et al. |
| 2007/0255282 A1 | 11/2007 | Simonton et al. |
| 2007/0260251 A1 | 11/2007 | Weier et al. |
| 2007/0260279 A1 | 11/2007 | Hotter et al. |
| 2007/0265704 A1 | 11/2007 | Mayer et al. |
| 2007/0270856 A1 | 11/2007 | Morales et al. |
| 2007/0270878 A1 | 11/2007 | Leisinger |
| 2007/0276387 A1 | 11/2007 | Morales et al. |
| 2007/0288023 A1 | 12/2007 | Pellegrino et al. |
| 2008/0009904 A1 | 1/2008 | Bourque et al. |
| 2008/0027430 A1 | 1/2008 | Montgomery et al. |
| 2008/0027440 A1 | 1/2008 | Marissen et al. |
| 2008/0027446 A1 | 1/2008 | Stone et al. |
| 2008/0033549 A1 | 2/2008 | Marshall et al. |
| 2008/0046009 A1 | 2/2008 | Albertorio et al. |
| 2008/0051834 A1 | 2/2008 | Mazzocca et al. |
| 2008/0051836 A1 | 2/2008 | Foerster et al. |
| 2008/0058787 A1 | 3/2008 | Gertner |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0086138 A1 | 4/2008 | Stone et al. |
| 2008/0097430 A1 | 4/2008 | Bernstein et al. |
| 2008/0103528 A1 | 5/2008 | Zirps et al. |
| 2008/0114460 A1 | 5/2008 | Willobee et al. |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0133007 A1 | 6/2008 | Donnelly et al. |
| 2008/0137624 A1 | 6/2008 | Silverstrim et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0147127 A1 | 6/2008 | Tipirneni et al. |
| 2008/0147187 A1 | 6/2008 | Bollinger et al. |
| 2008/0154260 A1 | 6/2008 | Hoof |
| 2008/0154314 A1 | 6/2008 | Mcdevitt |
| 2008/0161806 A1 | 7/2008 | Donnelly et al. |
| 2008/0161852 A1 | 7/2008 | Kaiser et al. |
| 2008/0161861 A1 | 7/2008 | Huebner |
| 2008/0161864 A1 | 7/2008 | Beck et al. |
| 2008/0166421 A1 | 7/2008 | Buhr et al. |
| 2008/0172097 A1 | 7/2008 | Lerch et al. |
| 2008/0177302 A1 | 7/2008 | Shurnas |
| 2008/0183290 A1 | 7/2008 | Baird et al. |
| 2008/0188933 A1 | 8/2008 | Koob et al. |
| 2008/0188935 A1 | 8/2008 | Saylor et al. |
| 2008/0188936 A1 | 8/2008 | Ball et al. |
| 2008/0208252 A1 | 8/2008 | Holmes |
| 2008/0217263 A1 | 9/2008 | Higgins et al. |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0228271 A1 | 9/2008 | Stone et al. |
| 2008/0234730 A1 | 9/2008 | Cotton et al. |
| 2008/0243260 A1 | 10/2008 | Lee et al. |
| 2008/0243261 A1 | 10/2008 | Wyss et al. |
| 2008/0243262 A1 | 10/2008 | Lee |
| 2008/0255613 A1 | 10/2008 | Kaiser et al. |
| 2008/0257363 A1 | 10/2008 | Schoenefeld et al. |
| 2008/0262544 A1 | 10/2008 | Burkhart |
| 2008/0268064 A1 | 10/2008 | Woodell-may |
| 2008/0269674 A1 | 10/2008 | Stone |
| 2008/0275469 A1 | 11/2008 | Fanton et al. |

(56) References Cited

U.S. PATENT DOCUMENTS

| | | |
|---|---|---|
| 2008/0275477 A1 | 11/2008 | Sterrett et al. |
| 2008/0281428 A1 | 11/2008 | Meyers et al. |
| 2008/0288070 A1 | 11/2008 | Lo |
| 2008/0300611 A1 | 12/2008 | Houser et al. |
| 2008/0312689 A1 | 12/2008 | Denham et al. |
| 2008/0319478 A1 | 12/2008 | Foerster et al. |
| 2009/0018589 A1 | 1/2009 | Smisson, III et al. |
| 2009/0018654 A1 | 1/2009 | Schmieding et al. |
| 2009/0018655 A1 | 1/2009 | Brunelle et al. |
| 2009/0043342 A1 | 2/2009 | Freedland |
| 2009/0054928 A1 | 2/2009 | Denham et al. |
| 2009/0062847 A1 | 3/2009 | Ken |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0084491 A1 | 4/2009 | Uthgenannt et al. |
| 2009/0099598 A1 | 4/2009 | Mcdevitt et al. |
| 2009/0105717 A1 | 4/2009 | Bluechel |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0182335 A1 | 7/2009 | Struhl |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0216325 A1 | 8/2009 | May et al. |
| 2009/0228015 A1 | 9/2009 | Ellis |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0234451 A1 | 9/2009 | Manderson |
| 2009/0240251 A1 | 9/2009 | Gabele |
| 2009/0240335 A1 | 9/2009 | Arcenio et al. |
| 2009/0241497 A1 | 10/2009 | Imai et al. |
| 2009/0248091 A1 | 10/2009 | Teague et al. |
| 2009/0254089 A1 | 10/2009 | Tipirneni et al. |
| 2009/0265014 A1 | 10/2009 | May et al. |
| 2009/0265015 A1 | 10/2009 | May et al. |
| 2009/0287215 A1 | 11/2009 | Fisher et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0312793 A1 | 12/2009 | Huxel et al. |
| 2009/0318960 A1 | 12/2009 | Burkhart |
| 2009/0318961 A1 | 12/2009 | Stone et al. |
| 2009/0318965 A1 | 12/2009 | Burkhart |
| 2010/0016891 A1 | 1/2010 | Kennedy et al. |
| 2010/0016899 A1 | 1/2010 | Gelfand |
| 2010/0030321 A1 | 2/2010 | Mach |
| 2010/0042114 A1 | 2/2010 | Schaffhausen et al. |
| 2010/0063540 A1 | 3/2010 | Maiorino |
| 2010/0063541 A1 | 3/2010 | Brunelle et al. |
| 2010/0087857 A1 | 4/2010 | Stone et al. |
| 2010/0094341 A1 | 4/2010 | Raju |
| 2010/0094355 A1 | 4/2010 | Trenhaile |
| 2010/0106254 A1 | 4/2010 | Delsignore |
| 2010/0121348 A1 | 5/2010 | Van Der et al. |
| 2010/0145384 A1 | 6/2010 | Stone et al. |
| 2010/0152752 A1 | 6/2010 | Denove et al. |
| 2010/0191319 A1 | 7/2010 | Lilburn et al. |
| 2010/0191342 A1 | 7/2010 | Byrd et al. |
| 2010/0204700 A1 | 8/2010 | Falahee |
| 2010/0211071 A1 | 8/2010 | Lettmann et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0274282 A1 | 10/2010 | Olson |
| 2010/0292792 A1 | 11/2010 | Stone et al. |
| 2010/0298872 A1 | 11/2010 | Berndt et al. |
| 2010/0298952 A1 | 11/2010 | Busold et al. |
| 2010/0305698 A1 | 12/2010 | Metzger et al. |
| 2010/0305709 A1 | 12/2010 | Metzger et al. |
| 2010/0305710 A1 | 12/2010 | Metzger |
| 2010/0312245 A1 | 12/2010 | Tipirneni et al. |
| 2010/0312341 A1 | 12/2010 | Kaiser et al. |
| 2010/0324676 A1 | 12/2010 | Albertorio |
| 2010/0331881 A1 | 12/2010 | Hart |
| 2011/0009885 A1 | 1/2011 | Graf et al. |
| 2011/0022083 A1 | 1/2011 | Dimatteo et al. |
| 2011/0026141 A1 | 2/2011 | Barrows |
| 2011/0040387 A1 | 2/2011 | Ries et al. |
| 2011/0046733 A1 | 2/2011 | Eggli |
| 2011/0087225 A1 | 4/2011 | Fritzinger |
| 2011/0087280 A1 | 4/2011 | Albertorio |
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0112537 A1 | 5/2011 | Bernstein et al. |
| 2011/0112538 A1 | 5/2011 | Dell'oca |
| 2011/0124954 A1 | 5/2011 | Ogdahl et al. |
| 2011/0125153 A1 | 5/2011 | Tyber et al. |
| 2011/0160767 A1 | 6/2011 | Stone et al. |
| 2011/0160768 A1 | 6/2011 | Stone et al. |
| 2011/0166608 A1 | 7/2011 | Duggal et al. |
| 2011/0184227 A1 | 7/2011 | Altman et al. |
| 2011/0208239 A1 | 8/2011 | Stone et al. |
| 2011/0208240 A1 | 8/2011 | Stone et al. |
| 2011/0213367 A1 | 9/2011 | Tyber et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0245868 A1 | 10/2011 | Teeslink et al. |
| 2011/0264141 A1 | 10/2011 | Denham et al. |
| 2011/0270278 A1 | 11/2011 | Overes et al. |
| 2011/0270306 A1 | 11/2011 | Denham et al. |
| 2011/0295284 A1 | 12/2011 | Purdue et al. |
| 2011/0319932 A1 | 12/2011 | Avelar et al. |
| 2012/0004669 A1 | 1/2012 | Overes et al. |
| 2012/0024134 A1 | 2/2012 | Dow et al. |
| 2012/0029561 A1 | 2/2012 | Olson |
| 2012/0041485 A1 | 2/2012 | Kaiser et al. |
| 2012/0041486 A1 | 2/2012 | Stone et al. |
| 2012/0041496 A1 | 2/2012 | Walker |
| 2012/0042768 A1 | 2/2012 | Chou et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0059468 A1 | 3/2012 | Mattern et al. |
| 2012/0060278 A1 | 3/2012 | Mccurdy |
| 2012/0083837 A1 | 4/2012 | Ferragamo et al. |
| 2012/0089193 A1 | 4/2012 | Stone et al. |
| 2012/0095470 A1 | 4/2012 | Kaiser et al. |
| 2012/0109156 A1 | 5/2012 | Overes et al. |
| 2012/0116409 A1 | 5/2012 | Stone |
| 2012/0116450 A1 | 5/2012 | Mcdevitt et al. |
| 2012/0116452 A1 | 5/2012 | Stone et al. |
| 2012/0123447 A1 | 5/2012 | Corrao et al. |
| 2012/0123474 A1 | 5/2012 | Zajac et al. |
| 2012/0123541 A1 | 5/2012 | Albertorio et al. |
| 2012/0130423 A1 | 5/2012 | Sengun et al. |
| 2012/0130492 A1 | 5/2012 | Eggli et al. |
| 2012/0143215 A1 | 6/2012 | Corrao et al. |
| 2012/0150223 A1 | 6/2012 | Manos et al. |
| 2012/0150297 A1 | 6/2012 | Denham et al. |
| 2012/0165864 A1 | 6/2012 | Hernandez et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0192455 A1 | 8/2012 | Hansen et al. |
| 2012/0197271 A1 | 8/2012 | Astorino et al. |
| 2012/0215257 A1 | 8/2012 | Mcdevitt et al. |
| 2012/0239159 A1 | 9/2012 | Metzger et al. |
| 2012/0245585 A1 | 9/2012 | Kaiser et al. |
| 2012/0265219 A1 | 10/2012 | Rushdy et al. |
| 2012/0265294 A1 | 10/2012 | Nishigishi |

(56)         References Cited

U.S. PATENT DOCUMENTS

| | | |
|---|---|---|
| 2012/0271403 A1 | 10/2012 | Gries |
| 2012/0273085 A1 | 11/2012 | David et al. |
| 2012/0290002 A1 | 11/2012 | Astorino |
| 2012/0290003 A1 | 11/2012 | Dreyfuss |
| 2012/0290004 A1 | 11/2012 | Lombardo et al. |
| 2012/0296427 A1 | 11/2012 | Conner et al. |
| 2012/0310245 A1 | 12/2012 | Hoeppner et al. |
| 2013/0018375 A1 | 1/2013 | Dell'oca |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone |
| 2013/0035722 A1 | 2/2013 | Mcdevitt et al. |
| 2013/0046341 A1 | 2/2013 | Stone et al. |
| 2013/0060323 A1 | 3/2013 | Mchugo |
| 2013/0090720 A1 | 4/2013 | Mahr et al. |
| 2013/0090731 A1 | 4/2013 | Walker |
| 2013/0103082 A1 | 4/2013 | Kaiser et al. |
| 2013/0110165 A1 | 5/2013 | Burkhart et al. |
| 2013/0110251 A1 | 5/2013 | Metzger et al. |
| 2013/0116730 A1 | 5/2013 | Denham |
| 2013/0123810 A1 | 5/2013 | Brown et al. |
| 2013/0123813 A1 | 5/2013 | Stone et al. |
| 2013/0131722 A1 | 5/2013 | Marchand et al. |
| 2013/0138123 A1 | 5/2013 | Stone et al. |
| 2013/0144337 A1 | 6/2013 | Stone et al. |
| 2013/0144338 A1 | 6/2013 | Stone et al. |
| 2013/0158599 A1 | 6/2013 | Hester et al. |
| 2013/0158601 A1 | 6/2013 | Stone et al. |
| 2013/0172942 A1 | 7/2013 | Lewis et al. |
| 2013/0190818 A1 | 7/2013 | Norton |
| 2013/0190819 A1 | 7/2013 | Norton |
| 2013/0204276 A1 | 8/2013 | Stone et al. |
| 2013/0211452 A1 | 8/2013 | Stone et al. |
| 2013/0231700 A1 | 9/2013 | Gedet et al. |
| 2013/0237997 A1 | 9/2013 | Arai et al. |
| 2013/0245761 A1 | 9/2013 | Conner et al. |
| 2013/0267956 A1 | 10/2013 | Terrill et al. |
| 2013/0274812 A1 | 10/2013 | Dell'oca |
| 2013/0289564 A1 | 10/2013 | Bernstein et al. |
| 2013/0317621 A1 | 11/2013 | Metzger et al. |
| 2013/0331742 A1 | 12/2013 | Aupperle et al. |
| 2013/0331848 A1 | 12/2013 | Kaiser et al. |
| 2014/0005754 A1 | 1/2014 | Finley et al. |
| 2014/0018804 A1 | 1/2014 | Foerster |
| 2014/0046367 A1 | 2/2014 | Stone et al. |
| 2014/0046368 A1 | 2/2014 | Kaiser et al. |
| 2014/0052179 A1 | 2/2014 | Dreyfuss et al. |
| 2014/0058436 A1 | 2/2014 | Rosenbluth et al. |
| 2014/0067081 A1 | 3/2014 | Stone |
| 2014/0081322 A1 | 3/2014 | Sengun et al. |
| 2014/0088655 A1 | 3/2014 | Stone et al. |
| 2014/0094913 A1 | 4/2014 | Berelsman et al. |
| 2014/0128985 A1 | 5/2014 | Sanders et al. |
| 2014/0135835 A1 | 5/2014 | Stone et al. |
| 2014/0163613 A1 | 6/2014 | Stone et al. |
| 2014/0163614 A1 | 6/2014 | Denham et al. |
| 2014/0194927 A1 | 7/2014 | Kaiser et al. |
| 2014/0200583 A1 | 7/2014 | Stone et al. |
| 2014/0257378 A1 | 9/2014 | Norton et al. |
| 2014/0276992 A1 | 9/2014 | Stone et al. |
| 2014/0277447 A1 | 9/2014 | Berelsman et al. |
| 2014/0324101 A1 | 10/2014 | Denham et al. |
| 2014/0330311 A1 | 11/2014 | Denham et al. |
| 2014/0336760 A1 | 11/2014 | Eggli |
| 2014/0350674 A1 | 11/2014 | Stone et al. |
| 2015/0012094 A1 | 1/2015 | Denham et al. |
| 2015/0032216 A1 | 1/2015 | Metzger et al. |
| 2015/0057665 A1 | 2/2015 | Neal et al. |
| 2015/0057757 A1 | 2/2015 | Metzger et al. |
| 2015/0066081 A1 | 3/2015 | Martin |
| 2015/0119890 A1 | 4/2015 | Kaiser et al. |
| 2015/0127051 A1 | 5/2015 | Kaiser et al. |
| 2015/0128792 A1 | 5/2015 | Zachariades et al. |
| 2015/0134000 A1 | 5/2015 | Denham et al. |
| 2015/0143981 A1 | 5/2015 | Dunker |
| 2015/0148888 A1 | 5/2015 | Milner et al. |
| 2015/0173753 A1 | 6/2015 | Spivey et al. |
| 2015/0173887 A1 | 6/2015 | Berelsman et al. |
| 2015/0257750 A1 | 9/2015 | Kaiser et al. |
| 2015/0320026 A1 | 11/2015 | Toddes |
| 2016/0000483 A1 | 1/2016 | Stone |
| 2016/0022261 A1 | 1/2016 | Stone et al. |
| 2016/0038187 A1 | 2/2016 | Mcdonnell |
| 2016/0058436 A1 | 3/2016 | Stone et al. |
| 2016/0058484 A1 | 3/2016 | Mccombs-stearnes et al. |
| 2016/0074049 A1 | 3/2016 | Russell et al. |
| 2016/0081789 A1 | 3/2016 | Denham et al. |
| 2016/0106414 A1 | 4/2016 | Stone et al. |
| 2016/0128684 A1 | 5/2016 | Stone et al. |
| 2016/0183935 A1 | 6/2016 | Stone |
| 2016/0199053 A1 | 7/2016 | Norton et al. |
| 2016/0213369 A1 | 7/2016 | Stone et al. |
| 2016/0242760 A1 | 8/2016 | Kaiser et al. |
| 2017/0014225 A1 | 1/2017 | Denham et al. |
| 2017/0020507 A1 | 1/2017 | Denham et al. |
| 2017/0020569 A1 | 1/2017 | Grant |
| 2017/0035411 A1 | 2/2017 | Kaiser et al. |
| 2017/0049557 A1 | 2/2017 | Denham et al. |
| 2017/0065278 A1 | 3/2017 | Stone |
| 2017/0071593 A1 | 3/2017 | Stone |
| 2017/0071595 A1 | 3/2017 | Stone et al. |
| 2017/0086816 A1 | 3/2017 | Norton |
| 2017/0119382 A1 | 5/2017 | Denham et al. |
| 2017/0128061 A1 | 5/2017 | Stone et al. |
| 2017/0181746 A1 | 6/2017 | Denham et al. |
| 2017/0189011 A1 | 7/2017 | Stone et al. |
| 2017/0189197 A1 | 7/2017 | Werber et al. |
| 2017/0202587 A1 | 7/2017 | Stone et al. |
| 2017/0273686 A1 | 9/2017 | Denham et al. |
| 2017/0311947 A1 | 11/2017 | Kaiser et al. |
| 2017/0319194 A1 | 11/2017 | Mayeski et al. |
| 2017/0319195 A1 | 11/2017 | Denham et al. |
| 2017/0319204 A1 | 11/2017 | Norton et al. |
| 2017/0325808 A1 | 11/2017 | Stone et al. |
| 2017/0333176 A1 | 11/2017 | Stone et al. |
| 2017/0360425 A1 | 12/2017 | Stone et al. |
| 2018/0000477 A1 | 1/2018 | Kaiser et al. |
| 2018/0014864 A1 | 1/2018 | Stone et al. |
| 2018/0020762 A1 | 1/2018 | Jamison |
| 2018/0021036 A1 | 1/2018 | Kaiser et al. |
| 2018/0021125 A1 | 1/2018 | Berelsman et al. |
| 2018/0042609 A1 | 2/2018 | Denham et al. |
| 2018/0098858 A1 | 4/2018 | Valderrabano et al. |
| 2018/0125476 A1 | 5/2018 | Kaiser et al. |
| 2018/0125477 A1 | 5/2018 | Stone |
| 2018/0153538 A1 | 6/2018 | Kaiser et al. |
| 2018/0153558 A1 | 6/2018 | Bake et al. |
| 2018/0161030 A1 | 6/2018 | Stone et al. |
| 2018/0177501 A1 | 6/2018 | Kaiser et al. |
| 2018/0193015 A1 | 7/2018 | Denham et al. |
| 2018/0221017 A1 | 8/2018 | Stone et al. |
| 2018/0235747 A1 | 8/2018 | Berelsman et al. |
| 2018/0249997 A1 | 9/2018 | Stone et al. |
| 2018/0256153 A1 | 9/2018 | Stone et al. |
| 2019/0083233 A1 | 3/2019 | Denham et al. |
| 2019/0150909 A1 | 5/2019 | Stone et al. |
| 2019/0150923 A1 | 5/2019 | Stone et al. |
| 2019/0231348 A1 | 8/2019 | Stone et al. |
| 2019/0254652 A1 | 8/2019 | Stone et al. |
| 2019/0274681 A1 | 9/2019 | Denham et al. |
| 2019/0282227 A1 | 9/2019 | Norton |
| 2019/0290258 A1 | 9/2019 | Denham et al. |
| 2019/0298345 A1 | 10/2019 | Denham et al. |
| 2019/0328382 A1 | 10/2019 | Stone et al. |
| 2019/0365376 A1 | 12/2019 | Stone et al. |
| 2020/0029955 A1 | 1/2020 | Stone et al. |
| 2020/0085562 A1 | 3/2020 | Stone et al. |
| 2020/0178959 A1 | 6/2020 | Denham et al. |
| 2020/0187932 A1 | 6/2020 | Kaiser et al. |
| 2020/0187933 A1 | 6/2020 | Kaiser et al. |
| 2020/0197002 A1 | 6/2020 | Stone et al. |
| 2020/0297338 A1 | 9/2020 | Stone et al. |

(56) References Cited

U.S. PATENT DOCUMENTS

| | | | |
|---|---|---|---|
| 2020/0367880 | A1 | 11/2020 | Stone et al. |
| 2021/0177397 | A1 | 6/2021 | Stone et al. |
| 2021/0228203 | A1 | 7/2021 | Denham et al. |
| 2021/0361286 | A1 | 11/2021 | Stone et al. |
| 2022/0015757 | A1 | 1/2022 | Stone et al. |
| 2022/0054123 | A1 | 2/2022 | Kaiser et al. |
| 2022/0096074 | A1 | 3/2022 | Denham et al. |
| 2022/0096081 | A1 | 3/2022 | Denham et al. |
| 2022/0133296 | A1 | 5/2022 | Stone et al. |
| 2023/0000484 | A1 | 1/2023 | Kaiser et al. |
| 2023/0084732 | A1 | 3/2023 | Norton |
| 2023/0146316 | A1 | 5/2023 | Stone et al. |
| 2023/0165580 | A1 | 6/2023 | Kaiser et al. |
| 2023/0172602 | A1 | 6/2023 | Kaiser et al. |
| 2023/0248356 | A1 | 8/2023 | Stone et al. |
| 2023/0293165 | A1 | 9/2023 | Stone et al. |

FOREIGN PATENT DOCUMENTS

| | | | |
|---|---|---|---|
| AU | 4381268 | A | 4/1970 |
| AU | 5850469 | A | 1/1971 |
| AU | 5963869 | A | 2/1971 |
| AU | 1505470 | A | 11/1971 |
| AU | 2223767 | A | 5/1973 |
| AU | 3615171 | A | 5/1973 |
| AU | 440266 | B2 | 9/1973 |
| AU | 5028569 | A | 9/1973 |
| AU | 7110887 | A | 10/1987 |
| AU | 639410 | A | 11/1989 |
| AU | 1713188 | A | 11/1989 |
| AU | 651929 | B2 | 8/1994 |
| AU | 3877493 | B2 | 8/1994 |
| BE | 1010569 | A6 | 10/1998 |
| CN | 1720872 | A | 1/2006 |
| CN | 1777450 | A | 5/2006 |
| CN | 101083954 | A | 12/2007 |
| CN | 101584592 | A | 11/2009 |
| CN | 105208970 | A | 12/2015 |
| DE | 2529669 | A1 | 3/1976 |
| DE | 2747312 | A1 | 4/1979 |
| DE | 2818254 | A1 | 10/1979 |
| DE | 2919009 | A1 | 11/1979 |
| DE | 3027138 | A1 | 12/1981 |
| DE | 3225620 | A1 | 2/1983 |
| DE | 3136083 | A1 | 3/1983 |
| DE | 233303 | A1 | 2/1986 |
| DE | 4127550 | A1 | 2/1993 |
| DE | 4302397 | A | 7/1993 |
| DE | 29621340 | U1 | 4/1998 |
| DE | 19841252 | A1 | 3/2000 |
| DE | 29922088 | U1 | 4/2000 |
| DE | 20207781 | U1 | 8/2002 |
| EP | 0019062 | A1 | 11/1980 |
| EP | 0108912 | A2 | 5/1984 |
| EP | 0129422 | A2 | 12/1984 |
| EP | 0129442 | A1 | 12/1984 |
| EP | 0172130 | A2 | 2/1986 |
| EP | 0241240 | A2 | 10/1987 |
| EP | 0241792 | A1 | 10/1987 |
| EP | 0260970 | A2 | 3/1988 |
| EP | 0270704 | A1 | 6/1988 |
| EP | 0282789 | A2 | 9/1988 |
| EP | 0315371 | A2 | 5/1989 |
| EP | 0317406 | A1 | 5/1989 |
| EP | 0340159 | A1 | 11/1989 |
| EP | 0346183 | A1 | 12/1989 |
| EP | 0349173 | A1 | 1/1990 |
| EP | 0374088 | A1 | 6/1990 |
| EP | 0409364 | A2 | 1/1991 |
| EP | 0415915 | A1 | 3/1991 |
| EP | 0440991 | A1 | 8/1991 |
| EP | 0441065 | A2 | 8/1991 |
| EP | 0447065 | A2 | 9/1991 |
| EP | 0451932 | A1 | 10/1991 |
| EP | 0464480 | A1 | 1/1992 |
| EP | 0490417 | A1 | 6/1992 |
| EP | 0497079 | A1 | 8/1992 |
| EP | 0502509 | A1 | 9/1992 |
| EP | 0502698 | A1 | 9/1992 |
| EP | 0520177 | A1 | 12/1992 |
| EP | 0546726 | A1 | 6/1993 |
| EP | 0552950 | A1 | 7/1993 |
| EP | 0574707 | A1 | 12/1993 |
| EP | 0582514 | A1 | 2/1994 |
| EP | 0591991 | A2 | 4/1994 |
| EP | 0598219 | A2 | 5/1994 |
| EP | 0611551 | A1 | 8/1994 |
| EP | 0627203 | A2 | 12/1994 |
| EP | 0651979 | A1 | 5/1995 |
| EP | 0669110 | A2 | 8/1995 |
| EP | 0686373 | A1 | 12/1995 |
| EP | 0702933 | A1 | 3/1996 |
| EP | 0775473 | A1 | 5/1997 |
| EP | 0913123 | A1 | 5/1999 |
| EP | 0913131 | A2 | 5/1999 |
| EP | 0995409 | A1 | 4/2000 |
| EP | 1013229 | A2 | 6/2000 |
| EP | 1093773 | A1 | 4/2001 |
| EP | 1093774 | A1 | 4/2001 |
| EP | 1555945 | A2 | 7/2005 |
| EP | 1741412 | A2 | 1/2007 |
| EP | 1864617 | A2 | 12/2007 |
| EP | 2238944 | A2 | 10/2010 |
| EP | 2544607 | A1 | 1/2013 |
| EP | 2709557 | A1 | 3/2014 |
| EP | 2895112 | A1 | 7/2015 |
| EP | 2934379 | A1 | 10/2015 |
| EP | 2434987 | B1 | 6/2016 |
| EP | 2775935 | B1 | 5/2017 |
| FR | 2622790 | A1 | 5/1989 |
| FR | 2634373 | A1 | 1/1990 |
| FR | 2655840 | A1 | 6/1991 |
| FR | 2663837 | A1 | 1/1992 |
| FR | 2682867 | A1 | 4/1993 |
| FR | 2687911 | A1 | 9/1993 |
| FR | 2688689 | A1 | 9/1993 |
| FR | 2704140 | A3 | 10/1994 |
| FR | 2717070 | A1 | 9/1995 |
| FR | 2723528 | A1 | 2/1996 |
| FR | 2734709 | A1 | 12/1996 |
| FR | 2744010 | A1 | 8/1997 |
| FR | 2745999 | A1 | 9/1997 |
| FR | 2770764 | A1 | 5/1999 |
| GB | 401677 | A | 11/1933 |
| GB | 1413477 | A | 11/1975 |
| GB | 1485681 | A | 9/1977 |
| GB | 2083751 | A | 3/1982 |
| GB | 2118474 | A | 11/1983 |
| GB | 2129306 | A | 5/1984 |
| GB | 2227175 | A | 7/1990 |
| GB | 2253147 | A | 9/1992 |
| GB | 2312376 | A | 10/1997 |
| GB | 2403416 | A | 1/2005 |
| GB | 2454251 | A | 5/2009 |
| JP | 5362911 | U | 5/1978 |
| JP | 5362912 | U | 5/1978 |
| JP | 5374942 | U | 6/1978 |
| JP | 5378230 | U | 6/1978 |
| JP | 54166092 | U | 11/1979 |
| JP | 54166093 | U | 11/1979 |
| JP | 54176284 | U | 12/1979 |
| JP | 54178988 | U | 12/1979 |
| JP | 5362911 | A | 7/1987 |
| JP | 62159647 | A | 7/1987 |
| JP | 62159647 | U | 10/1987 |
| JP | 62295657 | A | 12/1987 |
| JP | 5269160 | A | 10/1993 |
| JP | 5300917 | A | 11/1993 |
| JP | 751292 | A | 2/1995 |
| JP | 10127672 | A | 5/1998 |
| JP | 10211213 | A | 8/1998 |
| JP | 5362911 | B2 | 12/2013 |
| JP | 5362912 | B2 | 12/2013 |
| JP | 5374942 | B2 | 12/2013 |

(56) References Cited

FOREIGN PATENT DOCUMENTS

| JP | 5378230 B2 | 12/2013 |
| RU | 2051647 C1 | 1/1996 |
| RU | 2076667 C1 | 4/1997 |
| WO | WO-8300615 A1 | 3/1983 |
| WO | WO-8603666 A1 | 7/1986 |
| WO | WO-8701270 A1 | 3/1987 |
| WO | WO-8901767 A1 | 3/1989 |
| WO | WO-8909030 A1 | 10/1989 |
| WO | WO-8910096 A1 | 11/1989 |
| WO | WO-9008510 A1 | 8/1990 |
| WO | WO-9203980 A1 | 3/1992 |
| WO | WO-9314705 A1 | 8/1993 |
| WO | WO-9315694 A1 | 8/1993 |
| WO | WO-9502373 A1 | 1/1995 |
| WO | WO-9503003 A1 | 2/1995 |
| WO | WO-9529637 A1 | 11/1995 |
| WO | WO-9532670 A1 | 12/1995 |
| WO | WO-9609797 A1 | 4/1996 |
| WO | WO-9629029 A1 | 9/1996 |
| WO | WO-9737603 A1 | 10/1997 |
| WO | WO-9812991 A1 | 4/1998 |
| WO | WO-9812992 A1 | 4/1998 |
| WO | WO-9822047 A1 | 5/1998 |
| WO | WO-9822048 A1 | 5/1998 |
| WO | WO-9901084 A2 | 1/1999 |
| WO | WO-9912480 A1 | 3/1999 |
| WO | WO-9937219 A1 | 7/1999 |
| WO | WO-9944544 A1 | 9/1999 |
| WO | WO-9952472 A1 | 10/1999 |
| WO | WO-0004159 A1 | 1/2000 |
| WO | WO-0040159 A1 | 7/2000 |
| WO | WO-0139671 A1 | 6/2001 |
| WO | WO-0236020 A1 | 5/2002 |
| WO | WO-03005914 A1 | 1/2003 |
| WO | WO-03071962 A2 | 9/2003 |
| WO | WO-03077772 A1 | 9/2003 |
| WO | WO-03092551 A1 | 11/2003 |
| WO | WO-2004091412 A1 | 10/2004 |
| WO | WO-05104992 A1 | 11/2005 |
| WO | WO-2005122954 A1 | 12/2005 |
| WO | WO-2006011786 A1 | 2/2006 |
| WO | WO-2006023661 A2 | 3/2006 |
| WO | WO-2006055823 A2 | 5/2006 |
| WO | WO-2007045460 A2 | 4/2007 |
| WO | WO-2007103562 A2 | 9/2007 |
| WO | WO-2007109280 A2 | 9/2007 |
| WO | WO-2007119057 A1 | 10/2007 |
| WO | WO-2008002550 A2 | 1/2008 |
| WO | WO-2008015171 A1 | 2/2008 |
| WO | WO-2008073588 A2 | 6/2008 |
| WO | WO-2009012021 A1 | 1/2009 |
| WO | WO-2009083047 A1 | 7/2009 |
| WO | WO-2009131820 A1 | 10/2009 |
| WO | WO-2010138832 A1 | 12/2010 |
| WO | WO-2011112371 A1 | 9/2011 |
| WO | WO-2011150238 A1 | 12/2011 |
| WO | WO-2012134999 A1 | 10/2012 |
| WO | WO-2012158583 A1 | 11/2012 |
| WO | WO-2013066974 A1 | 5/2013 |
| WO | WO-2013074525 A1 | 5/2013 |
| WO | WO-2014043078 A1 | 3/2014 |
| WO | WO-2014100109 A1 | 6/2014 |
| WO | WO-2014151766 A1 | 9/2014 |

OTHER PUBLICATIONS

"AperFix® System Surgical Technique Guide. Single Tunnel Double Bundle.™", Cayenne Medical brochure, (Aug. 2008), 8 pgs.
"U.S. Appl. No. 10/984,624, Final Office Action mailed Jan. 5, 2009", 9 pgs.
"U.S. Appl. No. 10/984,624, Non Final Office Action mailed Jul. 10, 2008", 9 pgs.
"U.S. Appl. No. 10/984,624, Notice of Allowance mailed Jun. 12, 2009", 9 pgs.
"U.S. Appl. No. 10/984,624, Response filed Apr. 1, 2009 to Final Office Action mailed Jan. 5, 2009", 16 pgs.
"U.S. Appl. No. 10/984,624, Response filed Apr. 15, 2008 to Restriction Requirement mailed Mar. 24, 2008", 1 pg.
"U.S. Appl. No. 10/984,624, Response filed Oct. 10, 2008 to Non Final Office Action mailed Jul. 10, 2008", 12 pgs.
"U.S. Appl. No. 10/984,624, Restriction Requirement mailed Mar. 24, 2008", 5 pgs.
"U.S. Appl. No. 11/294,694, Final Office Action mailed Sep. 1, 2010", 14 pgs.
"U.S. Appl. No. 11/294,694, Non Final Office Action mailed Mar. 16, 2010", 19 pgs.
"U.S. Appl. No. 11/294,694, Notice of Allowance mailed Nov. 17, 2010", 4 pgs.
"U.S. Appl. No. 11/294,694, Preliminary Amendment filed Jan. 13, 2010", 9 pgs.
"U.S. Appl. No. 11/294,694, Response filed Jun. 16, 2010 to Non Final Office Action mailed Mar. 16, 2010", 16 pgs.
"U.S. Appl. No. 11/294,694, Response filed Nov. 1, 2010 to Final Office Action mailed Sep. 1, 2010", 10 pgs.
"U.S. Appl. No. 11/294,694, Response filed Dec. 22, 2009 to Restriction Requirement mailed Nov. 25, 2009", 1 pg.
"U.S. Appl. No. 11/294,694, Restriction Requirement mailed Nov. 25, 2009", 9 pgs.
"U.S. Appl. No. 11/347,661, Examiner Interview Summary mailed Sep. 11, 2009", 2 pgs.
"U.S. Appl. No. 11/347,661, Final Office Action mailed Mar. 3, 2009", 15 pgs.
"U.S. Appl. No. 11/347,661, Non Final Office Action mailed Aug. 13, 2009", 19 pgs.
"U.S. Appl. No. 11/347,661, Non Final Office Action mailed Aug. 21, 2008", 11 pgs.
"U.S. Appl. No. 11/347,661, Notice of Allowance mailed Feb. 24, 2010", 8 pgs.
"U.S. Appl. No. 11/347,661, Notice of Allowance mailed May 5, 2010", 8 pgs.
"U.S. Appl. No. 11/347,661, Response filed May 29, 2008 to Restriction Requirement mailed Apr. 30, 2008", 1 pg.
"U.S. Appl. No. 11/347,661, Response filed Jun. 3, 2009 to Final Office Action mailed Mar. 3, 2009", 19 pgs.
"U.S. Appl. No. 11/347,661, Response filed Nov. 6, 2009 to Non Final Office Action mailed Aug. 13, 2009", 16 pgs.
"U.S. Appl. No. 11/347,661, Response filed Nov. 19, 2008 to Non Final Office Action mailed Aug. 21, 2008", 12 pgs.
"U.S. Appl. No. 11/347,661, Restriction Requirement mailed Apr. 30, 2008", 6 pgs.
"U.S. Appl. No. 11/347,662, Examiner Interview Summary mailed Jun. 24, 2010", 3 pgs.
"U.S. Appl. No. 11/347,662, Examiner Interview Summary mailed Nov. 9, 2009", 3 pgs.
"U.S. Appl. No. 11/347,662, Final Office Action mailed Sep. 16, 2009", 13 pgs.
"U.S. Appl. No. 11/347,662, Final Office Action mailed Oct. 26, 2010", 10 pgs.
"U.S. Appl. No. 11/347,662, Non Final Office Action mailed Mar. 9, 2009", 11 pgs.
"U.S. Appl. No. 11/347,662, Non Final Office Action mailed May 21, 2010", 19 pgs.
"U.S. Appl. No. 11/347,662, Non Final Office Action mailed Oct. 28, 2008", 13 pgs.
"U.S. Appl. No. 11/347,662, Response filed Jan. 16, 2009 to Non Final Office Action mailed Oct. 28, 2008", 16 pgs.
"U.S. Appl. No. 11/347,662, Response filed Feb. 12, 2010 to Final Office Action mailed Sep. 16, 2009", 21 pgs.
"U.S. Appl. No. 11/347,662, Response filed Jun. 5, 2009 to Non Final Office Action mailed Mar. 9, 2009", 13 pgs.
"U.S. Appl. No. 11/347,662, Response filed Aug. 20, 2010 to Non Final Office Action mailed May 21, 2010", 13 pgs.
"U.S. Appl. No. 11/386,071, Advisory Action mailed Dec. 23, 2010", 3 pgs.
"U.S. Appl. No. 11/386,071, Examiner Interview Summary mailed Jan. 31, 2011", 3 pgs.

(56)  References Cited

OTHER PUBLICATIONS

"U.S. Appl. No. 11/386,071, Examiner Interview Summary mailed Jul. 21, 2010", 3 pgs.
"U.S. Appl. No. 11/386,071, Final Office Action mailed Oct. 27, 2010", 10 pgs.
"U.S. Appl. No. 11/386,071, Non Final Office Action mailed May 12, 2010", 13 pgs.
"U.S. Appl. No. 11/386,071, Notice of Allowance mailed Jun. 6, 2011", 6 pgs.
"U.S. Appl. No. 11/386,071, Response filed Jan. 26, 2011 to Advisory Action mailed Dec. 23, 2010", 13 pgs.
"U.S. Appl. No. 11/386,071, Response filed Aug. 12, 2010 to Non Final Office Action mailed May 12, 2010", 14 pgs.
"U.S. Appl. No. 11/386,071, Response filed Dec. 15, 2010 to Final Office Action mailed Oct. 27, 2010", 14 pgs.
"U.S. Appl. No. 11/408,282, Final Office Action mailed Dec. 15, 2008", 8 pgs.
"U.S. Appl. No. 11/408,282, Non Final Office Action mailed May 23, 2008", 12 pgs.
"U.S. Appl. No. 11/408,282, Response filed Aug. 21, 2008 to Non Final Office Action mailed May 23, 2008", 10 pgs.
"U.S. Appl. No. 11/504,882, Examiner Interview Summary mailed Sep. 2, 2010", 3 pgs.
"U.S. Appl. No. 11/504,882, Final Office Action mailed Dec. 21, 2010", 7 pgs.
"U.S. Appl. No. 11/504,882, Non Final Office Action mailed Jun. 19, 2014", 11 pgs.
"U.S. Appl. No. 11/504,882, Non Final Office Action mailed Jun. 23, 2010", 8 pgs.
"U.S. Appl. No. 11/504,882, Non Final Office Action mailed Nov. 13, 2013", 13 pgs.
"U.S. Appl. No. 11/504,882, Notice of Allowance mailed Dec. 1, 2014", 9 pgs.
"U.S. Appl. No. 11/504,882, Response filed Feb. 10, 2014 to Non Final Office Action mailed Nov. 13, 2013", 11 pgs.
"U.S. Appl. No. 11/504,882, Response filed Mar. 18, 2011 to Final Office Action mailed Dec. 21, 2010", 11 pgs.
"U.S. Appl. No. 11/504,882, Response filed Sep. 17, 2014 to Non Final Office Action mailed Jun. 19, 2014", 14 pgs.
"U.S. Appl. No. 11/504,882, Response filed Sep. 23, 2010 to Non Final Office Action mailed Jun. 23, 2010", 12 pgs.
"U.S. Appl. No. 11/504,882, Supplemental Notice of Allowability mailed Mar. 12, 2015", 5 pgs.
"U.S. Appl. No. 11/541,505, Non Final Office Action mailed May 19, 2009", 7 pgs.
"U.S. Appl. No. 11/541,505, Notice of Allowance mailed Sep. 18, 2009", 8 pgs.
"U.S. Appl. No. 11/541,505, Response filed Apr. 9, 2009 to Restriction Requirement mailed Mar. 9, 2009", 1 pg.
"U.S. Appl. No. 11/541,505, Response filed Jun. 18, 2009 to Non Final Office Action mailed May 19, 2009", 5 pgs.
"U.S. Appl. No. 11/541,505, Restriction Requirement mailed Mar. 9, 2009", 9 pgs.
"U.S. Appl. No. 11/541,506, Notice of Allowance mailed Jun. 1, 2009", 10 pgs.
"U.S. Appl. No. 11/541,506, Notice of Allowance mailed Jun. 29, 2009", 8 pgs.
"U.S. Appl. No. 11/541,506, Response filed Apr. 9, 2009 to Restriction Requirement mailed Mar. 9, 2009", 1 pg.
"U.S. Appl. No. 11/541,506, Restriction Requirement mailed Mar. 9, 2009", 6 pgs.
"U.S. Appl. No. 11/739,768, Examiner Interview Summary mailed May 11, 2011", 3 pgs.
"U.S. Appl. No. 11/739,768, Examiner Interview Summary mailed Oct. 4, 2011", 3 pgs.
"U.S. Appl. No. 11/739,768, Final Office Action mailed Aug. 22, 2011", 14 pgs.
"U.S. Appl. No. 11/739,768, Non Final Office Action mailed Mar. 4, 2011", 11 pgs.

"U.S. Appl. No. 11/739,768, Notice of Allowance mailed Nov. 15, 2011", 5 pgs.
"U.S. Appl. No. 11/739,768, Response filed Jun. 6, 2011 to Non Final Office Action mailed Mar. 4, 2011", 15 pgs.
"U.S. Appl. No. 11/739,768, Response filed Oct. 26, 2011 to Final Office Action mailed Aug. 22, 2011", 14 pgs.
"U.S. Appl. No. 11/740,035, Final Office Action mailed Aug. 7, 2008", 9 pgs.
"U.S. Appl. No. 11/740,035, Non Final Office Action mailed Jan. 3, 2008", 9 pgs.
"U.S. Appl. No. 11/740,035, Response filed Apr. 3, 2008 to Non Final Office Action mailed Jan. 3, 2008", 6 pgs.
"U.S. Appl. No. 11/784,821, Corrected Notice of Allowance mailed Dec. 24, 2014", 4 pgs.
"U.S. Appl. No. 11/784,821, Examiner Interview Summary mailed Jun. 26, 2014", 3 pgs.
"U.S. Appl. No. 11/784,821, Examiner Interview Summary mailed Nov. 17, 2009", 3 pgs.
"U.S. Appl. No. 11/784,821, Final Office Action mailed Mar. 10, 2010", 11 pgs.
"U.S. Appl. No. 11/784,821, Non Final Office Action mailed Mar. 28, 2014", 14 pgs.
"U.S. Appl. No. 11/784,821, Non Final Office Action mailed Sep. 4, 2009", 12 pgs.
"U.S. Appl. No. 11/784,821, Notice of Allowance mailed Oct. 21, 2014", 10 pgs.
"U.S. Appl. No. 11/784,821, Response filed Jun. 10, 2010 to Final Office Action mailed Mar. 10, 2010", 20 pgs.
"U.S. Appl. No. 11/784,821, Response filed Jun. 15, 2009 to Restriction Requirement mailed May 13, 2009", 2 pgs.
"U.S. Appl. No. 11/784,821, Response filed Jun. 26, 2014 to Non Final Office Action mailed Mar. 28, 2014", 16 pgs.
"U.S. Appl. No. 11/784,821, Response filed Nov. 23, 2009 to Non Final Office Action mailed Sep. 4, 2009", 17 pgs.
"U.S. Appl. No. 11/784,821, Restriction Requirement mailed May 13, 2009", 6 pgs.
"U.S. Appl. No. 11/869,440, Examiner Interview Summary mailed Mar. 25, 2010", 3 pgs.
"U.S. Appl. No. 11/869,440, Non Final Office Action mailed Mar. 1, 2010", 13 pgs.
"U.S. Appl. No. 11/869,440, Notice of Allowance mailed Aug. 19, 2010", 10 pgs.
"U.S. Appl. No. 11/869,440, Response filed Jun. 1, 2010 to Non Final Office Action mailed Mar. 1, 2010", 14 pgs.
"U.S. Appl. No. 11/935,681, Examiner Interview Summary mailed Jul. 19, 2010", 3 pgs.
"U.S. Appl. No. 11/935,681, Non Final Office Action mailed May 24, 2010", 12 pgs.
"U.S. Appl. No. 11/935,681, Notice of Allowance mailed Nov. 8, 2010", 10 pgs.
"U.S. Appl. No. 11/935,681, Response filed Apr. 19, 2010 to Restriction Requirement mailed Mar. 17, 2010", 4 pgs.
"U.S. Appl. No. 11/935,681, Response filed Aug. 24, 2010 to Non Final Office Action mailed May 24, 2010", 13 pgs.
"U.S. Appl. No. 11/935,681, Restriction Requirement mailed Mar. 17, 2010", 6 pgs.
"U.S. Appl. No. 12/014,340, Examiner Interview Summary mailed Jun. 22, 2010", 3 pgs.
"U.S. Appl. No. 12/014,340, Non Final Office Action mailed May 25, 2010", 12 pgs.
"U.S. Appl. No. 12/014,340, Notice of Allowance mailed Nov. 8, 2010", 9 pgs.
"U.S. Appl. No. 12/014,340, Preliminary Amendment filed May 21, 2010", 11 pgs.
"U.S. Appl. No. 12/014,340, Response filed Apr. 26, 2010 to Restriction Requirement mailed Mar. 25, 2010", 2 pgs.
"U.S. Appl. No. 12/014,340, Response filed Aug. 25, 2010 to Non Final Office Action mailed May 25, 2010", 16 pgs.
"U.S. Appl. No. 12/014,340, Restriction Requirement mailed Mar. 25, 2010", 9 pgs.
"U.S. Appl. No. 12/014,399, Examiner Interview Summary mailed Jun. 23, 2010", 3 pgs.

(56)                    References Cited

OTHER PUBLICATIONS

"U.S. Appl. No. 12/014,399, Non Final Office Action mailed May 26, 2010", 13 pgs.
"U.S. Appl. No. 12/014,399, Notice of Allowance mailed Nov. 12, 2010", 11 pgs.
"U.S. Appl. No. 12/014,399, Preliminary Amendment filed May 25, 2010", 10 pgs.
"U.S. Appl. No. 12/014,399, Response filed May 5, 2010 to Restriction Requirement mailed Apr. 6, 2010", 2 pgs.
"U.S. Appl. No. 12/014,399, Response filed Aug. 25, 2010 to Non Final Office Action mailed May 26, 2010", 14 pgs.
"U.S. Appl. No. 12/014,399, Restriction Requirement mailed Apr. 6, 2010", 9 pgs.
"U.S. Appl. No. 12/029,861, Examiner Interview Summary mailed Jan. 27, 2012", 3 pgs.
"U.S. Appl. No. 12/029,861, Final Office Action mailed Dec. 8, 2011", 11 pgs.
"U.S. Appl. No. 12/029,861, Non Final Office Action mailed Jul. 26, 2011", 11 pgs.
"U.S. Appl. No. 12/029,861, Notice of Allowance mailed Apr. 26, 2012", 5 pgs.
"U.S. Appl. No. 12/029,861, Response filed Jan. 26, 2012 to Final Office Action mailed Dec. 8, 2011", 15 pgs.
"U.S. Appl. No. 12/029,861, Response filed May 6, 2011 to Restriction Requirement mailed Apr. 7, 2011", 10 pgs.
"U.S. Appl. No. 12/029,861, Response filed Jun. 23, 2011 to Restriction Requirement mailed May 24, 2011", 1 pgs.
"U.S. Appl. No. 12/029,861, Response filed Oct. 14, 2011 to Non Final Office Action mailed Jul. 26, 2011", 11 pgs.
"U.S. Appl. No. 12/029,861, Restriction Requirement mailed Apr. 7, 2011", 8 pgs.
"U.S. Appl. No. 12/029,861, Restriction Requirement mailed May 24, 2011", 6 pgs.
"U.S. Appl. No. 12/107,437, Examiner Interview Summary mailed May 10, 2010", 4 pgs.
"U.S. Appl. No. 12/107,437, Non Final Office Action mailed Mar. 17, 2010", 9 pgs.
"U.S. Appl. No. 12/107,437, Preliminary Amendment filed Feb. 23, 2010", 9 pgs.
"U.S. Appl. No. 12/107,437, Response filed Jan. 29, 2010 to Restriction Requirement mailed Jan. 13, 2010", 1 pgs.
"U.S. Appl. No. 12/107,437, Restriction Requirement mailed Jan. 13, 2010", 7 pgs.
"U.S. Appl. No. 12/196,398, Examiner Interview Summary mailed Nov. 8, 10", 3 pgs.
"U.S. Appl. No. 12/196,398, Notice of Allowance mailed Feb. 3, 2011", 12 pgs.
"U.S. Appl. No. 12/196,398, Preliminary Amendment filed Nov. 10, 2008", 3 pgs.
"U.S. Appl. No. 12/196,398, Preliminary Amendment filed Dec. 1, 2010", 12 pgs.
"U.S. Appl. No. 12/196,398, Preliminary Amendment filed Dec. 9, 2008", 46 pgs.
"U.S. Appl. No. 12/196,398, Response filed Oct. 29, 2010 to Restriction Requirement mailed Sep. 29, 2010", 2 pgs.
"U.S. Appl. No. 12/196,398, Restriction Requirement mailed Sep. 29, 2010", 6 pgs.
"U.S. Appl. No. 12/196,398, Supplemental Notice of Allowability mailed Mar. 9, 2011", 4 pgs.
"U.S. Appl. No. 12/196,398, Supplemental Notice of Allowability mailed Apr. 15, 2011", 4 pgs.
"U.S. Appl. No. 12/196,405, Examiner Interview Summary mailed Jun. 20, 2011", 3 pgs.
"U.S. Appl. No. 12/196,405, Non Final Office Action mailed Apr. 11, 2011", 13 pgs.
"U.S. Appl. No. 12/196,405, Notice of Allowance mailed Oct. 26, 2011", 11 pgs.
"U.S. Appl. No. 12/196,405, Preliminary Amendment filed Nov. 10, 2008", 3 pgs.

"U.S. Appl. No. 12/196,405, Response filed Mar. 16, 2011 to Restriction Requirement mailed Feb. 14, 2011", 1 pgs.
"U.S. Appl. No. 12/196,405, Response filed Jul. 12, 2011 to Non Final Office Action mailed Apr. 11, 2011", 19 pgs.
"U.S. Appl. No. 12/196,405, Restriction Requirement mailed Feb. 14, 2011", 6 pgs.
"U.S. Appl. No. 12/196,405, Supplemental Amendment filed Oct. 3, 2011", 12 pgs.
"U.S. Appl. No. 12/196,407, Examiner Interview Summary mailed Jul. 14, 2011", 3 pgs.
"U.S. Appl. No. 12/196,407, Non Final Office Action mailed May 4, 2011", 11 pgs.
"U.S. Appl. No. 12/196,407, Notice of Allowance mailed Oct. 26, 2011", 10 pgs.
"U.S. Appl. No. 12/196,407, Preliminary Amendment filed Nov. 10, 2008", 3 pgs.
"U.S. Appl. No. 12/196,407, Response filed Apr. 20, 2011 to Restriction Requirement mailed Mar. 22, 2011", 12 pgs.
"U.S. Appl. No. 12/196,407, Response filed Aug. 2, 2011 to Non Final Office Action mailed May 4, 2011", 27 pgs.
"U.S. Appl. No. 12/196,407, Restriction Requirement mailed Mar. 22, 2011", 6 pgs.
"U.S. Appl. No. 12/196,407, Supplemental Response to Non Final Office Action filed Oct. 3, 2011", 18 pgs.
"U.S. Appl. No. 12/196,410, Examiner Interview Summary mailed Jul. 14, 2011", 3 pgs.
"U.S. Appl. No. 12/196,410, Non Final Office Action mailed May 9, 2011", 9 pgs.
"U.S. Appl. No. 12/196,410, Notice of Allowance mailed Oct. 13, 2011", 8 pgs.
"U.S. Appl. No. 12/196,410, Response filed Apr. 20, 2011 to Restriction Requirement mailed Mar. 22, 2011", 13 pgs.
"U.S. Appl. No. 12/196,410, Response filed Aug. 1, 2011 to Non Final Office Action mailed May 9, 2011", 23 pgs.
"U.S. Appl. No. 12/196,410, Restriction Requirement mailed Mar. 22, 2011", 6 pgs.
"U.S. Appl. No. 12/196,410, Supplemental Amendment filed Oct. 3, 2011", 15 pgs.
"U.S. Appl. No. 12/398,548, Examiner Interview Summary mailed Jul. 12, 2011", 3 pgs.
"U.S. Appl. No. 12/398,548, Non Final Office Action mailed Apr. 12, 2011", 7 pgs.
"U.S. Appl. No. 12/398,548, Notice of Allowance mailed Oct. 18, 2011", 7 pgs.
"U.S. Appl. No. 12/398,548, Response filed Jul. 12, 2011 to Non Final Office Action mailed Apr. 12, 2011", 15 pgs.
"U.S. Appl. No. 12/398,548, Supplemental Preliminary Amendment filed Sep. 7, 2010", 11 pgs.
"U.S. Appl. No. 12/419,491, Examiner Interview Summary mailed May 30, 2012", 3 pgs.
"U.S. Appl. No. 12/419,491, Examiner Interview Summary mailed Nov. 29, 2011", 3 pgs.
"U.S. Appl. No. 12/419,491, Final Office Action mailed Apr. 12, 2012", 12 pgs.
"U.S. Appl. No. 12/419,491, Non Final Office Action mailed Sep. 22, 2011", 12 pgs.
"U.S. Appl. No. 12/419,491, Notice of Allowance mailed Jul. 13, 2012", 10 pgs.
"U.S. Appl. No. 12/419,491, Response filed May 30, 2012 to Final Office Action mailed Apr. 12, 2012", 12 pgs.
"U.S. Appl. No. 12/419,491, Response filed Dec. 9, 2011 to Non Final Office Action mailed Sep. 22, 2011", 17 pgs.
"U.S. Appl. No. 12/474,802, Notice of Allowance mailed Aug. 31, 2011", 13 pgs.
"U.S. Appl. No. 12/474,802, Notice of Allowance mailed Oct. 26, 2011", 4 pgs.
"U.S. Appl. No. 12/474,802, Response filed Mar. 28, 2011 to Restriction Requirement mailed Feb. 24, 2011", 12 pgs.
"U.S. Appl. No. 12/474,802, Restriction Requirement mailed Feb. 24, 2011", 6 pgs.
"U.S. Appl. No. 12/489,168, Examiner Interview Summary mailed Feb. 21, 2012", 3 pgs.

(56)　　　　　References Cited

OTHER PUBLICATIONS

"U.S. Appl. No. 12/489,168, Non Final Office Action mailed Dec. 7, 2011", 10 pgs.

"U.S. Appl. No. 12/489,168, Notice of Allowance mailed Apr. 26, 2012", 8 pgs.

"U.S. Appl. No. 12/489,168, Notice of Allowance mailed Sep. 5, 2012", 8 pgs.

"U.S. Appl. No. 12/489,168, Preliminary Amendment filed Oct. 22, 2009", 3 pgs.

"U.S. Appl. No. 12/489,168, Response filed Feb. 27, 2012 to Non Final Office Action mailed Dec. 7, 2011", 15 pgs.

"U.S. Appl. No. 12/489,168, Response filed Nov. 11, 2011 to Restriction Requirement mailed Oct. 20, 2011", 1 pg.

"U.S. Appl. No. 12/489,168, Restriction Requirement mailed Oct. 20, 2011", 8 pgs.

"U.S. Appl. No. 12/489,181, Examiner Interview Summary mailed Feb. 13, 2012", 3 pgs.

"U.S. Appl. No. 12/489,181, Non Final Office Action mailed Jan. 3, 2012", 9 pgs.

"U.S. Appl. No. 12/489,181, Notice of Allowance mailed May 23, 2012", 9 pgs.

"U.S. Appl. No. 12/489,181, Preliminary Amendment filed Mar. 31, 2011", 10 pgs.

"U.S. Appl. No. 12/489,181, Preliminary Amendment filed Oct. 22, 2009", 3 pgs.

"U.S. Appl. No. 12/489,181, Response filed Mar. 27, 2012 to Non Final Office Action mailed Jan. 3, 2012", 12 pgs.

"U.S. Appl. No. 12/489,181, Response filed Dec. 5, 2011 to Restriction Requirement mailed Nov. 4, 2011", 1 pg.

"U.S. Appl. No. 12/489,181, Restriction Requirement mailed Nov. 4, 2011", 7 pgs.

"U.S. Appl. No. 12/570,854, Examiner Interview Summary mailed Apr. 16, 2012", 3 pgs.

"U.S. Appl. No. 12/570,854, Non Final Office Action mailed Feb. 10, 2012", 8 pgs.

"U.S. Appl. No. 12/570,854, Notice of Allowance mailed Jun. 29, 2012", 10 pgs.

"U.S. Appl. No. 12/570,854, Notice of Allowance mailed Sep. 19, 2012", 6 pgs.

"U.S. Appl. No. 12/570,854, Response filed May 10, 2012 to Non Final Office Action mailed Feb. 10, 2012", 27 pgs.

"U.S. Appl. No. 12/570,854, Response filed Dec. 20, 2011 to Restriction Requirement mailed Dec. 14, 2011", 1 pg.

"U.S. Appl. No. 12/570,854, Restriction Requirement mailed Dec. 14, 2011", 6 pgs.

"U.S. Appl. No. 12/702,067, Non Final Office Action mailed Mar. 5, 2013", 8 pgs.

"U.S. Appl. No. 12/702,067, Notice of Allowance mailed Oct. 7, 2013", 11 pgs.

"U.S. Appl. No. 12/702,067, Preliminary Amendment filed Jan. 11, 2011", 13 pgs.

"U.S. Appl. No. 12/702,067, Response filed Jun. 5, 2013 to Non Final Office Action mailed Mar. 5, 2013", 17 pgs.

"U.S. Appl. No. 12/702,067, Response filed Oct. 2, 2012 to Restriction Requirement mailed Sep. 4, 2012", 1 pg.

"U.S. Appl. No. 12/702,067, Restriction Requirement mailed Sep. 4, 2012", 9 pgs.

"U.S. Appl. No. 12/719,337, Advisory Action mailed Sep. 30, 2014", 4 pgs.

"U.S. Appl. No. 12/719,337, Examiner Interview Summary mailed Apr. 4, 2014", 4 pgs.

"U.S. Appl. No. 12/719,337, Examiner Interview Summary mailed May 14, 2013", 3 pgs.

"U.S. Appl. No. 12/719,337, Examiner Interview Summary mailed Sep. 18, 2014", 3 pgs.

"U.S. Appl. No. 12/719,337, Final Office Action mailed Mar. 12, 2013", 8 pgs.

"U.S. Appl. No. 12/719,337, Final Office Action mailed Jul. 18, 2014", 15 pgs.

"U.S. Appl. No. 12/719,337, Non Final Office Action mailed Jan. 10, 2014", 14 pgs.

"U.S. Appl. No. 12/719,337, Non Final Office Action mailed Sep. 5, 2012", 7 pgs.

"U.S. Appl. No. 12/719,337, Notice of Allowance mailed Mar. 11, 2015", 10 pgs.

"U.S. Appl. No. 12/719,337, Notice of Non-Compliant Amendment mailed May 2, 2014", 3 pgs.

"U.S. Appl. No. 12/719,337, Response filed Apr. 10, 2014 to Non Final Office Action mailed Jan. 10, 2014", 16 pgs.

"U.S. Appl. No. 12/719,337, Response filed May 25, 2012 to Restriction Requirement mailed Apr. 26, 2012", 9 pgs.

"U.S. Appl. No. 12/719,337, Response filed Jun. 5, 2013 to Final Office Action mailed Mar. 12, 2013", 16 pgs.

"U.S. Appl. No. 12/719,337, Response filed Jun. 25, 2014 to Notice of Non-Compliant Amendment mailed May 2, 2014", 10 pgs.

"U.S. Appl. No. 12/719,337, Response filed Sep. 18, 2014 to Final Office Action mailed Jul. 18, 2014", 13 pgs.

"U.S. Appl. No. 12/719,337, Response filed Nov. 28, 2012 to Non Final Office Action mailed Sep. 5, 2012", 14 pgs.

"U.S. Appl. No. 12/719,337, Restriction Requirement mailed Apr. 26, 2012", 8 pgs.

"U.S. Appl. No. 12/788,966, Examiner Interview Summary mailed Jun. 1, 2012", 3 pgs.

"U.S. Appl. No. 12/788,966, Final Office Action mailed May 4, 2012", 16 pgs.

"U.S. Appl. No. 12/788,966, Non Final Office Action mailed Jan. 4, 2012", 12 pgs.

"U.S. Appl. No. 12/788,966, Notice of Allowance mailed Aug. 16, 2012", 10 pgs.

"U.S. Appl. No. 12/788,966, Notice of Allowance mailed Nov. 23, 2012", 2 pgs.

"U.S. Appl. No. 12/788,966, Response filed Apr. 4, 2012 to Non Final Office Action mailed Jan. 4, 2012", 15 pgs.

"U.S. Appl. No. 12/788,966, Response filed Aug. 6, 2012 to Final Office Action mailed May 4, 2012", 12 pgs.

"U.S. Appl. No. 12/788,966, Response filed Dec. 16, 2011 to Restriction Requirement mailed Dec. 7, 2011", 11 pgs.

"U.S. Appl. No. 12/788,966, Restriction Requirement mailed Dec. 7, 2011", 9 pgs.

"U.S. Appl. No. 12/788,973, Advisory Action mailed Jan. 23, 2013", 3 pgs.

"U.S. Appl. No. 12/788,973, Advisory Action mailed Dec. 27, 2012", 8 pgs.

"U.S. Appl. No. 12/788,973, Final Office Action mailed Sep. 18, 2012", 16 pgs.

"U.S. Appl. No. 12/788,973, Non Final Office Action mailed May 8, 2012", 12 pgs.

"U.S. Appl. No. 12/788,973, Notice of Allowance mailed Mar. 21, 2013", 6 pgs.

"U.S. Appl. No. 12/788,973, Response filed Jan. 16, 2013 to Advisory Action mailed Dec, 27, 2012", 9 pgs.

"U.S. Appl. No. 12/788,973, Response filed Jul. 19, 2012 to Non Final Office Action mailed May 8, 2012", 21 pgs.

"U.S. Appl. No. 12/788,973, Response filed Dec. 16, 2011 to Restriction Requirement mailed Dec. 6, 2011", 11 pgs.

"U.S. Appl. No. 12/788,973, Response filed Dec. 17, 2012 to Final Office Action mailed Sep. 18, 2012", 15 pgs.

"U.S. Appl. No. 12/788,973, Restriction Requirement mailed Dec. 6, 2011", 9 pgs.

"U.S. Appl. No. 12/788,973, Supplemental Notice of Allowance mailed May 24, 2013", 2 pgs.

"U.S. Appl. No. 12/788,978, Advisory Action mailed Dec. 24, 2013", 4 pgs.

"U.S. Appl. No. 12/788,978, Applicant's Summary of Examiner Interview filed Dec. 12, 2013", 2 pgs.

"U.S. Appl. No. 12/788,978, Corrected Notice of Allowance mailed Apr. 30, 2014", 2 pgs.

"U.S. Appl. No. 12/788,978, Examiner Interview Summary mailed Jan. 28, 2014", 3 pgs.

"U.S. Appl. No. 12/788,978, Examiner Interview Summary mailed Mar. 22, 2013", 3 pgs.

(56)　　　　References Cited

OTHER PUBLICATIONS

"U.S. Appl. No. 12/788,978, Examiner Interview Summary mailed Sep. 11, 2012", 3 pgs.
"U.S. Appl. No. 12/788,978, Examiner Interview Summary mailed Oct. 29, 2013", 4 pgs.
"U.S. Appl. No. 12/788,978, Examiner Interview Summary mailed Dec. 16, 2013", 3 pgs.
"U.S. Appl. No. 12/788,978, Examiner Interview Summary mailed Dec. 27, 2012", 3 pgs.
"U.S. Appl. No. 12/788,978, Final Office Action mailed Aug. 20, 2013", 17 pgs.
"U.S. Appl. No. 12/788,978, Final Office Action mailed Nov. 2, 2012", 14 pgs.
"U.S. Appl. No. 12/788,978, Non Final Office Action mailed Jan. 11, 2013", 16 pgs.
"U.S. Appl. No. 12/788,978, Non Final Office Action mailed Jul. 13, 2012", 17 pgs.
"U.S. Appl. No. 12/788,978, Notice of Allowance mailed Jan. 24, 2014", 9 pgs.
"U.S. Appl. No. 12/788,978, Notice of Non-Compliant Amendment mailed Jun. 6, 2013", 3 pgs.
"U.S. Appl. No. 12/788,978, Response filed Jan. 2, 2013 to Final Office Action mailed Nov. 2, 2012", 13 pgs.
"U.S. Appl. No. 12/788,978, Response filed Jan. 20, 2014 to Advisory Action mailed Dec. 24, 2013", 4 pgs.
"U.S. Appl. No. 12/788,978, Response filed Apr. 8, 2013 to Non Final Office Action mailed Jan. 11, 2013", 16 pgs.
"U.S. Appl. No. 12/788,978, Response filed May 21, 2012 to Restriction Requirement mailed Apr. 20, 2012", 12 pgs.
"U.S. Appl. No. 12/788,978, Response filed Jul. 3, 2013 to Notice of Non-Compliant Amendment mailed Jun. 6, 2013", 17 pgs.
"U.S. Appl. No. 12/788,978, Response filed Oct. 5, 2012 to Non Final Office Action mailed Jul. 13, 2012", 20 pgs.
"U.S. Appl. No. 12/788,978, Response filed Nov. 20, 2013 to Final Office Action mailed Aug. 20, 2013", 15 pgs.
"U.S. Appl. No. 12/788,978, Restriction Requirement mailed Apr. 20, 2012", 8 pgs.
"U.S. Appl. No. 12/828,977, Examiner Interview Summary mailed Jul. 9, 2012", 3 pgs.
"U.S. Appl. No. 12/828,977, Non Final Office Action mailed May 3, 2012", 9 pgs.
"U.S. Appl. No. 12/828,977, Notice of Allowance mailed Sep. 5, 2012", 9 pgs.
"U.S. Appl. No. 12/828,977, Preliminary Amendment filed Jul. 19, 2011", 10 pgs.
"U.S. Appl. No. 12/828,977, Response filed Mar. 14, 2012 to Restriction Requirement mailed Feb. 13, 2012", 9 pgs.
"U.S. Appl. No. 12/828,977, Response filed Jul. 25, 2012 to Non Final Office Action mailed May 3, 2012", 11 pgs.
"U.S. Appl. No. 12/828,977, Restriction Requirement mailed Feb. 13, 2012", 7 pgs.
"U.S. Appl. No. 12/915,962, Examiner Interview Summary mailed Jul. 25, 2012", 3 pgs.
"U.S. Appl. No. 12/915,962, Non Final Office Action mailed May 7, 2012", 11 pgs.
"U.S. Appl. No. 12/915,962, Non Final Office Action mailed Oct. 15, 2012", 9 pgs.
"U.S. Appl. No. 12/915,962, Notice of Allowance mailed Jun. 10, 2013", 12 pgs.
"U.S. Appl. No. 12/915,962, Response filed Jan. 10, 2013 to Non Final Office Action mailed Oct. 15, 2012", 21 pgs.
"U.S. Appl. No. 12/915,962, Response filed Mar. 16, 2012 to Restriction Requirement mailed Feb. 15, 2012", 15 pgs.
"U.S. Appl. No. 12/915,962, Response filed Aug. 7, 2012 to Non Final Office Action mailed May 7, 2012", 26 pgs.
"U.S. Appl. No. 12/915,962, Restriction Requirement mailed Feb. 15, 2012", 8 pgs.
"U.S. Appl. No. 12/938,902, Examiner Interview Summary mailed Dec. 3, 2012", 3 pgs.
"U.S. Appl. No. 12/938,902, Non Final Office Action mailed Sep. 17, 2012", 11 pgs.
"U.S. Appl. No. 12/938,902, Notice of Allowance mailed Jun. 21, 2013", 13 pgs.
"U.S. Appl. No. 12/938,902, Notice of Allowance mailed Oct. 1, 2013", 9 pgs.
"U.S. Appl. No. 12/938,902, Response filed Aug. 6, 2012 to Restriction Requirement mailed Jul. 6, 2012", 14 pgs.
"U.S. Appl. No. 12/938,902, Response filed Dec. 10, 2012 to Non Final Office Action mailed Sep. 17, 2012", 20 pgs.
"U.S. Appl. No. 12/938,902, Restriction Requirement mailed Jul. 6, 2012", 8 pgs.
"U.S. Appl. No. 12/976,328, Examiner Interview Summary mailed Feb. 13, 2012", 3 pgs.
"U.S. Appl. No. 12/976,328, Non Final Office Action mailed Dec. 15, 2011", 13 pgs.
"U.S. Appl. No. 12/976,328, Notice of Allowance mailed Apr. 30, 2012", 9 pgs.
"U.S. Appl. No. 12/976,328, Response filed Mar. 2, 2012 to Non Final Office Action mailed Dec. 15, 2011", 15 pgs.
"U.S. Appl. No. 13/045,689, Examiner Interview Summary mailed May 14, 2012", 3 pgs.
"U.S. Appl. No. 13/045,689, Non Final Office Action mailed Mar. 20, 2012", 11 pgs.
"U.S. Appl. No. 13/045,689, Notice of Allowance mailed Aug. 10, 2012", 10 pgs.
"U.S. Appl. No. 13/045,689, Notice of Allowance mailed Sep. 24, 2012", 7 pgs.
"U.S. Appl. No. 13/045,689, Response filed Jan. 30, 2012 to Restriction Requirement mailed Dec. 29, 2011", 13 pgs.
"U.S. Appl. No. 13/045,689, Response filed Jun. 8, 2012 to Non Final Office Action mailed Mar. 20, 2012", 15 pgs.
"U.S. Appl. No. 13/045,689, Restriction Requirement mailed Dec. 29, 2011", 6 pgs.
"U.S. Appl. No. 13/045,691, Examiner Interview Summary mailed May 14, 2012", 3 pgs.
"U.S. Appl. No. 13/045,691, Non Final Office Action mailed Mar. 20, 2012", 12 pgs.
"U.S. Appl. No. 13/045,691, Notice of Allowance mailed Jun. 19, 2012", 10 pgs.
"U.S. Appl. No. 13/045,691, Response filed Feb. 9, 2012 to Restriction Requirement mailed Jan. 9, 2012", 1 pg.
"U.S. Appl. No. 13/045,691, Response filed Jun. 8, 2012 to Non Final Office Action mailed Mar. 20, 2012", 17 pgs.
"U.S. Appl. No. 13/045,691, Restriction Requirement mailed Jan. 9, 2012", 6 pgs.
"U.S. Appl. No. 13/071,563, Final Office Action mailed May 23, 2014", 13 pgs.
"U.S. Appl. No. 13/071,563, Non Final Office Action mailed Oct. 23, 2013", 18 pgs.
"U.S. Appl. No. 13/071,563, Notice of Allowance mailed Aug. 15, 2014", 7 pgs.
"U.S. Appl. No. 13/071,563, Preliminary Amendment filed May 1, 2012", 8 pgs.
"U.S. Appl. No. 13/071,563, Preliminary Amendment filed Dec. 6, 2011", 7 pgs.
"U.S. Appl. No. 13/071,563, Response filed Jan. 21, 2014 to Non Final Office Action mailed Oct. 23, 2013", 13 pgs.
"U.S. Appl. No. 13/071,563, Response filed Jul. 23, 2014 to Final Office Action mailed May 23, 2014", 14 pgs.
"U.S. Appl. No. 13/071,563, Response filed Sep. 19, 2013 to Restriction Requirement mailed Aug. 19, 2013", 11 pgs.
"U.S. Appl. No. 13/071,563, Restriction Requirement mailed Aug. 19, 2013", 7 pgs.
"U.S. Appl. No. 13/098,897, Examiner Interview Summary mailed Nov. 27, 2012", 3 pgs.
"U.S. Appl. No. 13/098,897, Non Final Office Action mailed Sep. 21, 2012", 9 pgs.
"U.S. Appl. No. 13/098,897, Notice of Allowance mailed Jun. 11, 2013", 13 pgs.
"U.S. Appl. No. 13/098,897, Response filed Aug. 30, 2012 to Restriction Requirement mailed Jul. 30, 2012", 16 pgs.

(56)　　　　　References Cited

OTHER PUBLICATIONS

"U.S. Appl. No. 13/098,897, Response filed Dec. 18, 2012 to Non Final Office Action mailed Sep. 21, 2012", 21 pgs.
"U.S. Appl. No. 13/098,897, Restriction Requirement mailed Jul. 30, 2012", 8 pgs.
"U.S. Appl. No. 13/098,927, Advisory Action mailed Aug. 8, 2013", 3 pgs.
"U.S. Appl. No. 13/098,927, Applicant's Summary of Examiner Interview filed Sep. 23, 2013", 12 pgs.
"U.S. Appl. No. 13/098,927, Examiner Interview Summary mailed Jun. 28, 2013", 3 pgs.
"U.S. Appl. No. 13/098,927, Examiner Interview Summary mailed Sep. 20, 2013", 3 pgs.
"U.S. Appl. No. 13/098,927, Final Office Action mailed May 22, 2013", 10 pgs.
"U.S. Appl. No. 13/098,927, Non Final Office Action mailed Sep. 24, 2012", 12 pgs.
"U.S. Appl. No. 13/098,927, Notice of Allowance mailed Jan. 8, 2014", 5 pgs.
"U.S. Appl. No. 13/098,927, Notice of Allowance mailed Sep. 26, 2013", 14 pgs.
"U.S. Appl. No. 13/098,927, Response filed Jul. 22, 2015 to Final Office Action mailed May 22, 2013", 17 pgs.
"U.S. Appl. No. 13/098,927, Response filed Aug. 27, 2012 to Restriction Requirement mailed Jul. 25, 2012", 14 pgs.
"U.S. Appl. No. 13/098,927, Response filed Dec. 21, 2012 to Non Final Office Action mailed Sep. 24, 2012", 21 pgs.
"U.S. Appl. No. 13/098,927, Restriction Requirement mailed Jul. 25, 2012", 8 pgs.
"U.S. Appl. No. 13/102,182, Notice of Allowance mailed Mar. 22, 2012", 10 pgs.
"U.S. Appl. No. 13/109,667, Advisory Action mailed Feb. 4, 2014", 4 pgs.
"U.S. Appl. No. 13/109,667, Examiner Interview Summary mailed Dec. 20, 2013", 3 pgs.
"U.S. Appl. No. 13/109,667, Final Office Action mailed Oct. 11, 2013", 19 pgs.
"U.S. Appl. No. 13/109,667, Non Final Office Action mailed May 21, 2013", 21 pgs.
"U.S. Appl. No. 13/109,667, Notice of Allowance mailed Feb. 18, 2014", 10 pgs.
"U.S. Appl. No. 13/109,667, Response filed Jan. 13, 2014 to Final Office Action mailed Oct. 11, 2013", 20 pgs.
"U.S. Appl. No. 13/109,667, Response filed May 2, 2013 to Restriction Requirement mailed Apr. 2, 2013", 1 pg.
"U.S. Appl. No. 13/109,667, Response filed Aug. 21, 2013 to Non Final Office Action mailed May 21, 2013", 27 pgs.
"U.S. Appl. No. 13/109,667, Restriction Requirement mailed Apr. 2, 2013", 8 pgs.
"U.S. Appl. No. 13/109,667, Supplemental Notice of Allowability mailed Jun. 12, 2014", 3 pgs.
"U.S. Appl. No. 13/109,667, Supplemental Notice of Allowance mailed May 28, 2014", 2 pgs.
"U.S. Appl. No. 13/109,667, Supplemental Preliminary Amendment filed Feb. 4, 2014", 16 pgs.
"U.S. Appl. No. 13/109,672, 312 Amendment filed Jan. 15, 2015", 3 pgs.
"U.S. Appl. No. 13/109,672, Non Final Office Action mailed May 15, 2014", 10 pgs.
"U.S. Appl. No. 13/109,672, Notice of Allowance mailed Feb. 3, 2015", 2 pgs.
"U.S. Appl. No. 13/109,672, Notice of Allowance mailed Sep. 29, 2014", 9 pgs.
"U.S. Appl. No. 13/109,672, PTO Response to Rule 312 Communication mailed Jan. 27, 2015", 2 pgs.
"U.S. Appl. No. 13/109,672, Response filed Apr. 14, 2014 to Restriction Requirement mailed Feb. 14, 2014", 15 pgs.
"U.S. Appl. No. 13/109,672, Response filed Aug. 15, 2014 to Non Final Office Action mailed May 15, 2014", 20 pgs.

"U.S. Appl. No. 13/109,672, Response filed Nov. 4, 2013 to Restriction Requirement mailed Oct. 2, 2013", 10 pgs.
"U.S. Appl. No. 13/109,672, Restriction Requirement mailed Feb. 14, 2014", 7 pgs.
"U.S. Appl. No. 13/109,672, Restriction Requirement mailed Oct. 2, 2013", 7 pgs.
"U.S. Appl. No. 13/111,564, Corrected Notice of Allowance mailed Oct. 9, 2013", 2 pgs.
"U.S. Appl. No. 13/111,564, Examiner Interview Summary mailed Jun. 18, 2013", 3 pgs.
"U.S. Appl. No. 13/111,564, Non Final Office Action mailed Mar. 18, 2013", 8 pgs.
"U.S. Appl. No. 13/111,564, Notice of Allowance mailed Jun. 28, 2013", 12 pgs.
"U.S. Appl. No. 13/111,564, Response filed Feb. 4, 2013 to Restriction Requirement mailed Jan. 3, 2013", 20 pgs.
"U.S. Appl. No. 13/111,564, Response filed Jun. 18, 2013 to Non Final Office Action mailed Mar. 18, 2013", 25 pgs.
"U.S. Appl. No. 13/111,564, Restriction Requirement mailed Jan. 3, 2013", 5 pgs.
"U.S. Appl. No. 13/177,153, Final Office Action mailed May 28, 2013", 11 pgs.
"U.S. Appl. No. 13/177,153, Non Final Office Action mailed Oct. 2, 2012", 11 pgs.
"U.S. Appl. No. 13/177,153, Notice of Allowance mailed Jan. 7, 2014", 4 pgs.
"U.S. Appl. No. 13/177,153, Notice of Allowance mailed Sep. 17, 2013", 13 pgs.
"U.S. Appl. No. 13/177,153, Response filed Aug. 28, 2013 to Final Office Action mailed May 28, 2013", 19 pgs.
"U.S. Appl. No. 13/177,153, Response filed Sep. 4, 2012 to Restriction Requirement mailed Aug. 2, 2012", 15 pgs.
"U.S. Appl. No. 13/177,153, Response filed Dec. 20, 2012 to Non Final Office Action mailed Oct. 2, 2012", 16 pgs.
"U.S. Appl. No. 13/177,153, Restriction Requirement mailed Aug. 2, 2012", 9 pgs.
"U.S. Appl. No. 13/181,729, Examiner Interview Summary mailed May 9, 2013", 3 pgs.
"U.S. Appl. No. 13/181,729, Final Office Action mailed Mar. 13, 2013", 14 pgs.
"U.S. Appl. No. 13/181,729, Non Final Office Action mailed Oct. 2, 2012", 7 pgs.
"U.S. Appl. No. 13/181,729, Notice of Allowance mailed May 23, 2013", 9 pgs.
"U.S. Appl. No. 13/181,729, Response filed May 13, 2013 to Final Office Action mailed Mar. 13, 2013", 13 pgs.
"U.S. Appl. No. 13/181,729, Response filed Dec. 20, 2012 to Non Final Office Action mailed Oct. 2, 2012", 15 pgs.
"U.S. Appl. No. 13/269,097, Final Office Action mailed Aug. 8, 13", 7 pgs.
"U.S. Appl. No. 13/269,097, Non Final Office Action mailed Feb. 12, 13", 10 pgs.
"U.S. Appl. No. 13/269,097, Notice of Allowance mailed Feb. 3, 14", 5 pgs.
"U.S. Appl. No. 13/269,097, Notice of Allowance mailed Oct. 21, 13", 9 pgs.
"U.S. Appl. No. 13/269,097, Response filed May 13, 13 to Non Final Office Action mailed Feb. 12, 13", 17 pgs.
"U.S. Appl. No. 13/269,097, Response filed Oct. 8, 13 to Final Office Action mailed Aug. 8, 13", 12 pgs.
"U.S. Appl. No. 13/269,097, Response filed Nov. 13, 12 to Restriction Requirement mailed Oct. 17, 12", 1 pg.
"U.S. Appl. No. 13/269,097, Restriction Requirement mailed Oct. 17, 12", 8 pgs.
"U.S. Appl. No. 13/278,341, Notice of Allowance mailed Jun. 18, 13", 10 pgs.
"U.S. Appl. No. 13/278,341, Response filed Mar. 8, 13 to Restriction Requirement mailed Feb. 11, 13", 1 pg.
"U.S. Appl. No. 13/278,341, Restriction Requirement mailed Feb. 11, 2013", 6 pgs.
"U.S. Appl. No. 13/281,009, Corrected Notice of Allowance mailed Nov. 18, 2016", 4 pgs.

(56)                    References Cited

OTHER PUBLICATIONS

"U.S. Appl. No. 13/281,009, Corrected Notice of Allowance mailed Dec. 12, 2016", 2 pgs.

"U.S. Appl. No. 13/281,009, Examiner Interview Summary mailed Nov. 18, 2016", 2 pgs.

"U.S. Appl. No. 13/281,009, Non Final Office Action mailed Jun. 2, 2015", 9 pgs.

"U.S. Appl. No. 13/281,009, Notice of Allowance mailed Feb. 24, 2016", 9 pgs.

"U.S. Appl. No. 13/281,009, Notice of Allowance mailed Jun. 23, 2016", 9 pgs.

"U.S. Appl. No. 13/281,009, Notice of Allowance mailed Oct. 29, 2015", 8 pgs.

"U.S. Appl. No. 13/281,009, Response filed Sep. 2, 2015 to Non Final Office Action mailed Jun. 2, 2015", 13 pgs.

"U.S. Appl. No. 13/281,009, Restriction Requirement mailed Feb. 11, 2015", 6 pgs.

"U.S. Appl. No. 13/288,459, Corrected Notice of Allowance mailed Aug. 3, 2016", 4 pgs.

"U.S. Appl. No. 13/288,459, Corrected Notice of Allowance mailed Sep. 9, 2016", 4 pgs.

"U.S. Appl. No. 13/288,459, Corrected Notice of Allowance mailed Sep. 23, 2016", 4 pgs.

"U.S. Appl. No. 13/288,459, Examiner Interview Summary mailed Feb. 6, 2015", 3 pgs.

"U.S. Appl. No. 13/288,459, Examiner Interview Summary mailed Jan. 11, 2016", 1 pg.

"U.S. Appl. No. 13/288,459, Non Final Office Action mailed Jun. 24, 2015", 10 pgs.

"U.S. Appl. No. 13/288,459, Non Final Office Action mailed Nov. 4, 2014", 15 pgs.

"U.S. Appl. No. 13/288,459, Notice of Allowance mailed Jan. 11, 2016", 13 pgs.

"U.S. Appl. No. 13/288,459, Notice of Allowance mailed May 10, 2016", 7 pgs.

"U.S. Appl. No. 13/288,459, Response filed Mar. 3, 2015 to Non Final Office Action mailed Nov. 4, 2014", 16 pgs.

"U.S. Appl. No. 13/288,459, Response filed Oct. 13, 2014 to Restriction Requirement mailed Aug. 11, 2014", 15 pgs.

"U.S. Appl. No. 13/288,459, Response filed Oct. 23, 2015 to Non Final Office Action mailed Jun. 24, 2015", 14 pgs.

"U.S. Appl. No. 13/288,459, Restriction Requirement mailed Aug. 11, 2014", 9 pgs.

"U.S. Appl. No. 13/288,463, Examiner Interview Summary mailed Jun. 3, 2014", 3 pgs.

"U.S. Appl. No. 13/288,463, Non Final Office Action mailed Feb. 24, 2014", 13 pgs.

"U.S. Appl. No. 13/288,463, Notice of Allowance mailed Aug. 27, 2014", 9 pgs.

"U.S. Appl. No. 13/288,463, Response filed May 27, 2014 to Non Final Office Action mailed Feb. 24, 2014", 15 pgs.

"U.S. Appl. No. 13/288,463, Supplemental Notice of Allowability mailed Dec. 8, 2014", 5 pgs.

"U.S. Appl. No. 13/288,463, Supplemental Notice of Allowability mailed Dec. 19, 2014", 5 pgs.

"U.S. Appl. No. 13/293,825, Notice of Allowability mailed Jun. 22, 2015", 7 pgs.

"U.S. Appl. No. 13/293,825, Notice of Allowance mailed May 19, 2015", 9 pgs.

"U.S. Appl. No. 13/293,825, Response filed Apr. 15, 2015 to Restriction Requirement mailed Feb. 12, 2015", 17 pgs.

"U.S. Appl. No. 13/293,825, Restriction Requirement mailed Feb. 12, 2015", 9 pgs.

"U.S. Appl. No. 13/295,126, Non Final Office Action mailed May 19, 2015", 9 pgs.

"U.S. Appl. No. 13/295,126, Notice of Allowance mailed Oct. 22, 2015", 9 pgs.

"U.S. Appl. No. 13/295,126, Response filed Apr. 13, 2015 to Restriction Requirement mailed Feb. 12, 2015", 1 pgs.

"U.S. Appl. No. 13/295,126, Response filed Aug. 17, 2015 to Non Final Office Action mailed May 19, 2015", 21 pgs.

"U.S. Appl. No. 13/295,126, Restriction Requirement mailed Feb. 12, 2015", 9 pgs.

"U.S. Appl. No. 13/311,936, Examiner Interview Summary mailed Feb. 12, 2015", 2 pgs.

"U.S. Appl. No. 13/311,936, Non Final Office Action mailed Feb. 9, 2015", 13 pgs.

"U.S. Appl. No. 13/311,936, Non Final Office Action mailed Oct. 19, 2015", 8 pgs.

"U.S. Appl. No. 13/311,936, Notice of Allowance mailed Mar. 29, 2016", 8 pgs.

"U.S. Appl. No. 13/311,936, PTO Response to Rule 312 Communication mailed May 10, 2016", 2 pgs.

"U.S. Appl. No. 13/311,936, Response filed Jan. 18, 2016 to Non Final Office Action mailed Oct. 19, 2015", 8 pgs.

"U.S. Appl. No. 13/311,936, Response filed Jun. 9, 2015 to Non Final Office Action mailed Feb. 9, 2015", 12 pgs.

"U.S. Appl. No. 13/311,936, Response filed Oct. 3, 2014 to Restriction Requirement mailed Aug. 5, 2014", 10 pgs.

"U.S. Appl. No. 13/311,936, Restriction Requirement mailed Aug. 5, 2014", 7 pgs.

"U.S. Appl. No. 13/350,985, Final Office Action mailed Apr. 16, 2015", 8 pgs.

"U.S. Appl. No. 13/350,985, Non Final Office Action mailed Dec. 15, 2014", 8 pgs.

"U.S. Appl. No. 13/350,985, Notice of Allowance mailed Jul. 27, 2015", 5 pgs.

"U.S. Appl. No. 13/350,985, Response filed Mar. 13, 2015 to Non Final Office Action mailed Dec. 15, 2014", 10 pgs.

"U.S. Appl. No. 13/350,985, Response filed Jul. 9, 2015 to Final Office Action mailed Apr. 16, 2015", 8 pgs.

"U.S. Appl. No. 13/350,985, Response filed Dec. 2, 2014 to Restriction Requirement mailed Oct. 2, 2014", 9 pgs.

"U.S. Appl. No. 13/350,985, Restriction Requirement mailed Oct. 2, 2014", 6 pgs.

"U.S. Appl. No. 13/399,125, Corrected Notice of Allowance mailed Aug. 28, 2014", 2 pgs.

"U.S. Appl. No. 13/399,125, Examiner Interview Summary mailed May 17, 2013", 3 pgs.

"U.S. Appl. No. 13/399,125, Final Office Action mailed Mar. 20, 2013", 12 pgs.

"U.S. Appl. No. 13/399,125, Non Final Office Action mailed Oct. 24, 2012", 12 pgs.

"U.S. Appl. No. 13/399,125, Notice of Allowance mailed May 16, 2014", 8 pgs.

"U.S. Appl. No. 13/399,125, Response filed Jan. 10, 2013 to Non Final Office Action mailed Oct. 24, 2012", 15 pgs.

"U.S. Appl. No. 13/399,125, Response filed May 20, 2013 to Final Office Action mailed Mar. 20, 2013", 14 pgs.

"U.S. Appl. No. 13/412,105, Advisory Action mailed Feb. 24, 2014", 3 pgs.

"U.S. Appl. No. 13/412,105, Examiner Interview Summary mailed Feb. 6, 2014", 3 pgs.

"U.S. Appl. No. 13/412,105, Examiner Interview Summary mailed Oct. 11, 2013", 3 pgs.

"U.S. Appl. No. 13/412,105, Final Office Action mailed Dec. 13, 2013", 9 pgs.

"U.S. Appl. No. 13/412,105, Non Final Office Action mailed Jul. 15, 2013", 10 pgs.

"U.S. Appl. No. 13/412,105, Notice of Allowance mailed Aug. 18, 14", 9 pgs.

"U.S. Appl. No. 13/412,105, Response filed Feb. 10, 2014 to Final Office Action mailed Dec. 13, 2013", 14 pgs.

"U.S. Appl. No. 13/412,105, Response filed Mar. 13, 2014 to Advisory Action mailed Feb. 24, 2014", 19 pgs.

"U.S. Appl. No. 13/412,105, Response filed May 6, 2013 to Restriction Requirement mailed Apr. 5, 2013", 9 pgs.

"U.S. Appl. No. 13/412,105, Response filedmailed Jul. 15, 2013", 13 pgs.

"U.S. Appl. No. 13/412,105, Restriction Requirement mailed Apr. 5, 2013", 9 pgs.

(56)            References Cited

OTHER PUBLICATIONS

"U.S. Appl. No. 13/412,116, Corrected Notice of Allowance mailed Jun. 2, 2014", 2 pgs.

"U.S. Appl. No. 13/412,116, Examiner Interview Summary mailed Dec. 13, 2013", 3 pgs.

"U.S. Appl. No. 13/412,116, Non Final Office Action mailed Sep. 11, 2013", 9 pgs.

"U.S. Appl. No. 13/412,116, Notice of Allowance mailed Feb. 19, 2014", 9 pgs.

"U.S. Appl. No. 13/412,116, Response filed Jul. 3, 2013 to Restriction Requirement mailed Jun. 19, 2013", 1 pg.

"U.S. Appl. No. 13/412,116, Response filed Dec. 11, 2013 to Non Final Office Action mailed Sep. 11, 2013", 11 pgs.

"U.S. Appl. No. 13/412,116, Restriction Requirement mailed Jun. 19, 2013", 9 pgs.

"U.S. Appl. No. 13/412,127, Examiner Interview Summary mailed Nov. 5, 2013", 3 pgs.

"U.S. Appl. No. 13/412,127, Non Final Office Action mailed Aug. 7, 2013", 15 pgs.

"U.S. Appl. No. 13/412,127, Notice of Allowance mailed Dec. 24, 2013", 10 pgs.

"U.S. Appl. No. 13/412,127, Response filed May 23, 2013 to Restriction Requirement mailed Apr. 24, 2013", 2 pgs.

"U.S. Appl. No. 13/412,127, Response filedmailed Aug. 7, 2013", 16 pgs.

"U.S. Appl. No. 13/412,127, Restriction Requirement mailed Apr. 24, 2013", 10 pgs.

"U.S. Appl. No. 13/587,374, Final Office Action mailed Nov. 6, 2013", 9 pgs.

"U.S. Appl. No. 13/587,374, Non Final Office Action mailed Jul. 17, 2013", 8 pgs.

"U.S. Appl. No. 13/587,374, Notice of Allowance mailed Feb. 28, 2014", 5 pgs.

"U.S. Appl. No. 13/587,374, Preliminary Amendment filed Jun. 21, 2013", 9 pgs.

"U.S. Appl. No. 13/587,374, Response filed Jan. 24, 2014 to Final Office Action mailed Nov. 6, 2013", 15 pgs.

"U.S. Appl. No. 13/587,374, Response filed Oct. 14, 2013 to Non Final Office Action mailed Jul. 17, 2013", 14 pgs.

"U.S. Appl. No. 13/609,389, 312 Amendment filed Sep. 15, 2014", 4 pgs.

"U.S. Appl. No. 13/609,389, Examiner Interview Summary mailed Feb. 4, 2014", 4 pgs.

"U.S. Appl. No. 13/609,389, Final Office Action mailed May 5, 2014", 14 pgs.

"U.S. Appl. No. 13/609,389, Non Final Office Action mailed Nov. 27, 2013", 12 pgs.

"U.S. Appl. No. 13/609,389, Notice of Allowance mailed Jul. 23, 2014", 5 pgs.

"U.S. Appl. No. 13/609,389, PTO Response to Rule 312 Communication mailed Oct. 16, 2014", 2 pgs.

"U.S. Appl. No. 13/609,389, Response filed Feb. 27, 2014 to Non Final Office Action mailed Nov. 27, 2013", 18 pgs.

"U.S. Appl. No. 13/609,389, Response filed Jul. 10, 2014 to Final Office Action mailed May 5, 2014", 12 pgs.

"U.S. Appl. No. 13/625,413, Final Office Action mailed Oct. 30, 2015", 8 pgs.

"U.S. Appl. No. 13/625,413, Non Final Office Action mailed Jun. 8, 2015", 11 pgs.

"U.S. Appl. No. 13/625,413, Notice of Allowance mailed Apr. 1, 2016", 8 pgs.

"U.S. Appl. No. 13/625,413, Notice of Allowance mailed Dec. 11, 2015", 9 pgs.

"U.S. Appl. No. 13/625,413, Response filed May 11, 2015 to Restriction Requirement mailed Mar. 10, 2015", 1 pg.

"U.S. Appl. No. 13/625,413, Response filed Sep. 8, 2015 to Non Final Office Action mailed Jun. 8, 2015", 16 pgs.

"U.S. Appl. No. 13/625,413, Response filed Dec. 1, 2015 to Final Office Action mailed Oct. 30, 2015", 9 pgs.

"U.S. Appl. No. 13/625,413, Restriction Requirement mailed Mar. 10, 2015", 7 pgs.

"U.S. Appl. No. 13/645,964, Advisory Action mailed Feb. 4, 2016", 2 pgs.

"U.S. Appl. No. 13/645,964, Final Office Action mailed Oct. 6, 2015", 17 pgs.

"U.S. Appl. No. 13/645,964, Non Final Office Action mailed Mar. 15, 2016", 15 pgs.

"U.S. Appl. No. 13/645,964, Non Final Office Action mailed Mar. 17, 2015", 15 pgs.

"U.S. Appl. No. 13/645,964, Notice of Allowance mailed Jul. 21, 2016", 9 pgs.

"U.S. Appl. No. 13/645,964, Response filed Jun. 13, 2016 to Non Final Office Action mailed Mar. 15, 2016", 11 pgs.

"U.S. Appl. No. 13/645,964, Response filed Jul. 17, 2015 to Non Final Office Action mailed Mar. 17, 2015", 17 pgs.

"U.S. Appl. No. 13/645,964, Response filed Dec. 4, 2015 to Final Office Action mailed Oct. 6, 2015", 14 pgs.

"U.S. Appl. No. 13/656,821, Notice of Allowance mailed Jun. 18, 2015", 11 pgs.

"U.S. Appl. No. 13/656,821, Response filed May 11, 2015 to Restriction Requirement mailed Mar. 10, 2015", 1 pg.

"U.S. Appl. No. 13/656,821, Restriction Requirement mailed Mar. 10, 2015", 6 pgs.

"U.S. Appl. No. 13/720,631, Final Office Action mailed Jun. 25, 2014", 10 pgs.

"U.S. Appl. No. 13/720,631, Non Final Office Action mailed Mar. 6, 2014", 7 pgs.

"U.S. Appl. No. 13/720,631, Notice of Allowance mailed Jul. 25, 2014", 5 pgs.

"U.S. Appl. No. 13/720,631, Response filed Jun. 6, 2014 to Non Final Office Action mailed Mar. 6, 2014", 11 pgs.

"U.S. Appl. No. 13/720,631, Response filed Jul. 14, 2014 to Final Office Action mailed Jun. 25, 2014", 6 pgs.

"U.S. Appl. No. 13/720,631, Supplemental Notice of Allowance mailed Sep. 8, 2014", 2 pgs.

"U.S. Appl. No. 13/720,648, Final Office Action mailed Nov. 16, 2015", 7 pgs.

"U.S. Appl. No. 13/720,648, Non Final Office Action mailed Jun. 10, 2015", 11 pgs.

"U.S. Appl. No. 13/720,648, Notice of Allowance mailed Feb. 5, 2016", 11 pgs.

"U.S. Appl. No. 13/720,648, Response filed Jan. 13, 2016 to Final Office Action mailed Nov. 16, 2015", 9 pgs.

"U.S. Appl. No. 13/720,648, Response filed May 11, 2015 to Restriction Requirement mailed Mar. 10, 2015", 8 pgs.

"U.S. Appl. No. 13/720,648, Response filed Oct. 9, 2015 to Non Final Office Action mailed Jun. 10, 2015", 12 pgs.

"U.S. Appl. No. 13/720,648, Restriction Requirement mailed Mar. 10, 2015", 8 pgs.

"U.S. Appl. No. 13/721,970, Notice of Allowance mailed Aug. 12, 2013", 13 pgs.

"U.S. Appl. No. 13/721,970, Preliminary Amendment filed Mar. 15, 2013", 13 pgs.

"U.S. Appl. No. 13/721,970, Response filed May 8, 2013 to Restriction Requirement mailed Apr. 11, 2013", 1 pgs.

"U.S. Appl. No. 13/721,970, Restriction Requirement mailed Apr. 11, 2013", 6 pgs.

"U.S. Appl. No. 13/751,846, Final Office Action mailed Nov. 17, 2015", 9 pgs.

"U.S. Appl. No. 13/751,846, Non Final Office Action mailed Jun. 15, 2015", 10 pgs.

"U.S. Appl. No. 13/751,846, Notice of Allowance mailed Mar. 16, 2016", 11 pgs.

"U.S. Appl. No. 13/751,846, Notice of Allowance mailed Jul. 6, 2016", 9 pgs.

"U.S. Appl. No. 13/751,846, Response filed Feb. 5, 2016 to Final Office Action mailed Nov. 17, 2015", 14 pgs.

"U.S. Appl. No. 13/751,846, Response filed May 11, 2015 to Restriction Requirement mailed Mar. 10, 2015", 15 pgs.

"U.S. Appl. No. 13/751,846, Response filed Oct. 9, 2015 to Non Final Office Action mailed Jun. 15, 2015", 20 pgs.

(56)　　　　　References Cited

OTHER PUBLICATIONS

"U.S. Appl. No. 13/751,846, Restriction Requirement mailed Mar. 10, 2015", 7 pgs.
"U.S. Appl. No. 13/757,003, Non Final Office Action mailed Jun. 25, 2015", 8 pgs.
"U.S. Appl. No. 13/757,003, Notice of Allowance mailed Feb. 8, 2016", 10 pgs.
"U.S. Appl. No. 13/757,003, Response filed May 12, 2015 to Restriction Requirement mailed Mar. 12, 2015", 9 pgs.
"U.S. Appl. No. 13/757,003, Response filed Oct. 26, 2015 to Non Final Office Action mailed Jul. 25, 2015", 8 pgs.
"U.S. Appl. No. 13/757,003, Restriction Requirement mailed Mar. 12, 2015", 6 pgs.
"U.S. Appl. No. 13/757,019, Non Final Office Action mailed Jun. 25, 2015", 11 pgs.
"U.S. Appl. No. 13/757,019, Notice of Allowance mailed Dec. 10, 2015", 10 pgs.
"U.S. Appl. No. 13/757,019, Response filed May 11, 2015 to Restriction Requirement mailed Mar. 11, 2015", 9 pgs.
"U.S. Appl. No. 13/757,019, Response filed Oct. 26, 2015 to Non Final Office Action mailed Jun. 25, 2015", 9 pgs.
"U.S. Appl. No. 13/757,019, Restriction Requirement mailed Mar. 11, 2015", 10 pgs.
"U.S. Appl. No. 13/767,401, Non Final Office Action mailed Aug. 26, 2015", 9 pgs.
"U.S. Appl. No. 13/767,401, Notice of Allowance mailed Apr. 8, 2016", 9 pgs.
"U.S. Appl. No. 13/767,401, Notice of Allowance mailed Dec. 30, 2015", 9 pgs.
"U.S. Appl. No. 13/767,401, Response filed May 18, 2015 to Restriction Requirement mailed Mar. 17, 2015", 15 pgs.
"U.S. Appl. No. 13/767,401, Response filed Nov. 6, 2015 to Non Final Office Action mailed Aug. 26, 2015", 12 pgs.
"U.S. Appl. No. 13/767,401, Restriction Requirement mailed Mar. 17, 2015", 8 pgs.
"U.S. Appl. No. 13/790,982, Examiner Interview Summary mailed Jun. 9, 2015", 3 pgs.
"U.S. Appl. No. 13/790,982, Non Final Office Action mailed Sep. 16, 2015", 11 pgs.
"U.S. Appl. No. 13/790,982, Notice of Allowance mailed Feb. 24, 2016", 10 pgs.
"U.S. Appl. No. 13/790,982, Response filed Jun. 2, 2015 to Restriction Requirement mailed Apr. 2, 2015", 11 pgs.
"U.S. Appl. No. 13/790,982, Response filed Dec. 16, 2015 to Non Final Office Action mailed Sep. 16, 2015", 10 pgs.
"U.S. Appl. No. 13/790,982, Restriction Requirement mailed Apr. 2, 2015", 10 pgs.
"U.S. Appl. No. 13/790,997, Examiner Interview Summary mailed Jun. 8, 2015", 3 pgs.
"U.S. Appl. No. 13/790,997, Non Final Office Action mailed Sep. 21, 2015", 8 pgs.
"U.S. Appl. No. 13/790,997, Notice of Allowance mailed Mar. 2, 2016", 9 pgs.
"U.S. Appl. No. 13/790,997, Response filed Jun. 2, 2015 to Restriction Requirement mailed Apr. 2, 2015", 12 pgs.
"U.S. Appl. No. 13/790,997, Response filed Dec. 18, 2015 to Non Final Office Action mailed Sep. 21, 2015", 9 pgs.
"U.S. Appl. No. 13/790,997, Restriction Requirement mailed Apr. 2, 2015", 8 pgs.
"U.S. Appl. No. 13/791,014, Final Office Action mailed Jan. 8, 2016", 11 pgs.
"U.S. Appl. No. 13/791,014, Non Final Office Action mailed Aug. 14, 2015", 9 pgs.
"U.S. Appl. No. 13/791,014, Notice of Allowability mailed Jul. 27, 2017", 2 pgs.
"U.S. Appl. No. 13/791,014, Notice of Allowance mailed Jan. 10, 2017", 15 pgs.
"U.S. Appl. No. 13/791,014, Notice of Allowance mailed Apr. 27, 2017", 8 pgs.

"U.S. Appl. No. 13/791,014, Response filed Jun. 6, 2016 to Final Office Action mailed Jan. 8, 2016", 13 pgs.
"U.S. Appl. No. 13/791,014, Response filed Aug. 3, 2015 to Restriction Requirement mailed May 1, 2015", 9 pgs.
"U.S. Appl. No. 13/791,014, Response filed Nov. 10, 2015 to Non Final Office Action mailed Aug. 14, 2015", 13 pgs.
"U.S. Appl. No. 13/791,014, Restriction Requirement mailed May 1, 2015", 6 pgs.
"U.S. Appl. No. 13/833,567, Advisory Action mailed Apr. 28, 2016", 3 pgs.
"U.S. Appl. No. 13/833,567, Final Office Action mailed Mar. 9, 2016", 9 pgs.
"U.S. Appl. No. 13/833,567, Non Final Office Action mailed May 27, 2016", 9 pgs.
"U.S. Appl. No. 13/833,567, Non Final Office Action mailed Oct. 23, 2015", 10 pgs.
"U.S. Appl. No. 13/833,567, Notice of Allowance mailed Sep. 27, 2016", 9 pgs.
"U.S. Appl. No. 13/833,567, Response filed Jan. 22, 2016 to Non Final Office Action mailed Oct. 23, 2015", 11 pgs.
"U.S. Appl. No. 13/833,567, Response filed Apr. 20, 2016 to Final Office Action mailed Mar. 9, 2016", 10 pgs.
"U.S. Appl. No. 13/833,567, Response filed Jun. 25, 2015 to Restriction Requirement mailed Apr. 3, 2015", 10 pgs.
"U.S. Appl. No. 13/833,567, Response filed Aug. 4, 2016 to Non Final Office Action mailed May 27, 2016", 11 pgs.
"U.S. Appl. No. 13/833,567, Restriction Requirement mailed Apr. 3, 2015", 6 pgs.
"U.S. Appl. No. 13/838,755, Final Office Action mailed Feb. 22, 2016", 9 pgs.
"U.S. Appl. No. 13/838,755, Non Final Office Action mailed Sep. 17, 2015", 11 pgs.
"U.S. Appl. No. 13/838,755, Notice of Allowance mailed Apr. 27, 2016", 7 pgs.
"U.S. Appl. No. 13/838,755, Notice of Allowance mailed Aug. 3, 2016", 8 pgs.
"U.S. Appl. No. 13/838,755, Response filed Apr. 15, 2016 to Final Office Action mailed Feb. 22, 2016", 11 pgs.
"U.S. Appl. No. 13/838,755, Response filed Jun. 8, 2015 to Restriction Requirement mailed Apr. 6, 2015", 1 pg.
"U.S. Appl. No. 13/838,755, Response filed Dec. 1, 2015 to Non Final Office Action mailed Sep. 17, 2015", 13 pgs.
"U.S. Appl. No. 13/838,755, Restriction Requirement mailed Apr. 6, 2015", 6 pgs.
"U.S. Appl. No. 13/889,851, Non Final Office Action mailed Apr. 6, 2015", 10 pgs.
"U.S. Appl. No. 13/889,851, Notice of Allowance mailed Aug. 12, 2015", 8 pgs.
"U.S. Appl. No. 13/889,851, Response filed Feb. 26, 2015 to Restriction Requirement mailed Jan. 21, 2015", 12 pgs.
"U.S. Appl. No. 13/889,851, Response filed Jul. 6, 2015 to Non Final Office Action mailed Apr. 6, 2015", 14 pgs.
"U.S. Appl. No. 13/889,851, Restriction Requirement mailed Jan. 21, 2015", 6 pgs.
"U.S. Appl. No. 13/889,851, Supplemental Amendment and Response filed Jul. 6, 2015 to Non Final Office Action mailed Apr. 6, 2015", 8 pgs.
"U.S. Appl. No. 13/959,145, Examiner Interview Summary mailed Sep. 16, 2015", 3 pgs.
"U.S. Appl. No. 13/959,145, Final Office Action mailed Jan. 29, 2016", 16 pgs.
"U.S. Appl. No. 13/959,145, Final Office Action mailed Feb. 5, 2015", 22 pgs.
"U.S. Appl. No. 13/959,145, Non Final Office Action mailed Jul. 31, 2015", 21 pgs.
"U.S. Appl. No. 13/959,145, Non Final Office Action mailed Sep. 15, 2014", 20 pgs.
"U.S. Appl. No. 13/959,145, Notice of Allowability mailed Jun. 14, 2016", 2 pgs.
"U.S. Appl. No. 13/959,145, Notice of Allowance mailed Apr. 13, 2016", 5 pgs.
"U.S. Appl. No. 13/959,145, Response filed Mar. 28, 2016 to Final Office Action mailed Jan. 29, 2016", 10 pgs.

(56) References Cited

OTHER PUBLICATIONS

"U.S. Appl. No. 13/959,145, Response filed Jul. 6, 2015 to Final Office Action mailed Feb. 5, 2015", 18 pgs.
"U.S. Appl. No. 13/959,145, Response filed Oct. 30, 2015 to Non Final Office Action mailed Jul. 31, 2015", 14 pgs.
"U.S. Appl. No. 13/959, 145, Response filed Dec. 15, 2014 to Non Final Office Action mailed Sep. 15, 2014", 21 pgs.
"U.S. Appl. No. 14/055,172, Final Office Action mailed Dec. 22, 2016", 8 pgs.
"U.S. Appl. No. 14/055,172, Non Final Office Action mailed Jul. 14, 2016", 12 pgs.
"U.S. Appl. No. 14/055,172, Notice of Allowance mailed Mar. 29, 2017", 10 pgs.
"U.S. Appl. No. 14/055,172, Response filed Feb. 22, 2017 to Final Office Action mailed Dec. 22, 2016", 11 pgs.
"U.S. Appl. No. 14/055,172, Response filed May 4, 2016 to Restriction Requirement mailed Mar. 4, 2016", 8 pgs.
"U.S. Appl. No. 14/055,172, Response filed Nov. 14, 2016 to Non Final Office Action mailed Jul. 14, 2016", 19 pgs.
"U.S. Appl. No. 14/055,172, Restriction Requirement mailed Mar. 4, 2016", 6 pgs.
"U.S. Appl. No. 14/055,191, Non Final Office Action mailed May 16, 2016", 8 pgs.
"U.S. Appl. No. 14/055,191, Notice of Allowability mailed Sep. 8, 2016", 7 pgs.
"U.S. Appl. No. 14/055,191, Notice of Allowance mailed Aug. 31, 2016", 13 pgs.
"U.S. Appl. No. 14/055,191, Response filed Apr. 29, 2016 to Restriction Requirement mailed Mar. 7, 2016", 8 pgs.
"U.S. Appl. No. 14/055,191, Response filed Aug. 3, 2016 to Non Final Office Action mailed May 16, 2016", 11 pgs.
"U.S. Appl. No. 14/055,191, Restriction Requirement mailed Mar. 7, 2016", 6 pgs.
"U.S. Appl. No. 14/071,295, Non Final Office Action mailed Aug. 15, 14", 6 pgs.
"U.S. Appl. No. 14/071,295, Notice of Allowance mailed Dec. 10, 2014", 8 pgs.
"U.S. Appl. No. 14/071,295, Response filed Nov. 17, 2014 to Non Final Office Action mailed Aug. 15, 2014", 14 pgs.
"U.S. Appl. No. 14/071,295, Supplemental Notice of Allowability mailed Jan. 26, 2015", 2 pgs.
"U.S. Appl. No. 14/094,311, Corrected Notice of Allowance mailed Mar. 28, 2017", 5 pgs.
"U.S. Appl. No. 14/094,311, Notice of Allowance mailed Aug. 16, 2016", 12 pgs.
"U.S. Appl. No. 14/094,311, Notice of Allowance mailed Dec. 27, 2016", 8 pgs.
"U.S. Appl. No. 14/094,311, Response filed Jul. 26, 2016 to Restriction Requirement mailed Jun. 22, 2016", 10 pgs.
"U.S. Appl. No. 14/094,311, Restriction Requirement mailed Jun. 22, 2016", 6 pgs.
"U.S. Appl. No. 14/095,614, Non Final Office Action mailed Jan. 19, 2017", 9 pgs.
"U.S. Appl. No. 14/095,614, Notice of Allowance mailed May 8, 2017", 8 pgs.
"U.S. Appl. No. 14/095,614, Notice of Allowance mailed Nov. 6, 2017", 9 pgs.
"U.S. Appl. No. 14/095,614, Preliminary Amendment filed Apr. 15, 2014", 17 pgs.
"U.S. Appl. No. 14/095,614, Response filed Mar. 2, 2017 to Non Final Office Action mailed Jan. 19, 2017", 14 pgs.
"U.S. Appl. No. 14/095,614, Response filed Sep. 12, 2016 to Restriction Requirement mailed Jul. 11, 2016", 11 pgs.
"U.S. Appl. No. 14/095,614, Restriction Requirement mailed Jul. 11, 2016", 8 pgs.
"U.S. Appl. No. 14/095,639, Non Final Office Action mailed Jan. 18, 2017", 10 pgs.
"U.S. Appl. No. 14/095,639, Notice of Allowance mailed Apr. 13, 2017", 9 pgs.
"U.S. Appl. No. 14/095,639, Notice of Allowance mailed Oct. 30, 2017", 9 pgs.
"U.S. Appl. No. 14/095,639, Response filed Mar. 2, 2017 to Non Final Office Action mailed Jan. 18, 2017", 9 pgs.
"U.S. Appl. No. 14/095,639, Response filed Sep. 12, 2016 to Restriction Requirement mailed Jul. 19, 2016", 7 pgs.
"U.S. Appl. No. 14/095,639, Restriction Requirement mailed Jul. 19, 2016", 8 pgs.
"U.S. Appl. No. 14/107,350, Notice of Allowance mailed Feb. 26, 2016", 11 pgs.
"U.S. Appl. No. 14/107,350, Notice of Allowance mailed Jul. 27, 2016", 7 pgs.
"U.S. Appl. No. 14/107,350, Preliminary Amendment filed Feb. 28, 2014", 4 pgs.
"U.S. Appl. No. 14/159,094, Examiner Interview Summary mailed Nov. 29, 2016", 1 pg.
"U.S. Appl. No. 14/159,094, Non Final Office Action mailed Jun. 29, 2016", 15 pgs.
"U.S. Appl. No. 14/159,094, Notice of Allowance mailed Nov. 29, 2016", Examiner Interview Summary from Nov. 29, 2016 included, 11 pgs.
"U.S. Appl. No. 14/159,094, Response filed Jun. 3, 2016 to Restriction Requirement mailed Apr. 20, 2016", 9 pgs.
"U.S. Appl. No. 14/159,094, Response filed Sep. 19, 2016 to Non Final Office Action mailed Jun. 29, 2016", 13 pgs.
"U.S. Appl. No. 14/159,094, Restriction Requirement mailed Apr. 20, 2016", 6 pgs.
"U.S. Appl. No. 14/182,038, Advisory Action mailed Mar. 1, 2017", 3 pgs.
"U.S. Appl. No. 14/182,038, Final Office Action mailed Dec. 19, 2016", 8 pgs.
"U.S. Appl. No. 14/182,038, Non Final Office Action mailed Jul. 19, 2016", 10 pgs.
"U.S. Appl. No. 14/182,038, Notice of Allowance mailed May 24, 2017", 9 pgs.
"U.S. Appl. No. 14/182,038, Response filed Feb. 20, 2017 to Final Office Action mailed Dec. 19, 2016", 11 pgs.
"U.S. Appl. No. 14/182,038, Response filed Jun. 27, 2016 to Restriction Requirement mailed Apr. 26, 2016", 8 pgs.
"U.S. Appl. No. 14/182,038, Response filed Oct. 19, 2016 to Non Final Office Action mailed Jul. 19, 2016", 15 pgs.
"U.S. Appl. No. 14/182,038, Restriction Requirement mailed Apr. 26, 2016", 7 pgs.
"U.S. Appl. No. 14/182,046, Corrected Notice of Allowance mailed Jan. 20, 2017", 6 pgs.
"U.S. Appl. No. 14/182,046, Non Final Office Action mailed Jul. 15, 2016", 9 pgs.
"U.S. Appl. No. 14/182,046, Notice of Allowance mailed Dec. 8, 2016", 7 pgs.
"U.S. Appl. No. 14/182,046, Response filed Jun. 27, 2016 to Restriction Requirement mailed Apr. 26, 2016", 7 pgs.
"U.S. Appl. No. 14/182,046, Response filed Oct. 17, 2016 to Non Final Office Action mailed Jul. 15, 2016", 11 pgs.
"U.S. Appl. No. 14/182,046, Restriction Requirement mailed Apr. 26, 2016", 6 pgs.
"U.S. Appl. No. 14/211,977, Notice of Allowance mailed Jul. 12, 2016", 9 pgs.
"U.S. Appl. No. 14/211,977, Preliminary Amendment filed Mar. 2, 2016", 7 pgs.
"U.S. Appl. No. 14/211,977, Response filed Apr. 29, 2016 to Restriction Requirement mailed Mar. 11, 2016", 8 pgs.
"U.S. Appl. No. 14/211,977, Restriction Requirement mailed Mar. 11, 2016", 6 pgs.
"U.S. Appl. No. 14/215,550, Corrected Notice of Allowance mailed Jul. 27, 2017", 2 pgs.
"U.S. Appl. No. 14/215,550, Examiner Interview Summary mailed Mar. 9, 2017", 3 pgs.
"U.S. Appl. No. 14/215,550, Final Office Action mailed Feb. 1, 2017", 11 pgs.
"U.S. Appl. No. 14/215,550, Non Final Office Action mailed Jul. 19, 2016", 12 pgs.
"U.S. Appl. No. 14/215,550, Notice of Allowance mailed Jun. 21, 2017", 8 pgs.

(56)     References Cited

OTHER PUBLICATIONS

"U.S. Appl. No. 14/215,550, Response filed May 1, 2017 to Final Office Action mailed Feb. 1, 2017", 10 pgs.

"U.S. Appl. No. 14/215,550, Response filed Jun. 22, 2016 to Restriction Requirement mailed Apr. 28, 2016", 7 pgs.

"U.S. Appl. No. 14/215,550, Response filed Dec. 5, 2016 to Non Final Office Action mailed Jul. 19, 2016", 13 pgs.

"U.S. Appl. No. 14/215,550, Restriction Requirement mailed Apr. 28, 2016", 6 pgs.

"U.S. Appl. No. 14/275,548, Examiner Interview Summary mailed May 25, 2016", 3 pgs.

"U.S. Appl. No. 14/275,548, Non Final Office Action mailed Feb. 19, 2016", 14 pgs.

"U.S. Appl. No. 14/275,548, Notice of Allowance mailed Jul. 27, 2016", 7 pgs.

"U.S. Appl. No. 14/275,548, Response filed May 19, 2016 to Non Final Office Action mailed Feb. 19, 2016", 19 pgs.

"U.S. Appl. No. 14/324,688, Corrected Notice of Allowance mailed Sep. 22, 2016", 2 pgs.

"U.S. Appl. No. 14/324,688, Non Final Office Action mailed Jan. 8, 2016", 18 pgs.

"U.S. Appl. No. 14/324,688, Notice of Allowance mailed Jun. 9, 2016", 7 pgs.

"U.S. Appl. No. 14/324,688, Response filed Apr. 8, 2016 to Non Final Office Action mailed Jan. 8, 2016", 15 pgs.

"U.S. Appl. No. 14/456,286, Advisory Action mailed Jun. 21, 2016", 3 pgs.

"U.S. Appl. No. 14/456,286, Final Office Action mailed May 27, 2016", 15 pgs.

"U.S. Appl. No. 14/456,286, Non Final Office Action mailed Oct. 17, 2016", 17 pgs.

"U.S. Appl. No. 14/456,286, Non Final Office Action mailed Dec. 30, 2015", 16 pgs.

"U.S. Appl. No. 14/456,286, Notice of Allowance mailed Feb. 15, 2017", 9 pgs.

"U.S. Appl. No. 14/456,286, Response filed Mar. 30, 2016 to Non Final Office Action mailed Dec. 30, 2015", 15 pgs.

"U.S. Appl. No. 14/456,286, Response filed Jun. 13, 2016 to Final Office Action mailed May 27, 2016", 10 pgs.

"U.S. Appl. No. 14/456,286, Response filed Nov. 16, 2016 to Non Final Office Action mailed Oct. 17, 2016", 9 pgs.

"U.S. Appl. No. 14/456,286, Response filed Dec. 11, 2015 to Restriction Requirement mailed Oct. 29, 2015", 6 pgs.

"U.S. Appl. No. 14/456,286, Restriction Requirement mailed Oct. 29, 2015", 9 pgs.

"U.S. Appl. No. 14/492,590, Notice of Allowance mailed Oct. 5, 2016", 10 pgs.

"U.S. Appl. No. 14/492,590, Response filed Sep. 15, 2016 to Restriction Requirement mailed Jul. 25, 2015", 7 pgs.

"U.S. Appl. No. 14/492,590, Restriction Requirement mailed Jul. 25, 2016", 6 pgs.

"U.S. Appl. No. 14/492,590, Supplemental Response filed Sep. 26, 2016 to Restriction Requirement mailed Jul. 25, 2016", 10 pgs.

"U.S. Appl. No. 14/514,453, Final Office Action mailed Mar. 17, 2016", 17 pgs.

"U.S. Appl. No. 14/514,453, Non Final Office Action mailed Sep. 24, 2015", 11 pgs.

"U.S. Appl. No. 14/514,453, Response filed Dec. 16, 2015 to Non Final Office Action mailed Sep. 24, 2015", 14 pgs.

"U.S. Appl. No. 14/532,333, Response filed Apr. 7, 2016 to Restriction Requirement mailed Feb. 8, 2016", 10 pgs.

"U.S. Appl. No. 14/532,333, Restriction Requirement mailed Feb. 8, 2016", 6 pgs.

"U.S. Appl. No. 14/589,101, Advisory Action mailed Feb. 21, 2017", 5 pgs.

"U.S. Appl. No. 14/589,101, Advisory Action mailed May 22, 2018", 3 pgs.

"U.S. Appl. No. 14/589, 101, Examiner Interview Summary mailed Jan. 30, 2017", 3 pgs.

"U.S. Appl. No. 14/589,101, Final Office Action mailed Feb. 22, 2018", 15 pgs.

"U.S. Appl. No. 14/589,101, Final Office Action mailed Oct. 2, 2015", 10 pgs.

"U.S. Appl. No. 14/589,101, Final Office Action mailed Nov. 16, 2016", 12 pgs.

"U.S. Appl. No. 14/589,101, Non Final Office Action mailed Feb. 12, 2015", 10 pgs.

"U.S. Appl. No. 14/589,101, Non Final Office Action mailed May 5, 2016", 14 pgs.

"U.S. Appl. No. 14/589,101, Non Final Office Action mailed Sep. 14, 2017", 13 pgs.

"U.S. Appl. No. 14/589,101, Response filed Jan. 23, 2017 to Final Office Action mailed Nov. 16, 2016", 9 pgs.

"U.S. Appl. No. 14/589,101, Response filed Apr. 10, 2018 to Final Office Action mailed Feb. 22, 2018", 10 pgs.

"U.S. Appl. No. 14/589,101, Response filed Jun. 12, 2015 to Non Final Office Action mailed Feb. 12, 2015", 11 pgs.

"U.S. Appl. No. 14/589,101, Response filed Nov. 13, 2017 to Non Final Office Action mailed Sep. 14, 2017", 10 pgs.

"U.S. Appl. No. 14/589,101, Response filed Dec. 29, 2015 to Final Office Action mailed Oct. 2, 2015", 15 pgs.

"U.S. Appl. No. 14/589,191, Response filed Aug. 5, 2016 to Non Final Office Action mailed May 5, 2016", 16 pgs.

"U.S. Appl. No. 14/594,285, Final Office Action mailed May 22, 2017", 12 pgs.

"U.S. Appl. No. 14/594,285, Non Final Office Action mailed Jan. 11, 2017", 15 pgs.

"U.S. Appl. No. 14/594,285, Notice of Allowance mailed Jun. 27, 2017", 10 pgs.

"U.S. Appl. No. 14/594,285, Response filed Apr. 11, 2017 to Non Final Office Action mailed Jan. 11, 2017", 12 pgs.

"U.S. Appl. No. 14/594,285, Response filed Jun. 14, 2017 to Final Office Action mailed May 22, 2017", 9 pgs.

"U.S. Appl. No. 14/594,285, Response filed Dec. 14, 2016 to Restriction Requirement mailed Nov. 7, 2016", 8 pgs.

"U.S. Appl. No. 14/594,285, Restriction Requirement mailed Nov. 7, 2016", 6 pgs.

"U.S. Appl. No. 14/599,909, Non Final Office Action mailed Jul. 27, 2017", 18 pgs.

"U.S. Appl. No. 14/599,909, Notice of Allowance mailed Feb. 13, 2018", 9 pgs.

"U.S. Appl. No. 14/599,909, Response filed Sep. 21, 2017 to Non Final Office Action mailed Jul. 27, 2017", 10 pgs.

"U.S. Appl. No. 14/635,055, Non Final Office Action mailed Aug. 28, 2017", 8 pgs.

"U.S. Appl. No. 14/635,055, Notice of Allowance mailed Feb. 28, 2018", 11 pgs.

"U.S. Appl. No. 14/635,055, Response filed Jun. 27, 2017 to Restriction Requirement mailed Apr. 27, 2017", 11 pgs.

"U.S. Appl. No. 14/635,055, Response filed Nov. 28, 2017 to Non Final Office Action mailed Aug. 28, 2017", 13 pgs.

"U.S. Appl. No. 14/635,055, Restriction Requirement mailed Apr. 27, 2017", 7 pgs.

"U.S. Appl. No. 14/697,140, Advisory Action mailed Aug. 11, 2017", 3 pgs.

"U.S. Appl. No. 14/697,140, Final Office Action mailed Jun. 30, 2017", 13 pgs.

"U.S. Appl. No. 14/697,140, Final Office Action mailed Sep. 23, 2016", 10 pgs.

"U.S. Appl. No. 14/697,140, Non Final Office Action mailed Jan. 10, 2017", 12 pgs.

"U.S. Appl. No. 14/697,140, Non Final Office Action mailed Apr. 8, 2016", 8 pgs.

"U.S. Appl. No. 14/697,140, Notice of Allowance mailed Sep. 5, 2017", 7 pgs.

"U.S. Appl. No. 14/697,140, Response filed Mar. 1, 2017 to Non Final Office Action mailed Jan. 10, 2017", 11 pgs.

"U.S. Appl. No. 14/697,140, Response filed Jun. 13, 2016 to Non Final Office Action mailed Apr. 8, 2016", 10 pgs.

"U.S. Appl. No. 14/697,140, Response filed Jul. 27, 2017 to Final Office Action mailed Jun. 30, 2017", 10 pgs.

(56)     References Cited

OTHER PUBLICATIONS

"U.S. Appl. No. 14/697,140, Response filed Nov. 16, 2016 to Final Office Action mailed Sep. 23, 2016", 13 pgs.

"U.S. Appl. No. 14/794,309, Final Office Action mailed Mar. 20, 2017", 18 pgs.

"U.S. Appl. No. 14/794,309, Non Final Office Action mailed Jun. 20, 2017", 16 pgs.

"U.S. Appl. No. 14/794,309, Non Final Office Action mailed Nov. 22, 2016", 13 pgs.

"U.S. Appl. No. 14/794,309, Notice of Allowance mailed Sep. 18, 2017", 5 pgs.

"U.S. Appl. No. 14/794,309, Preliminary Amendment filed Sep. 22, 2015", 6 pgs.

"U.S. Appl. No. 14/794,309, Response filed Feb. 22, 2017 to Non Final Office Action mailed Nov. 22, 2016", 12 pgs.

"U.S. Appl. No. 14/794,309, Response filed May 22, 2017 to Final Office Action mailed Mar. 20, 2017", 13 pgs.

"U.S. Appl. No. 14/794,309, Response filed Aug. 17, 2017 to Non Final Office Action mailed Jun. 20, 2017", 12 pgs.

"U.S. Appl. No. 14/794,309, Supplemental Preliminary Amendment filed Mar. 3, 2016", 8 pgs.

"U.S. Appl. No. 14/854,308, Notice of Allowance mailed Mar. 16, 2018", 11 pgs.

"U.S. Appl. No. 14/854,308, Response filed Dec. 20, 2017 to Restriction Requirement mailed Oct. 20, 2017", 8 pgs.

"U.S. Appl. No. 14/854,308, Restriction Requirement mailed Oct. 20, 2017", 8 pgs.

"U.S. Appl. No. 14/854,308, Supplemental Preliminary Amendment Filed Aug. 31, 2017", 3 pgs.

"U.S. Appl. No. 14/876,167, Final Office Action mailed Jul. 31, 2018", 8 pgs.

"U.S. Appl. No. 14/876,167, Non Final Office Action mailed Mar. 13, 2018", 8 pgs.

"U.S. Appl. No. 14/876,167, Notice of Allowance mailed Dec. 10, 2018", 8 pgs.

"U.S. Appl. No. 14/876,167, Preliminary Amendment filed Oct. 27, 2015", 8 pgs.

"U.S. Appl. No. 14/876,167, Response filed Jan. 9, 2018 to Restriction Requirement mailed Nov. 22, 2017", 6 pgs.

"U.S. Appl. No. 14/876,167, Response filed Jun. 6, 2018 to Non Final Office Action mailed Mar. 13, 2018", 9 pgs.

"U.S. Appl. No. 14/876,167, Response filed Sep. 28, 2018 to Final Office Action mailed Jul. 31, 2018", 10 pgs.

"U.S. Appl. No. 14/876,167, Restriction Requirement mailed Nov. 22, 2017", 9 pgs.

"U.S. Appl. No. 14/936,831, Advisory Action mailed Jan. 29, 2019", 3 pgs.

"U.S. Appl. No. 14/936,831, Final Office Action mailed Nov. 20, 2018", 8 pgs.

"U.S. Appl. No. 14/936,831, Non Final Office Action mailed May 16, 2018", 11 pgs.

"U.S. Appl. No. 14/936,831, Notice of Allowance mailed Jul. 3, 2019", 8 pgs.

"U.S. Appl. No. 14/936,831, Notice of Non-Compliant Amendment mailed Mar. 14, 2018", 2 pgs.

"U.S. Appl. No. 14/936,831, Preliminary Amendment filed Nov. 11, 2015", 6 pgs.

"U.S. Appl. No. 14/936,831, Response filed Jan. 10, 2018 to Restriction Requirement mailed Nov. 22, 2017", 6 pgs.

"U.S. Appl. No. 14/936,831, Response filed Jan. 21, 2019 to Final Office Action mailed Nov. 20, 2018", 9 pgs.

"U.S. Appl. No. 14/936,831, Response filed Mar. 26, 2018 to Notice of Non-Compliant Amendment mailed Mar. 14, 2018", 6 pgs.

"U.S. Appl. No. 14/936,831, Response filed Aug. 16, 2018 to Non Final Office Action mailed May 16, 2018", 9 pgs.

"U.S. Appl. No. 14/936,831, Restriction Requirement mailed Nov. 22, 2017", 8 pgs.

"U.S. Appl. No. 14/956,724, Examiner Interview Summary mailed Jun. 20, 2017", 3 pgs.

"U.S. Appl. No. 14/956,724, Non Final Office Action mailed Mar. 31, 2017", 17 pgs.

"U.S. Appl. No. 14/956,724, Notice of Allowance mailed Aug. 23, 2017", 9 pgs.

"U.S. Appl. No. 14/956,724, Preliminary Amendment filed Dec. 7, 2015", 8 pgs.

"U.S. Appl. No. 14/956,724, Response filed Jun. 16, 2017 to Non Final Office Action mailed Mar. 31, 2017", 12 pgs.

"U.S. Appl. No. 14/956,724, Supplemental Preliminary Amendment filed Feb. 11, 2016", 7 pgs.

"U.S. Appl. No. 14/956,724, Supplemental Preliminary Amendment filed Oct. 3, 2016", 8 pgs.

"U.S. Appl. No. 14/983,108, Final Office Action mailed Aug. 30, 2018", 9 pgs.

"U.S. Appl. No. 14/983,108, Non Final Office Action mailed Apr. 10, 2018", 7 pgs.

"U.S. Appl. No. 14/983,108, Non Final Office Action mailed Nov. 5, 2018", 8 pgs.

"U.S. Appl. No. 14/983,108, Notice of Allowance mailed Mar. 8, 2019", 8 pgs.

"U.S. Appl. No. 14/983,108, Preliminary Amendment filed Dec. 30, 2015", 7 pgs.

"U.S. Appl. No. 14/983,108, Response filed Jan. 24, 2018 to Restriction Requirement mailed Dec. 4, 2017", 6 pgs.

"U.S. Appl. No. 14/983,108, Response filed Feb. 4, 2019 to Non Final Office Action mailed Nov. 5, 2018", 8 pgs.

"U.S. Appl. No. 14/983,108, Response filed Jun. 13, 2018 to Non Final Office Action mailed Apr. 10, 2018", 10 pgs.

"U.S. Appl. No. 14/983,108, Response filed Oct. 22, 2018 to Final Office Action mailed Aug. 30, 2018", 9 pgs.

"U.S. Appl. No. 14/983,108, Restriction Requirement mailed Dec. 4, 2017", 7 pgs.

"U.S. Appl. No. 14/983,747, Non Final Office Action mailed Apr. 9, 2018", 13 pgs.

"U.S. Appl. No. 14/983,747, Notice of Allowance mailed Sep. 24, 2018", 14 pgs.

"U.S. Appl. No. 14/983,747, Preliminary Amendment filed Jan. 4, 2016", 5 pgs.

"U.S. Appl. No. 14/983,747, Response filed Jan. 24, 2018 to Restriction Requirement mailed Dec. 20, 2017", 5 pgs.

"U.S. Appl. No. 14/983,747, Response filed Jun. 13, 2018 to Non Final Office Action mailed Apr. 9, 2018", 9 pgs.

"U.S. Appl. No. 14/983,747, Restriction Requirement mailed Dec. 20, 2017", 7 pgs.

"U.S. Appl. No. 14/983,747, Supplemental Response to Restriction Requirement filed Jan. 24, 2018", 5 pgs.

"U.S. Appl. No. 15/060,007, Corrected Notice of Allowability mailed May 1, 2019", 2 pgs.

"U.S. Appl. No. 15/060,007, Final Office Action mailed Jan. 3, 2019", 9 pgs.

"U.S. Appl. No. 15/060,007, Non Final Office Action mailed Nov. 9, 2018", 17 pgs.

"U.S. Appl. No. 15/060,007, Notice of Allowance mailed Mar. 6, 2019", 5 pgs.

"U.S. Appl. No. 15/060,007, Preliminary Amendment filed Mar. 9, 2016", 9 pgs.

"U.S. Appl. No. 15/060,007, Response filed Feb. 15, 2019 to Final Office Action mailed Jan. 3, 2019", 9 pgs.

"U.S. Appl. No. 15/060,007, Response filed Nov. 26, 2018 to Non Final Office Action mailed Nov. 9, 2018", 10 pgs.

"U.S. Appl. No. 15/061,352, Corrected Notice of Allowance mailed Feb. 12, 2018", 2 pgs.

"U.S. Appl. No. 15/061,352, Non Final Office Action mailed Nov. 17, 2017", 6 pgs.

"U.S. Appl. No. 15/061,352, Notice of Allowance mailed Jan. 19, 2018", 10 pgs.

"U.S. Appl. No. 15/061,352, Preliminary Amendment filed Mar. 7, 2016", 8 pgs.

"U.S. Appl. No. 15/061,352, Response filed Dec. 12, 2017 to Non Final Office Action mailed Nov. 17, 2017", 9 pgs.

"U.S. Appl. No. 15/074,553, Corrected Notice of Allowance mailed Feb. 12, 2018", 2 pgs.

(56) References Cited

OTHER PUBLICATIONS

"U.S. Appl. No. 15/074,553, Non Final Office Action mailed Nov. 17, 2017", 6 pgs.

"U.S. Appl. No. 15/074,553, Notice of Allowance mailed Jan. 19, 2018", 10 pgs.

"U.S. Appl. No. 15/074,553, Preliminary Amendment filed Mar. 21, 2016", 8 pgs.

"U.S. Appl. No. 15/074,553, Response filed Dec. 12, 2017 to Non Final Office Action mailed Nov. 17, 2017", 8 pgs.

"U.S. Appl. No. 15/131,663, Non Final Office Action mailed Oct. 2, 2018", 7 pgs.

"U.S. Appl. No. 15/131,663, Notice of Allowance mailed Mar. 19, 2019", 8 pgs.

"U.S. Appl. No. 15/131,663, Preliminary Amendment filed Dec. 21, 2016", 6 pgs.

"U.S. Appl. No. 15/131,663, Response Filed Jan. 2, 2019 to Non-Final Office Action Mailed Oct. 2, 2018", 9 pgs.

"U.S. Appl. No. 15/131,663, Response filed Jul. 13, 2018 to Restriction Requirement mailed May 18, 2018", 8 pgs.

"U.S. Appl. No. 15/131,663, Restriction Requirement mailed May 18, 2018", 7 pgs.

"U.S. Appl. No. 15/166,480, Notice of Allowance mailed Sep. 20, 2018", 12 pgs.

"U.S. Appl. No. 15/166,480, Response filed Jul. 18, 2018 to Restriction Requirement mailed May 21, 2018", 6 pgs.

"U.S. Appl. No. 15/166,480, Restriction Requirement mailed May 21, 2018", 6 pgs.

"U.S. Appl. No. 15/166,480, Supplemental Preliminary Amendment filed Jul. 18, 2017", 7 pgs.

"U.S. Appl. No. 15/200,546, Non Final Office Action mailed Oct. 15, 2018", 10 pgs.

"U.S. Appl. No. 15/200,546, Notice of Allowance mailed Mar. 19, 2019", 7 pgs.

"U.S. Appl. No. 15/200,546, Preliminary Amendment filed Dec. 21, 2016", 6 pgs.

"U.S. Appl. No. 15/200,546, Response Filed Jan. 15, 2019 to Non-Final Office Action Mailed Oct. 15, 2018", 10 pgs.

"U.S. Appl. No. 15/200,546, Response Filed Sep. 17, 2018 to Restriction Requirement Mailed Jul. 16, 2018", 8 pgs.

"U.S. Appl. No. 15/200,546, Restriction Requirement mailed Jul. 16, 2018", 6 pgs.

"U.S. Appl. No. 15/278,777, Non Final Office Action mailed Feb. 28, 2018", 14 pgs.

"U.S. Appl. No. 15/278,777, Notice of Allowance mailed Jul. 16, 2018", 8 pgs.

"U.S. Appl. No. 15/278,777, Preliminary Amendment filed Oct. 3, 2016", 7 pgs.

"U.S. Appl. No. 15/278,777, Response filed May 29, 2018 to Non Final Office action mailed Feb. 28, 2018", 11 pgs.

"U.S. Appl. No. 15/288,183, Corrected Notice of Allowability mailed Jun. 21, 2019", 7 pgs.

"U.S. Appl. No. 15/288,183, Non Final Office Action mailed Dec. 10, 2018", 13 pgs.

"U.S. Appl. No. 15/288,183, Notice of Allowance mailed May 9, 2019", 11 pgs.

"U.S. Appl. No. 15/288,183, Preliminary Amendment filed Oct. 31, 2016", 7 pgs.

"U.S. Appl. No. 15/288,183, Response filed Feb. 27, 2019 to Non Final Office Action mailed Dec. 10, 2018", 11 pgs.

"U.S. Appl. No. 15/288,183, Response filed Oct. 25, 2018 to Restriction Requirement mailed Sep. 12, 2018", 7 pgs.

"U.S. Appl. No. 15/288,183, Restriction Requirement mailed Sep. 12, 2018", 6 pgs.

"U.S. Appl. No. 15/288,183, Supplemental Preliminary Amendment filed Jul. 27, 2017", 7 pgs.

"U.S. Appl. No. 15/294,994, Examiner Interview Summary mailed Feb. 26, 2019", 3 pgs.

"U.S. Appl. No. 15/294,994, Final Office Action mailed Jan. 25, 2019", 13 pgs.

"U.S. Appl. No. 15/294,994, Non Final Office Action mailed Aug. 9, 2018", 9 pgs.

"U.S. Appl. No. 15/294,994, Notice of Allowance mailed May 22, 2019", 10 pgs.

"U.S. Appl. No. 15/294,994, Preliminary Amendment filed Jan. 25, 2017", 8 pgs.

"U.S. Appl. No. 15/294,994, Response filed Feb. 27, 2019 to Final Office Action mailed Jan. 25, 2019", 9 pgs.

"U.S. Appl. No. 15/294,994, Response filed Oct. 25, 2018 to Non Final Office Action mailed Aug. 9, 2018", 10 pgs.

"U.S. Appl. No. 15/294,994, Supplemental Preliminary Amendment filed May 31, 2017", 6 pgs.

"U.S. Appl. No. 15/297,844, Notice of Allowance mailed Aug. 30, 2018", 10 pgs.

"U.S. Appl. No. 15/297,844, Preliminary Amendment filed Oct. 20, 2016", 7 pgs.

"U.S. Appl. No. 15/297,844, Supplemental Preliminary Amendment filed Jan. 25, 2018", 6 pgs.

"U.S. Appl. No. 15/332,590, Notice of Allowance mailed Dec. 5, 2018", 13 pgs.

"U.S. Appl. No. 15/332,590, Preliminary Amendment filed Nov. 22, 2016", 5 pgs.

"U.S. Appl. No. 15/361,917, Advisory Action mailed Nov. 19, 2019", 3 pgs.

"U.S. Appl. No. 15/361,917, Final Office Action mailed Sep. 3, 2019", 8 pgs.

"U.S. Appl. No. 15/361,917, Non Final Office Action mailed Apr. 19, 2019", 11 pgs.

"U.S. Appl. No. 15/361,917, Notice of Allowance mailed Mar. 4, 2020", 8 pgs.

"U.S. Appl. No. 15/361,917, Preliminary Amendment filed Nov. 30, 2016", 6 pgs.

"U.S. Appl. No. 15/361,917, Response filed Feb. 14, 2019 to Restriction Requirement mailed Jan. 3, 2019", 6 pgs.

"U.S. Appl. No. 15/361,917, Response filed Jun. 19, 2019 to Non Final Office Action mailed Apr. 19, 2019", 9 pgs.

"U.S. Appl. No. 15/361,917, Response filed Nov. 4, 2019 to Final Office Action mailed Sep. 3, 2019", 8 pgs.

"U.S. Appl. No. 15/361,917, Restriction Requirement mailed Jan. 3, 2019", 6 pgs.

"U.S. Appl. No. 15/401,768, Non Final Office Action mailed Jul. 22, 2019", 10 pgs.

"U.S. Appl. No. 15/401,768, Notice of Allowance mailed Nov. 20, 2019", 9 pgs.

"U.S. Appl. No. 15/401,768, Preliminary Amendment filed Mar. 23, 2017", 6 pgs.

"U.S. Appl. No. 15/401,768, Response filed May 15, 2019 to Restriction Requirement mailed Mar. 15, 2019", 7 pgs.

"U.S. Appl. No. 15/401,768, Response filed Aug. 28, 2019 to Non Final Office Action mailed Jul. 22, 2019", 10 pgs.

"U.S. Appl. No. 15/401,768, Restriction Requirement mailed Mar. 15, 2019", 6 pgs.

"U.S. Appl. No. 15/401,768, Supplemental Preliminary Amendment filed Jun. 22, 2017", 7 pgs.

"U.S. Appl. No. 15/412,676, Non Final Office Action mailed Jul. 23, 2019", 11 pgs.

"U.S. Appl. No. 15/412,676, Notice of Allowance mailed Dec. 30, 2019", 8 pgs.

"U.S. Appl. No. 15/412,676, Preliminary Amendment filed Jul. 3, 2017", 7 pgs.

"U.S. Appl. No. 15/412,676, Response filed May 15, 2019 to Restriction Requirement mailed Mar. 15, 2019", 7 pgs.

"U.S. Appl. No. 15/412,676, Response filed Oct. 23, 2019 to Non Final Office Action mailed Jul. 23, 2019", 12 pgs.

"U.S. Appl. No. 15/412,676, Restriction Requirement mailed Mar. 15, 2019", 6 pgs.

"U.S. Appl. No. 15/455,895, Examiner Interview Summary mailed Nov. 25, 2019", 3 pgs.

"U.S. Appl. No. 15/455,895, Non Final Office Action mailed Sep. 5, 2019", 11 pgs.

"U.S. Appl. No. 15/455,895, Notice of Allowance mailed Feb. 13, 2020", 7 pgs.

(56)     References Cited

OTHER PUBLICATIONS

"U.S. Appl. No. 15/455,895, Preliminary Amendment filed Mar. 13, 2017", 6 pgs.

"U.S. Appl. No. 15/455,895, Response filed Jan. 28, 2020 to Non Final Office Action mailed Sep. 5, 2019", 14 pgs.

"U.S. Appl. No. 15/455,895, Supplemental Preliminary Amendment filed May 24, 2019", 6 pgs.

"U.S. Appl. No. 15/461,675, Non Final Office Action mailed Aug. 9, 2019", 10 pgs.

"U.S. Appl. No. 15/461,675, Notice of Allowance mailed Jan. 30, 2020", 7 pgs.

"U.S. Appl. No. 15/461,675, Preliminary Amendment filed Jun. 24, 2017", 6 pgs.

"U.S. Appl. No. 15/461,675, Response filed May 24, 2019 to Restriction Requirement mailed Mar. 26, 2019", 6 pgs.

"U.S. Appl. No. 15/461,675, Response filed Nov. 12, 2019 to Non Final Office Action mailed Aug. 9, 2019", 11 pgs.

"U.S. Appl. No. 15/461,675, Restriction Requirement mailed Mar. 26, 2019", 6 pgs.

"U.S. Appl. No. 15/461,675, Supplemental Preliminary Amendment filed Jun. 28, 2018", 7 pgs.

"U.S. Appl. No. 15/622,718, Examiner Interview Summary mailed Nov. 22, 2019", 3 pgs.

"U.S. Appl. No. 15/622,718, Non Final Office Action mailed Aug. 28, 2019", 14 pgs.

"U.S. Appl. No. 15/622,718, Notice of Allowance mailed Feb. 13, 2020", 8 pgs.

"U.S. Appl. No. 15/622,718, Preliminary Amendment filed Jun. 15, 2017", 7 pgs.

"U.S. Appl. No. 15/622,718, Response filed Jan. 28, 2020 to Non Final Office Action mailed Aug. 28, 2019", 11 pgs.

"U.S. Appl. No. 15/622,718, Response filed Jul. 31, 2019 to Restriction Requirement mailed Jun. 7, 2019", 8 pgs.

"U.S. Appl. No. 15/622,718, Restriction Requirement mailed Jun. 7, 2019", 6 pgs.

"U.S. Appl. No. 15/626,384, Non Final Office Action mailed May 3, 2019", 14 pgs.

"U.S. Appl. No. 15/626,384, Notice of Allowability mailed Oct. 18, 2019", 2 pgs.

"U.S. Appl. No. 15/626,384, Notice of Allowance mailed Aug. 21, 2019", 7 pgs.

"U.S. Appl. No. 15/626,384, Preliminary Amendment filed Aug. 10, 2018", 11 pgs.

"U.S. Appl. No. 15/626,384, Response filed Jul. 31, 2019 to Non-Final Office Action mailed May 3, 2019", 13 pgs.

"U.S. Appl. No. 15/654,386, Non Final Office Action mailed Nov. 7, 2019", 10 pgs.

"U.S. Appl. No. 15/654,386, Notice of Allowance mailed Feb. 20, 2020", 8 pgs.

"U.S. Appl. No. 15/654,386, Preliminary Amendment filed Aug. 30, 2017", 11 pgs.

"U.S. Appl. No. 15/654,386, Response filed Feb. 5, 2020 to Non Final Office Action mailed Nov. 7, 2019", 12 pgs.

"U.S. Appl. No. 15/654,386, Response filed Aug. 23, 2019 to Restriction Requirement mailed Jul. 16, 2019", 9 pgs.

"U.S. Appl. No. 15/654,386, Restriction Requirement mailed Jul. 16, 2019", 6 pgs.

"U.S. Appl. No. 15/659,689, Non Final Office Action mailed Oct. 31, 2018", 13 pgs.

"U.S. Appl. No. 15/659,689, Preliminary Amendment filed Jul. 26, 2017", 7 pgs.

"U.S. Appl. No. 15/662,572, Non Final Office Action mailed Oct. 10, 2019", 14 pgs.

"U.S. Appl. No. 15/662,572, Notice of Allowance mailed Mar. 11, 2020", 9 pgs.

"U.S. Appl. No. 15/662,572, Preliminary Amendment filed Jul. 31, 2017", 7 pgs.

"U.S. Appl. No. 15/662,572, Response filed Jan. 8, 2020 to Non Final Office Action mailed Oct. 10, 2019", 10 pgs.

"U.S. Appl. No. 15/662,572, Response filed Aug. 23, 2019 to Retsriction Requirement mailed Jul. 1, 2019", 8 pgs.

"U.S. Appl. No. 15/662,572, Restriction Requirement mailed Jul. 1, 2019", 6 pgs.

"U.S. Appl. No. 15/664,572, Non Final Office Action mailed May 15, 2019", 8 pgs.

"U.S. Appl. No. 15/664,572, Notice of Allowance mailed Jun. 12, 2019", 8 pgs.

"U.S. Appl. No. 15/664,572, Preliminary Amendment filed Aug. 3, 2017", 7 pgs.

"U.S. Appl. No. 15/664,572, Response filed May 17, 2019 to Non Final Office Action mailed May 15, 2019", 9 pgs.

"U.S. Appl. No. 15/682,187, Non Final Office Action mailed Dec. 16, 2019", 10 pgs.

"U.S. Appl. No. 15/682,187, Notice of Allowance mailed Mar. 25, 2020", 9 pgs.

"U.S. Appl. No. 15/682,187, Preliminary Amendment filed Sep. 7, 2017", 6 pgs.

"U.S. Appl. No. 15/682,187, Response filed Feb. 27, 2020 to Non Final Office Action mailed Dec. 16, 2019", 11 pgs.

"U.S. Appl. No. 15/682,187, Response filed Sep. 18, 2019 to Restriction Requirement mailed Aug. 9, 2019", 7 pgs.

"U.S. Appl. No. 15/682,187, Restriction Requirement mailed Aug. 9, 2019", 6 pgs.

"U.S. Appl. No. 15/703,727, Non Final Office Action mailed Aug. 1, 2019", 11 pgs.

"U.S. Appl. No. 15/703,727, Notice of Allowance mailed Nov. 20, 2019", 7 pgs.

"U.S. Appl. No. 15/703,727, Preliminary Amendment filed Sep. 14, 2017", 7 pgs.

"U.S. Appl. No. 15/703,727, Response filed Nov. 1, 2019 to Non Final Office Action mailed Aug. 1, 2019", 10 pgs.

"U.S. Appl. No. 15/715,731, Non Final Office Action mailed Jan. 21, 2020", 8 pgs.

"U.S. Appl. No. 15/715,731, Notice of Allowance mailed Apr. 8, 2020", 9 pgs.

"U.S. Appl. No. 15/715,731, Preliminary Amendment Filed Sep. 26, 2017", 9 pgs.

"U.S. Appl. No. 15/715,731, Response filed Feb. 27, 2020 to Non Final Office Action mailed Jan. 21, 2020", 12 pgs.

"U.S. Appl. No. 15/715,731, Response Filed Nov. 4, 2019 to Restriction Requirement Mailed Sep. 4, 2019", 9 pgs.

"U.S. Appl. No. 15/715,731, Restriction Requirement mailed Sep. 4, 2019", 6 pgs.

"U.S. Appl. No. 15/715,731, Supplemental Preliminary Amendment filed Dec. 29, 2017", 8 pgs.

"U.S. Appl. No. 15/720,997, Advisory Action mailed Jun. 15, 2021", 3 pgs.

"U.S. Appl. No. 15/720,997, Advisory Action mailed Oct. 13, 2020", 2 pgs.

"U.S. Appl. No. 15/720,997, Final Office Action mailed Apr. 7, 2021", 9 pgs.

"U.S. Appl. No. 15/720,997, Final Office Action mailed Aug. 4, 2020", 10 pgs.

"U.S. Appl. No. 15/720,997, Non Final Office Action mailed Jan. 6, 2020", 10 pgs.

"U.S. Appl. No. 15/720,997, Non Final Office Action mailed Jul. 16, 2019", 11 pgs.

"U.S. Appl. No. 15/720,997, Non Final Office Action mailed Nov. 23, 2020", 7 pgs.

"U.S. Appl. No. 15/720,997, Notice of Allowance mailed Jul. 29, 2021", 7 pgs.

"U.S. Appl. No. 15/720,997, Preliminary Amendment filed Oct. 2, 2017", 6 pgs.

"U.S. Appl. No. 15/720,997, Response filed Jan. 25, 2021 to Non Final Office Action mailed Nov. 23, 2020", 9 pgs.

"U.S. Appl. No. 15/720,997, Response filed Mar. 27, 2020 to Non Final Office Action mailed Jan. 6, 2020", 10 pgs.

"U.S. Appl. No. 15/720,997, Response filed Jun. 2, 2021 to Final Office Action mailed Apr. 7, 2021", 9 pgs.

"U.S. Appl. No. 15/720,997, Response filed Jul. 7, 2021 to Advisory Action mailed Jun. 15, 2021", 6 pgs.

(56)                    References Cited

OTHER PUBLICATIONS

"U.S. Appl. No. 15/720,997, Response filed Sep. 30, 2020 to Final Office Action mailed Aug. 4, 2020", 11 pgs.

"U.S. Appl. No. 15/720,997, Response filed Oct. 3, 2019 to Non-Final Office Action mailed Jul. 16, 2019", 9 pgs.

"U.S. Appl. No. 15/722,002, Non Final Office Action mailed Feb. 4, 2020", 8 pgs.

"U.S. Appl. No. 15/722,002, Notice of Allowance mailed Apr. 8, 2020", 7 pgs.

"U.S. Appl. No. 15/722,002, Preliminary Amendment filed Jun. 29, 2018", 5 pgs.

"U.S. Appl. No. 15/722,002, Response filed Mar. 5, 2020 to Non Final Office Action mailed Feb. 4, 2020", 7 pgs.

"U.S. Appl. No. 15/722,002, Response filed Nov. 14, 2019 to Restriction Requirement mailed Sep. 17, 2019", 6 pgs.

"U.S. Appl. No. 15/722,002, Restriction Requirement mailed Sep. 17, 2019", 6 pgs.

"U.S. Appl. No. 15/793,216, Examiner Interview Summary mailed Nov. 4, 2019", 4 pgs.

"U.S. Appl. No. 15/793,216, Non Final Office Action mailed Aug. 1, 2019", 21 pgs.

"U.S. Appl. No. 15/793,216, Notice of Allowance mailed Mar. 23, 2020", 7 pgs.

"U.S. Appl. No. 15/793,216, Preliminary Amendment filed Oct. 26, 2017", 8 pgs.

"U.S. Appl. No. 15/793,216, Response filed Jan. 28, 2020 to Non Final Office Action mailed Aug. 1, 2019", 13 pgs.

"U.S. Appl. No. 15/865,938, Notice of Allowance mailed Sep. 17, 2019", 11 pgs.

"U.S. Appl. No. 15/865,938, Preliminary Amendment filed Jan. 10, 2018", 7 pgs.

"U.S. Appl. No. 15/866,089, Corrected Notice of Allowability mailed Aug. 27, 2020", 2 pgs.

"U.S. Appl. No. 15/866,089, Final Office Action mailed Mar. 25, 2020", 15 pgs.

"U.S. Appl. No. 15/866,089, Non Final Office Action mailed Dec. 4, 2019", 16 pgs.

"U.S. Appl. No. 15/866,089, Notice of Allowance mailed Jul. 15, 2020", 5 pgs.

"U.S. Appl. No. 15/866,089, Preliminary Amendment filed Jan. 10, 2018", 10 pgs.

"U.S. Appl. No. 15/866,089, Response filed Feb. 27, 2020 to Non Final Office Action mailed Dec. 4, 2019", 10 pgs.

"U.S. Appl. No. 15/866,089, Response filed Jun. 18, 2020 to Final Office Action mailed Mar. 25, 2020", 11 pgs.

"U.S. Appl. No. 15/886,712, Non Final Office Action mailed Sep. 27, 2019", 8 pgs.

"U.S. Appl. No. 15/886,712, Notice of Allowance mailed Nov. 14, 2019", 7 pgs.

"U.S. Appl. No. 15/886,712, Preliminary Amendment filed Feb. 2, 2018", 8 pgs.

"U.S. Appl. No. 15/886,712, Response filed Oct. 18, 2019 to Non Final Office Action mailed Sep. 27, 2019", 9 pgs.

"U.S. Appl. No. 15/891,049, Examiner Interview Summary mailed Aug. 10, 2020", 3 pgs.

"U.S. Appl. No. 15/891,049, Examiner Interview Summary mailed Dec. 4, 2020", 2 pgs.

"U.S. Appl. No. 15/891,049, Final Office Action mailed Nov. 10, 2020", 10 pgs.

"U.S. Appl. No. 15/891,049, Non Final Office Action mailed Jul. 14, 2020", 16 pgs.

"U.S. Appl. No. 15/891,049, Notice of Allowance mailed Dec. 22, 2020", 8 pgs.

"U.S. Appl. No. 15/891,049, Preliminary Amendment filed Feb. 8, 2018", 6 pgs.

"U.S. Appl. No. 15/891,049, Response filed May 29, 2020 to Restriction Requirement mailed May 5, 2020", 9 pgs.

"U.S. Appl. No. 15/891,049, Response filed Aug. 17, 2020 to Non Final Office Action mailed Jul. 14, 2020", 18 pgs.

"U.S. Appl. No. 15/891,049, Response filed Dec. 1, 2020 to Final Office Action mailed Nov. 10, 2020", 12 pgs.

"U.S. Appl. No. 15/891,049, Restriction Requirement mailed May 5, 2020", 6 pgs.

"U.S. Appl. No. 15/891,049, Supplemental Preliminary Amendment filed Dec. 20, 2019", 8 pgs.

"U.S. Appl. No. 15/903,261, Notice of Allowance mailed Mar. 26, 2020", 9 pgs.

"U.S. Appl. No. 15/903,261, Preliminary Amendment filed Feb. 28, 2018", 6 pgs.

"U.S. Appl. No. 15/917,143, Non Final Office Action mailed Aug. 7, 2020", 6 pgs.

"U.S. Appl. No. 15/917,143, Notice of Allowance mailed Feb. 24, 2021", 8 pgs.

"U.S. Appl. No. 15/917,143, Preliminary Amendment filed Mar. 14, 2018", 7 pgs.

"U.S. Appl. No. 15/917,143, Response filed Jun. 17, 2020 to Restriction Requirement mailed May 5, 2020", 8 pgs.

"U.S. Appl. No. 15/917,143, Response filed Oct. 29, 2020 to Non Final Office Action mailed Aug. 7, 2020", 11 pgs.

"U.S. Appl. No. 15/917,143, Restriction Requirement mailed May 5, 2020", 6 pgs.

"U.S. Appl. No. 15/941,481, Non Final Office Action mailed Aug. 14, 2020", 21 pgs.

"U.S. Appl. No. 15/941,481, Notice of Allowance mailed Dec. 3, 2020", 8 pgs.

"U.S. Appl. No. 15/941,481, Preliminary Amendment filed Mar. 30, 2018", 7 pgs.

"U.S. Appl. No. 15/941,481, Response filed Jun. 24, 2020 to Restriction Requirement mailed May 19, 2020", 8 pgs.

"U.S. Appl. No. 15/941,481, Response filed Nov. 16, 2020 to Non Final Office Action mailed Aug. 14, 2020", 15 pgs.

"U.S. Appl. No. 15/941,481, Restriction Requirement mailed May 19, 2020", 7 pgs.

"U.S. Appl. No. 15/945,425, Non Final Office Action mailed Aug. 25, 2020", 11 pgs.

"U.S. Appl. No. 15/945,425, Notice of Allowance mailed Dec. 24, 2020", 8 pgs.

"U.S. Appl. No. 15/945,425, Preliminary Amendment filed Apr. 5, 2018", 8 pgs.

"U.S. Appl. No. 15/945,425, Response filed Jun. 24, 2020 to Restriction Requirement mailed May 19, 2020", 7 pgs.

"U.S. Appl. No. 15/945,425, Response filed Nov. 23, 2020 to Non Final Office Action mailed Aug. 25, 2020", 10 pgs.

"U.S. Appl. No. 15/945,425, Restriction Requirement mailed May 19, 2020", 7 pgs.

"U.S. Appl. No. 15/945,425, Supplemental Preliminary Amendment filed May 10, 2018", 6 pgs.

"U.S. Appl. No. 15/956,444, Non Final Office Action mailed Dec. 7, 2020", 7 pgs.

"U.S. Appl. No. 15/956,444, Notice of Allowance mailed Mar. 11, 2021", 8 pgs.

"U.S. Appl. No. 15/956,444, Preliminary Amendment filed Apr. 19, 2018", 7 pgs.

"U.S. Appl. No. 15/956,444, PTO Response to Rule 312 Communication mailed Jun. 8, 2021", 2 pgs.

"U.S. Appl. No. 15/956,444, Response filed Feb. 23, 2021 to Non Final Office Action mailed Dec. 7, 2020", 11 pgs.

"U.S. Appl. No. 15/956,444, Response filed Sep. 14, 2020 to Restriction Requirement mailed Jul. 14, 2020", 8 pgs.

"U.S. Appl. No. 15/956,444, Restriction Requirement mailed Jul. 14, 2020", 7 pgs.

"U.S. Appl. No. 15/972,646, Non Final Office Action mailed Dec. 7, 2020", 11 pgs.

"U.S. Appl. No. 15/972,646, Notice of Allowance mailed Apr. 21, 2021", 8 pgs.

"U.S. Appl. No. 15/972,646, Preliminary Amendment filed May 9, 2018", 6 pgs.

"U.S. Appl. No. 15/972,646, Response filed Feb. 22, 2021 to Non Final Office Action mailed Dec. 7, 2020", 13 pgs.

"U.S. Appl. No. 15/972,646, Response filed Sep. 21, 2020 to Restriction Requirement mailed Jul. 27, 2020", 7 pgs.

(56)  References Cited

OTHER PUBLICATIONS

"U.S. Appl. No. 15/972,646, Restriction Requirement mailed Jul. 27, 2020", 6 pgs.
"U.S. Appl. No. 16/160,559, 312 Amendment filed Dec. 9, 2021", 7 pgs.
"U.S. Appl. No. 16/160,559, Non Final Office Action mailed May 14, 2021", 12 pgs.
"U.S. Appl. No. 16/160,559, Notice of Allowance mailed Sep. 16, 2021", 14 pgs.
"U.S. Appl. No. 16/160,559, Preliminary Amendment filed Oct. 17, 2018", 6 pgs.
"U.S. Appl. No. 16/160,559, PTO Response to Rule 312 Communication mailed Dec. 24, 2021", 2 pgs.
"U.S. Appl. No. 16/160,559, Response filed Mar. 2, 2021 to Restriction Requirement mailed Jan. 27, 2021", 7 pgs.
"U.S. Appl. No. 16/160,559, Response filed Aug. 11, 2021 to Non Final Office Action mailed May 14, 2021", 10 pgs.
"U.S. Appl. No. 16/160,559, Restriction Requirement mailed Jan. 27, 2021", 6 pgs.
"U.S. Appl. No. 16/251,342, Notice of Allowance mailed Jul. 26, 2021", 8 pgs.
"U.S. Appl. No. 16/251,342, Preliminary Amendment filed Jan. 21, 2019", 6 pgs.
"U.S. Appl. No. 16/251,342, Response filed May 3, 2021 to Restriction Requirement mailed Apr. 30, 2021", 8 pgs.
"U.S. Appl. No. 16/251,342, Restriction Requirement mailed Apr. 30, 2021", 6 pgs.
"U.S. Appl. No. 16/251,342, Supplemental Preliminary Amendment filed Oct. 28, 2020", 7 pgs.
"U.S. Appl. No. 16/251,342, Supplemental Preliminary Amendment filed Nov. 4, 2020", 7 pgs.
"U.S. Appl. No. 16/255,300 Supplemental Preliminary Amendment Filed Nov. 12, 2020", 8 pgs.
"U.S. Appl. No. 16/255,300, Notice of Allowance mailed Jul. 19, 2021", 10 pgs.
"U.S. Appl. No. 16/255,300, Preliminary Amendment filed Jan. 24, 2019", 6 pgs.
"U.S. Appl. No. 16/380,742, Notice of Allowance mailed Jan. 3, 2022", 13 pgs.
"U.S. Appl. No. 16/380,742, Preliminary Amendment filed Apr. 12, 2019", 6 pgs.
"U.S. Appl. No. 16/380,742, Response filed Oct. 20, 2021 to Restriction Requirement mailed Aug. 20, 2021", 6 pgs.
"U.S. Appl. No. 16/380,742, Restriction Requirement mailed Aug. 20, 2021", 7 pgs.
"U.S. Appl. No. 16/380,742, Supplemental Preliminary Amendment filed Mar. 1, 2021", 5 pgs.
"U.S. Appl. No. 16/400,199, Non Final Office Action mailed Feb. 10, 2022", 8 pgs.
"U.S. Appl. No. 16/400,199, Notice of Allowance mailed May 11, 2022", 8 pgs.
"U.S. Appl. No. 16/400,199, Preliminary Amendment filed May 7, 2019", 7 pgs.
"U.S. Appl. No. 16/400,199, Response filed Apr. 13, 2022 to Non Final Office Action mailed Feb. 10, 2022", 11 pgs.
"U.S. Appl. No. 16/400,199, Response filed Nov. 15, 2021 to Restriction Requirement mailed Oct. 1, 2021", 8 pgs.
"U.S. Appl. No. 16/400,199, Restriction Requirement mailed Oct. 1, 2021", 7 pgs.
"U.S. Appl. No. 16/420,676, Non Final Office Action mailed Jul. 20, 2021", 11 pgs.
"U.S. Appl. No. 16/420,676, Notice of Allowance mailed Nov. 15, 2021", 9 pgs.
"U.S. Appl. No. 16/420,676, Preliminary Amendment filed Jun. 3, 2019", 5 pgs.
"U.S. Appl. No. 16/420,676, Response filed Oct. 20, 2021 to Non Final Office Action mailed Jul. 20, 2021", 14 pgs.
"U.S. Appl. No. 16/428,277, Corrected Notice of Allowability mailed Sep. 16, 2022", 6 pgs.
"U.S. Appl. No. 16/428,277, Non Final Office Action mailed May 24, 2022", 7 pgs.
"U.S. Appl. No. 16/428,277, Notice of Allowance mailed Aug. 25, 2022", 9 pgs.
"U.S. Appl. No. 16/428,277, Preliminary Amendment filed Jun. 3, 2019", 5 pgs.
"U.S. Appl. No. 16/428,277, Response filed Apr. 11, 2022 to Restriction Requirement mailed Feb. 11, 2022", 8 pgs.
"U.S. Appl. No. 16/428,277, Response filed Aug. 3, 2022 to Non Final Office Action mailed May 24, 2022", 8 pgs.
"U.S. Appl. No. 16/428,277, Restriction Requirement mailed Feb. 11, 2022", 6 pgs.
"U.S. Appl. No. 16/436,023, Examiner Interview Summary mailed Aug. 23, 2021", 2 pgs.
"U.S. Appl. No. 16/436,023, Non Final Office Action mailed May 19, 2021", 18 pgs.
"U.S. Appl. No. 16/436,023, Notice of Allowance mailed Oct. 27, 2021", 8 pgs.
"U.S. Appl. No. 16/436,023, Preliminary Amendment filed Jun. 12, 2019", 6 pgs.
"U.S. Appl. No. 16/436,023, Response filed Aug. 19, 2021 to Non Final Office actio mailed May 19, 2021", 9 pgs.
"U.S. Appl. No. 16/443,391, Non Final Office Action mailed Aug. 31, 2021", 11 pgs.
"U.S. Appl. No. 16/443,391, Notice of Allowance mailed Jan. 7, 2022", 5 pgs.
"U.S. Appl. No. 16/443,391, Preliminary Amendment filed Jun. 19, 2019", 6 pgs.
"U.S. Appl. No. 16/443,391, Response filed Nov. 15, 2021 to Non Final Office Action mailed Aug. 31, 2021", 9 pgs.
"U.S. Appl. No. 16/508,764, Notice of Allowance mailed Oct. 20, 2021", 10 pgs.
"U.S. Appl. No. 16/508,764, Preliminary Amendment filed Jul. 12, 2019", 7 pgs.
"U.S. Appl. No. 16/508,764, Supplemental Amendment filed Sep. 30, 2021", 6 pgs.
"U.S. Appl. No. 16/544,293, Corrected Notice of Allowability mailed Mar. 17, 2023", 7 pgs.
"U.S. Appl. No. 16/544,293, Non Final Office Action mailed Sep. 21, 2022", 14 pgs.
"U.S. Appl. No. 16/544,293, Notice of Allowance mailed Mar. 8, 2023", 11 pgs.
"U.S. Appl. No. 16/544,293, Preliminary Amendment filed Aug. 21, 2019", 7 pgs.
"U.S. Appl. No. 16/544,293, Response filed Aug. 15, 2022 to Restriction Requirement mailed Jul. 7, 2022", 7 pgs.
"U.S. Appl. No. 16/544,293, Response filed Nov. 28, 2022 to Non-Final Office Action mailed Sep. 21, 2022", 10 pgs.
"U.S. Appl. No. 16/544,293, Restriction Requirement mailed Jul. 7, 2022", 6 pgs.
"U.S. Appl. No. 16/544,293, Supplemental Preliminary Amendment filed Oct. 28, 2020", 6 pgs.
"U.S. Appl. No. 16/593,022, Preliminary Amendment filed Oct. 30, 2019", 8 pgs.
"U.S. Appl. No. 16/593,022, Response filed Sep. 9, 2022 to Restriction Requirement mailed Sep. 6, 2022", 8 pgs.
"U.S. Appl. No. 16/593,022, Response filed Nov. 4, 2022 to Restriction Requirement mailed Oct. 31, 2022", 8 pgs.
"U.S. Appl. No. 16/593,022, Restriction Requirement mailed Sep. 6, 2022", 6 pgs.
"U.S. Appl. No. 16/593,022, Restriction Requirement mailed Oct. 31, 2022", 6 pgs.
"U.S. Appl. No. 16/593,022, Supplemental Amendment filed Nov. 7, 2022 to Restriction Requirement mailed Oct. 31, 2022", 9 pgs.
"U.S. Appl. No. 16/593,022, Supplemental Preliminary Amendment filed Oct. 21, 2020", 8 pgs.
"U.S. Appl. No. 16/593,022, Supplemental Preliminary Amendment filed Dec. 5, 2019", 8 pgs.
"U.S. Appl. No. 16/593,022, Supplemental Preliminary Amendment filed Dec. 20, 2019", 5 pgs.
"U.S. Appl. No. 16/690,671, Non Final Office Action mailed Nov. 15, 2021", 8 pgs.

(56) References Cited

OTHER PUBLICATIONS

"U.S. Appl. No. 16/690,671, Notice of Allowance mailed Mar. 2, 2022", 7 pgs.
"U.S. Appl. No. 16/690,671, Preliminary Amendment filed Dec. 11, 2019", 7 pgs.
"U.S. Appl. No. 16/690,671, Response filed Feb. 4, 2022 to Non Final Office Action mailed Nov. 15, 2021", 10 pgs.
"U.S. Appl. No. 16/795,181, Examiner Interview Summary mailed Apr. 15, 2022", 2 pgs.
"U.S. Appl. No. 16/795,181, Final Office Action mailed Jun. 7, 2022", 12 pgs.
"U.S. Appl. No. 16/795,181, Non Final Office Action mailed Jan. 24, 2022", 12 pgs.
"U.S. Appl. No. 16/795,181, Notice of Allowance mailed Aug. 25, 2022", 7 pgs.
"U.S. Appl. No. 16/795,181, Preliminary Amendment filed Feb. 20, 2020", 6 pgs.
"U.S. Appl. No. 16/795,181, Response filed Apr. 14, 2022 to Non Final Office Action mailed Jan. 24, 2022", 9 pgs.
"U.S. Appl. No. 16/795,181, Response filed Aug. 3, 2022 to Final Office Action mailed Jun. 7, 2022", 8 pgs.
"U.S. Appl. No. 16/802,228, Notice of Allowance mailed Jun. 15, 2022", 10 pgs.
"U.S. Appl. No. 16/802,228, Preliminary Amendment filed Mar. 4, 2020", 7 pgs.
"U.S. Appl. No. 16/802,248, Non Final Office Action mailed Jun. 17, 2022", 18 pgs.
"U.S. Appl. No. 16/802,248, Notice of Allowance mailed Oct. 28, 2022", 9 pgs.
"U.S. Appl. No. 16/802,248, Preliminary Amendment filed Mar. 5, 2020", 8 pgs.
"U.S. Appl. No. 16/802,248, Response filed Sep. 14, 2022 to Non Final Office Action mailed Jun. 17, 2022", 12 pgs.
"U.S. Appl. No. 16/806,611, Notice of Allowance mailed Feb. 15, 2023", 10 pgs.
"U.S. Appl. No. 16/806,611, Preliminary Amendment filed Mar. 4, 2020", 7 pgs.
"U.S. Appl. No. 16/806,611, Response filed Sep. 9, 2022 to Restriction Requirement mailed Aug. 26, 2022", 9 pgs.
"U.S. Appl. No. 16/806,611, Response filed Nov. 7, 2022 to Restriction Requirement mailed Nov. 1, 2022", 9 pgs.
"U.S. Appl. No. 16/806,611, Restriction Requirement mailed Aug. 26, 2022", 6 pgs.
"U.S. Appl. No. 16/806,611, Restriction Requirement mailed Nov. 1, 2022", 6 pgs.
"U.S. Appl. No. 16/895,246, Non Final Office Action mailed Dec. 13, 2022", 8 pgs.
"U.S. Appl. No. 16/895,246, Notice of Allowance mailed Apr. 5, 2023", 13 pgs.
"U.S. Appl. No. 16/895,246, Preliminary Amendment filed Jun. 9, 2020", 6 pgs.
"U.S. Appl. No. 16/895,246, Response filed Jan. 11, 2023 to Non Final Office Action mailed Dec. 13, 2022", 8 pgs.
"U.S. Appl. No. 16/895,246, Response filed Sep. 28, 2022 to Restriction Requirement mailed Sep. 9, 2022", 7 pgs.
"U.S. Appl. No. 16/895,246, Restriction Requirement mailed Sep. 9, 2022", 6 pgs.
"U.S. Appl. No. 16/987,001, Notice of Allowance mailed Feb. 17, 2023", 15 pgs.
"U.S. Appl. No. 16/989,386, Non Final Office Action mailed Mar. 15, 2023", 13 pgs.
"U.S. Appl. No. 16/989,386, Notice of Allowance mailed Jul. 26, 2023", 9 pgs.
"U.S. Appl. No. 16/989,386, PTO Response to Rule 312 Communication mailed Oct. 19, 2023", 2 pgs.
"U.S. Appl. No. 16/989,386, Response filed May 19, 2023 to Non Final Office Action mailed Mar. 15, 2023", 11 pgs.
"U.S. Appl. No. 16/989,386, Response filed Dec. 5, 2022 to Restriction Requirement mailed Nov. 14, 2022", 9 pgs.

"U.S. Appl. No. 16/989,386, Restriction Requirement mailed Nov. 14, 2022", 6 pgs.
"U.S. Appl. No. 16/989,386, Supplemental Preliminary Amendment filed Oct. 21, 2020", 8 pgs.
"U.S. Appl. No. 17/190,686, Notice of Allowance mailed Oct. 5, 2023", 8 pgs.
"U.S. Appl. No. 17/190,686, Preliminary Amendment filed Mar. 10, 2021", 7 pgs.
"U.S. Appl. No. 17/190,686, Restriction Requirement mailed Jun. 6, 2023", 7 pgs.
"U.S. Appl. No. 17/190,686, Supplemental Amendment filed Apr. 12, 2023", 9 pgs.
"U.S. Appl. No. 17/232,672, Preliminary Amendment filed Apr. 19, 2021", 5 pgs.
"U.S. Appl. No. 17/392,971, Preliminary Amendment filed Aug. 18, 2021", 9 pgs.
"U.S. Appl. No. 17/492,082, Notice of Allowance mailed Apr. 17, 2023", 8 pgs.
"U.S. Appl. No. 17/492,082, Preliminary Amendment filed Oct. 25, 2021", 6 pgs.
"U.S. Appl. No. 17/516,664, Preliminary Amendment filed Nov. 10, 2021", 6 pgs.
"U.S. Appl. No. 17/545,668, Notice of Allowance mailed Jun. 22, 2023", 7 pgs.
"U.S. Appl. No. 17/545,668, Preliminary Amendment filed Dec. 9, 2021", 5 pgs.
"U.S. Appl. No. 17/550,074, Preliminary Amendment filed Dec. 15, 2021", 5 pgs.
"U.S. Appl. No. 17/577,188, Preliminary Amendment filed Jan. 19, 2022", 7 pgs.
"U.S. Appl. No. 17/940,022, Preliminary Amendment filed Sep. 26, 2022", 6 pgs.
"U.S. Appl. No. 17/991,832, Preliminary Amendment filed Dec. 14, 2022", 6 pgs.
"U.S. Appl. No. 17/190,686, Response filed Aug. 3, 2023 to Restriction Requirement mailed Jun. 6, 2023", 9 pgs.
"U.S. Appl. No. 18/093,114, Supplemental Amendment filed Jan. 11, 2023", 6 pgs.
"U.S. Appl. No. 18/101,490, Supplemental Preliminary Amendment filed Jan. 26, 2023", 7 pgs.
"U.S. Appl. No. 18/102,518, Preliminary Amendment filed Jan. 30, 2023", 6 pgs.
"U.S. Appl. No. 18/126,022, Preliminary Amendment filed Apr. 28, 2023", 6 pgs.
"U.S. Appl. No. 18/134,897, Supplemental Amendment filed Nov. 1, 2023", 8 pgs.
"U.S. Appl. No. 18/134,897, Supplemental Preliminary Amendment filed Apr. 17, 2023", 6 pgs.
"U.S. Appl. No. 18/235,540, Supplemental Preliminary Amendment filed Aug. 30, 2023", 5 pgs.
"U.S. Appl. No. 18/471,089, Supplemental Preliminary Amendment filed Sep. 21, 2023", 7 pgs.
"U.S. Appl. No. 18/497,342, Supplemental Amendment filed Nov. 1, 2023", 7 pgs.
"U.S. Appl. No. 18/514,936, Preliminary Amendment filed Nov. 20, 2023", 4 pgs.
"U.S. Appl. No. 18/514,936, Supplemental Amendment filed Nov. 22, 2023", 6 pgs.
"Arthroscopic Meniscal Repair using the Meniscal Cinch™", Surgical Technique brochure. Arthrex®, 6 sheets, (2008), 6 sheets.
"Australian Application Serial No. 2014236885, First Examination Report mailed Dec. 11, 2017", 2 pgs.
"Australian Application Serial No. 2014236885, Response filed Feb. 14, 2018 to First Examination Report mailed Dec. 11, 2017", 6 pgs.
"Bio-Intrafix Tibial Soft Tissue Fastener, Building on the Legacy of IntraFix", DePuy Mitek brochure, (Feb. 2007), 6 pgs.
"Bio-Intrafix (TCP/PLA) & Intrafix, Tibial Soft Tissue Fasteners", DePuy Mitek, ((date unknown)), 6 pgs.
"Biomechanical Evaluation of the Biomet Sports Medicine JurggerKnot™ Soft Anchor in Porcine Bone", Study completed Jan. 2010. Biomet Sports Medicine Research and Develo ment, Warsaw, Indiana, (Jan. 2010), 2 pgs.

(56)                    References Cited

OTHER PUBLICATIONS

"Canadian Application Serial No. 2906596, Office Action mailed Feb. 26, 2018", 3 pgs.
"Chinese Application Serial No. 201480027708.4, Office Action mailed Feb. 14, 2017", (W/ English Translation), 18 pgs.
"Chinese Application Serial No. 201480027708.4, Office Action mailed May 26, 2016", W/ English Translation, 15 pgs.
"Chinese Application Serial No. 201480027708.4, Office Action mailed Aug. 18, 2017", (W/ English Translation), 8 pgs.
"Chinese Application Serial No. 201480027708.4, Response filed May 2, 2017 to Office Action mailed Feb. 14, 2017", (W/ English Translation), 17 pgs.
"Chinese Application Serial No. 201480027708.4, Response filed Oct. 10, 2016 to Office Action mailed May 26, 2016", (W/ English Translation of Claims), 14 pgs.
"Chinese Application Serial No. 201480027708.4, Response filed Oct. 31, 2017 to Office Action mailed Aug. 18, 2017", (W/ English Claims), 7 pgs.
"Declaration of John White regarding PSCD and Customized Device and Exhibits 1-5".
"Do your next distal tendon repair with . . . The Lubbers Technique", Teno Fix® brochure, Ortheon® Medical, (2003), 2 pgs.
"European Application No. 16168202.6, Extended European Search Report mailed Aug. 16, 2017", 11 pgs.
"European Application No. 16168202.6, Response filed Nov. 3, 2017 to Extended European Search Report mailed Aug. 16, 2017", 9 pgs.
"European Application Serial No. 10727548.9, Examination Notification Art. 94(3) mailed Sep. 18, 2014", 6 pgs.
"European Application Serial No. 10727548.9, Office Action mailed Jan. 11, 2016", 6 pgs.
"European Application Serial No. 10727548.9, Office Action mailed Jan. 19, 2012", 2 pgs.
"European Application Serial No. 10727548.9, Response filed Mar. 19, 2015 to Examination Notification Art. 94(3) mailed Sep. 18, 2014", 23 pgs.
"European Application Serial No. 11707316.3, Examination Notification Art. 94(3) mailed Feb. 4, 2014", 3 pgs.
"European Application Serial No. 11707316.3, Examination Notification Art. 94(3) mailed Dec. 17, 2014", 5 pgs.
"European Application Serial No. 11707316.3, Office Action mailed Nov. 10, 2015", 6 pgs.
"European Application Serial No. 11707316.3, Response filed Jun. 5, 2014 to Examination Notification Art. 94(3) mailed Feb. 4, 2014", 7 pgs.
"European Application Serial No. 11707316.3, Response filed Jun. 29, 2015 to Examination Notification Art. 94(3) mailed Dec. 17, 2014", 25 pgs.
"European Application Serial No. 12721676.0, Communication pursuant to Article 94(3) EPC mailed Sep. 30, 2015", 4 pgs.
"European Application Serial No. 12721676.0, Office Action mailed Jan. 3, 2014", 2 pgs.
"European Application Serial No. 12721676.0, Preliminary Amendment filed Nov. 19, 2013", 9 pgs.
"European Application Serial No. 12721676.0, Response filed Apr. 11, 2016 to Communication pursuant to Article 94(3) EPC mailed Sep. 30, 2015", 38 pgs.
"European Application Serial No. 12721676.0, Response filed Jul. 10, 2014 to Office Action mailed Jan. 3, 2014", 2 pgs.
"European Application Serial No. 12791902.5, Examination Notification Art. 94(3) mailed Aug. 14, 2015", 4 pgs.
"European Application Serial No. 12791902.5, Office Action mailed Jul. 15, 2014", 2 pgs.
"European Application Serial No. 12791902.5, Response filed Feb. 23, 2016 to Examination Notification Art. 94(3) mailed Aug. 14, 2015", 12 pgs.
"European Application Serial No. 12806211.4, Examination Notification Art. 94(3) mailed Aug. 13, 2015", 5 pgs.
"European Application Serial No. 12806211.4, Office Action mailed Jul. 18, 2014", 2 pgs.

"European Application Serial No. 12806211.4, Response filed Feb. 23, 2016 to Communication Pursuant to Article 94(3) EPC mailed Aug. 13, 2015", 11 pgs.
"European Application Serial No. 13818131.8, Office Action mailed Jul. 28, 2015", 2 pgs.
"European Application Serial No. 13818131.8, Response filed Feb. 8, 2016 to Office Action mailed Jul. 28, 2015", 14 pgs.
"European Application Serial No. 14716173.1, Communication Pursuant to Article 94(3) EPC mailed Jul. 13, 2020", 4 pgs.
"European Application Serial No. 14716173.1, Office Action mailed Nov. 5, 2015", 2 pgs.
"European Application Serial No. 14716173.1, Response filed May 16, 2016 to Communication pursuant to Rules 161(1) and 162 EPC mailed Nov. 5, 2015", 10 pgs.
"European Application Serial No. 14716173.1, Response filed Sep. 25, 2017 to Office Action mailed Mar. 14, 2017", 12pgs.
"European Application Serial No. 16168202.6, Communication Pursuant to Article 94(3) EPC mailed Apr. 25, 2018", 5 pgs.
"European Application Serial No. 16168202.6, Communication pursuant to Article 94(3) EPC mailed Dec. 11, 2018", 6 pgs.
"European Application Serial No. 16168202.6, Partial European Search Report mailed May 9, 2017", 12 pgs.
"European Application Serial No. 16168202.6, Response filed Sep. 5, 2018 to Communication Pursuant to Article 94(3) EPC mailed Apr. 25, 2018", 13 pgs.
"European Application Serial No. 17169003.5, Extended European Search Report mailed May 11, 2018", 8 pgs.
"European Application Serial No. 17169003.5, Response Filed Dec. 19, 2018 to Extended European Search Report mailed May 11, 2018", 22 pgs.
"European Application Serial No. 12806211.4, Communication Pursuant to Article 94(3) EPC mailed Jun. 23, 2016", 4 pgs.
"EZ Loc Femoral Fixation Device", copyright 2005 Arthrotek, Inc, (2005), 8 pgs.
"Information of Polydioxanone", Dolphin Sutures, [Online] Retrieved from the internet: <https://www.dolphinsutures.com/resoucres/information-on-polydioxanone>, (2018), 2 pgs.
"International Application Serial No. PCT/US2009/039580, International Preliminary Report on Patentability mailed Nov. 4, 2010", 9 pgs.
"International Application Serial No. PCT/US2009/039580, International Search Report mailed Jul. 30, 2009", 4 pgs.
"International Application Serial No. PCT/US2009/039580, Written Opinion mailed Jul. 30, 2009", 7 pgs.
"International Application Serial No. PCT/US2010/036602, International Preliminary Report on Patentability mailed Dec. 8, 2011", 9 pgs.
"International Application Serial No. PCT/US2010/036602, International Search Report mailed Nov. 8, 2010", 6 pgs.
"International Application Serial No. PCT/US2010/036602, Written Opinion mailed Nov. 8, 2010", 7 pgs.
"International Application Serial No. PCT/US2011/026349, International Preliminary Report on Patentability mailed Sep. 20, 2012", 11 pgs.
"International Application Serial No. PCT/US2011/026349, International Search Report mailed Jul. 28, 2011", 6 pgs.
"International Application Serial No. PCT/US2011/026349, Invitation to Pay Additional Fees mailed Jun. 9, 2011", 5 pgs.
"International Application Serial No. PCT/US2011/026349, Written Opinion mailed Jul. 28, 2011", 9 pgs.
"International Application Serial No. PCT/US2011/038188, International Preliminary Report on Patentability mailed Dec. 6, 2012", 14 pgs.
"International Application Serial No. PCT/US2011/038188, International Search Report mailed Oct. 14, 2011", 6 pgs.
"International Application Serial No. PCT/US2011/038188, Invitation to Pay Additional Fees mailed Aug. 5, 2011", 5 pgs.
"International Application Serial No. PCT/US2011/038188, Written Opinion mailed Oct. 14, 2011", 12 pgs.
"International Application Serial No. PCT/US2012/030294, International Preliminary Report on Patentability mailed Oct. 10, 2013", 9 pgs.

(56)         References Cited

OTHER PUBLICATIONS

"International Application Serial No. PCT/US2012/030294, International Search Report mailed May 23, 2012", 6 pgs.
"International Application Serial No. PCT/US2012/030294, Written Opinion mailed May 23, 2012", 7 pgs.
"International Application Serial No. PCT/US2012/037703, International Preliminary Report on Patentability mailed Nov. 28, 2013", 10 pgs.
"International Application Serial No. PCT/US2012/037703, International Search Report mailed Sep. 21, 2012", 6 pgs.
"International Application Serial No. PCT/US2012/037703, Invitation to Pay Additional Fees mailed Jul. 19, 2012", 7 pgs.
"International Application Serial No. PCT/US2012/037703, Written Opinion mailed Sep. 21, 2012", 8 pgs.
"International Application Serial No. PCT/US2012/062738, International Preliminary Report on Patentability mailed May 15, 2014", 9 pgs.
"International Application Serial No. PCT/US2012/062738, International Search Report mailed Mar. 6, 2013", 6 pgs.
"International Application Serial No. PCT/US2012/062738, Written Opinion mailed Mar. 6, 2013", 7 pgs.
"International Application Serial No. PCT/US2012/064832, International Preliminary Report on Patentability mailed May 30, 2014", 9 pgs.
"International Application Serial No. PCT/US2012/064832, International Search Report mailed Feb. 6, 2013", 3 pgs.
"International Application Serial No. PCT/US2012/064832, Written Opinion mailed Feb. 6, 2013", 7 pgs.
"International Application Serial No. PCT/US2013/058921, International Preliminary Report on Patentability mailed Mar. 26, 2015", 9 pgs.
"International Application Serial No. PCT/US2013/058921, International Search Report mailed Oct. 21, 2013", 5 pgs.
"International Application Serial No. PCT/US2013/058921, Written Opinion mailed Oct. 21, 2013", 6 pgs.
"International Application Serial No. PCT/US2013/075989, International Preliminary Report on Patentability mailed Jul. 2, 2015", 10 pgs.
"International Application Serial No. PCT/US2013/075989, International Search Report mailed Mar. 6, 2014", 4 pgs.
"International Application Serial No. PCT/US2013/075989, Written Opinion mailed Mar. 6, 2014", 7 pgs.
"International Application Serial No. PCT/US2014/026413, International Preliminary Report on Patentability mailed Sep. 24, 2015", 10 pgs.
"International Application Serial No. PCT/US2014/026413, International Search Report mailed Jun. 6, 2014", 5 pgs.
"International Application Serial No. PCT/US2014/026413, Written Opinion mailed Jun. 6, 2014", 8 pgs.
"JuggerKnot™ Soft Anchor Midfoot Repair", brochure. Biomet Sports Medicine, (Jul. 2011), 12 pgs.
"JuggerKnot™ Soft Anchor. It's Small. It's strong. And it's all suture . . . ", Ordering Information brochure. Biomet Sports Medicine, (Jun. 2011), 2 pgs.
"JuggerKnot™ Soft Anchor. Labral Repair", brochure. Biomet Sports Medicine, (Apr. 2011), 12 pgs.
"JuggerKnot™ Soft Anchor: Arthroscopic and Mini-Open Rotator Cuff Repair Using JuggerKnot™ Soft Anchor—2.9mm with ALLthread™ Knotless Anchor Surgical Technique", brochure, Biomet® Sports Medicine, (2013), 16 pgs.
"Make your next tendon repair an open-and-shut case. The Teno Fix® Tendon Repair System", Teno Fix® brochure, Ortheon® Medical, (2003), 2 pgs.
"Mallory-Head Modular Calcar Revision System", Biomet Orthopedics, Inc., (2006), 20 pgs.
"Next Generation in Knee Ligament Reconstruction & Repair Technology", Suture Tensioner w/Tensiometer, Arthrex®, Inc. catalog, (2009).
"PANALOK Anchor with PDS II and ETHIBOND Suture", Mitek Products ETHICON, (1997), 2 pgs.

"Rapid Sternal Closure", KLS Martin L.P., [Online] retrieved from the internet: U.S. Appl. No. 13/645,964 , (2006).
"Rotator Cuff Fixation", Acufex Fastenator System: Shoulder Arthroscopy; H-2-H-22, 22 pgs.
"SE Graft Tensioning System Surgical Technique", Linvatec Corporation copyright 2003, (2004), 12 pgs.
"SportMesh™ Soft Tissue Reinforcment, Made from . . . Artelon® optimal tissue repair", Biomet® Sports Medicine, Inc., (2007), 8 pgs.
"Sternal Cable System", Pioneer®, [Online] retrieved from the internet: U.S. Appl. No. 13/645,964 , (2010).
"The AutoCuff System", Opus Medical, [Online]. Retrieved from the Internet: <www.opusmedical.com>, (2003), 4 pgs.
"Toggleloc™ Femoral Fixation Device", Arthrotek, (Mar. 31, 2006), 8 pgs.
"TriTis™ Tibial Fixation System and Implant", brochure. Scandius Biomedical, (2006).
Albritton, Mark J, et al., "Toggleloc Fixation Device with Ziploop Technology: Biceps Tendon Reattachment", Biomet Sports Medicine, a Biomet Company Brochure 2099, (2011), 1-12.
Alford, J Winslow, et al., "Cartilage Restoration, Part 1. Basic Science, Historical Perspective, Patient Evaluation, and Treatment Options", The American Journal of Sports Medicine, 33(2), (2005), 295-306.
Andrews, James R, "Toggleloc™ Fixation Device with Ziploop™ Technology: ACL Reconstruction Bone-Tendon-Bone", Biomet Sports Medicine, a Biomet Company Brochure, (2013), 1-20.
Anitua, Eduardo, et al., "Autologous platelets as a source of proteins for healing and tissue regeneration", Thromb Haemost, vol. 91, (2004), 4-15.
Arthrotek, "A Biomet Company; Sure fire Hybrid Meniscal Device", Fall AANA, (2004), 37 pgs.
Barber, Alan F, "Uses and Abuses of Sutures and Anchors", Shoulder Scope, San Diego Shoulder Arthroscopy Library, (Jul. 1999), 6 pgs.
Barber, Alan F, "Using Sutures and Anchors", San Diego Shoulder Arthroscopy Course, 17th Annual Meetina, (Jun. 14, 2000), 9 pgs.
Charlton, Timothy, "Ziptight™ Fixation System Featuring Zip Loop™ Technology. Ankle Syndesmosis. Surgical Protocol", Biomet Sports® Medicine brochure, (Jun. 15, 2011), 8 pgs.
Edwards, Andrew, et al., "The Attachments of the Fiber Bundles of the Posterior Cruciate ligament: An Anatomic Study", Arthroscopy: The Journal of Arthroscopic and Related Surgery, vol. 23, No. 3, (Mar. 2008), 284-290.
Flavia, Namie Azato, "Traction endurance biomechanical study of metallic suture anchors at different insertion angles", Acta Ortop. Bras., vol. 11, No. 1, Sao Paulo, (Jan./Mar. 2003), pp. 25-31.
Floryan, K, et al., "Home Study Program: Intraoperative use of Autologous Platelet-Rich and Platelet-Poor Plasma for Orthopedic Surgery Patients", AORN Journal: Home Study Program, 80(4), (Oct. 2004), 667-678.
Fromm, Stuart M.D. E, "", Rapidloc, Meniscal Repair System, Mitek Products, Ethicon, (2001), 6 pgs.
Haynesworth, S E, et al., "Mitogenic Stimulation of Human Mesenchymal Stem Cells by Platelet Releasate Suggests a Mechanism for Enhancement of Bone Repair by Platelet Concentrate", 48th Annual Meeting of the Orthopaedic Research Society Poster No. 0462, (2002), 1 pg.
Hecker, AT, et al., "Pull-out strength of suture anchors for rotator cuff and Bankart lesion repairs", The American Journal of Sports Medicine 21(6), (1993), 874-879.
Hunt, Patrick, et al., "Development of a Perforated Biodegradable Interference Screw; Arthroscopy:", The Journal of Arthroscopic and Related Surgery, vol. 21, No. 3;, (Mar. 2005), 258-265.
Lawhorn, M D, et al., "MaxFire™ Meniscal Repair Device with Zip Loop™ Technology", Biomet Sports Medicine, (Feb. 29, 2008), 12 pgs.
Majors, MD, Roy Alan, "Meniscal repairs: proven techniques and current trends", Lippincott Williams & Wilkins, Inc.;, (2002), 30-36.
Miller, Mark D, et al., "Pitfalls Associated with FasT-Fix Meniscal Repair", Arthroscopy: The Journal of Arthroscopic and Related Surgery, vol. 18 No. 8 :, (Oct. 2002), 939-943.

(56)  References Cited

OTHER PUBLICATIONS

Mithoefer, Kai MD, et al., "The Microfracture Technique for the Treatment of Articular Cartilage Lesions in the Knee. A Prospective Cohort Study", The Journal of Bone and Joint Surgery 87(9), (Sep. 2005), 1911-1920.

Nixon, A J, "Platelet Enriched Plasma Provides an Intensely Anabolic Vehicle for Sustained Chondrocyte Function After Implantation", 52nd Annual Meeting of the Orthopedic Research Society: Paper No. 1416, (2005), 2 pgs.

Roseberg, MD, Thomas D, "ACL Reconstruction with Acufex Director Drill Guide and Endobutton CL Fixation System", Smith & Nephew: Knee Series, Technique Guide, (2005), 12 pgs.

Saxena, Pankaj, et al., "Use of Double Wires in Sternal Closure, A Useful Technique", Texas Heart® Institute. Journal List> Tex Heart Inst J > v.33(4), (2006).

Smith, et al., "Endoscopic Meniscal Repair Using the T-Fix", (1996), 16 pgs.

Smith, et al., "Fast-Fix", Meniscal Repair System;, (2001), 3 pgs.

Steadman, et al., "Microfracture: Surgical Technique and Rehabilitation to Treat Chondral Defects", Clinical Orthopaedics and Related Research 391, (2001), S362-S369.

Thomas, Roseberg D, "Technique for ACL Reconstruction with Acufex Director Drill Guide and Endobutton CL", Smith & Nephew, Technique Guide, (1999), 18 pgs.

Weiler, A, et al., "Biodegradierbare Interferenzschrauben in der Kreuzbandchirurgie", OPJOURNAL 14, (1998), 278-284.

Zeitani, Jacob M.D, "A New Sternal Reinforcement Device to Prevent and Treat Sternal Dehiscence", CTSNet, [Online]. Retrieved from the Internet: <URL: http://www.ctsnet.org/print/article/new-sternal-reinforcement-device-prevent-and-treat-sternal-dehiscence>, (Jun. 30, 2008), 6 pgs.

U.S. Appl. No. 11/784,821 U.S. Pat. No. 9,017,381, filed Apr. 10, 2007, Adjustable Knotless Loops.

U.S. Appl. No. 14/697,140 U.S. Pat. No. 9,861,351, filed Apr. 27, 2015, Adjustable Knotless Loops.

U.S. Appl. No. 11/541,506 U.S. Pat. No. 7,601,165, filed Sep. 29, 2006, Method and Apparatus for Forming a Self-locking Adjustable Suture Loop.

U.S. Appl. No. 15/720,997 U.S. Pat. No. 11,185,320, filed Sep. 29, 2017, Adjustable Knotless Loops.

U.S. Appl. No. 15/903,261 U.S. Pat. No. 10,729,423, filed Feb. 23, 2018, Adjustable Knotless Loops.

U.S. Appl. No. 17/516,664, filed Nov. 1, 2021, Adjustable Knotless Loops.

U.S. Appl. No. 11/347,661 U.S. Pat. No. 7,749,250, filed Feb. 3, 2006, Soft Tissue Repair Assembly and Associated Method.

U.S. Appl. No. 12/828,977 U.S. Pat. No. 8,409,253, filed Jul. 1, 2010, Soft Tissue Repair Assembly and Associated Method.

U.S. Appl. No. 13/767,401 U.S. Pat. No. 9,414,833, filed Feb. 14, 2013, Soft Tissue Repair Assembly and Associated Method.

U.S. Appl. No. 14/936,831 U.S. Pat. No. 10,441,264, filed Nov. 10, 2015, Soft Tissue Repair Assembly and Associated Method.

U.S. Appl. No. 15/361,917 U.S. Pat. No. 10,702,259, filed Nov. 28, 2016, Soft Tissue Repair Assembly and Associated Method.

U.S. Appl. No. 16/251,342 U.S. Pat. No. 11,116,495, filed Jan. 18, 2019, Soft Tissue Repair Assembly and Associated Method.

U.S. Appl. No. 16/544,293 U.S. Pat. No. 11,730,464, filed Aug. 19, 2019, Soft Tissue Repair Assembly and Associated Method.

U.S. Appl. No. 11/541,505 U.S. Pat. No. 7,658,751, filed Sep. 29, 2006, Method for Implanting Soft Tissue.

U.S. Appl. No. 12/702,067 U.S. Pat. No. 8,672,968, filed Feb. 8, 2010, Method for Implanting Soft Tissue.

U.S. Appl. No. 14/211,977 U.S. Pat. No. 9,486,211, filed Mar. 14, 2014, Method for Implanting Soft Tissue.

U.S. Appl. No. 15/061,352 U.S. Pat. No. 10,004,493, filed Mar. 4, 2016, Method for Implanting Soft Tissue.

U.S. Appl. No. 15/664,572 U.S. Pat. No. 10,398,430, filed Jul. 31, 2017, Method for Implanting Soft Tissue.

U.S. Appl. No. 16/508,764 U.S. Pat. No. 11,259,794, filed Jul. 11, 2019, Method for Implanting Soft Tissue.

U.S. Appl. No. 17/492,082 U.S. Pat. No. 11,672,527, filed Oct. 1, 2021, Method for Implanting Soft Tissue.

U.S. Appl. No. 11/935,681 U.S. Pat. No. 7,905,903, filed Nov. 6, 2007, Method for Tissue Fixation.

U.S. Appl. No. 12/196,398 U.S. Pat. No. 7,959,650, filed Aug. 22, 2008, Adjustable Knotless Loops.

U.S. Appl. No. 13/102,182 U.S. Pat. No. 8,231,654, filed May 6, 2011, Adjustable Knotless Loops.

U.S. Appl. No. 10/984,624 U.S. Pat. No. 7,608,098, filed Nov. 9, 2004, Bone Fixation Device.

U.S. Appl. No. 11/294,694 U.S. Pat. No. 7,914,539, filed Dec. 5, 2005, Tissue Fixation Device.

U.S. Appl. No. 11/408,282, filed Apr. 20, 2006, Soft Tissue Conduit Device.

U.S. Appl. No. 12/419,491 U.S. Pat. No. 8,317,825, filed Apr. 7, 2009, Soft Tissue Conduit Device and Method.

U.S. Appl. No. 11/869,440 U.S. Pat. No. 7,857,830, filed Oct. 9, 2007, Soft Tissue Repair and Conduit Device.

U.S. Appl. No. 12/976,328 U.S. Pat. No. 8,273,106, filed Dec. 22, 2010, Soft Tissue Repair and Conduit Device.

U.S. Appl. No. 12/489,168 U.S. Pat. No. 8,361,113, filed Jun. 22, 2009, Method and Apparatus for Coupling Soft Tissue to a Bone.

U.S. Appl. No. 13/751,846 U.S. Pat. No. 9,492,158, filed Jan. 28, 2013, Method and Apparatus for Coupling Soft Tissue to a Bone.

U.S. Appl. No. 14/983,747 U.S. Pat. No. 10,154,837, filed Dec. 30, 2015, Method and Apparatus for Coupling Soft Tissue to a Bone.

U.S. Appl. No. 15/941,481 U.S. Pat. No. 10,973,507, filed Mar. 30, 2018, Method and Apparatus for Coupling Soft Tissue to a Bone.

U.S. Appl. No. 16/400,199 U.S. Pat. No. 11,446,019, filed May 1, 2019, Method and Apparatus for Coupling Soft Tissue to a Bone.

U.S. Appl. No. 17/190,686, filed Mar. 3, 2021, Method and Apparatus for Coupling Soft Tissue to a Bone.

U.S. Appl. No. 18/514,936, filed Nov. 20, 2023, Method and Apparatus for Coupling Soft Tissue to a Bone.

U.S. Appl. No. 12/014,399 U.S. Pat. No. 7,909,851, filed Jan. 15, 2008, Soft Tissue Repair Assembly and Associated Method.

U.S. Appl. No. 13/045,691 U.S. Pat. No. 8,292,921, filed Mar. 11, 2011, Soft Tissue Repair Assembly and Associated Method.

U.S. Appl. No. 13/656,821 U.S. Pat. No. 9,173,651, filed Oct. 22, 2012, Soft Tissue Repair Device and Associated Methods.

U.S. Appl. No. 14/876,167 U.S. Pat. No. 10,251,637, filed Oct. 6, 2015, Soft Tissue Repair Device and Associated Methods.

U.S. Appl. No. 15/891,049 U.S. Pat. No. 10,932,770, filed Feb. 7, 2018, Soft Tissue Repair Device and Associated Methods.

U.S. Appl. No. 16/593,022 U.S. Pat. No. 11,617,572, filed Oct. 4, 2019, Soft Tissue Repair Device and Associated Methods.

U.S. Appl. No. 16/989,386 U.S. Pat. No. 11,819,205, filed Aug. 10, 2020, Soft Tissue Repair Device and Associated Methods.

U.S. Appl. No. 18/471,089, filed Sep. 20, 2023, Soft Tissue Repair Device and Associated Methods.

U.S. Appl. No. 12/014,340 U.S. Pat. No. 7,905,904, filed Jan. 15, 2008, Soft Tissue Repair Assembly and Associated Method.

U.S. Appl. No. 13/045,689 U.S. Pat. No. 8,337,525, filed Mar. 11, 2011, Soft Tissue Repair Assembly and Associated Method.

U.S. Appl. No. 13/721,970 U.S. Pat. No. 8,632,569, filed Dec. 20, 2012, Soft Tissue Repair Assembly and Associated Method.

U.S. Appl. No. 13/838,755 U.S. Pat. No. 9,510,819, filed Mar. 15, 2013, Soft Tissue Repair Device and Associated Methods.

U.S. Appl. No. 13/833,567 U.S. Pat. No. 9,561,025, filed Mar. 15, 2013, Soft Tissue Repair Device and Associated Methods.

U.S. Appl. No. 14/159,094 U.S. Pat. No. 9,622,736, filed Jan. 20, 2014, Soft Tissue Repair Device and Associated Methods.

U.S. Appl. No. 15/412,676, filed Jan. 23, 2017, Soft Tissue Repair Device and Associated Methods.

U.S. Appl. No. 16/806,611 U.S. Pat. No. 11,612,391, filed Mar. 2, 2020, Soft Tissue Repair Device and Associated Methods.

U.S. Appl. No. 18/126,022, filed Mar. 24, 2023, Soft Tissue Repair Device and Associated Methods.

U.S. Appl. No. 12/489,181 U.S. Pat. No. 8,298,262, filed Jun. 22, 2009, Method for Tissue Fixation.

U.S. Appl. No. 13/625,413 U.S. Pat. No. 9,402,621, filed Sep. 24, 2012, Method for Tissue Fixation.

(56)     References Cited

OTHER PUBLICATIONS

U.S. Appl. No. 14/983,108 U.S. Pat. No. 10,321,906, filed Dec. 29, 2015, Method for Tissue Fixation.
U.S. Appl. No. 15/945,425 U.S. Pat. No. 10,987,099, filed Apr. 4, 2018, Method for Tissue Fixation.
U.S. Appl. No. 16/380,742 U.S. Pat. No. 11,311,287, filed Apr. 10, 2019, Method for Tissue Fixation.
U.S. Appl. No. 17/577,188, filed Jan. 17, 2022, Method for Tissue Fixation.
U.S. Appl. No. 18/531,362, filed Dec. 6, 2023, Method for Tissue Fixation.
U.S. Appl. No. 10/983,236, filed Nov. 5, 2004, Tissue Repair Assembly.
U.S. Appl. No. 11/347,662, filed Feb. 3, 2006, Tissue Repair Assembly.
U.S. Appl. No. 16/795,181 U.S. Pat. No. 11,534,159, filed Feb. 19, 2020, Method and Apparatus for Coupling Soft Tissue to a Bone.
U.S. Appl. No. 17/550,074, filed Dec. 14, 2021, Method and Apparatus for Coupling Soft Tissue to a Bone.
U.S. Appl. No. 12/196,410 U.S. Pat. No. 8,118,836, filed Aug. 22, 2008, Method and Apparatus for Coupling Soft Tissue to a Bone.
U.S. Appl. No. 13/399,125 U.S. Pat. No. 8,840,645, filed Feb. 17, 2012, Method and Apparatus for Coupling Soft Tissue to a Bone.
U.S. Appl. No. 14/492,590 U.S. Pat. No. 9,572,655, filed Sep. 22, 2014, Method and Apparatus for Coupling Soft Tissue to a Bone.
U.S. Appl. No. 14/956,724 U.S. Pat. No. 9,801,708, filed Dec. 2, 2015, Method and Apparatus for Coupling Soft Tissue to a Bone.
U.S. Appl. No. 15/278,777 U.S. Pat. No. 10,092,288, filed Sep. 28, 2016, Method and Apparatus for Coupling Soft Tissue to a Bone.
U.S. Appl. No. 15/455,895 U.S. Pat. No. 10,695,052, filed Mar. 10, 2017, Method and Apparatus for Coupling Soft Tissue to a Bone.
U.S. Appl. No. 15/622,718 U.S. Pat. No. 10,687,803, filed Jun. 14, 2017, Method and Apparatus for Coupling Soft Tissue to a Bone.
U.S. Appl. No. 15/793,216 U.S. Pat. No. 10,729,430, filed Oct. 25, 2017, Method and Apparatus for Coupling Soft Tissue to a Bone.
U.S. Appl. No. 16/420,676 U.S. Pat. No. 11,284,884, filed May 23, 2019, Method and Apparatus for Coupling Soft Tissue to a Bone.
U.S. Appl. No. 18/235,540, filed Aug. 18, 2023, Method and Apparatus for Coupling Anatomical Features.
U.S. Appl. No. 12/196,407 U.S. Pat. No. 8,137,382, filed Aug. 22, 2008, Method and Apparatus for Coupling Anatomical Features.
U.S. Appl. No. 13/412,116 U.S. Pat. No. 8,771,316, filed Mar. 5, 2012, Method and Apparatus for Coupling Anatomical Features.
U.S. Appl. No. 14/324,688 U.S. Pat. No. 9,498,204, filed Jul. 7, 2014, Method and Apparatus for Coupling Anatomical Features.
U.S. Appl. No. 13/412,127 U.S. Pat. No. 8,721,684, filed Mar. 5, 2012, Method and Apparatus for Coupling Anatomical Features.
U.S. Appl. No. 14/275,548 U.S. Pat. No. 9,510,821, filed May 12, 2014, Method and Apparatus for Coupling Anatomical Features.
U.S. Appl. No. 15/288,183 U.S. Pat. No. 10,398,428, filed Oct. 7, 2016, Method and Apparatus for Coupling Anatomical Features.
U.S. Appl. No. 15/662,572 U.S. Pat. No. 10,716,557, filed Jul. 28, 2017, Method and Apparatus for Coupling Anatomical Features.
U.S. Appl. No. 16/436,023 U.S. Pat. No. 11,259,792, filed Jun. 10, 2019, Method and Apparatus for Coupling Anatomical Features.
U.S. Appl. No. 17/545,668 U.S. Pat. No. 11,786,236, filed Dec. 8, 2021, Method and Apparatus for Coupling Anatomical Features.
U.S. Appl. No. 12/196,405 U.S. Pat. No. 8,128,658, filed Aug. 22, 2008, Method and Apparatus for Coupling Soft Tissue to Bone.
U.S. Appl. No. 13/181,729 U.S. Pat. No. 8,551,140, filed Jul. 13, 2011, Method and Apparatus for Coupling Soft Tissue to Bone.
U.S. Appl. No. 13/412,105 U.S. Pat. No. 8,932,331, filed Mar. 5, 2012, Method and Apparatus for Coupling Soft Tissue to Bone.
U.S. Appl. No. 14/594,285 U.S. Pat. No. 9,801,620, filed Jan. 12, 2015, Method and Apparatus for Coupling Soft Tissue to Bone.
U.S. Appl. No. 15/703,727 U.S. Pat. No. 10,603,029, filed Sep. 13, 2017, Method and Apparatus for Coupling Soft Tissue to Bone.
U.S. Appl. No. 16/802,248 U.S. Pat. No. 11,589,859, filed Feb. 26, 2020, Method and Apparatus for Coupling Soft Tissue to Bone.

U.S. Appl. No. 18/101,490, filed Jan. 25, 2023, Method and Apparatus for Coupling Soft Tissue to Bone.
U.S. Appl. No. 18/102,518, filed Jan. 27, 2023, Method and Apparatus for Coupling Soft Tissue to a Bone.
U.S. Appl. No. 12/474,802 U.S. Pat. No. 8,088,130, filed May 29, 2009, Method and Apparatus for Coupling Soft Tissue to a Bone.
U.S. Appl. No. 13/278,341 U.S. Pat. No. 8,608,777, filed Oct. 21, 2011, Method and Apparatus for Coupling Soft Tissue to a Bone.
U.S. Appl. No. 14/107,350 U.S. Pat. No. 9,532,777, filed Dec. 16, 2013, Method and Apparatus for Coupling Soft Tissue to a Bone.
U.S. Appl. No. 15/074,553 U.S. Pat. No. 10,004,489, filed Mar. 18, 2016, Method and Apparatus for Coupling Soft Tissue to a Bone.
U.S. Appl. No. 15/297,844 U.S. Pat. No. 10,098,629, filed Oct. 19, 2016, Method and Apparatus for Coupling Soft Tissue to a Bone.
U.S. Appl. No. 15/865,938 U.S. Pat. No. 10,542,967, filed Jan. 9, 2018, Method and Apparatus for Coupling Soft Tissue to a Bone.
U.S. Appl. No. 15/886,712 U.S. Pat. No. 10,595,851, filed Feb. 1, 2018, Method and Apparatus for Coupling Soft Tissue to a Bone.
U.S. Appl. No. 16/802,228 U.S. Pat. No. 11,471,147, filed Feb. 26, 2020, Method and Apparatus for Coupling Soft Tissue to a Bone.
U.S. Appl. No. 17/940,022, filed Sep. 8, 2022, Method and Apparatus for Coupling Soft Tissue to a Bone.
U.S. Appl. No. 12/570,854 U.S. Pat. No. 8,303,604, filed Sep. 30, 2009, Soft Tissue Repair Device and Method.
U.S. Appl. No. 13/645,964 U.S. Pat. No. 9,504,460, filed Oct. 5, 2012, Soft Tissue Repair Device and Method.
U.S. Appl. No. 15/332,590 U.S. Pat. No. 10,265,064, filed Oct. 24, 2016, Soft Tissue Repair Device and Method.
U.S. Appl. No. 16/255,300 U.S. Pat. No. 11,109,857, filed Jan. 23, 2019, Soft Tissue Repair Device and Method.
U.S. Appl. No. 17/392,971, filed Aug. 3, 2021, Soft Tissue Repair Device and Method.
U.S. Appl. No. 12/719,337 U.S. Pat. No. 9,078,644, filed Mar. 8, 2010, Fracture Fixation Device.
U.S. Appl. No. 14/794,309 U.S. Pat. No. 9,833,230, filed Jul. 8, 2015, Fracture Fixation Device.
U.S. Appl. No. 15/060,007 U.S. Pat. No. 10,349,931, filed Mar. 3, 2016, Fracture Fixation Device.
U.S. Appl. No. 15/866,089 U.S. Pat. No. 10,835,232, filed Jan. 9, 2018, Fracture Fixation Device.
U.S. Appl. No. 12/915,962 U.S. Pat. No. 8,562,647, filed Oct. 29, 2010, Method and Apparatus for Securing Soft Tissue to Bone.
U.S. Appl. No. 14/055,172 U.S. Pat. No. 9,724,090, filed Oct. 16, 2013, Method and Apparatus for Attaching Soft Tissue to Bone.
U.S. Appl. No. 15/654,386 U.S. Pat. No. 10,695,045, filed Jul. 19, 2017, Method and Apparatus for Attaching Soft Tissue to Bone.
U.S. Appl. No. 12/938,902 U.S. Pat. No. 8,597,327, filed Nov. 3, 2010, Method and Apparatus for Securing Soft Tissue to Bone.
U.S. Appl. No. 14/094,311 U.S. Pat. No. 9,642,661, filed Dec. 2, 2013, Method and Apparatus for Sternal Closure.
U.S. Appl. No. 15/461,675 U.S. Pat. No. 10,675,073, filed Mar. 17, 2017, Method and Apparatus for Sternal Closure.
U.S. Appl. No. 11/504,882 U.S. Pat. No. 8,998,949, filed Aug. 16, 2006, Soft Tissue Conduit Device.
U.S. Appl. No. 12/029,861 U.S. Pat. No. 8,251,998, filed Feb. 12, 2008, Chondral Defect Repair.
U.S. Appl. No. 13/587,374 U.S. Pat. No. 8,777,956, filed Aug. 16, 2012, Chondral Defect Repair.
U.S. Appl. No. 11/740,035, filed Apr. 25, 2007, Method for Treating Cartilage Defects.
U.S. Appl. No. 11/739,768 U.S. Pat. No. 8,137,354, filed Apr. 25, 2007, Localized Cartilage Defect Therapy.
U.S. Appl. No. 13/350,985 U.S. Pat. No. 9,198,673, filed Jan. 16, 2012, Localized Cartilage Defect Therapy.
U.S. Appl. No. 14/923,506, filed Oct. 27, 2015, Localized Cartilage Defect Therapy.
U.S. Appl. No. 13/111,564 U.S. Pat. No. 8,574,235, filed May 19, 2011, Method for Trochanteric Reattachment.
U.S. Appl. No. 14/071,295 U.S. Pat. No. 9,005,287, filed Nov. 4, 2013, Method for Bone Reattachment.
U.S. Appl. No. 13/288,459 U.S. Pat. No. 9,468,433, filed Nov. 3, 2011, Method and Apparatus for Forming a Self-Locking Adjustable Loop.

(56)                    References Cited

OTHER PUBLICATIONS

U.S. Appl. No. 15/294,994 U.S. Pat. No. 10,517,587, filed Oct. 17, 2016, Method and Apparatus for Forming a Self-Locking Adjustable Loop.
U.S. Appl. No. 16/443,391 U.S. Pat. No. 11,317,907, filed Jun. 17, 2019, Method and Apparatus for Forming a Self-Locking Adjustable Loop.
U.S. Appl. No. 13/288,463 U.S. Pat. No. 8,936,621, filed Nov. 3, 2011, Method and Apparatus for Forming a Self-Locking Adjustable Loop.
U.S. Appl. No. 14/599,909 U.S. Pat. No. 9,993,241, filed Jan. 19, 2015, Method and Apparatus for Forming a Self-Locking Adjustable Loop.
U.S. Appl. No. 15/917,143 U.S. Pat. No. 11,039,826, filed Mar. 9, 2018, Method and Apparatus for Forming a Self-Locking Adjustable Loop.
U.S. Appl. No. 17/232,672, filed Apr. 16, 2021, Method and Apparatus for Forming a Self-Locking Adjustable Loop.
U.S. Appl. No. 18/531,431, filed Dec. 6, 2023, Method and Apparatus for Forming a Self-Locking Adjustable Loop.
U.S. Appl. No. 13/720,648 U.S. Pat. No. 9,357,991, filed Dec. 19, 2012, Method and Apparatus for Stitching Tendons.
U.S. Appl. No. 15/166,480 U.S. Pat. No. 10,265,159, filed May 27, 2016, Method and Apparatus for Stitching Tendons.
U.S. Appl. No. 16/160,559 U.S. Pat. No. 11,241,305, filed Oct. 15, 2018, Method and Apparatus for Stitching Tendons.
U.S. Appl. No. 14/095,639 U.S. Pat. No. 9,918,827, filed Dec. 3, 2013, Scaffold for Spring Ligament Repair.
U.S. Appl. No. 14/095,614 U.S. Pat. No. 9,918,826, filed Dec. 3, 2013, Scaffold for Spring Ligament Repair.
U.S. Appl. No. 15/722,002 U.S. Pat. No. 10,758,221, filed Oct. 2, 2017, Scaffold for Spring Ligament Repair.
U.S. Appl. No. 13/098,897 U.S. Pat. No. 8,562,645, filed May 2, 2011, Method and Apparatus for Forming a Self-Locking Adjustable Loop.
U.S. Appl. No. 14/055,191 U.S. Pat. No. 9,539,003, filed Oct. 16, 2013, Method and Apparatus for Forming a Self-Locking Adjustable Loop.
U.S. Appl. No. 15/401,768 U.S. Pat. No. 10,610,217, filed Jan. 9, 2017, Method and Apparatus for Forming a Self-Locking Adjustable Loop.
U.S. Appl. No. 15/972,646 U.S. Pat. No. 11,096,684, filed May 7, 2018, Method and Apparatus for Forming a Self-Locking Adjustable Loop.
U.S. Appl. No. 13/098,927 U.S. Pat. No. 8,652,171, filed May 2, 2011, Method and Apparatus for Soft Tissue Fixation.
U.S. Appl. No. 14/182,038 U.S. Pat. No. 9,763,656, filed Feb. 17, 2014, Method and Apparatus for Soft Tissue Fixation.
U.S. Appl. No. 15/682,187 U.S. Pat. No. 10,729,421, filed Aug. 21, 2017, Method and Apparatus for Soft Tissue Fixation.
U.S. Appl. No. 16/895,246 U.S. Pat. No. 11,723,648, filed Jun. 8, 2020, Method and Apparatus for Soft Tissue Fixation.
U.S. Appl. No. 18/093,114, filed Jan. 4, 2023, Method and Apparatus for Soft Tissue Fixation.
U.S. Appl. No. 18/134,897, filed Apr. 14, 2023, Method and Apparatus for Soft Tissue Fixation.
U.S. Appl. No. 18/497,342, filed Oct. 30, 2023, Method and Apparatus for Soft Tissue Fixation.
U.S. Appl. No. 12/788,978 U.S. Pat. No. 8,801,783, filed May 27, 2010, Prosthetic Ligament System for Knee Joint.
U.S. Appl. No. 14/456,286 U.S. Pat. No. 9,681,940, filed Aug. 11, 2014, Ligament System for Knee Joint.
U.S. Appl. No. 15/626,384 U.S. Pat. No. 10,517,714, filed Jun. 19, 2017, Ligament System for Knee Joint.
U.S. Appl. No. 16/690,671 U.S. Pat. No. 11,376,115, filed Nov. 21, 2019, Prosthetic Ligament System for Knee Joint.

U.S. Appl. No. 11/386,071 U.S. Pat. No. 8,034,090, filed Mar. 21, 2006, Bone Fixation Device.
U.S. Appl. No. 13/293,825 U.S. Pat. No. 9,149,267, filed Nov. 10, 2011, Method and Apparatus for Coupling Soft Tissue to a Bone.
U.S. Appl. No. 14/854,308 U.S. Pat. No. 10,022,118, filed Sep. 15, 2015, Method and Apparatus for Coupling Soft Tissue to a Bone.
U.S. Appl. No. 13/071,563 U.S. Pat. No. 8,926,613, filed Mar. 25, 2011, Method and Apparatus for Forming a Bone Hole.
U.S. Appl. No. 14/589,101, filed Jan. 5, 2015, Method and Apapratus for Forming a Bone Hole.
U.S. Appl. No. 13/311,936 U.S. Pat. No. 9,408,599, filed Dec. 6, 2011, Method and Apparatus for Coupling Soft Tissue to a Bone.
U.S. Appl. No. 15/231,074, filed Aug. 8, 2016, Method and Apparatus for Coupling Soft Tissue to a Bone.
U.S. Appl. No. 13/757,003 U.S. Pat. No. 9,357,992, filed Feb. 1, 2013, Method for Coupling Soft Tissue to a Bone.
U.S. Appl. No. 13/295,126 U.S. Pat. No. 9,271,713, filed Nov. 14, 2011, Method and Apparatus for Tensioning a Suture.
U.S. Appl. No. 13/281,009 U.S. Pat. No. 9,538,998, filed Oct. 25, 2011, Method and Apparatus for Fracture Fixation.
U.S. Appl. No. 13/269,097 U.S. Pat. No. 8,672,969, filed Oct. 7, 2011, Fracture Fixation Device.
U.S. Appl. No. 14/215,550 U.S. Pat. No. 9,788,876, filed Mar. 17, 2014, Fracture Fixation Device.
U.S. Appl. No. 15/715,731 U.S. Pat. No. 10,743,925, filed Sep. 26, 2017, Fracture Fixation Device.
U.S. Appl. No. 13/757,019 U.S. Pat. No. 9,314,241, filed Feb. 1, 2013, Apparatus for Coupling Soft Tissue to a Bone.
U.S. Appl. No. 15/131,663 U.S. Pat. No. 10,368,856, filed Apr. 18, 2016, Apparatus for Coupling Soft Tissue to a Bone.
U.S. Appl. No. 13/790,982 U.S. Pat. No. 9,370,350, filed Mar. 8, 2013, Apparatus for Coupling Soft Tissue to a Bone.
U.S. Appl. No. 13/790,997 U.S. Pat. No. 9,381,013, filed Mar. 8, 2013, Method for Coupling Soft Tissue to a Bone.
U.S. Appl. No. 15/200,546 U.S. Pat. No. 10,363,028, filed Jul. 1, 2016, Method for Coupling Soft Tissue to a Bone.
U.S. Appl. No. 16/428,277 U.S. Pat. No. 11,534,157, filed May 31, 2019, Method for Coupling Soft Tissue to a Bone.
U.S. Appl. No. 17/991,832, filed Nov. 21, 2022, Method for Coupling Soft Tissue to a Bone.
U.S. Appl. No. 12/788,973 U.S. Pat. No. 8,500,818, filed May 27, 2010, Knee Prosthesis Assembly With Ligament Link.
U.S. Appl. No. 13/959,145 U.S. Pat. No. 9,414,925, filed Aug. 5, 2013, Method of Implanting a Knee Prosthesis Assembly With a Ligament Link.
U.S. Appl. No. 13/109,672 U.S. Pat. No. 8,968,364, filed May 17, 2011, Method and Apparatus for Fixation of an ACL Graft.
U.S. Appl. No. 14/635,055 U.S. Pat. No. 10,004,588, filed Mar. 2, 2015, Method and Apparatus for Fixation of an ACL Graft.
U.S. Appl. No. 15/956,444 U.S. Pat. No. 11,065,103, filed Apr. 18, 2018, Method and Apparatus for Fixation of an ACL Graft.
U.S. Appl. No. 13/109,667 U.S. Pat. No. 8,771,352, filed May 17, 2011, Method and Apparatus for Tibial Fixation of an ACL Graft.
U.S. Appl. No. 13/889,851 U.S. Pat. No. 9,216,078, filed May 8, 2013, Method and Apparatus for Tibial Fixation of an ACL Graft.
U.S. Appl. No. 14/974,516, filed Dec. 18, 2015, Method and Apparatus for Tibial Fixation of an ACL Graft.
U.S. Appl. No. 13/177,153 U.S. Pat. No. 8,652,172, filed Jul. 6, 2011, Flexible Anchors for Tissue Fixation.
U.S. Appl. No. 14/182,046 U.S. Pat. No. 9,603,591, filed Feb. 17, 2014, Flexible Anchors for Tissue Fixation.
U.S. Appl. No. 12/107,437, filed Apr. 22, 2008, Method and Apparatus for Attaching Soft Tissue to Bone.
U.S. Appl. No. 12/398,548 U.S. Pat. No. 8,118,868, filed Mar. 5, 2009, Method and Apparatus for Attaching Soft Tissue to Bone.

* cited by examiner

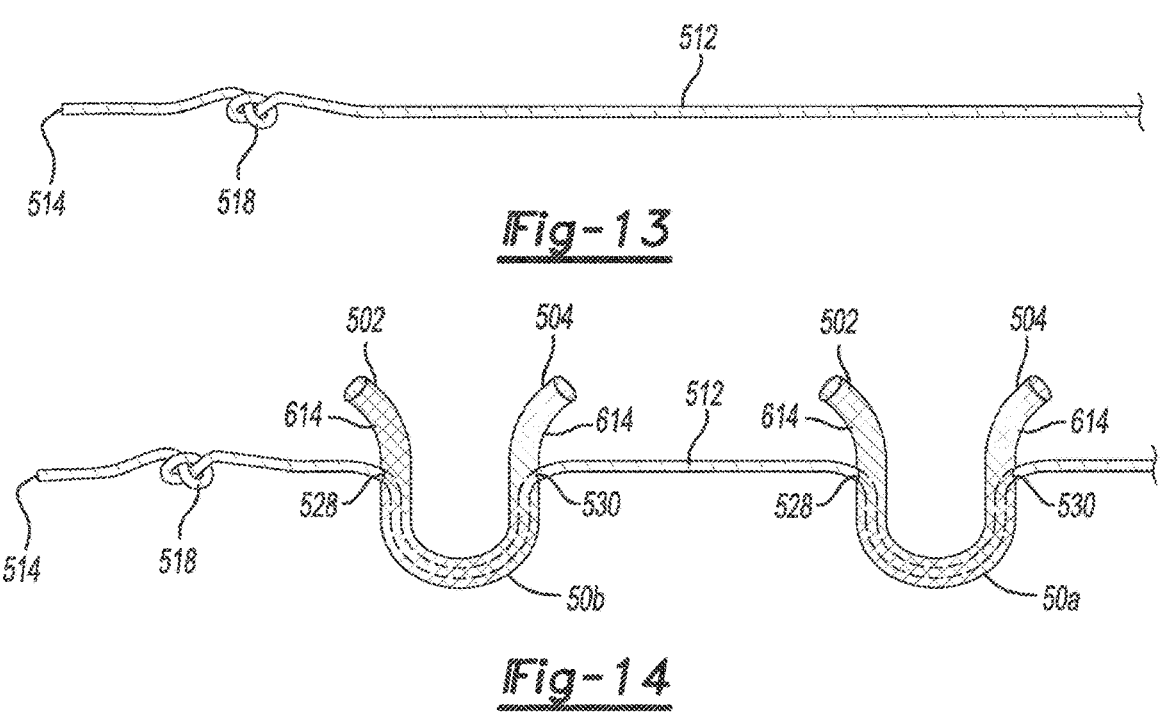
*Fig-13*
*Fig-14*
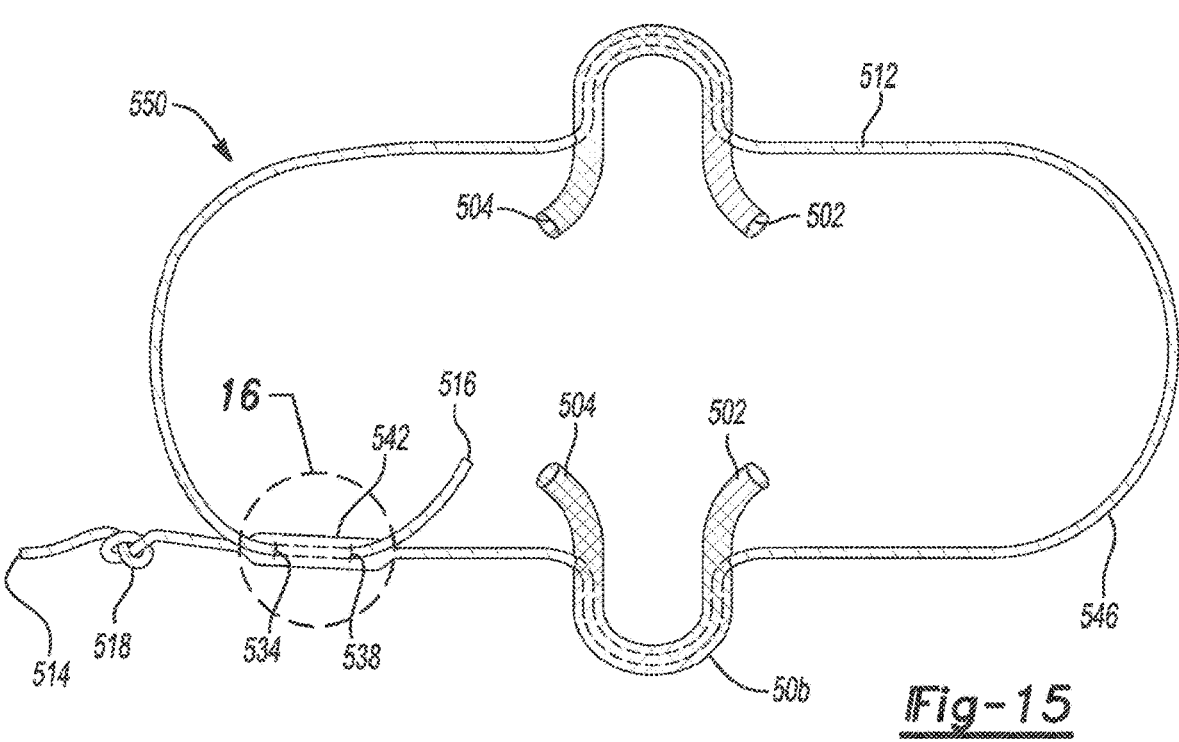
*Fig-15*

SOFT TISSUE REPAIR DEVICE AND METHOD

CROSS-REFERENCE TO RELATED APPLICATIONS

This application is a continuation of U.S. patent application Ser. No. 17/392,971 filed Aug. 3, 2021, which is a continuation of Ser. No. 16/255,300 filed Jan. 23, 2019, now issued as U.S. Pat. No. 11,109,857, which is a continuation of U.S. patent application Ser. No. 15/332,590 filed Oct. 24, 2016, now issued as U.S. Pat. No. 10,265,064, which is a continuation of U.S. patent application Ser. No. 13/645,964 filed Oct. 5, 2012, now issued as U.S. Pat. No. 9,504,460, which is a divisional of U.S. patent application Ser. No. 12/570,854 filed Sep. 30, 2009, now issued as U.S. Pat. No. 8,303,604.

The disclosures of all of the above applications are hereby incorporated by reference.

FIELD

The present teachings relate generally to soft tissue repair and, more particularly, to a device and associated method for repairing a tear in soft tissue.

INTRODUCTION

Tears caused by trauma or disease in soft tissue, such as cartilage, ligament, or muscle, can be repaired by suturing. Various repair devices have been developed for facilitating suturing and are effective for their intended purposes. Nevertheless, tissue repair devices for facilitating suturing are still desirable.

SUMMARY

This section provides a general summary of the disclosure, and is not a comprehensive disclosure of its full scope or all of its features.

According to one aspect, the present teachings provide a soft tissue repair device. The device can include a housing having a handle, a deployment system having an actuation member, and an insertion system having an inserter and a slider. The slider can be coupled to the actuation member and movable relative to the inserter between deployed and retracted positions. At least a portion of a first anchor can be carried on an external surface of the slider in a first position, and at least a portion of a second anchor can be carried on the external surface of the slider in a second position that is longitudinally spaced apart from the first anchor position such that the portions of the first and second anchors are co-axial with the slider and each other. A flexible strand can couple the first and second anchors. The insertion system can be operable to cooperate with the deployment system to move the slider from the retracted position to the deployed position to deploy the first anchor upon actuating the actuation member at a first time, and to move the slider from the retracted position to the deployed position to deploy the second anchor upon actuating the actuation member a second time after the first time.

According to another aspect, the present teachings provide a method for repairing a tear in soft tissue. The method can include coupling first and second flexible anchors with a flexible strand, providing an insertion device having a housing with a pistol grip handle, an inserter and a slider carried in the inserter such that the inserter and the slider each have a distal end extending from the housing. The first and second coupled anchors can be loaded on an external surface of the slider, and the inserter can be inserted though the soft tissue from a first side of the tear to a second side of the tear. An actuation member protruding from the pistol grip handle can be actuated at a first time to translate a distal end of the slider beyond a distal end of the inserter so as to deploy the first anchor. The actuation member can be released after deploying the first anchor, the inserter can be inserted through the soft tissue for a second time in a second position, and the actuation member can be actuated at a second time after the first time to extend the distal end of the slider beyond the distal end of the inserter and deploy the second anchor. The method can further include removing the inserter from the soft tissue, tensioning the flexible strand and reducing the tear.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The present teachings will become more fully understood from the detailed description, the appended claims and the following drawings. The drawings are for illustrative purposes only and are not intended to limit the scope of the present disclosure.

FIGS. 13, 14, 15 and 17 are sequential views illustrating an exemplary method and arrangement for coupling first and second flexible anchors with a flexible strand, and FIG. 16 shows a detail of FIG. 15 according to the present teachings;

FIG. 18 is a perspective view of a flexible anchor coupled with a flexible strand according to the present teachings;

DESCRIPTION OF VARIOUS ASPECTS

Figures 1, 2:
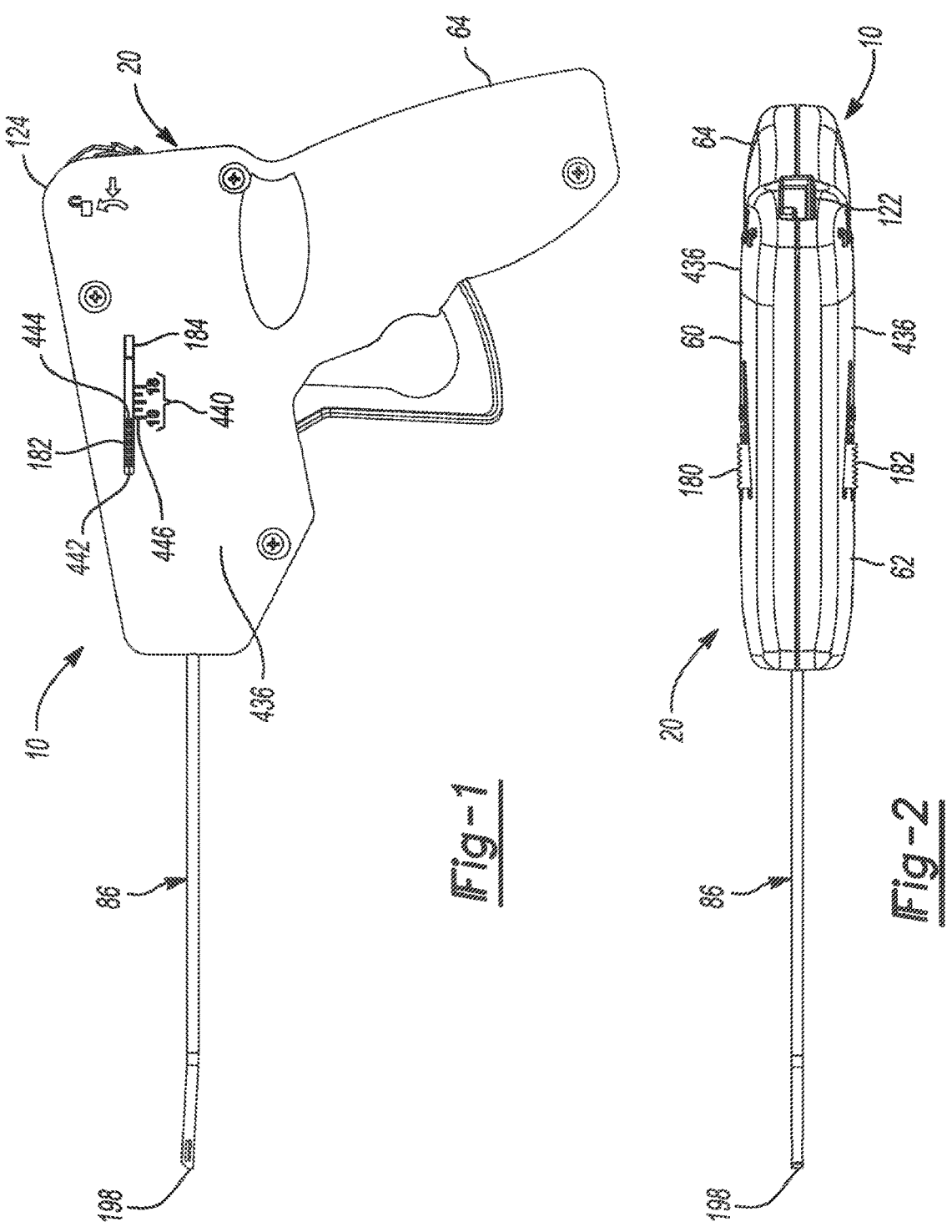
FIG. 1 is a side view of an exemplary tissue repair device according to the present teachings.
FIG. 2 is a top view of the exemplary tissue repair device according to the present teachings.
Figure 3:
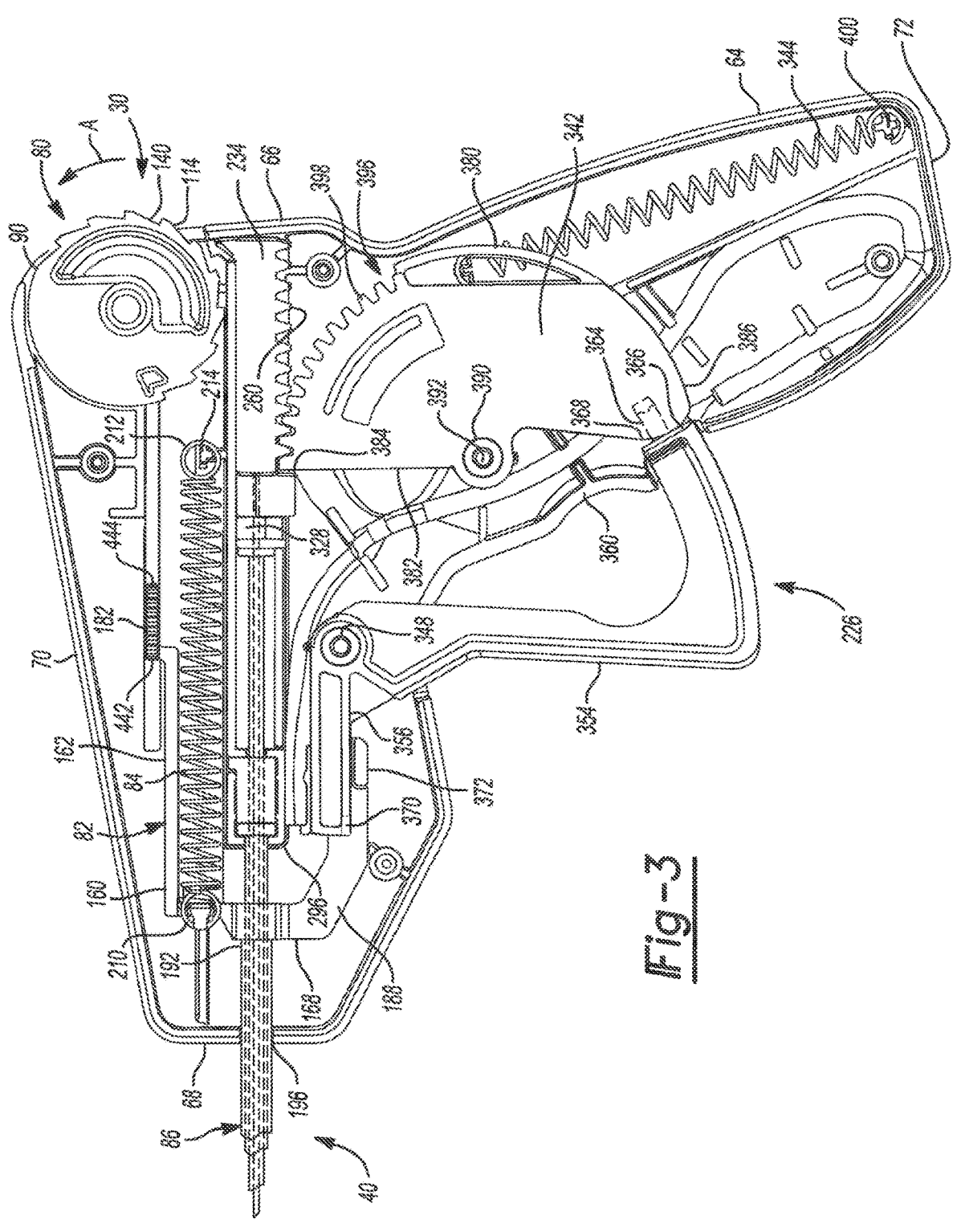
FIG. 3 is a partial side view of an exemplary configuration of the tissue repair device shown with a portion of the casing removed according to the present teachings.

The following description is merely exemplary in nature and is in no way intended to limit the present disclosure, its application, or uses. For example, although the present teachings are illustrated in an application for meniscus repair in knee surgery, the present teachings can also be used for repairing any fibrous tissue, such as muscle, ligament or tendon in an arthroscopic or other open procedure, including rotator cuff reconstruction, acromioclavicular (AC) reconstruction, anterior cruciate ligament reconstruction (ACL) and generally for fastening tendons, grafts, or strands to fibrous tissue and bone.

With initial reference to FIGS. 1-6, an exemplary tissue repair device 10 according to the present teachings is illustrated. As will be further described below, the device 10 can include a casing 20 housing a depth limiting or positioning system 30 that cooperates with an insertion system 40, which can be preloaded with one or more flexible suture anchors 50 configured to be delivered into soft tissue. Two flexible suture anchors 50 are illustrated in various Figures, including FIG. 6, and will be generally referred to hereinafter as first and second flexible anchors 50a, 50b for clarification purposes. The casing 20 can include a two-part casing having a first half portion 60 arranged to engage a second half portion 62, such that together the half portions 60, 62 can form a pistol grip handle portion 64. Each casing portion 60, 62 can include a proximal end 66, a distal end 68, a top 70 and a bottom 72 generally located at a distal end of pistol grip handle portion 64. Casing 20 can be formed from plastic or any other suitable material.

The depth positioning system 30 can include a rotatable cam member 80, an axially moving translation member 82, a biasing member 84, and an axially moveable outer cannula 86. With continuing reference to FIGS. 1-6 and additional reference to FIGS. 7-9B, cam member 80 can include a thumbwheel 90 having a first side 92, a second side 94 and an outer periphery 96. The first side 92 can include a central first projection or post 98 extending from a center thereof that can be positioned in a corresponding slot 100 in first casing portion 60. In a similar manner, second side 94 can likewise include a central second projection or post 104 extending therefrom in an opposite direction as post 98 and can be positioned in a corresponding slot 108 in second casing portion 62. Slots 100, 108 can have a longitudinal length greater than a diameter of respective posts 98, 104 so as to provide for both translation and rotation of thumbwheel 90, as will be described in greater detail below.

Thumbwheel 90 can further include a toothed portion 114 disposed around a portion of outer periphery 96 and configured to be engagable by a user of the device 10. Casing portions 60, 62 can each include respective recesses 118, 120 that together form an opening 122 to facilitate a portion of thumbwheel 90 extending through the opening 122 and beyond a periphery 124 of casing 20, as shown for example in FIGS. 1 and 3. First side 92 can further include a first rotation limiting surface 130, a first cam surface 132 positioned adjacent thereto, and second and third rotation limiting surfaces 134 and 136, respectively, the operation of which will be described in greater detail below. A recess area 138 can be formed in outer periphery 96 so as to provide access to surfaces 130-136.

The toothed portion 114 can include a plurality of teeth 140 with each tooth having an inclined or ramped surface 142 that mates with second surface 144 orientated generally normal to the outer periphery 96 of thumbwheel 90. The ramped surfaces 142 can be orientated such that they incline away from the outer periphery in a counter-clockwise direction shown by arrow A in FIG. 3.

Figure 4:
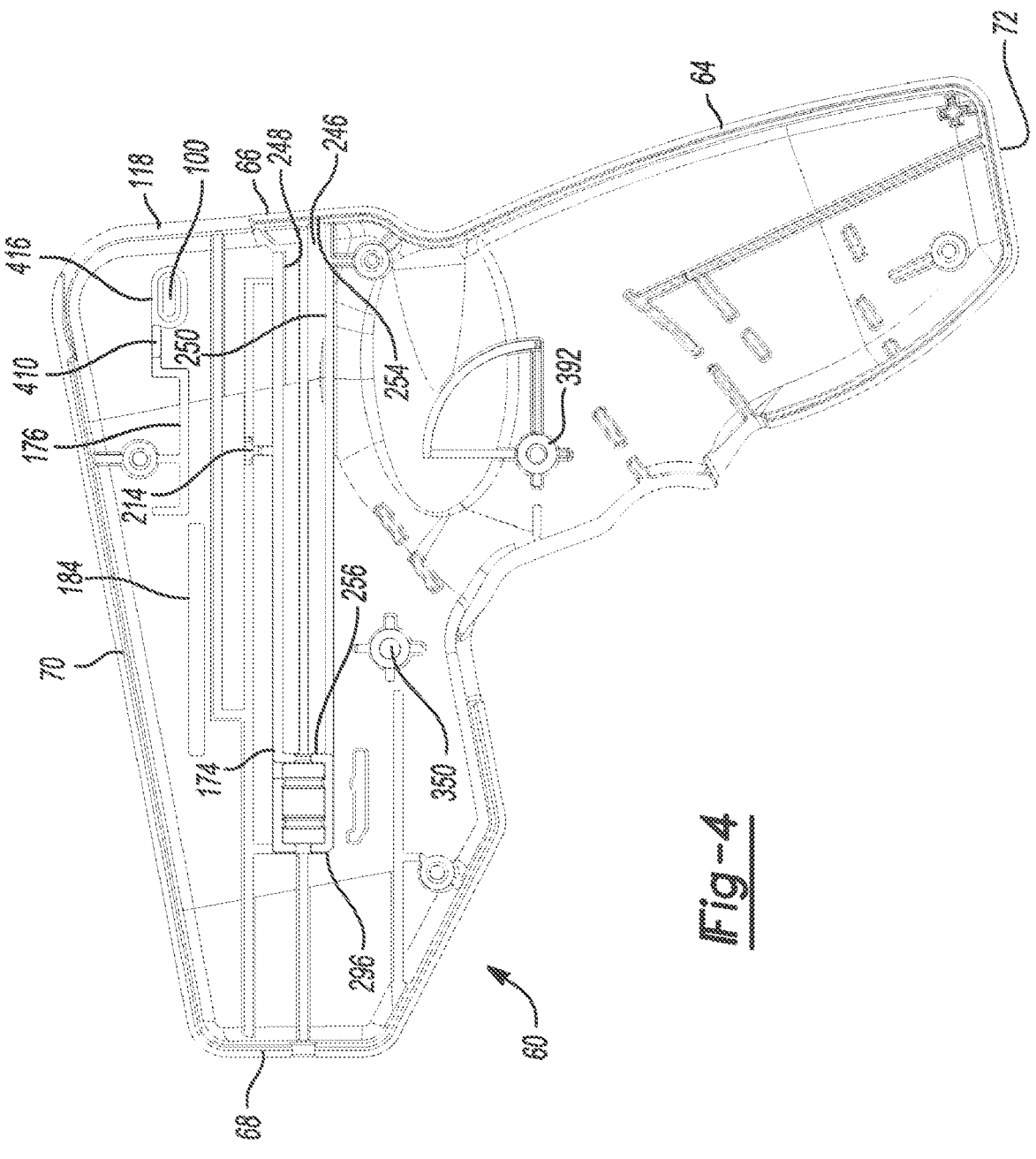
FIG. 4 is a side view of a portion of the casing of the device of FIG. 1 according to the present teachings.
Figure 5:
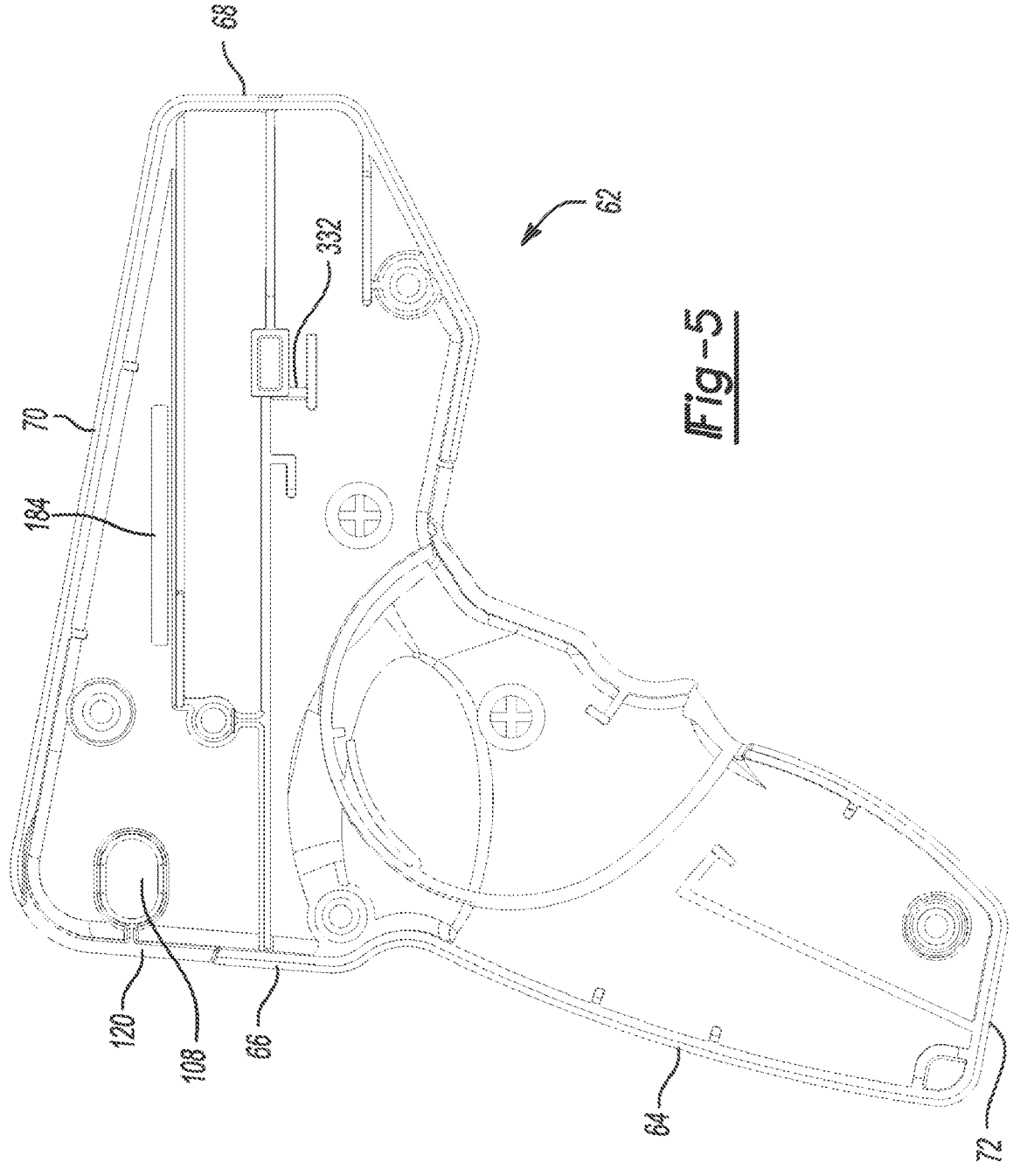
FIG. 5 is a side view of another portion of the casing of the device of FIG. 1 according to the present teachings.
Figure 6:
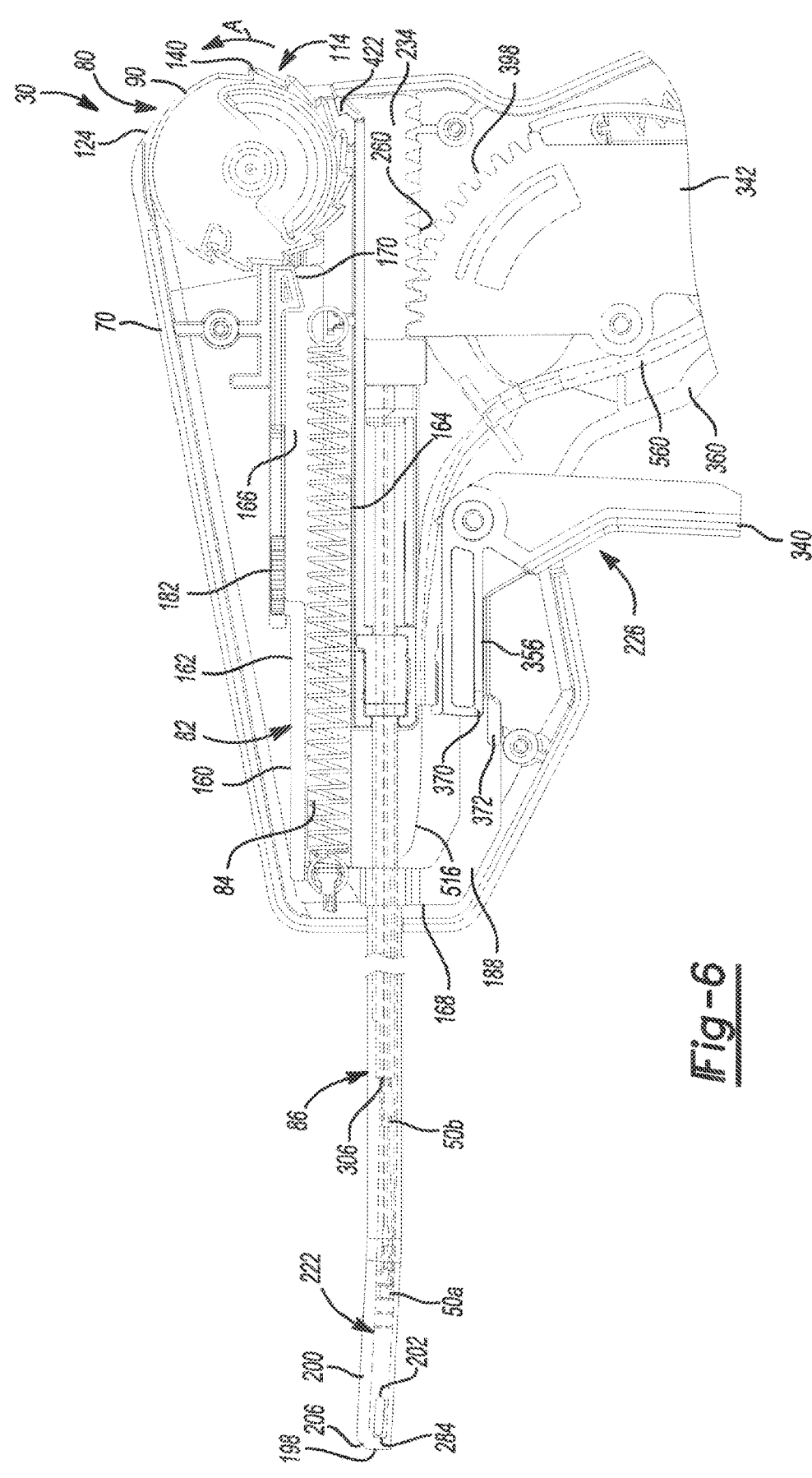
FIG. 6 is a partial side view of the device of FIG. 1, shown in an exemplary configuration according to the present teachings.

Translation member 82 can include a longitudinally extending portion 160 having a top 162, a bottom 164, a side portion 166 connecting the top and bottom 162, 164, a distal end 168 and a proximal end 170, as shown for example in FIG. 6. Translation member 82 can be positioned in casing 20 such that bottom 164 is adjacent a flange portion 174 of first casing portion 60 and top 162 is adjacent a flange portion 176 also of first casing portion 60, as generally shown in FIG. 4 with reference to FIG. 6. Flange portions 174, 176 can form a channel that guides translation member 82 during translation. A pair of position indication members 180, 182 can extend transversely in opposite directions from top 162 so as to extend through slots 184 in respective casing portions 60, 62 as shown in FIGS. 1 and 2.

Translation member 82 can further include an L-shaped portion 188 extending from distal end 168, as shown for example in FIG. 6. A proximal end 192 of outer cannula 86 can be coupled to L-shaped portion 188 such that outer cannula 86 can slidably protrude through an aperture 196 formed by casing portions 60, 62. A distal end 198 of outer cannula 86 can include a curved or inclined portion 200 as well as a pair of elongated apertures 202 positioned in alignment on opposite sides of cannula 86, as shown for example in FIG. 11C. Outer cannula 86 can also include a beveled or chamfered end 206 at a distal most end thereof adjacent to apertures 202. Chamfered end 206 can include a rounded or smooth end for placement adjacent to or abutting tissue without piercing the tissue. It should be appreciated that distal end 198 of outer cannula 86 can also be straight or non-inclined, arcuate, angled, etc. depending on a desired use or application, and can also be provided with or without apertures 202 and chamfered end 206.

Biasing member 84 can be connected at a first end 210 to the distal end 168 of translation member 82 and at a second end 212 to a tab 214 fixed to first casing portion 60. Biasing member 84 can be any suitable device, such as a coil spring, configured for expanding and contracting while also exerting a biasing force that biases the proximal end 170 of translation member 82 into engagement with thumbwheel 90.

Figure 10:
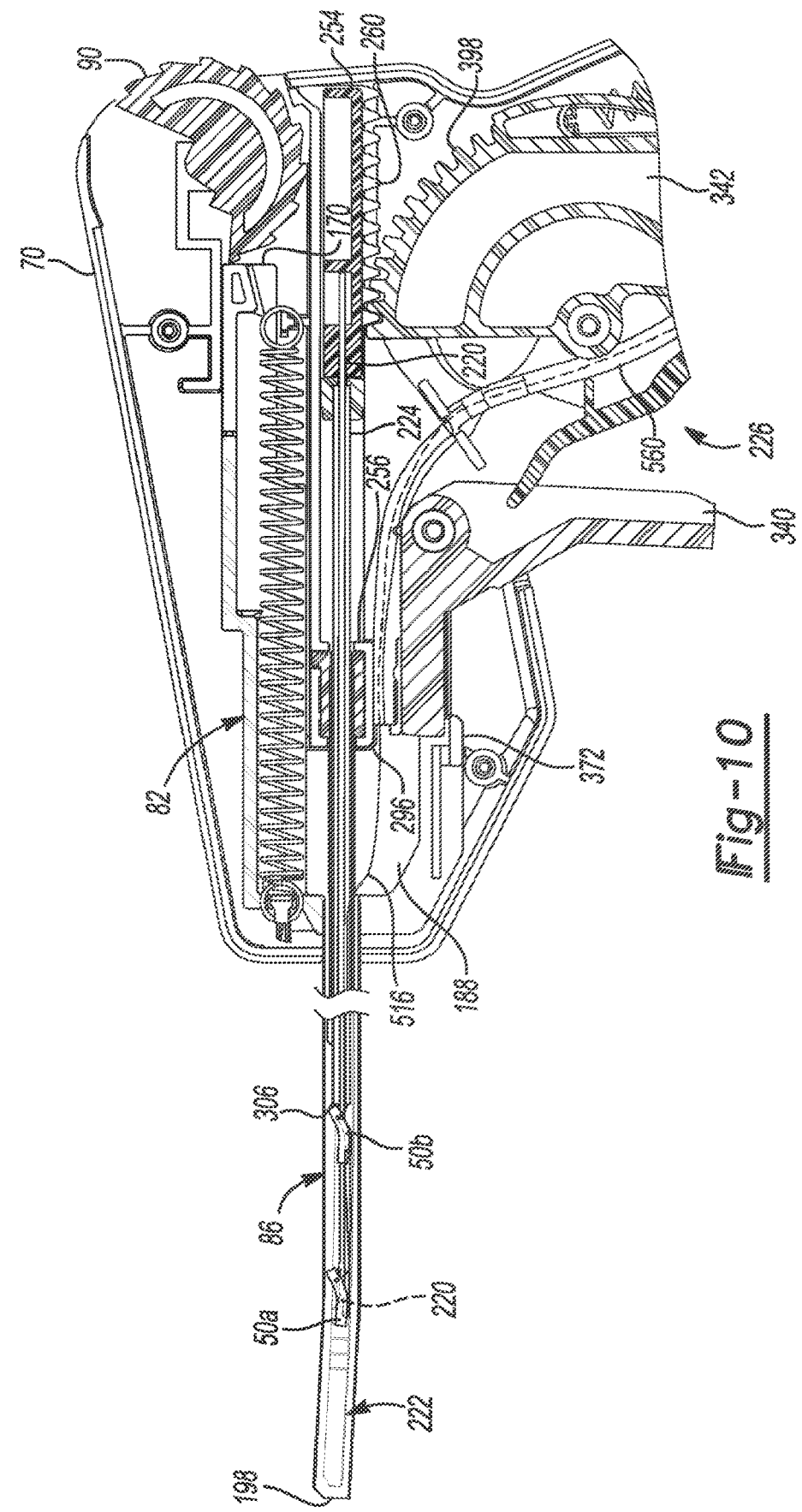
FIG. 10 is a partial sectional view of the device of FIG. 1, shown in an exemplary configuration according to the present teachings.
Figure 11:
FIG. 11 is an exploded perspective view of an exemplary carrying wire, positioning member, insertion member and outer cannula of the device of FIG. 1 according to the present teachings.
Figure 12:
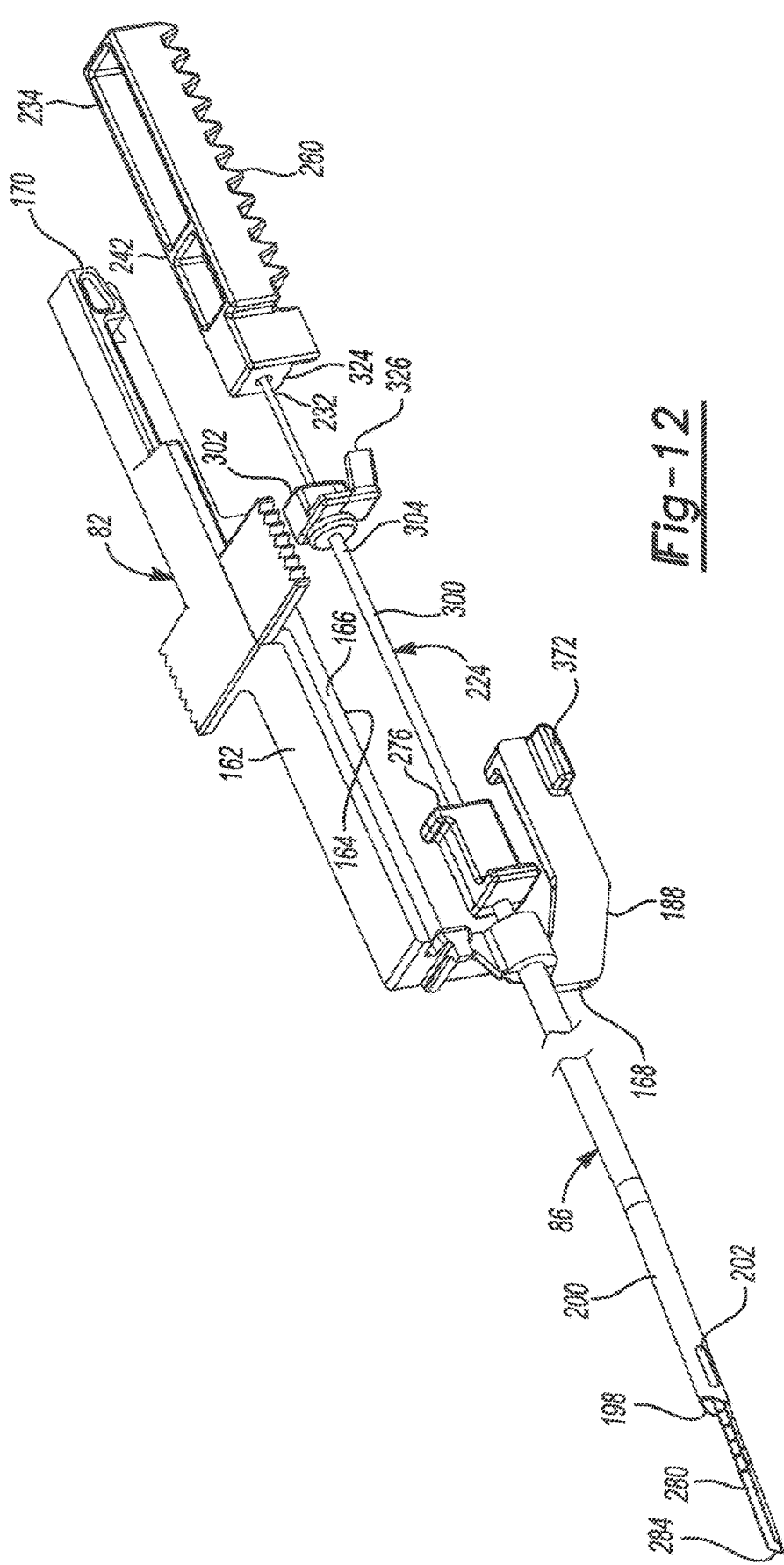
FIG. 12 is a perspective view of the components of FIG. 11, shown in an exemplary assembled configuration according to the present teachings.

With additional reference to FIGS. 10-12, the insertion system 40 will now be described. Insertion system 40 can include a slider or carrying wire 220, an insertion member 222, a loading or positioning member 224, and a deployment system 226. Carrying wire 220 can include a solid, semi-rigid construction 230 with a proximal end 232 fixedly coupled to a cam follower 234 and a distal end 236 having a suture anchor engagement portion 238. Cam follower 234 can include a generally rectangular shape 242 that can be configured to translate in a track 246 defined by flanges 248 and 250 in first casing portion 60. Track 246 can further include proximal and distal ends 254 and 256 serving to limit travel of the cam follower 234 therebetween, as shown in FIGS. 4 and 10. A lower surface of cam follower 234 can include a plurality of gear teeth 260 configured for meshing engagement with a cam member 342 to translate carrying wire 220 between a stowed position where cam follower 234 abuts proximal end 254 and a deployed position where cam follower 234 abuts distal end 256, as will be further described below.

The insertion member 222 can include a tubular portion 274 extending from a body member 276 at a proximal end 278 and a trough portion 280 mating with the tubular portion 274 and extending therefrom to a distal end 284. The trough portion 280 can include an inclined portion 286 complimentary to the inclined portion 200 of cannula 86. It should be appreciated that insertion member 222 can be provided with a straight or non-inclined distal end that could correspond to a straight distal end of outer cannula 86. Inclined portion 286 can include depth indicator markers 290, as well as a pointed and chamfered distal most end 292 capable of piercing skin and soft tissue. Body member 276 can be configured for positioning in a correspondingly shaped cavity 296 to fix insertion member 222 relative to casing 20 and outer cannula 86. The distal end 284 of insertion member 222 can be received in outer cannula 86 such that at least a portion of trough portion 280 and tubular portion 274 can reside within cannula 86 as shown for example in FIGS. 11 and 12.

The positioning member 224 can include a tubular portion 300 fixedly coupled to an engagement member 302 at a proximal end 304, and a distal end 306 configured to engage suture anchor 50b, as will be described in greater detail below in connection with the operation of device 10. Tubular portion 300 can include an inside diameter larger than the suture engagement portion 238 of carrying wire 220 but an outside diameter less than an inside diameter 314 of insertion member 222. Engagement member 302 can include a generally square or rectangular shape 316 configured to mate with the dimensions of track 246 such that engagement member 302 can be slidably received within track 246. Tubular portion 300 can be slidably received within the tubular portion 274 of insertion member 222 such that distal end 306 and a portion of tubular portion 300 are slidably housed within insertion member 222, as shown in FIGS. 11 and 12.

Figure 19:
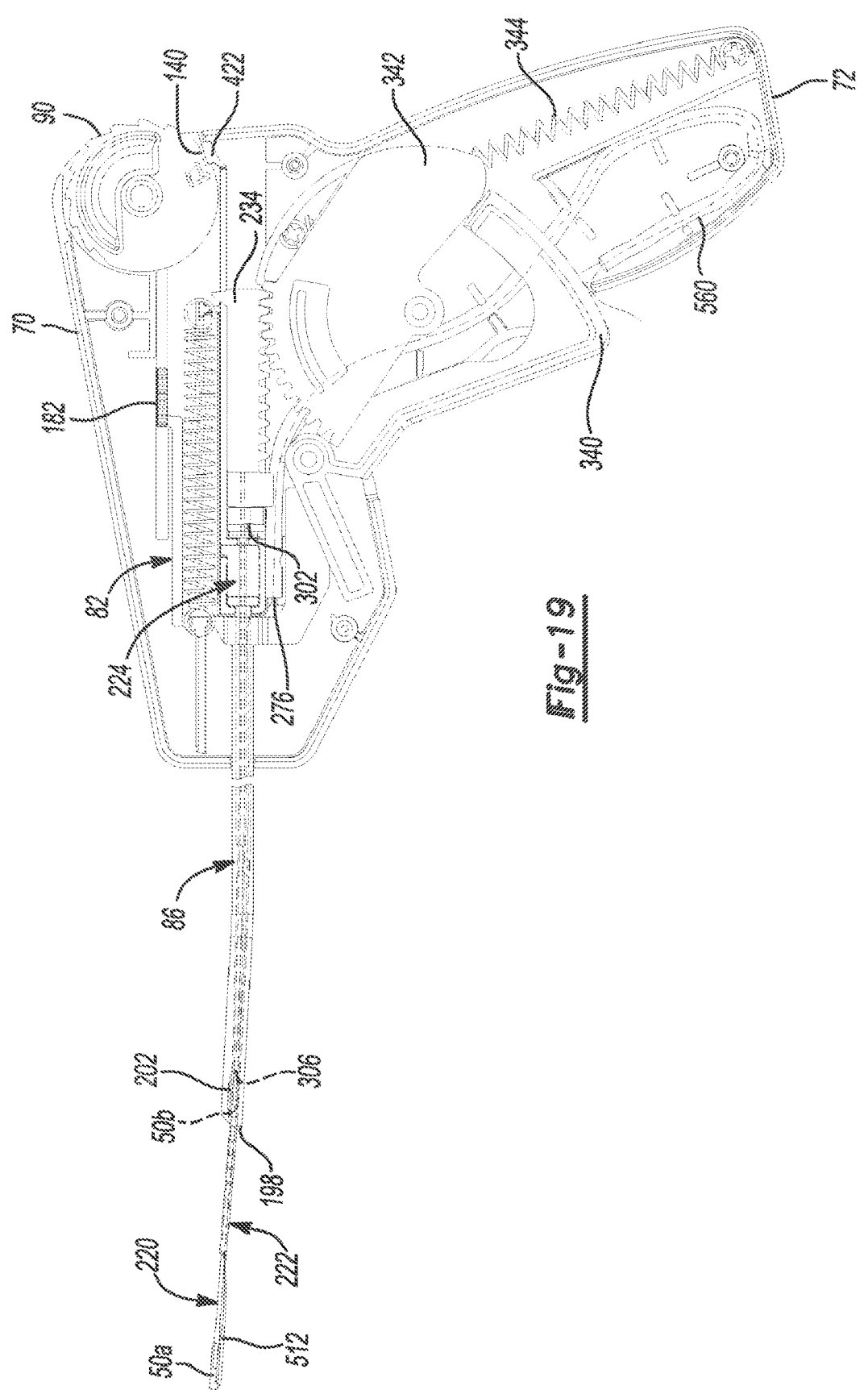
FIG. 19 is a partial side view of the device of FIG. 1, shown in an exemplary configuration according to the present teachings.

Carrying wire 220 can be inserted through positioning member 224 via aperture 320 such that positioning member 224 can translate on and relative to carrying wire 220. With carrying wire 220 disposed through positioning member 224, engagement member 302 and cam follower 234 can be positioned in track 246 such that engagement member 302 abuts a distal end 324 of cam follower 234 when cam follower 234 is in the stowed position. A retention tab 326 can also extend from a top portion 328 of engagement member 302. Retention tab 326 can be configured to engage a flange 332 extending from casing portion 62 so as to retain engagement member 302 relative to flange 332 when cam follower 234 is translated to the deployed position, as shown in FIG. 19 with reference to FIGS. 5 and 12.

Deployment system 226 can include a trigger 340, a cam member 342 and a biasing member 344. Trigger 340 can include an aperture 348 for pivotally coupling trigger 340 to a pivot post 350 of first casing portion 60, a user engageable portion 354 and a flange member 356. User engageable portion 354 can protrude through an aperture 360 formed by respective casing portions 60, 62 so as to be accessible by a user, as will be further described below. A coupling member 364 can extend from an end 366 of trigger 340 that is configured to abut cam member 342 so as to engage and couple trigger 340 to an end 368 of cam member 342. Flange member 356 can extend from aperture 348 in a direction substantially orthogonal to user engageable portion 354. Flange member 356 can include a tab 370 protruding from a distal end thereof and configured to engage a corresponding tab 372 protruding from L-shaped portion 188, as shown for example in FIG. 6. When tabs 370 and 372 align, trigger 340 is locked such that it can not be rotated from the non-deployed position shown in FIG. 6.

Cam member 342 can include a generally semicircular shaped portion 380 and a generally planer portion 382 spanning between respective ends 384, 386 of portion 380. An aperture 390 can be centrally positioned between ends 384, 386 and configured to engage a pivot post 392 protruding from first casing portion 60 such that cam member 342 can pivot about post 392. Arcuate portion 380 can include a portion 396 having a plurality of gear teeth 398 adjacent to and configured for meshing engagement with the plurality of gear teeth 260 of cam follower 234. Biasing member 344 can be coupled at one end to a retention tab proximate arcuate portion 380 and at another end to a retention post 400 protruding from first casing portion 60. Biasing member 344 can include a coil spring or other device suitable for imparting a biasing force onto cam member 342 to bias trigger 340 to the non-deployed position, as shown for example in FIG. 6.

Figure 20:
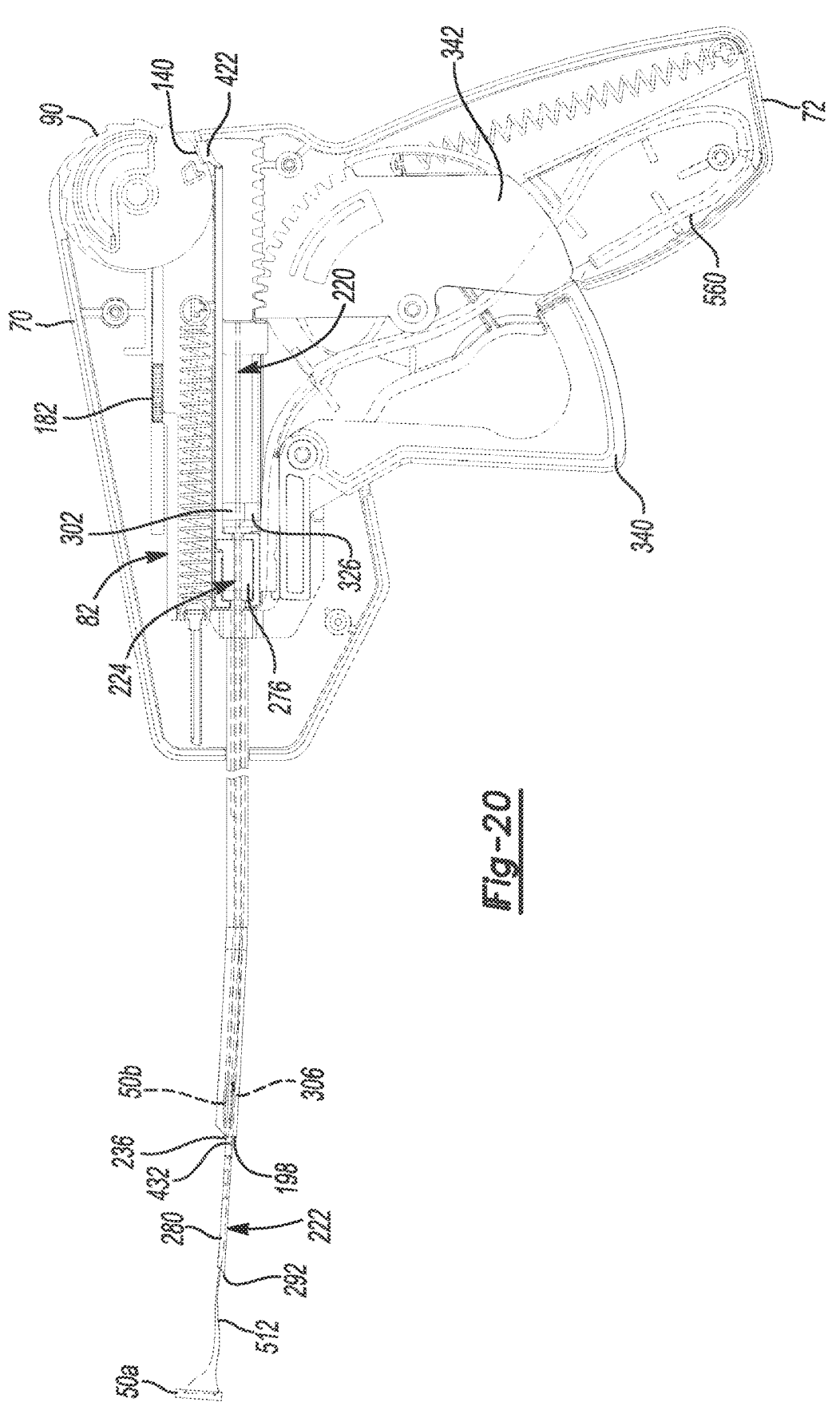
FIG. 20 is a partial side view of the device of FIG. 1, shown in another exemplary configuration according to the present teachings.

User engageable portion 354 of trigger 340 can be grasped by a user and squeezed or depressed so as to rotate trigger 340 about pivot post 350. Upon such rotation, trigger end 366 can drive cam member 342 to rotate about pivot post 392, which in turn will drivingly engage cam member gear teeth 398 with cam follower gear teeth 260 and translate cam follower 234 and carrying wire 220 forward from the stowed position to the deployed position, as generally shown in FIG. 19. Upon the user releasing trigger 340, the biasing force exerted by biasing member 344 can return cam follower 234, cam member 342 and trigger 340 to the non-deployed positions, as generally shown in FIGS. 6 and 20.

Returning to FIGS. 6-9B, operation of the depth positioning system 30 in connection with the insertion system 40 and trigger lock feature will now be described in greater detail. Thumbwheel 90 can be used to adjust a position of the outer cannula 86 relative to casing 20 and insertion member 222. More specifically, outer cannula 86 can be axially adjusted from a sheathed position to several use positions such that insertion member 222 extends at predetermined lengths relative to distal end 198 of outer cannula 86.

Figure 9A:
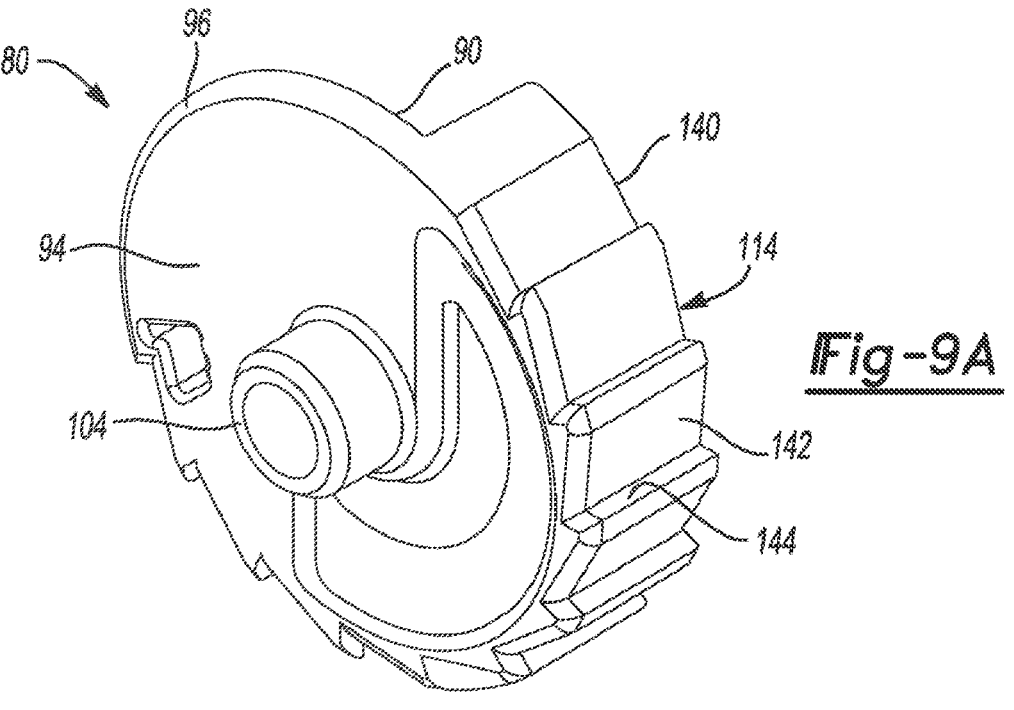
FIGS. 9A and 9B are perspective views of a cam member of the device of FIG. 1 according to the present teachings.
Figure 9B:
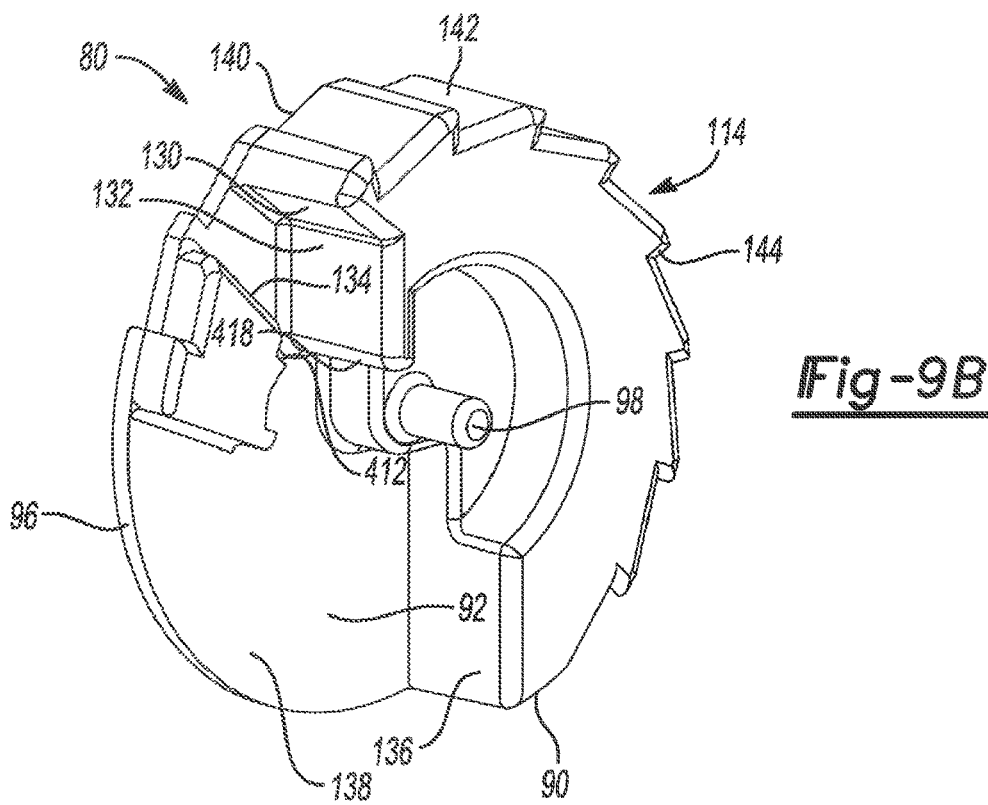

In the sheathed position, thumbwheel 90 can be positioned such that an engagement tab 410 protruding from first casing portion 60 is positioned between a projecting member 412 of rotation limiting surface 134 and an edge 418 of cam surface 132, as generally shown in FIG. 9B with reference to FIG. 4. In this position, thumbwheel 90 can be prevented from rotating and can engage the distal end of translation member 82 at the outer periphery 96 thereby positioning outer cannula 86 to a fully deployed or sheathed position, as shown in FIG. 6. In the sheathed position, outer cannula 86 can fully cover insertion member 222, carrying wire 220 and positioning member 224, as also shown in FIG. 6.

Figure 7:
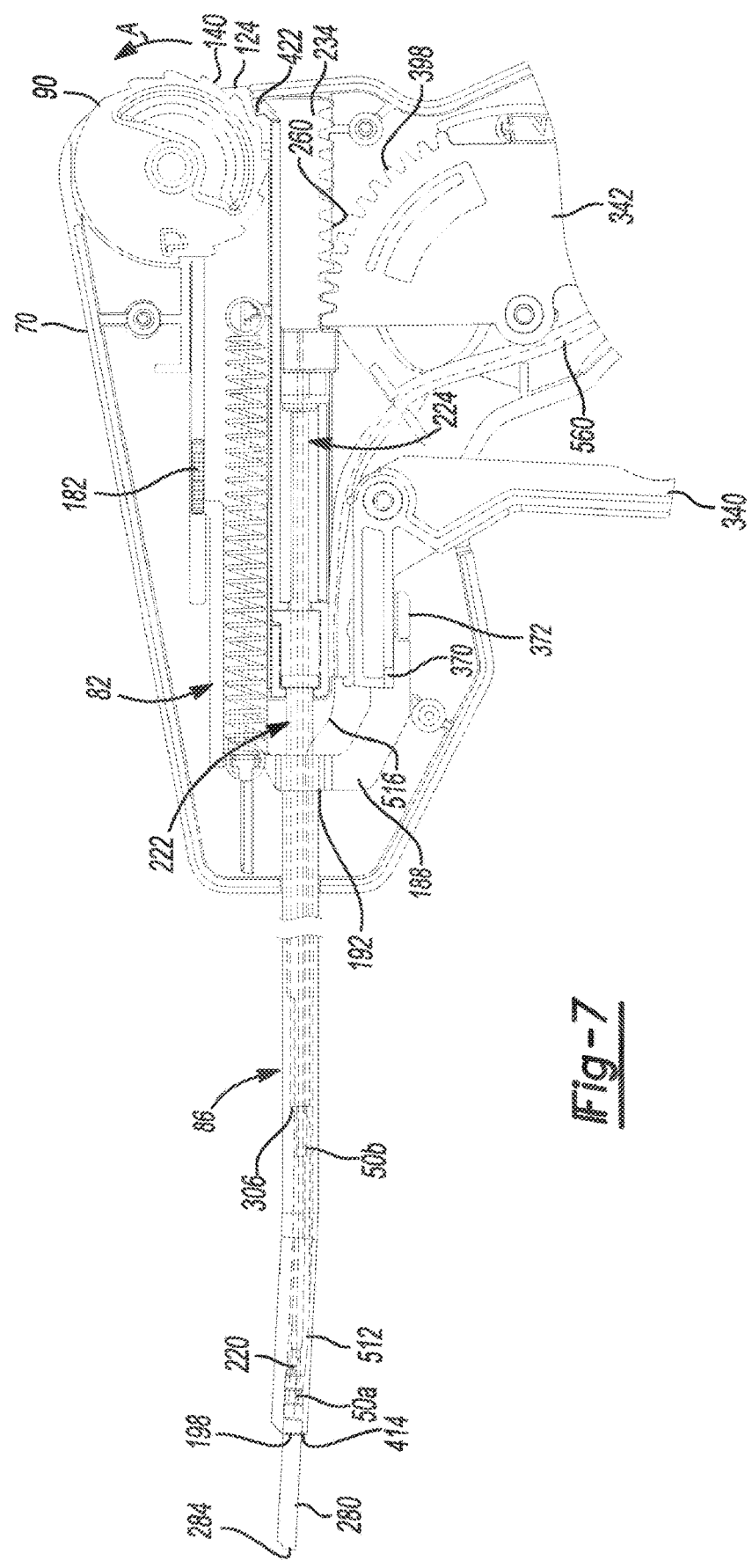
FIG. 7 is a partial side view of the device of FIG. 1, shown in another exemplary configuration according to the present teachings.

To move the depth positioning system 30 from the sheathed position to an initial use position, a user can push thumbwheel 90 to linearly translate thumbwheel 90 forward towards distal end 68 such that posts 98, 104 slide and translate forward in their respective slots 100, 108 and projection member 412 is disengaged from tab 410. Upon disengagement, thumbwheel 90 can be rotated counter-clockwise in the direction of arrow A such that recessed area 138 is now aligned with the proximal end 170 of translation member 82, as shown in FIG. 7. Biasing member 84 can then urge translation member 82 rearward into recess area 138 such that proximal end 170 engages first cam surface 132, as generally shown in FIG. 7 with additional reference to FIG. 9B. Cam surface 132 can be configured with a shape as shown that cooperates with proximal end 170 of translation member 82 and biasing member 84 to urge thumbwheel 90 to rotate in the direction of arrow A from the sheathed position to the initial use position. In the initial use position, the distal end 198 of outer cannula 86 can align with a first marker 414 of depth markers 290, and a tooth of the plurality of teeth 140 can engage a cooperating projection 422 of first casing portion 60, as also shown in FIG. 7.

Figure 8:
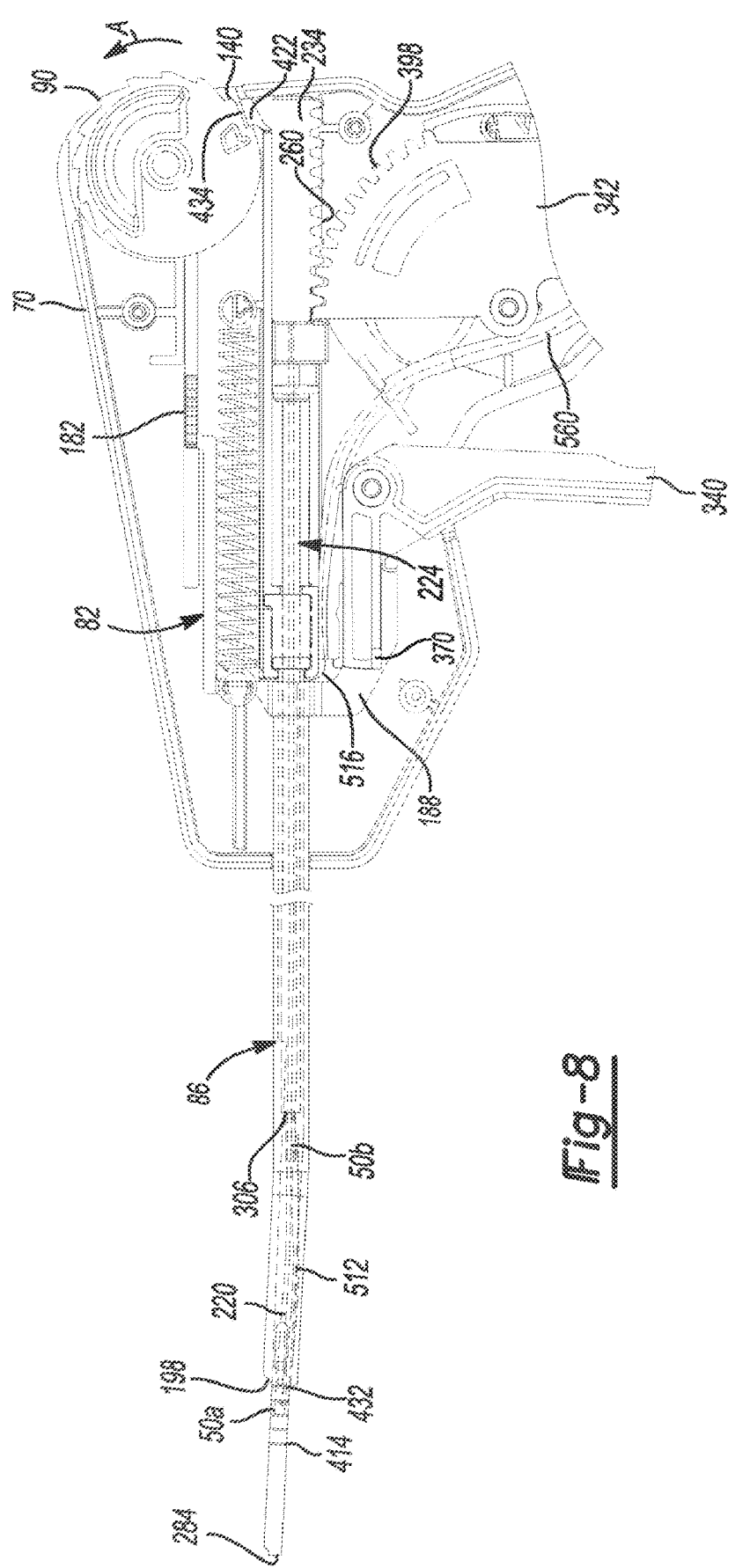
FIG. 8 is a partial side view of the device of FIG. 1, shown in another exemplary configuration according to the present teachings.

In the initial use position, outer cannula 86 can be partially translated rearward into casing 20 such that a distal end 284 of insertion member 222 is exposed. A user can now rotate thumbwheel 90 to adjust outer cannula 86 to a desired position relative to distal end 284 of insertion member 222. For example, a user could adjust outer cannula 86 relative to distal end 284 such that distal end 284 protrudes a prede-termined distance that corresponds to a desired distance in which insertion member 222 can be inserted into the anatomy. In one exemplary configuration, thumbwheel 90 can be used to adjust outer cannula 86 relative to insertion member 222 by 8 millimeters in 2 millimeter increments from first marker 414 to fifth marker 432, as generally shown in FIG. 8. It should be appreciated that the depth and positioning system 30 can be configured to provide various amounts of adjustment as may be desired for various pro-cedures. In this regard, thumbwheel 90 can include a plu-rality of discrete positions and/or infinite adjustment con-figurations as may be desired for various procedures.

Figures 11A, 11B, 11C:
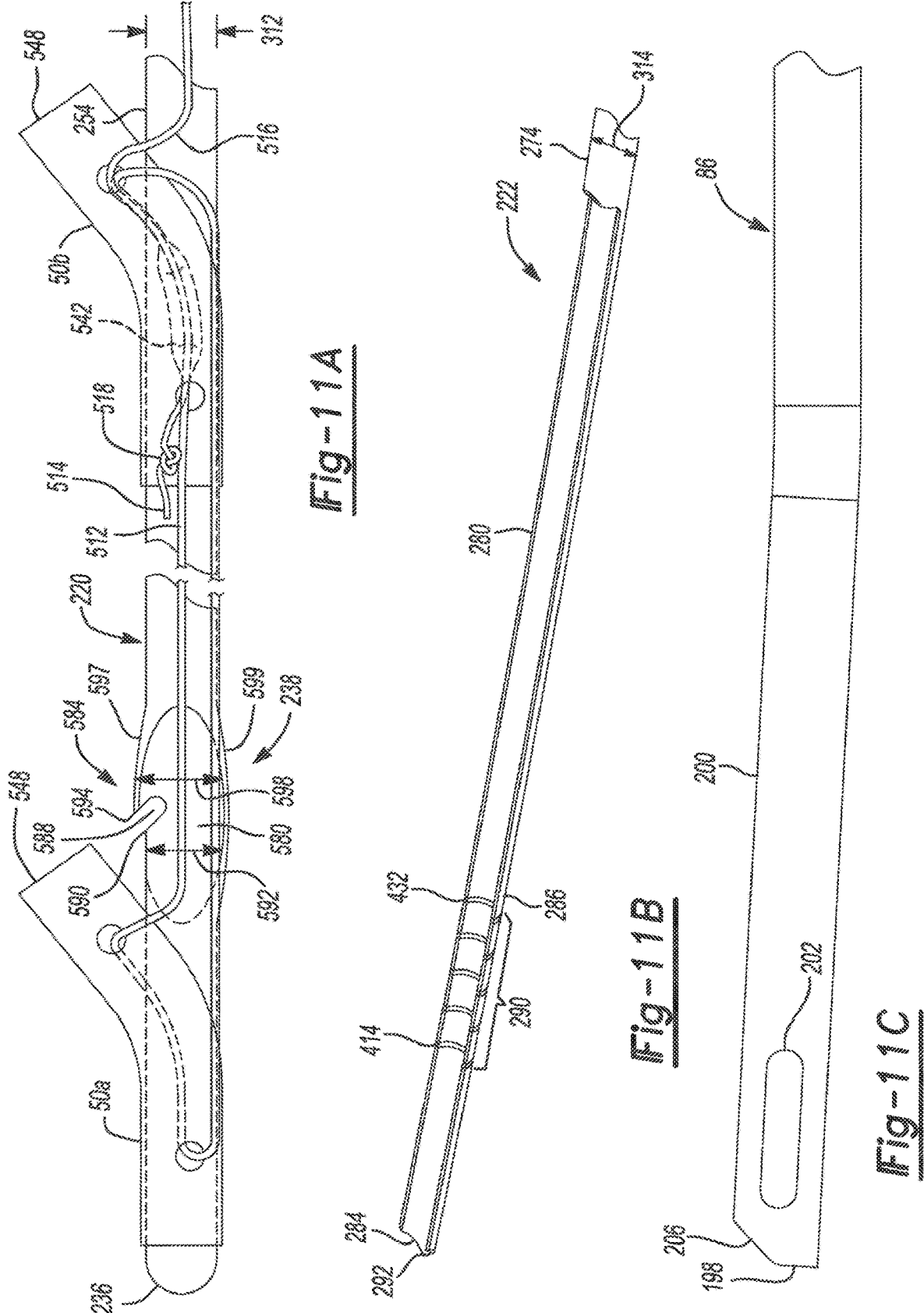
FIG. 11A is a partial exploded perspective view of the carrying wire of FIG. 11 having a pair of pre-loaded anchors according to the present teachings.
FIG. 11B is a partial exploded perspective view of the insertion member of FIG. 11 according to the present teachings.
FIG. 11C is a partial exploded perspective view of the outer cannula of FIG. 11 according to the present teachings.

With continuing reference to FIGS. 6-9B and additional reference to FIGS. 1 and 11B, depth markers 290 can be used to aid a user in positioning outer cannula 86 relative to insertion member 222. In an exemplary configuration, mark-ers 290 and can include five discrete markers or indicia, with the first marker 414 corresponding to a distance of 10 millimeters from the distal end 284 of insertion member 222 to the distal end 198 of outer cannula 86. Each successive marker in a rearward direction towards casing 20 can be separated by 2 millimeters such that the fifth marker 432 can correspond to a distance of 18 millimeters from distal end 284 to distal end 198.

In addition, respective sides 436 of casing 20 can also include depth indicator markings or indicia 440, as shown in FIG. 1. Markings 440 can similarly include five markers that correspond to the same five positions as the markers 290 on insertion member 222. A distal side 442 of position indicator members 180, 182 can be configured to align with markings 440 to provide a visual indication on casing 20 of a position of the distal end 284 of insertion member 222 relative to outer cannula 86, as shown for example in FIG. 1. It should also be noted that when insertion system 40 is in the sheathed position, a proximal side 444 of position indicator members 180, 182 can align with a first marker 446 of markings 440, as shown in FIG. 1.

Each tooth of the plurality of teeth 140 on thumbwheel 90 can be correspondingly spaced apart such that thumbwheel 90 can be used to advance or retract outer cannula 86 in the 2 millimeter increments described above. More specifically, to retract outer cannula 86 away from distal end 284 of insertion member 222, thumbwheel 90 can be pressed for-ward, such that teeth surfaces 144 clear cooperating projec-tion 422, and then rotated in the counter-clockwise direction of arrow A. For example, thumbwheel 90 can be translated forward and simultaneously rotated in the direction of arrow A to retract outer cannula 86 from the first marker 414 to the fifth marker 432 such that the distal end of insertion member 222 extends beyond outer cannula 86 by a distance of 18 millimeters, as shown in FIG. 8. In this position, second surface 144 adjacent an end of tooth 434 can engage cooperating projection 422 and rotation limiting surface 130 can engage surface 416 of first casing portion 60 adjacent engagement tab 410, as generally shown in FIGS. 8 and 9B. On the other hand, to advance outer cannula 86 towards distal end 284, thumbwheel 90 can be rotated in a direction opposite of arrow A with ramped surfaces 142 ratcheting against cooperating projection 422 to a desired position.

With reference to FIGS. 13-18, the flexible suture anchors 50*a*, 50*b* will now be described in greater detail. Each flexible anchor 50*a*, 50*b* can be an elongated member having first and second ends 502, 504. The first and second ends 502, 504 can be substantially perpendicular to the longitu-dinal axis of the flexible anchors 50*a*, 50*b*. The flexible anchors 50*a*, 50*b* can be made of resorbable or non-resorb-able materials, including braided suture, sponges and sponge-like materials in solid form, perforated materials, woven/braided from biocompatible materials or fibers, such as, for example, polymer, polyester, polyethylene, cotton, silk, or other natural or synthetic materials, including sponges and sponge-like materials. The flexible anchors 50*a*, 50*b* can have any properties that allow the flexible anchors 50*a*, 50*b* to change shape. The flexible anchors 50*a*, 50*b* can be, for example, compliant, flexible, foldable, squashable, squeezable, deformable, limp, flaccid, elastic, low-modulus, soft, spongy, perforated or any other flexible member which can change shape. In some aspects, the flexible anchors 50*a*, 50*b* can be coated with biological or biocompatible coatings, and can also be soaked in platelets and other biologics, which can be easily absorbed by the flexible anchors 50*a*, 50*b* in particular when, for example, the flexible anchors 50*a*, 50*b* are made from spongy, absor-bent material.

Figures 16, 17, 18:
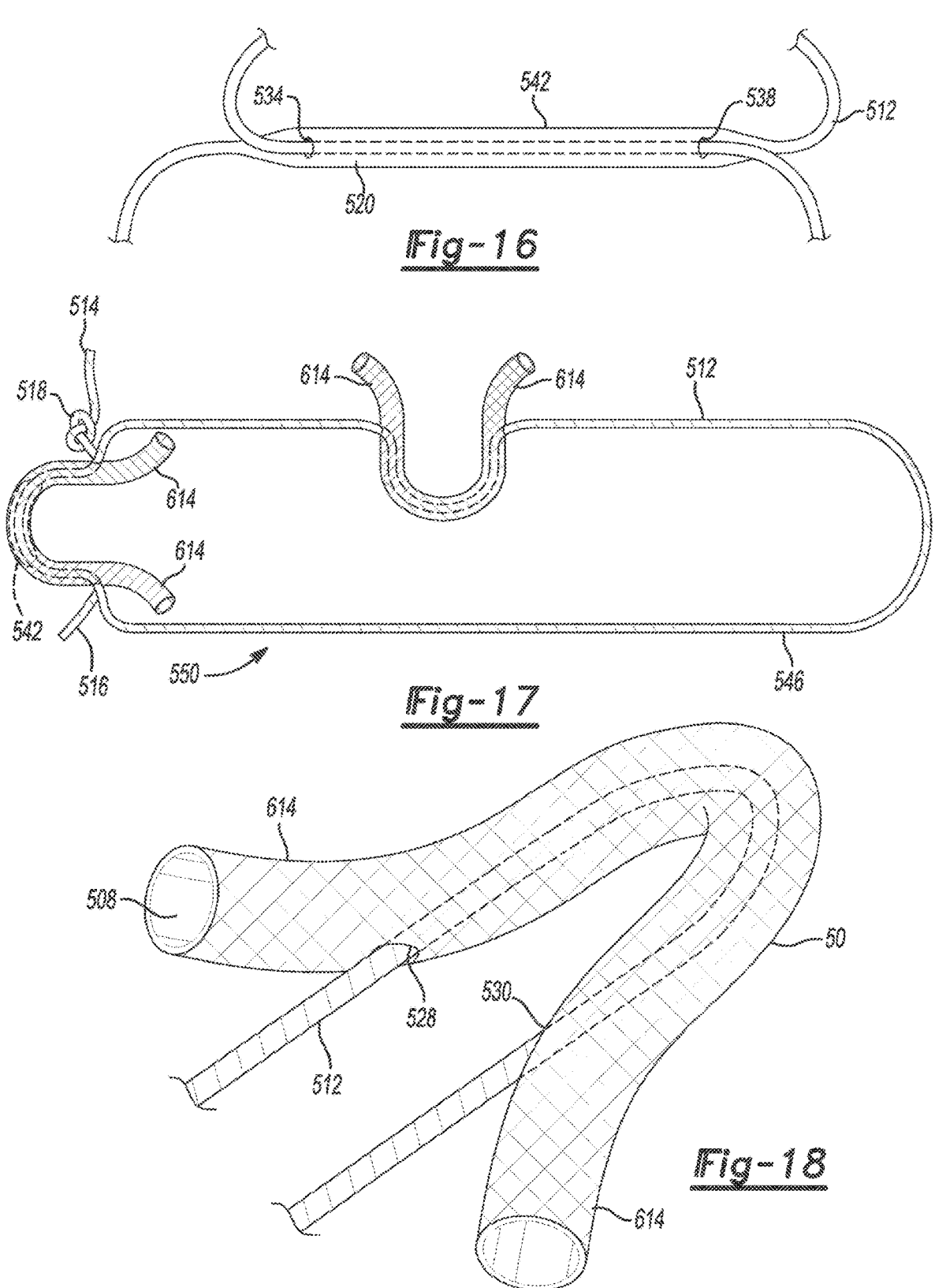

It should be understood by the above description that the flexible anchors 50*a*, 50*b* are not configured to pierce or otherwise penetrate tissue either with the first and second ends 502, 504, which are blunt or with any other portion thereof. The flexible anchors 50*a*, 50*b* can be loaded on the exterior of the distal end 256 of carrying wire 220, as will be discussed in greater detail below. The flexible anchors 50*a*, 50*b* can be in the form of an elongate flexible tube defining a bore 508 along their length, as shown in FIG. 18.

The first and second flexible suture anchors 50*a*, 50*b* can be coupled together with a flexible suture or strand 512. The flexible strand 512 can have first and second ends 514, 516 and can be made of braided filaments or fibers of biocom-patible material, including natural and synthetic fibers, such as cotton, silk, polymer, polyester, polyethylene, thin wire, suture, and other materials. The flexible strand 512 can be braided in a tubular or hollow form such that it forms an internal passage 520 between the first and second ends 514, 516.

A small knot or other retaining device 518 can be optionally formed adjacent the first end 514. The flexible strand 512 can be passed through a first opening 528 of each of the flexible anchors 50a, 50b, guided along the corresponding bore 508 and passed through a second opening 530 of each flexible anchor 50a, 50b, as for example shown in FIG. 18. The openings 528, 530 can be positioned intermediately between the first and second ends 502, 504 of each flexible anchor 50a, 50b at a distance of, for example, one-quarter length from the ends 502, 504 of each flexible anchor 50a, 50b. Furthermore, it will be appreciated that the openings 528, 530 can be apertures or voids in the woven fabric of the flexible anchors 50a, 50b, such that the openings 528, 530 do not disrupt or break the weave of flexible anchors 50a, 50b, when the flexible anchor 50a, 50b are made of braided or woven material.

After the flexible anchors 50a, 50b are mounted on the flexible strand 512, the second end 516 of the flexible strand 512 can be inserted into the internal passage 520 of the flexible strand 512 at an aperture 534, guided longitudinally along the passage 520, and led out of the passage 520 of the flexible strand 512 at an aperture 538. The portion of the strand 512 between apertures 534 and 538 can form an adjustment portion 542 between the optional knot 518 and the opening 528 of the second flexible anchor 50b, such that the flexible strand 512 defines a single adjustable knotless loop 546, as shown in FIGS. 15 and 16. The second flexible anchor 50b can be slidably moved along the flexible strand 512 until the adjustment portion 542 is within the bore 508 of the second flexible anchor 50b and the knot 518 is adjacent the opening 528 of the second flexible anchor 50b, as shown in FIG. 17. It will be appreciated, however, that the adjustment portion 542 can remain in the position shown in FIG. 15 outside of bore 508. The adjustable knotless loop 546 is self-locking and does not require the surgeon to tie a knot during a surgical procedure for securing the flexible strand 512. Further, once the adjustable knotless loop 546 is self-locked by pulling the second end 516 of the flexible strand 512 and tensioning the flexible strand 512, friction prevents the adjustable knotless loop 546 from being loosened, thereby providing a secure lock. Additional details regarding forming the knotless adjustable loop 546, and additional adjustable knotless loop configurations are disclosed in co-pending and commonly assigned U.S. patent application Ser. No. 11/541,506, filed on Sep. 29, 2006, the disclosure of which is incorporated herein by reference.

For discussion purposes, the anchors 50a, 50b, together with flexible strand 512 configured in the knotless loop 546 can be hereinafter referred to as the anchor system 550. With reference to FIGS. 6 and 11A, the anchor system 550 can be pre-loaded in an in-line configuration on the carrying wire 220 such that anchor 50a is positioned before flexible anchor engagement portion 238 and second anchor 50b is positioned after engagement portion 238. In the in-line configuration, carrying wire 220 can extend through a portion of bore 508 of anchors 50a, 50b and then pierce though each anchor thereby creating a tail portion 548 that is not coaxial with carrying wire 220, as shown for example in FIG. 11A. In this configuration, the anchors 50a, 50b can reside in the trough portion 280 of insertion member 222. The flexible strand 512 can be packaged within outer cannula 86 along side insertion member 222 and positioning member 224. Second end 516 of flexible strand 512 can extend out of outer cannula 86 through aperture 196 and into a tubular housing member 560 positioned in a handle portion of first casing portion 60, as shown for example in FIG. 6.

Returning to FIGS. 11 and 11A, the suture anchor engagement portion 238 of carrying wire 220 will now be described in greater detail. Suture engagement portion can have a flattened area 580 having a thickness less than the outside diameter 312 of carrying wire 220. Flattened area 580 can be formed so as to maintain the same cross-sectional area as a cross section through a non-flattened portion of carrying wire 220, thereby providing for the suture anchors 50a, 50b to be sized relative to the diameter of carrying wire 220 while ensuring that they can slide over the engagement portion 238, as will be further described below.

The engagement portion 238 can further include a one-way barb 584 configured such that flexible anchors 50a, 50b can slide or travel over barb 584 in only one direction of travel from the proximal end 254 of carrying wire 220 to the distal end 236 thereof. One-way barb 584 can be defined by a recess or cut-out 588 formed in the flattened section such that a distal end 590 of an open end of recess 588 mates with a portion of flattened area 580 having a first width 592. A proximal end 594 of the recess 588 also adjacent the opening can mate with another portion of the flattened area 580 having a second width 598 greater than the first width 592. Flattened area 580 can also include curved transition areas 597, 599 between the flattened area 580 and a non-flattened area of the carrying wire on a proximal side thereof, as shown in FIG. 11A.

In use, the larger second width 598 of flattened area 580 and the angled nature of one-way barb 584 provides for suture anchor 50b to be able to slide or travel over the barb 584 in a proximal to distal direction without being caught or stopped by barb 584. In a similar manner, carrying wire 220 can slide or travel relative to suture anchor 50b in a distal to proximal direction without barb 584 catching or stopping flexible anchor 50b. Conversely, the smaller first width 592 of flattened area 580 in cooperation with barb 584 provides for catching an interior surface of bore 508 of suture anchor 50b when carrying wire 220 moves in a proximal to distal direction relative to flexible anchor 50b.

Referring now to FIGS. 6-8 and 19-23, the soft tissue repair device 10 pre-loaded with suture anchors 50a, 50b can be used to repair a soft tissue defect 600, such as, for example, a tear, or other weakness in fibrous soft tissue 602, such as in meniscal tissue, cartilage, muscle or other fibrous tissue under the skin. An outer incision 601 can be made through the skin to access the soft tissue 602 and a user can insert the distal end 198 of outer cannula 86 to the surgical site. An appropriate insertion depth can be determined for the insertion member 222 and the user can translate and rotate thumbwheel 90, as discussed above, to unlock the depth and positioning system 30 from the sheathed position to the initial use position. The outer cannula 86 can then be adjusted relative to insertion member 222 such that distal end 284 extends beyond outer cannula 86 a distance corresponding to the desired insertion depth.

The exposed distal end 284 of insertion member 222 can be inserted through first entry point 604 into soft tissue 602 from a first side of the defect 600 until the distal end 284 can exit a second side 606 of the fibrous soft tissue 602, such as an outer surface or back side of a meniscus of a knee joint or other outer surface of a fibrous tissue. In this position, the distal end 198 of outer cannula 86 can be adjacent to or abutting the first entry point 604. It should be appreciated that the chamfered end 292 of insertion member 222 could alternatively be used to pierce the skin without requiring an incision 604.

Figure 21:
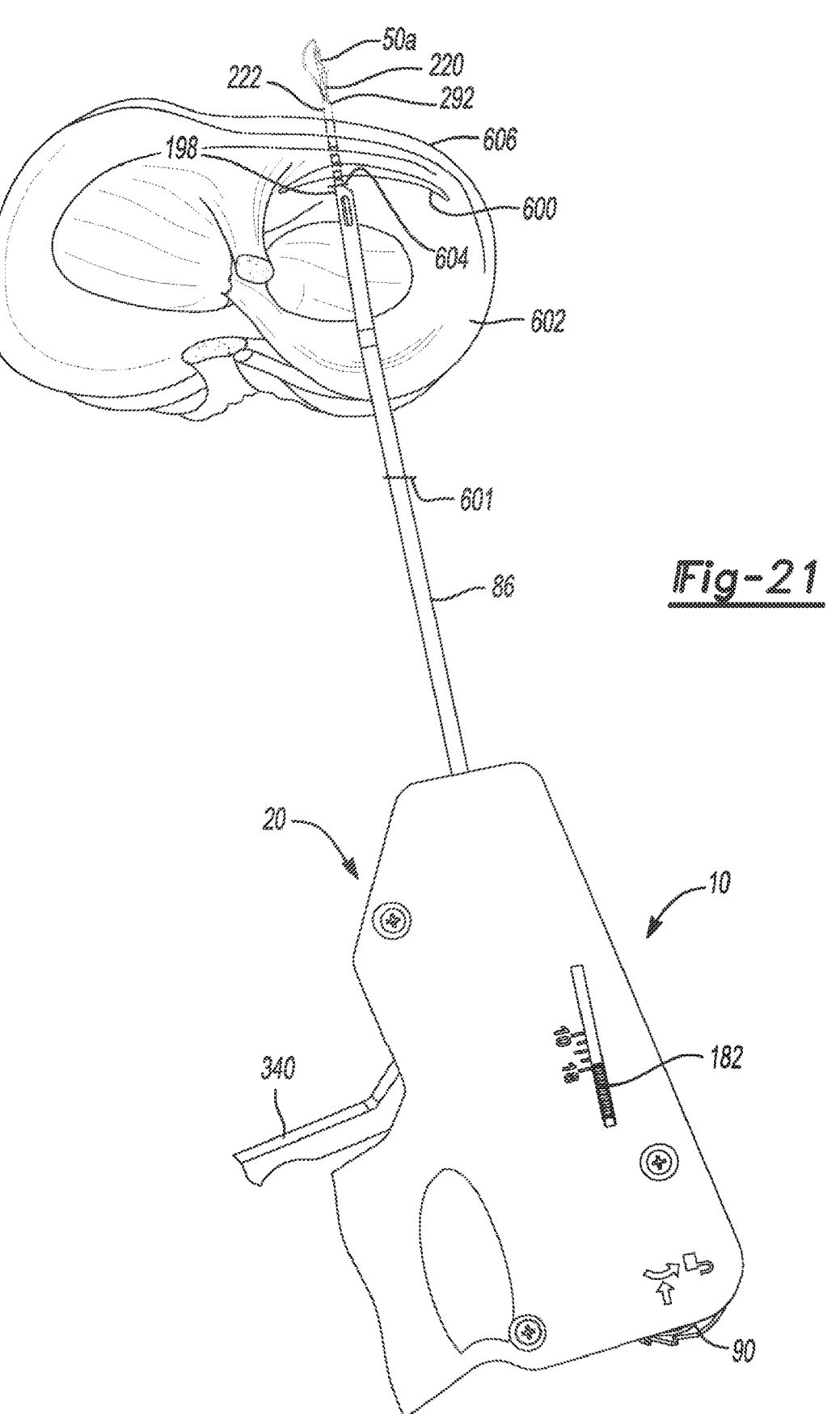
FIG. 21 is an exemplary environmental view showing a first anchor being deployed outside of soft tissue according to the present teachings.

With distal end 284 of insertion member 222 appropriately positioned, the trigger 340 can be squeezed or depressed to translate carrying wire 220 forward relative to insertion member 222 such that one-way barb 584 engages first flexible suture anchor 50*a* and delivers anchor 50*a* on the second side 606 of the soft tissue 602 at a first location, as shown in FIGS. 19 and 21. It should be appreciated that the manner and structure of the pre-assembled anchor system 550 in-line on carrying wire 220 allows the anchor 50*a* to pass through a narrow opening or slit, first entry point 604, formed in the tissue 602 by the chamfered end 292 of insertion member 222. It should also be appreciated that the U-shaped trough portion 280 of insertion member 222 requires a smaller insertion area than a fully enclosed, circular shaped insertion member would require and will not core a plug of tissue.

As cam follower 234 translates carrying wire 220 forward to deploy first anchor 50*a* in connection with depressing trigger 340, cam follower 234 also simultaneously translates positioning member 224 forward such that distal end 306 engages second flexible anchor 50*b* and moves anchor 50*b* forward towards distal end 198 of outer cannula 86, as shown in FIGS. 19 and 20. Tubular portion 300 of positioning member 224 can have a length such that when trigger 340 is fully depressed to deploy first anchor 50*a*, second anchor 50*b* will be carried forward to a position adjacent apertures 196 and distal end 198 of outer cannula 86. In this position, retention tab 326 can engage flange 332 to retain positioning member 224 and thus anchor 50*b* in this advanced position when trigger 340 is released. After the first anchor 50*a* has been deployed, the trigger 340 can be released thereby retracting the distal end 284 of insertion member 222 such that one-way barb 584 is positioned rearward of or within bore 508 of suture anchor 50*b*, as generally shown in FIGS. 19 and 21. When insertion member 222 is retracting, the tail portion 548 of suture anchor 50*a* can engage the soft tissue side 606 such that it will be removed from insertion member 222 as insertion member 220 retracts to the stowed position.

Figure 22:
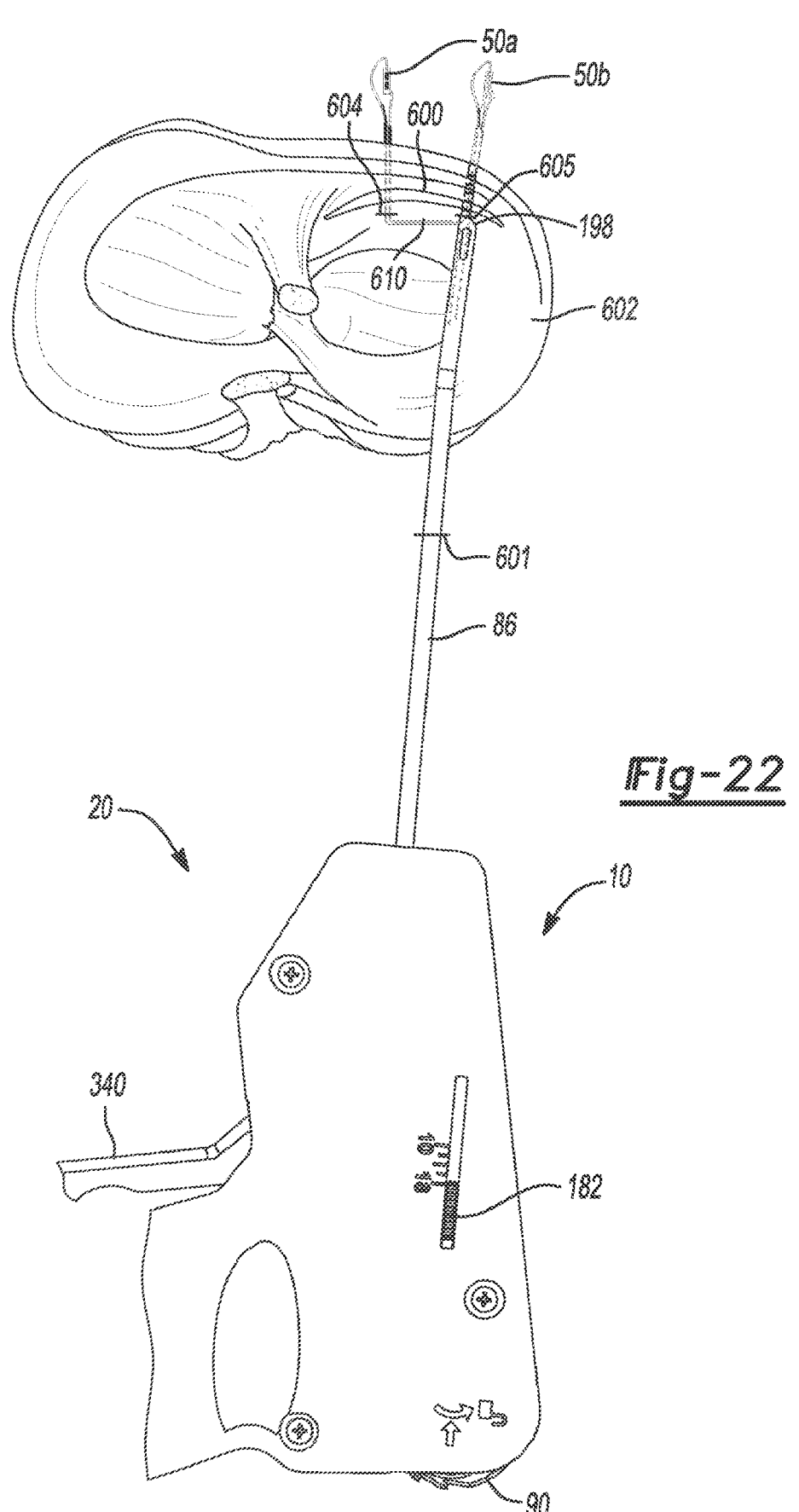
FIG. 22 is an exemplary environmental view showing first and second anchors being deployed outside of soft tissue according to the present teachings.
Figure 23:
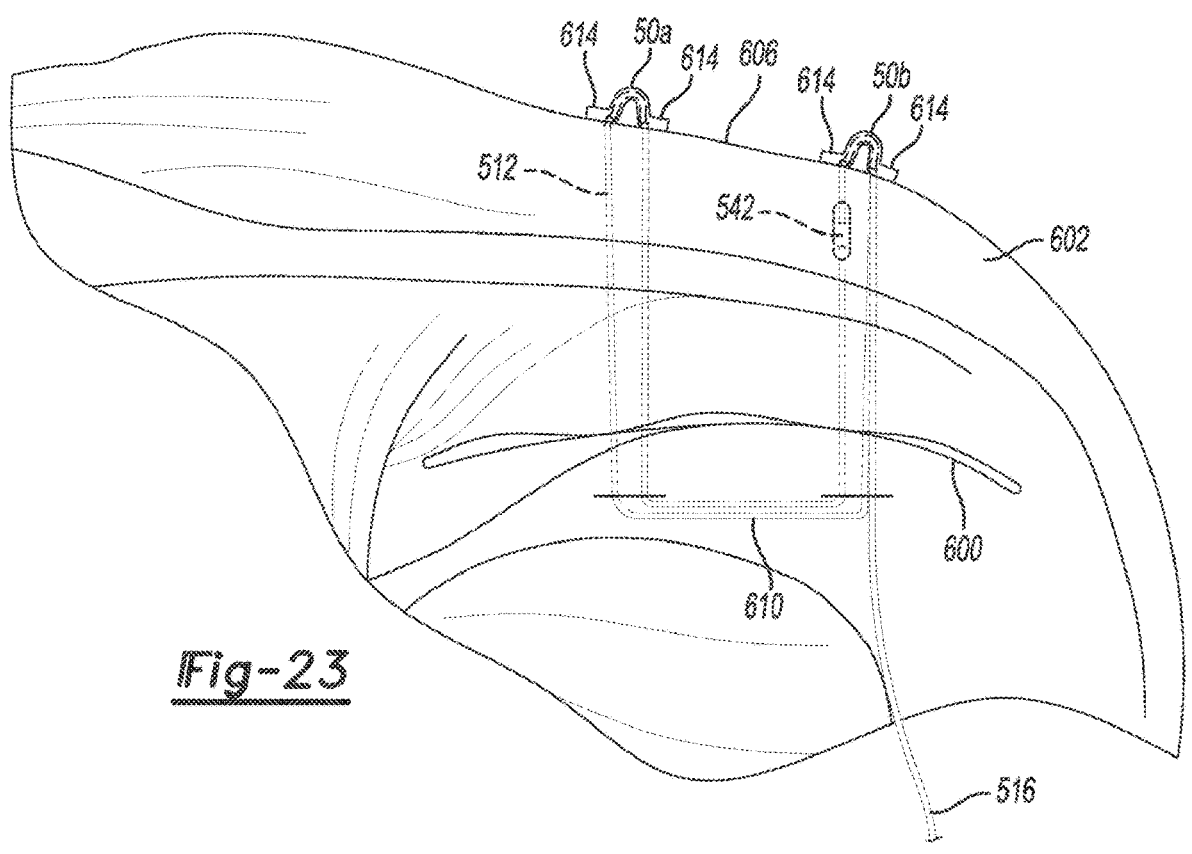
FIG. 23 is another exemplary environmental view showing first and second anchors being deployed outside of soft tissue according to the present teachings.

With the first anchor 50*a* deployed, the insertion device 10 can be removed from the soft tissue 602 while portions 610 of the knotless loop 546 can slide out from insertion device 10 as flexible anchor is retained in soft tissue 602. Insertion device 10 can then be inserted at a second location or entry point 605 on a second side of the soft tissue defect 600, as shown in FIG. 22. Once distal end 284 of insertion member 222 is appropriately positioned, such as beyond second side 606, trigger 340 can again be squeezed or depressed to deploy second anchor 50*b* adjacent to first anchor 50*a*. Depressing trigger 340 again translates carrying wire 220 forward such that one-way barb 584 engages an interior of bore 508 and deploys second flexible anchor 50*b* at the second location such that tail portion 548 of anchor 50*b* can engage soft tissue side 606 upon retraction on insertion member 222, as also generally shown in FIG. 22. Insertion device 10 can then be removed from the soft tissue 602 and the skin incision 601 with the second end 516 of the flexible strand 512 being removed from the soft tissue 602 along with insertion device 10, as also shown in FIG. 22. Once second anchor 50*b* is implanted and insertion device 10 removed from the soft tissue 602, any remaining portion of second flexible strand end 516 not removed from outer cannula 86 and housing member 560 can be subsequently removed.

Pulling the second, free end 516 of the flexible strand 512 can tighten the adjustable knotless loop 546, secure the first and second flexible anchors 50*a*, 50*b* against the second side surface 606 of the soft tissue 602, and reduce the defect 600. Further, portions 614 of the anchors 50*a*, 50*b* between the first and second ends 502, 504 and the corresponding first and second openings 528, 530, can define anchoring leg portions 614 that can provide additional resistance for securing the flexible anchors 50*a*, 50*b* on the surface 606 of the soft tissue 602, as these leg portions can be forced against surface 606 for anchoring, as shown for example in FIG. 23.

It will be appreciated from the above description and drawings that the present teachings provide flexible anchors that can be passed through tissue easily in a compact or low profile configuration and or orientation and then positioned outside tissue in a second orientation that provides anchoring without tissue penetration, preventing withdrawal from the tissue and reducing tissue injury. Further, the use of an inserter provided with preassembled anchors can help reduce the time length of the procedure and simplify manipulations required during the procedure.

It will be further understood that the various aspects of the depth positioning system, insertion system, deployment system and anchors can be mixed and matched or combined in ways other than those explicitly discussed above, without departing from the scope of the present teachings.

The foregoing discussion discloses and describes merely exemplary arrangements of the present disclosure. One skilled in the art will readily recognize from such discussion, and from the accompanying drawings and claims, that various changes, modifications and variations can be made therein without departing from the spirit and scope of the present teachings as defined in the following claims.

What is claimed is:

1. A meniscal tissue repair device, comprising:

a user-graspable casing that includes a first casing portion attached to a second casing portion;

an inserter extending from the user-graspable casing, the inserter including an open distal end and a longitudinal bore that extends through the inserter to the open distal end;

a first flexible suture anchor deployable from the inserter at a first location along an outer surface of a meniscus;

a second flexible suture anchor deployable from the inserter at a second location along the outer surface of the meniscus, wherein, in a pre-deployment condition of the meniscal tissue repair device, the second flexible suture anchor is located proximal of the first flexible suture anchor along the inserter;

a suture coupling the first flexible suture anchor to the second flexible suture anchor;

a cam pivotable about a pivot point that is located within the user-graspable casing, the cam including a first plurality of teeth that extend in an arcuate manner along the cam;

a cam follower including a second plurality of teeth that extend in a linear manner along the cam follower, the second plurality of teeth meshing with the first plurality of teeth such that pivoting the cam about the pivot point causes the cam follower to move linearly within the user-graspable casing;

a user-accessible element protruding from an aperture in the user-graspable casing so as to be accessible and movable by a user from outside the user-graspable casing, said aperture formed by attaching the first casing portion to the second casing portion, the user-accessible element coupled to the cam such that movement of the user-accessible element by the user causes the cam to pivot about the pivot point; and a carrying wire slidably received in the longitudinal bore of the inserter, the carrying wire including a proximal portion coupled to the cam follower such that linear movement of the cam follower within the user-graspable casing causes the carrying wire to move linearly within the longitudinal bore of the inserter, the carrying wire further including an anchor engagement portion distal of the proximal portion, wherein, in the pre-deployment condition of the meniscal tissue repair device, the carrying wire extends distally past the second flexible suture anchor toward the first flexible suture anchor to position the anchor engagement portion between the second flexible suture anchor and the first flexible suture anchor in the longitudinal bore of the inserter, wherein, from the pre-deployment condition of the meniscal tissue repair device, the cam is pivotable about the pivot point in a first rotational direction to advance the carrying wire within the longitudinal bore of the inserter and thereby force the first flexible suture anchor from the inserter via an engagement of the first flexible suture anchor with the anchor engagement portion, wherein the cam is pivotable about the pivot point in a second rotational direction opposite the first rotational direction to retract the carrying wire within the longitudinal bore of the inserter and thereby move the anchor engagement portion proximally past at least part of the second flexible suture anchor, and wherein the cam is pivotable about the pivot point in the first rotational direction to advance the carrying wire within the longitudinal bore of the inserter and thereby force the second flexible suture anchor from the inserter via an engagement of the second flexible suture anchor with the anchor engagement portion.

2. The meniscal tissue repair device of claim 1, wherein the user-accessible element includes an end portion adjoining the cam.

3. The meniscal tissue repair device of claim 2, wherein the end portion is rotatable about an axis.

4. The meniscal tissue repair device of claim 1, wherein the cam follower has a rectangular shape.

5. The meniscal tissue repair device of claim 1 further comprising an anchor stop, wherein, in the pre-deployment condition of the meniscal tissue repair device, the second flexible suture anchor is located between the first flexible suture anchor and the anchor stop.

6. A meniscal tissue repair device, comprising:
a user-graspable casing;
an inserter extending from the user-graspable casing, the inserter including an open distal end and a longitudinal bore that extends through the inserter to the open distal end;
a first flexible suture anchor deployable from the inserter at a first location along an outer surface of a meniscus;
a second flexible suture anchor deployable from the inserter at a second location along the outer surface of the meniscus, wherein, in a pre-deployment condition of the meniscal tissue repair device, the second flexible suture anchor is located proximal of the first flexible suture anchor along the inserter;
a suture coupling the first flexible suture anchor to the second flexible suture anchor;
a cam pivotable about a pivot point that is located within the user-graspable casing, the cam including a first plurality of teeth that extend in an arcuate manner along the cam;

a cam follower including a second plurality of teeth that extend in a linear manner along the cam follower, the second plurality of teeth meshing with the first plurality of teeth such that pivoting the cam about the pivot point causes the cam follower to move linearly within the user-graspable casing; and a carrying wire slidably received in the longitudinal bore of the inserter, the carrying wire including a proximal portion coupled to the cam follower such that linear movement of the cam follower within the user-graspable casing causes the carrying wire to move linearly within the longitudinal bore of the inserter, the carrying wire further including an anchor engagement portion distal of the proximal portion, wherein, in the pre-deployment condition of the meniscal tissue repair device, the carrying wire extends distally past the second flexible suture anchor toward the first flexible suture anchor to position the anchor engagement portion between the second flexible suture anchor and the first flexible suture anchor in the longitudinal bore of the inserter, wherein, from the pre-deployment condition of the meniscal tissue repair device, the cam is pivotable about the pivot point in a first rotational direction to advance the carrying wire within the longitudinal bore of the inserter and thereby force the first flexible suture anchor from the inserter via an engagement of the first flexible suture anchor with the anchor engagement portion, wherein the cam is pivotable about the pivot point in a second rotational direction opposite the first rotational direction to retract the carrying wire within the longitudinal bore of the inserter and thereby move the anchor engagement portion proximally past at least part of the second flexible suture anchor, and wherein the cam is pivotable about the pivot point in the first rotational direction to advance the carrying wire within the longitudinal bore of the inserter and thereby force the second flexible suture anchor from the inserter via an engagement of the second flexible suture anchor with the anchor engagement portion, wherein the carrying wire includes a non-flattened section that is located proximal of the anchor engagement portion, the non-flattened section having a non-flattened diameter and a non-flattened cross-sectional area, wherein the carrying wire also includes a flattened section that is part of the anchor engagement portion, the flattened section including at least a first flattened portion, wherein the first flattened portion has: (i) a first width that is greater than the non-flattened diameter of the non-flattened section of the carrying wire; (ii) a first thickness that is less than the non-flattened diameter of the non-flattened section of the carrying wire; and (iii) a first cross-sectional area that is equal to the cross-sectional area of the non-flattened section of the carrying wire.

7. The meniscal tissue repair device of claim 6, wherein the flattened section of the carrying wire also includes a second flattened portion having a second width that is greater than the first width.

8. The meniscal tissue repair device of claim 6, wherein the flattened section includes at least a first curved transition area distal of the non-flattened section of the carrying wire.

9. The meniscal tissue repair device of claim 6, wherein, in the pre-deployment condition of the meniscal tissue repair device, the carrying wire extends through the second flexible suture anchor.

10. The meniscal tissue repair device of claim 6, wherein the engagement of the first flexible suture anchor with the anchor engagement portion includes the anchor engagement portion contacting an intermediate portion of the first flexible suture anchor, the intermediate portion located between a first end and a second end of the first flexible suture anchor.

11. A meniscal tissue repair device, comprising:

a user-graspable casing that includes a first casing portion attached to a second casing portion;

an inserter extending from the user-graspable casing, the inserter including an open distal end and a longitudinal bore that extends through the inserter to the open distal end;

a first flexible suture anchor deployable from the inserter at a first location along an outer surface of a meniscus;

a second flexible suture anchor deployable from the inserter at a second location along the outer surface of the meniscus, wherein, in a pre-deployment condition of the meniscal tissue repair device, the second flexible suture anchor is located proximal of the first flexible suture anchor along the inserter;

a suture coupling the first flexible suture anchor to the second flexible suture anchor;

a cam pivotable about a pivot point that is located within the user-graspable casing, the cam including a first plurality of teeth that extend in an arcuate manner along the cam;

a cam follower including a second plurality of teeth that extend in a linear manner along the cam follower, the second plurality of teeth meshing with the first plurality of teeth such that pivoting the cam about the pivot point causes the cam follower to move linearly within the user-graspable casing;

a user-accessible element protruding from an aperture in the user-graspable casing so as to be accessible and movable by a user from outside the casing, the user-accessible element coupled to the cam such that movement of the user-accessible element by the user causes the cam to pivot about the pivot point; and a carrying wire slidably received in the longitudinal bore of the inserter, the carrying wire including a proximal portion coupled to the cam follower such that linear movement of the cam follower within the user-graspable casing causes the carrying wire to move linearly within the longitudinal bore of the inserter, the carrying wire further including an anchor engagement portion distal of the proximal portion, wherein, in the pre-deployment condition of the meniscal tissue repair device, the carrying wire extends distally past the second flexible suture anchor toward the first flexible suture anchor to position the anchor engagement portion between the second flexible suture anchor and the first flexible suture anchor in the longitudinal bore of the inserter, wherein the cam is pivotable about the pivot point: (i) a first time and in a first rotational direction to advance the carrying wire distally within the longitudinal bore of the inserter and thereby force the first flexible suture anchor from the inserter via an engagement of the first flexible suture anchor with the anchor engagement portion for deploying the first flexible suture anchor from the inserter at the first location along the outer surface of the meniscus; (ii) a second time and in a second rotational direction opposite the first rotational direction to retract the carrying wire proximally within the longitudinal bore of the inserter and thereby move the anchor engagement portion proximally past at least part of the second flexible suture anchor; and (iii) a third time and back in the first rotational direction to advance the carrying wire distally within the longitudinal bore of the inserter and thereby force the second flexible suture anchor from the inserter via an engagement of the second flexible suture anchor with the anchor engagement portion for deploying the second flexible suture anchor from the inserter at the second location along the outer surface of the meniscus, wherein the carrying wire includes a non-flattened section that is located proximal of the anchor engagement portion, wherein the carrying wire also includes a flattened section that is part of the anchor engagement portion.

12. The meniscal tissue repair device of claim 11, wherein the non-flattened section of the carrying wire has a non-flattened diameter and a non-flattened cross-sectional area.

13. The meniscal tissue repair device of claim 12, wherein the flattened section of the carrying wire includes at least a first flattened portion.

14. The meniscal tissue repair device of claim 13, wherein the first flattened portion has a first width that is greater than the non-flattened diameter of the non-flattened section of the carrying wire.

15. The meniscal tissue repair device of claim 14, wherein the flattened section includes at least a first curved transition area distal of the non-flattened section of the carrying wire.

16. The meniscal tissue repair device of claim 13, wherein the first flattened portion has a first thickness that is less than the non-flattened diameter of the non-flattened section of the carrying wire.

17. The meniscal tissue repair device of claim 16, wherein the flattened section includes at least a first curved transition area distal of the non-flattened section of the carrying wire.

18. The meniscal tissue repair device of claim 13, wherein the first flattened portion has a first cross-sectional area that is equal to the cross-sectional area of the non-flattened section of the carrying wire.

19. The meniscal tissue repair device of claim 18, wherein the flattened section includes at least a first curved transition area distal of the non-flattened section of the carrying wire.

20. The meniscal tissue repair device of claim 18, wherein the first flattened portion has a first width that is greater than the non-flattened diameter of the non-flattened section of the carrying wire.

21. The meniscal tissue repair device of claim 20, wherein the flattened section of the carrying wire also includes a second flattened portion having a second width that is greater than the first width.

22. The meniscal tissue repair device of claim 11 further comprising an anchor stop, wherein, in the pre-deployment condition of the meniscal tissue repair device, the second flexible suture anchor is located between the first flexible suture anchor and the anchor stop.

* * * * *